US008735137B2

(12) United States Patent
Hong et al.

(10) Patent No.: US 8,735,137 B2
(45) Date of Patent: May 27, 2014

(54) **USE OF *SACCHAROMYCES CEREVISIAE* SUC2 GENE IN *YARROWIA LIPOLYTICA* FOR SUCROSE UTILIZATION**

(75) Inventors: Seung-Pyo Hong, Hockessin, DE (US); John E. Seip, Alloway, NJ (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 184 days.

(21) Appl. No.: 13/296,524

(22) Filed: Nov. 15, 2011

(65) Prior Publication Data
US 2012/0171719 A1 Jul. 5, 2012

Related U.S. Application Data

(60) Provisional application No. 61/428,590, filed on Dec. 30, 2010.

(51) Int. Cl.
*C12N 1/15* (2006.01)
*C12N 15/56* (2006.01)
*C12N 9/26* (2006.01)
*C12N 9/60* (2006.01)

(52) U.S. Cl.
CPC .............. *C12N 9/2431* (2013.01); *C12N 9/60* (2013.01); *C07K 2319/006* (2013.01)
USPC ....... 435/254.2; 435/201; 435/69.9; 435/171; 435/134; 435/67; 435/106; 435/52; 435/125; 435/136; 435/155; 435/135; 435/133; 435/156

(58) Field of Classification Search
CPC combination set(s) only.
See application file for complete search history.

(56) References Cited

U.S. PATENT DOCUMENTS

| | | | |
|---|---|---|---|
| 5,212,087 A | 5/1993 | Fournier et al. | |
| 7,550,286 B2 | 6/2009 | Damude et al. | |
| 7,588,931 B2 | 9/2009 | Damude et al. | |
| 7,772,444 B2 | 8/2010 | Huang et al. | |
| 7,932,077 B2 | 4/2011 | Damude et al. | |
| 2009/0093543 A1 | 4/2009 | Xue et al. | |
| 2009/0142322 A1 | 6/2009 | Ye | |
| 2010/0317072 A1 | 12/2010 | Hong et al. | |

FOREIGN PATENT DOCUMENTS

| | | |
|---|---|---|
| EP | 0220864 B1 | 5/1987 |
| EP | 0329501 A1 | 8/1989 |
| EP | 0402226 A1 | 12/1990 |
| WO | 2007120423 A2 | 10/2007 |
| WO | 2008073367 A1 | 6/2008 |
| WO | 2008130372 A2 | 10/2008 |
| WO | 2008151149 A2 | 12/2008 |
| WO | 2009126890 A2 | 10/2009 |
| WO | 2010147907 A1 | 12/2010 |

OTHER PUBLICATIONS

International Search Report, Corresponding International Patent Application PCT/US2011/060788, Mailed Apr. 10, 2012.
Sreekrishna et al., Invertase Gene (SUC2) of *Saccharomyces cerevisiae* as a Dominant Marker for Transformation of *Pichia pastoris*, Gene, Elsevier, vol. 59., No. 1 (1987), pp. 115-125.
R. Taussig et al., Nucleotide Sequence of the Yeast SUC2 Gene for Invertase, Nucleic Acids Research, vol. 11, No. 6 (1983), pp. 1943-1954.
D. Perlman et al., Presecretory and Cytoplasmic Invertase Polypeptides Encoded by Distinct MRNAs Derived From the Same Structural Gene Differ by a Signal Sequence, Proc. Natl. Acad. Sci. USA, vol. 79 (1982), pp. 781-785.
Z. Lazar et al., Simultaneous Production of Citric Acid and Invertase by *Yarrowia lipolytica* SUC* Transformants, Bioresource Technology, vol. 102 (2011), pp. 6982-6989.
E. Walczak et al., Wzrost Z Sacharozy Klonow Drozdzy *Yarrowia lipolytica* Z Genem Inwertazy Z *Saccharomyces*, Acta Sci. Pol., Biotechnologia, vol. 8, No. 4 (2009) pp. 25-36. (Applicant Has Been Unable to Obtain a Translation at This Time).
S. Matoba et al., Intracellular Precursors and Secretion of Alkaline Extracellular Protease of *Yarrowia lipolytica*, Molecular and Cellular Biology, vol. 8, No. 11 (1988), pp. 4904-4916.
Park et al., Expression, Secretion and Processing of Rice, α-Amylase in the Yeast *Yarrowia lipolytica*, The Journal of Biological Chemistry, vol. 272, No. 11 (1997), pp. 6876-6881.
C. Kaiser et al., Secretion-Defective Mutations in the Signal Sequence for *Saccharomyces cerevisiae* Invertase, Molecular and Cellular Biology, vol. 6, No. 7 (1986), POO. 2382-2391.
J-M Nicaud et al., Expression of Invertase Activity in *Yarrowia lipolytica* and Its Use as a Selective Marker, Curr Genet, vol. 16 (1989), pp. 253-260.
L. S. Davidow et al., Cloning and Sequencing of the Alkaline Extracellular Protease Gene of *Yarrowia lipolytica*, Journal of Bacteriology, vol. 169, No. 1 (1987), pp. 4621-4629.
M. Carlson et al., Two Differentially Regulated MRNAs With Different 5' Ends Encode Secreted and Intracellular Forms of Yeast Invertase, Cell, vol. 28 (1982), pp. 145-154.
A. Foester et al., Citric Acid Production From Sucrose Using a Recombinant Strain of the Yeast *Yarrowia lipolytica*, Appl. Microiol. Biotechnol., vol. 75 (2007), pp. 1409-1417.
S-P Hong et al., Engineering *Yarrowia lipolytica* to Express Secretory Invertase With Strong FBA I in Promoter, Yeast, vol. 29 (2012), pp. 59-72. (Also Published Online in Wiley Online Library Dec. 29, 2011).

*Primary Examiner* — Rebecca Prouty

(57) ABSTRACT

Disclosed herein are transformed *Yarrowia lipolytica* comprising an exogenous polynucleotide encoding a polypeptide having sucrose invertase activity. Also disclosed are methods of using the transformed *Y. lipolytica*.

12 Claims, 9 Drawing Sheets

```
atg ctt ttg caa gct ttc ctt ttg gct ggt ttt gca gcc aaa      48
Met Leu Leu Gln Ala Phe Leu Leu Ala Gly Phe Ala Ala Lys
 1               5                  10              15 ata tct gca tca atg aca aac gaa act agc gat aga cct ttg gtc cac  96
Ile Ser Ala Ser Met Thr Asn Glu Thr Ser Asp Arg Pro Leu Val His
             20                  25                  30
```
└─────────── N-terminus of m-ScSUC2 ───────────┘

B

┌─ C-terminus of XPR2 pre/pro-region ─┐

```
tct ctc ccc gag att cct gct tct aat gcc aag cga gct atc cag    480
Ser Leu Pro Glu Ile Pro Ala Ser Asn Ala Lys Arg Ala Ile Gln
145                 150                 155             160 act act ccc gtc act caa tgg ggc ctg tct aga atc tct cat aag aag  528
Thr Thr Pro Val Thr Gln Trp Gly Leu Ser Arg Ile Ser His Lys Lys
                165                 170                 175 gcc cag act gga aac tac gcc tac gtt cga gag aca gtt ggc aag cac  576
Ala Gln Thr Gly Asn Tyr Ala Tyr Val Arg Glu Thr Val Gly Lys His
                180                 185                 190
```

USE OF *SACCHAROMYCES CEREVISIAE* SUC2 GENE IN *YARROWIA LIPOLYTICA* FOR SUCROSE UTILIZATION

This application claims the benefit of U.S. Provisional Application No. 61/428,590, filed Dec. 30, 2010, which is hereby incorporated by reference in its entirety.

FIELD OF THE INVENTION

This invention is in the field of biotechnology. More specifically, this invention pertains to a transformed *Yarrowia lipolytica* having the ability to use sucrose as a carbon source, wherein the transformed *Y. lipolytica* may also optionally be engineered to produce a non-native product of interest, such as polyunsaturated fatty acids ("PUFAs").

BACKGROUND OF THE INVENTION

Oleaginous yeast such as *Yarrowia lipolytica* have the natural ability to use glucose as their sole carbon source; however, this substrate is not always the most cost-effective carbon source. Using sucrose as a carbon source (whether alone or in combination with other carbon sources) as a carbon source instead of glucose may be advantageous due to its cost.

*Y. lipolytica* is not able to utilize sucrose as a carbon source since it does not have a gene encoding invertase, which catalyzes the conversion of sucrose (a disaccharide) into the monosaccharides glucose and fructose. Several previous investigators have fused a signal sequence to a heterologous gene encoding invertase (e.g., the *Saccharomyces cerevisiae* SUC2 gene), to engineer the yeast to secrete a mature invertase protein into the surrounding medium, where sucrose can then be hydrolyzed.

One well known signal sequence isolated from *Y. lipolytica* is that of the inducible alkaline extracellular protease ("AEP") (EP0220864 B1; Davidow, et al., *J. Bacteriol.*, 169:4621-4629 (1987); Matoba, et al., *Mol. Cell Biol.*, 8:4904-4916 (1988)). AEP is encoded by the XPR2 gene in *Y. lipolytica*. Furthermore, large amounts are naturally secreted extracellularly.

Nicaud et al. (*Current Genetics*, 16:253-260 (1989); EP 0402226 A1) reported chimeric expression of the *S. cerevisiae* SUC2 with a *Y. lipolytica* XPR2 promoter and its signal sequence, which resulted in a sucrose-utilizing (SUC+) phenotype in *Y. lipolytica*. Specifically, 23 N-terminal amino acids from XPR2 were fused to a truncated SUC2 (wherein the truncation removed the first 4 amino acids of the full-length protein). It was reported that about 10% of the invertase activity was observed in the culture broth (i.e., via extracellular secretion), whereas 90% of the activity was recovered using whole cells (i.e., invertase was secreted into the periplasm). Thus, the efficiency in extracellular sucrose hydrolysis was relatively low.

The methodology described by Nicaud et al. has been utilized by others, in their efforts to develop transformant *Y. lipolytica* strains producing citric acid using sucrose as a carbon source (Wojtatowicz, M., et al., *Pol. J. Food Nutr. Sci.*, 6/47(4): 49-54 (1997); Förster, A. et al., *Appl. Microbiol. Biotechnol.*, 75:1409-1417 (2007); Lazar, Z. et al., *Bioresour. Technol.*, 102:6982-6989 (2011)). Foster et al., above, reported that the majority (60-70%) of invertase activity was found on the cell surface (i.e., cell-bound activity detectable in whole cells, whereas 30-40% of the invertase was detectable in the cell-free culture medium; maximal invertase yield from biomass was 110 U/g dry weight biomass. Most recently, Lazar et al., above, identified a *Y. lipolytica* strain containing two copies of a fusion comprising the *Y. lipolytica* XPR2 promoter and its signal sequence and the *S. cerevisaie* SUC2 and demonstrated that most of the invertase activity was associated with the cells (2568 to 3736 U/g of cells), while about 232 to 589 U/g was extracellular (i.e., only 5-20% of the activity was extracellular).

Thus, engineering *Y. lipolytica* to have improved extracellular invertase activity is desirable, for it to better utilize sucrose as a carbon source.

SUMMARY OF THE INVENTION

In one embodiment, the invention concerns a transformed *Yarrowia lipolytica* comprising an exogenous polynucleotide encoding a polypeptide having sucrose invertase activity, wherein:

a) said polypeptide comprises a signal sequence fused to a polypeptide sequence encoding mature sucrose invertase; and, b) said signal sequence is selected from the group consisting of:

(i) a Xpr2 pre/pro-region and a N-terminal Xpr2 fragment; and, (ii) a sucrose invertase signal sequence, wherein the second amino acid of the sucrose invertase signal sequence can be any hydrophobic amino acid; and, c) said polypeptide sequence encoding mature sucrose invertase has at least 80% sequence identity based on the CLUSTALW method of alignment, when compared to SEQ ID NO:4 ("m-ScSUC2").

Preferably, the second amino acid of the sucrose invertase signal sequence described above is selected from the group consisting of: leucine, phenylalanine, isoleucine, valine and methionine.

In a second embodiment, the polypeptide sequence encoding mature sucrose invertase is set forth in SEQ ID NO:4 ("m-ScSUC2").

In a third embodiment, the Xpr2 pre/pro-region and N-terminal Xpr2 fragment is from *Y. lipolytica* and said sucrose invertase signal sequence is from *Saccharomyces cerevisiae*. Preferably, the Xpr2 pre/pro-region and N-terminal Xpr2 fragment comprises:

(i) a Xpr2 pre/pro-region comprising the N-terminal 157 amino acids of an alkaline extracellular protease precursor; and, (ii) a N-terminal Xpr2 fragment comprising the N-terminal 13 amino acids of a mature alkaline extracellular protease.

Preferably, the Xpr2 pre/pro-region and N-terminal Xpr2 fragment is set forth in SEQ ID NO:10 ["XPR2PP+13"].

In a fourth embodiment, the sucrose invertase signal sequence is set forth in SEQ ID NO:8 ["Suc2SS"].

In a fifth embodiment, the polypeptide comprising a signal sequence fused to a sucrose invertase coding sequence is selected from the group consisting of: SEQ ID NO:12 ["Suc2SS/m-ScSUC2"] and SEQ ID NO:20 ["XPR2PP+13/m-ScSUC2"].

In a sixth embodiment, the transformed *Y. lipolytica* is capable of growing under conditions wherein sucrose is the sole carbon source.

In a seventh embodiment, the transformed *Y. lipolytica* is capable of producing at least one non-native product of interest. Preferably, the at least one non-native product of interest is selected from the group consisting of: polyunsaturated fatty acids, carotenoids, amino acids, vitamins, sterols, flavonoids, organic acids, polyols and hydroxyesters, quinone-derived compounds and resveratrol.

In an eighth embodiment, any of the transformed *Y. lipolytica* of the invention herein, grown in a culture medium having at least sucrose as a carbon source, are capable of secreting at least 80% of the sucrose invertase extracellularly.

In a ninth embodiment, the invention concerns a method of producing at least one non-native product of interest comprising growing the transformed *Y. lipolytica* of the invention in a culture medium having at least one carbon source selected from the group consisting of:
 a) sucrose; and,
 b) glucose;
whereby the at least one non-native product of interest is produced, and optionally, recovering the at least one non-native product of interest.

Preferably, the at least one non-native product of interest is selected from the group consisting of: polyunsaturated fatty acids, carotenoids, amino acids, vitamins, sterols, flavonoids, organic acids, polyols and hydroxyesters, quinone-derived compounds and resveratrol.

In a tenth embodiment, the transformed *Y. lipolytica* is capable of secreting at least 80% of sucrose invertase extracellularly.

BRIEF DESCRIPTION OF THE DRAWINGS AND SEQUENCE DESCRIPTIONS

FIG. 1 provides a schematic summary of extracellular invertase expression constructs pYRH68 (SEQ ID NO:13), pYRH74 (SEQ ID NO:21), pYRH69 (SEQ ID NO:18) and pYRH73 (SEQ ID NO:15), as well as the resulting phenotype (i.e., sucrose-utilizing (SUC$^+$) or non-sucrose-utilizing (SUC$^-$)) when these constructs are expressed in *Y. lipolytica*.

FIG. 2A provides the nucleotide and translated amino acid sequence of the N-terminal portion of the *Saccharomyces cerevisiae* invertase ("ScSUC2"). More specifically, amino acids 1-32 of SEQ ID NO:2 are shown; the first 19 amino acids correspond to the invertase signal sequence set forth herein as Suc2SS (SEQ ID NO:8), while the remaining amino acids shown in the outlined box represent the N-terminus of the mature invertase protein, designated herein as m-ScSUC2 (SEQ ID NO:4).

FIG. 2B provides the nucleotide and translated amino acid sequence of a portion of the *Y. lipolytica* alkaline extracellular protease encoded by the XPR2 gene. Specifically, amino acids 145-192 of the alkaline extracellular protease precursor (SEQ ID NO:6) are shown. Of these, amino acids 145-157 shown in the dotted-lined box correspond to the C-terminus of the Xpr2 pre/pro-region, while amino acids 158-192 correspond to a N-terminal Xpr2 fragment of the mature protein. Underlined amino acids correspond to the 13 amino acids of the N-terminal Xpr2 fragment that are present in the Xpr2 pre/pro-region and N-terminal Xpr2 fragment referred to herein as the XPR2PP+13 (SEQ ID NO:10).

FIG. 3 provides a plasmid map for pZSUC.

FIG. 4 provides plasmid maps for the following: (A) pYRH68 and (B) pYRH70.

FIG. 5 provides plasmid maps for the following: (A) pYRH73 and (B) pYRH69.

Figure 1:
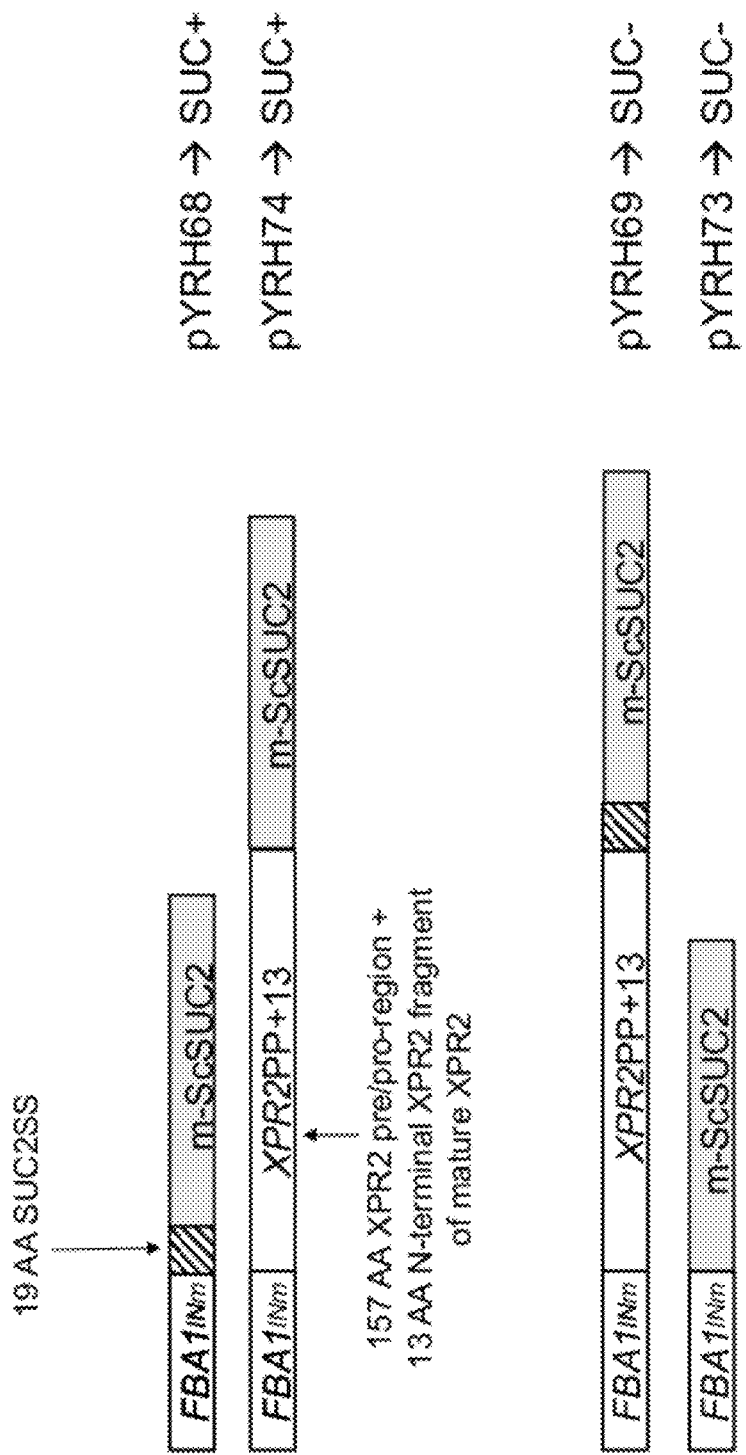

The following sequences comply with 37 C.F.R. §§1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-41 are ORFS encoding genes, proteins (or portions thereof), primers or plasmids, as identified in Table 1.

TABLE 1

Summary Of Nucleic Acid And Protein SEQ ID Numbers

| Description | Nucleic acid SEQ ID NO. | Protein SEQ ID NO. |
|---|---|---|
| *Saccharomyces cerevisiae* invertase ("ScSUC2"), comprising a signal sequence of 19 amino acids | 1 (1599 bp) | 2 (532 AA) |
| *Saccharomyces cerevisiae* invertase ("m-ScSUC2"), lacking the signal sequence of 19 amino acids | 3 (1542 bp) | 4 (513 AA) |
| *Yarrowia lipolytica* alkaline extracellular protease, comprising a signal sequence and a pre/pro-region of 157 amino acids | 5 (1365 bp) | 6 (454 AA) |
| Modified Suc2 signal sequence ("Suc2SS") derived from *Saccharomyces cerevisiae* invertase | 7 (57 bp) | 8 (19 AA) |
| Xpr2 pre/pro-region and a N-terminal Xpr2 fragment ("XPR2PP + 13"), derived from *Y. lipolytica* | 9 (510 bp) | 10 (170 AA) |
| SUC2SS/m-ScSUC2 fusion | 11 (1599 bp) | 12 (532 AA) |
| Vector pYRH68 | 13 (8743 bp) | — |
| Vector pYRH70 | 14 (11962 bp) | — |
| Vector pYRH73 | 15 (8689 bp) | — |
| XPR2PP + 13/SUC2SS/m-ScSUC2 fusion | 16 (2112 bp) | 17 (703 AA) |
| Vector pYRH69 | 18 (9256 bp) | — |
| XPR2PP + 13/m-ScSUC2 fusion | 19 (2058 bp) | 20 (685 AA) |
| Vector pYRH74 | 21 (9202 bp) | — |
| Plasmid pZSUC | 22 (9016 bp) | — |
| Primers Sc.SUC2-5' and Sc.SUC2-3' | 23, 24 | — |
| Plasmid pZKLY-PP2 | 25 (11180 bp) | — |
| Primer nSC.SUC2-3' | 26 | — |
| Primers Yl.XPR2-5' and Yl.XPR2-3' | 27, 28 | — |
| Plasmid pZKL3-9DP9N | 29 (13565 bp) | — |
| Synthetic mutant delta-9 elongase gene derived from *Euglena gracilis* ["EgD9eS-L35G"] | 30 (777 bp) | 31 (258 AA) |
| *Yarrowia lipolytica* delta-9 desaturase (GenBank Accession No. XM_501496) | 32 (1449 bp) | 33 (482 AA) |
| *Yarrowia lipolytica* choline-phosphate cytidylyl-transferase (GenBank Accession No. XM_502978) | 34 (1101 bp) | 35 (366 AA) |
| Primers YL427 and YL428 | 36, 37 | — |
| ClaI/HindIII fragment containing XPR2 promoter and 63 bp coding region | 38 (441 bp) | — |
| Primers YL429 and YL430 | 39, 40 | — |

TABLE 1-continued

Summary Of Nucleic Acid And Protein SEQ ID Numbers

| Description | Nucleic acid SEQ ID NO. | Protein SEQ ID NO. |
|---|---|---|
| HindIII/BsiWI fragment containing a truncated SUC2 gene | 41 (1581 bp) | — |

DETAILED DESCRIPTION OF THE INVENTION

All patents, patent applications, and publications cited herein are incorporated by reference in their entirety.

In this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

"Polyunsaturated fatty acid(s)" is abbreviated as "PUFA(s)".

"Triacylglycerols" are abbreviated as "TAGs".

"Total fatty acids" are abbreviated as "TFAs".

"Fatty acid methyl esters" are abbreviated as "FAMEs".

"Dry cell weight" is abbreviated as "DCW".

"Weight percent" is abbreviated as "wt %".

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

The term "secretory pathway" refers to the pathway by which a cell transports proteins out of the cell, in the process of secretion. Generally, proteins to be secreted are translated into the rough endoplasmic reticulum ["ER"], transported through the Golgi apparatus and then incorporated into a vesicle that ultimately fuses with the plasma membrane in a process of exocytosis, thereby releasing the protein. Secretion may occur constitutively or in a regulated fashion.

A "signal sequence" (also referred to as a "pre-" sequence region, "signal peptide", "targeting signal", "transit peptide", or "localization signal" in the art) is generally a short peptide sequence (i.e., about 3-60 amino acids in length at the N-most terminal portion of a polypeptide) that directs the transportation and localization of the remaining portion of the polypeptide within the cell or to the extracellular environment. The average length in eukaryotes is 22.6 amino acid. Signal sequences generally comprise defined peptide motifs for targeting proteins to their site of function via translocation across a membrane, e.g., the ER membrane. Following translocation, the signal sequence is usually subsequently cleaved by an endogenous signal peptidase. A protein comprising a signal sequence is referred to as a "pre-protein".

While there is no consensus sequence, almost all signal peptides possess a common structure: a short, positively charged amino region (n-region); a central hydrophobic region (h-region); and, a more polar region (c-region) containing the site that is cleaved by the signal peptidase (Nielsen, et al., *Protein Engineering*, 10:1-6 (1997)).

The terms "pro-protein" and "protein precursor" are used interchangeably herein and refer to a polypeptide that can be modified by cleavage of the N-terminal "pro-" sequence region. Removal of the "pro-" sequence region, usually by an endoprotease, results in the formation of a "mature protein". This "pro-" sequence region may be responsible for enhancing various post-translational modifications, may be a requirement for proper folding of the mature protein, or it may act to inhibit the activity of the mature protein until its post-translational removal.

A "pre/pro-protein" has a "pre/pro-" region attached to what will be the mature protein when the pre/pro region is removed. The "pre/pro-protein" comprises both a "pre-" sequence region (i.e., the N-terminal signal sequence) and a "pro-" sequence region (i.e., juxtaposed between the "pre-" sequence region and what will be the mature protein when the pre/pro region is removed).

The terms "invertase" and "beta-fructofuranosidase" refer to a protein (EC 3.2.1.26) having the ability to convert sucrose (i.e., a disaccharide composed of an alpha-D-glucose molecule and a beta-D-fructose molecule linked by an alpha-1, 4-glycosidic bond) into glucose and fructose via a hydrolysis reaction. In *Saccharomyces cerevisiae*, the gene encoding invertase is Suc2.

The term "extracellular invertase" refers to invertase that is secreted into culture medium in which a microbial cell is grown. Thus, extracellular invertase activity is typically measured within the culture medium itself. In contrast, "whole cell invertase" refers to invertase that is not secreted outside the cell, but instead secreted into the periplasmic spaces within the cell. Typically, whole cell invertase activity is measured within whole cells. The relative amount (i.e., percent) of extracellular invertase activity versus whole cell activity is determined as following: 100*invertase activity in culture medium/[(invertase activity in whole cells)+(invertase activity in culture medium)].

The term "alkaline extracellular protease" or "AEP" refers to a protein (EC 3.4.21.-) encoded by the XPR2 gene in *Y. lipolytica*. AEP is the major extracellular protein secreted by this yeast (over 1 gram per liter of culture) with 99% of the protein present in the cell-free medium supernatant. The N-terminus of the full-length protease contains a "pre/pro-" region, which is involved in processing and secretion of the mature protein.

The term "non-native product of interest" refers to any product that is not naturally produced in a wildtype microorganism. Typically, the non-native product of interest is produced via recombinant means, such that the appropriate heterologous gene(s) is introduced into the host microorganism to enable expression of the heterologous protein, which is the product of interest. Non-limiting examples of preferred non-native products of interest include, but are not limited to, polyunsaturated fatty acids, carotenoids, amino acids, vitamins, sterols, flavonoids, organic acids, polyols and hydroxyesters, quinone-derived compounds and resveratrol.

The term "at least one heterologous gene encoding a non-native product of interest" refers to a gene(s) derived from a different origin than of the host microorganism into which it is introduced. The heterologous gene facilitates production of a non-native product of interest in the host microorganism. In some cases, only a single heterologous gene may be needed to enable production of the product of interest, catalyzing conversion of a substrate directly into the desired product of interest without any intermediate steps or pathway intermediates. Alternatively, it may be desirable to introduce a series of genes encoding a novel biosynthetic pathway into the microorganism, such that a series of reactions occur to produce a desired non-native product of interest.

Generally, the term "oleaginous" refers to those organisms that tend to store their energy source in the form of oil (Weete, In: Fungal Lipid Biochemistry, 2nd Ed., Plenum, 1980). During this process, the cellular oil content of oleaginous microorganisms generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). For the purposes of the present application, the term "oleaginous" refers to those microorganisms that can accumulate at least about 25% of their dry cell weight ["DCW"] as oil.

The term "oleaginous yeast" refers to those oleaginous microorganisms classified as yeasts that can make oil, i.e., wherein the oil can accumulate in excess of about 25% of their DCW. Examples of oleaginous yeast include, but are no means limited to, the following genera: *Yarrowia, Candida, Rhodotorula, Rhodosporidium, Cryptococcus, Trichosporon* and *Lipomyces*. The ability to accumulate oil in excess of about 25% of the DCW of the yeast may be through efforts of recombinant engineering or through the natural abilities of the organism.

The term "carbon source" refers to a nutrient comprising carbon that a microorganism will metabolize to derive energy. For example, wildtype *Y. lipolytica* can use various carbon sources including glucose, fructose, glycerol, acetate, alcohols, alkanes, fatty acids, and triglycerides; however, it cannot use sucrose as the sole carbon source (Barth, G. and C. Gaillardin, *FEMS Microbiol. Rev.*, 19:219-237 (1997)). In contrast, the recombinant *Y. lipolytica* of the present invention can use sucrose either as the sole fermentable carbon source or in combination with other suitable carbon sources.

The terms "microbial host cell" and "microbial host organism" are used interchangeably herein and refer to a microorganism capable of receiving foreign or heterologous genes and capable of expressing those genes. A "recombinant microbial host cell" refers to a microbial host cell that has been recombinantly engineered (e.g., such that the microbial host cell has been transformed with an exogenous polynucleotide).

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in polymerase chain reaction ("PCR") in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine "Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Y. lipolytica* is provided in U.S. Pat. No. 7,125,672, incorporated herein by reference.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene (or "exogenous" gene) refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences", "transcription terminator" and "terminator" are used interchangeably herein and refer to DNA sequences located 3' downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "operably linked" refers to the association of nucleic acid sequences on a single nucleic acid fragment so that the function of one is affected by the other. For example, a promoter is operably linked with a coding sequence when it is capable of effecting the expression of that coding sequence. That is, the coding sequence is under the transcriptional control of the promoter. Coding sequences can be operably linked to regulatory sequences in sense or antisense orientation.

The term "expression", as used herein, refers to the transcription and stable accumulation of sense (mRNA) or antisense RNA. Expression may also refer to translation of mRNA into a polypeptide.

"Transformation" refers to the transfer of a nucleic acid molecule into a host organism. The nucleic acid molecule may be a plasmid that replicates autonomously; or, it may integrate into the genome of the host organism. Host organisms containing the transformed nucleic acid fragments are referred to as "transgenic" or "recombinant" or "transformed" organisms or "transformants".

"Stable transformation" refers to the transfer of a nucleic acid fragment into the genome of a host organism, including both nuclear and organellar genomes, resulting in genetically stable inheritance (i.e., the nucleic acid fragment is "stably integrated"). In contrast, "transient transformation" refers to the transfer of a nucleic acid fragment into the nucleus, or DNA-containing organelle, of a host organism resulting in gene expression without integration or stable inheritance.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, and may be linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., an open reading frame ("ORF")); and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.* 215:403-410 (1990)); 3) DNASTAR (DNASTAR, Inc. Madison, Wis.); 4) Sequencher (Gene Codes Corporation, Ann Arbor, Mich.); and 5) the FASTA program incorporating the Smith-Waterman algorithm (W. R. Pearson, Comput. *Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Sequence identity" or "identity" in the context of nucleic acid or polypeptide sequences refers to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology*

(von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences.

Multiple alignment of sequences can be performed using the "Clustal method of alignment" which encompasses several varieties of the algorithm including the "ClustalV method of alignment" and the "ClustalW method of alignment" (described by Higgins and Sharp, *CABIOS*, 5:151-153 (1989); Higgins, D. G. et al., *Comput. Appl. Biosci.*, 8:189-191 (1992)) and found in the MegAlign™ (version 8.0.2) program, above. After alignment of the sequences using either Clustal program, it is possible to obtain a "percent identity" by viewing the "sequence distances" table in the program.

Standard recombinant DNA and molecular cloning techniques used herein are well known in the art and are described by Sambrook, J., Fritsch, E. F. and Maniatis, T., Molecular Cloning: A Laboratory Manual, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

*Y. lipolytica* can be recombinantly engineered to use sucrose as a carbon source. This involved engineering the organism to express a gene encoding invertase, which catalyzes the conversion of sucrose into glucose and fructose. However, since the sucrose is present in the medium in which the yeast is grown, the sucrose needs to be transported into the cell prior to its hydrolysis by intracellular invertase or the invertase should be expressed extracellularly where it can hydrolyze the sucrose in the medium into glucose and fructose, which in turn can be transported into the cell. Preferably, a signal sequence is fused to a heterologous invertase gene so that invertase is secreted extracellularly into the surrounding medium.

*Saccharomyces cerevisiae* ferments sucrose because by expressing a functional invertase (EC 3.2.1.26; also referred to as "β-fructofuranosidase") that catalyzes the conversion of sucrose into glucose and fructose. There are two forms of invertase expressed from the same SUC2 allele in *S. cerevisiae*: a secreted glycosylated form regulated by glucose repression and an intracellular non-glycosylated form that is produced constitutively. The difference between these two forms is attributed to the presence or absence of the 5'-signal sequence required for synthesis of the secreted, glycosylated invertase. This signal sequence has been defined as the first 19 amino acids of the invertase protein (Perlman, D., et al., *Proc. Natl. Acad. Sci. U.S.A.*, 79:781-785 (1982); Carlson and Botstein, *Cell*, 28(1):145-54 (1982); Taussig and Carlson, *Nucleic Acids Res.*, 11:1943-54 (1983)).

Thus, the full-length *S. cerevisiae* SUC2 ["ScSUC2"] gene (SEQ ID NO:1) is 1599 nucleotides in length, encoding a full-length invertase of 532 amino acids (SEQ ID NO:2) that is secreted into the periplasm of *S. cerevisiae* in glycosylated form. In contrast, the "mature" ScSUC2 gene ["m-ScSUC2"] lacks the 19 amino acid length 5' signal sequence encoded by nucleotides 1-57 of SEQ ID NO:1; thus, the intracellular non-glycosylated form of m-ScSUC2 is encoded by the 1542 bp nucleotide sequence set forth as SEQ ID NO:3 (which corresponds to nucleotides 58-1599 of SEQ ID NO:1), and which is translated to yield a truncated m-ScSUC2 protein of 513 amino acids (SEQ ID NO:4).

Proteins secreted through the membrane of a cell are generally produced intracellularly as a "pre"-protein. In that form, the protein is fused to an additional "signal" polypeptide sequence which presumably assists in its secretion and localization, but is ultimately cleaved from the secreted "mature" protein during the secretion process. Although the signal peptides of pre-proteins share some similarities, their primary structures differ considerably. This suggests that each protein has evolved with a signal sequence which is particularly well suited for translocation of that particular protein through a cell membrane.

As discussed above, *Y. lipolytica* naturally secretes large amounts of AEP into the culture medium. The full-length *Y. lipolytica* AEP of SEQ ID NO:6 (454 amino acids in length) is encoded by the 1365 bp XPR2 gene (SEQ ID NO:5). The N-terminal 157 amino acid residues of the protease contains a signal sequence and a pre/pro-region which are involved in processing and secretion of the mature protein.

Detailed studies have shown that AEP is synthesized with a preproI-proII-proIII N-terminal region, and four different precursors of AEP were detected. Amino acid positions 1 to 13 contain a secretory signal sequence followed by positions 14 to 33 with a run of -Xaa-Ala- and -Xaa-Pro-, typical dipeptidyl aminopeptidase recognition sites. Amino acid position 54 or 60 is thought to be a cleavage site between the proI and proII regions, while position 129 or 131 is another cleavage site between the proII and proIII regions. Finally, amino acid position 157 of SEQ ID NO:6 is the cleavage site between proIII and mature AEP (Matoba, S. et al., *Mol. Cell. Biol.*, 8(11):4904-4916 (1988); see also U.S. Pat. No. 4,937,189 and EP 0220864 B1). It has been suggested that the pre/pro-region corresponding to amino acids 1-157 are involved in protein folding, efficient secretion, prevention of premature activation, etc.; without cleavage of the pre/pro-region, AEP protein is nonfunctional.

The Xpr2 prepro-region has been employed for secretion of various heterologous proteins in *Y. lipolytica*; however, use of the Xpr2 prepro-region for protein secretion has produced mixed outcomes (Madzak, C., et al., *Microbiology*, 145(1): 75-87 (1999)). Reasons for unsatisfactory protein expression include incomplete protein processing (Park, C. S., et al., *J. Biol. Chem.*, 272:6876-6881 (1997); Park, C. S., et al., *Appl. Biochem. Biotechnol.*, 87:1-15 (2000); Swennen, D., et al., *Microbiology*, 148:41-50 (2002)) and a lack of extracellular expression (Hamsa, P. V. and B. B. Chattoo, *Gene*, 143:165-70 (1994); Tharaud, C., et al., *Gene*, 121:111-119 (1992)). Therefore, it has been suggested that the pro-sequence might not be necessary or may even be deleterious for heterologous protein secretion (Madzak, C., et al., *J. Biotechnol.*, 109:63-81 (2004); Park, et al., *J. Biol. Chem.* (above); Tharaud, C., et al., above). This is shown by Tabuchi, M., et al. (*J. Bacteriol.*, 179:4179-4189 (1997)) in which the prepro-region of carboxypeptidase Y (CPY) was ineffective for secretion of Suc2 from *Schizosaccharomyces pombe*.

Constructs expressing the ScSuc2 signal sequence (corresponding to nucleotides 1-57 of SEQ ID NO:1 [ i.e., amino acids 1-19 of ScSUC2]) were mutated at amino acid position 2 to introduce a PciI restriction enzyme site. As a result, the wildtype Leu2 residue was mutated to Phe2, another hydrophobic residue, thereby maintaining the hydrophobicity of the signal sequence without affecting the secretory process for ScSuc2 (Kaiser, C. A., et al., *Science*, 235:312-317 (1987)). Thus, one suitable ScSuc2 signal sequence of the present invention (i.e., "Suc2SS") is set forth herein as SEQ ID NOs:7 and 8.

Constructs including the Xpr2 pre/pro-region were designed to encode amino acids 1-170 of SEQ ID NO:10. Although the Xpr2 pre/pro-region was described herein as encompassing only amino acids 1-157 of SEQ ID NO:6, an additional 13 amino acids of the protease after the pre/pro-region (i.e., a N-terminal Xpr2 fragment) were included as a "linker" to ensure access of the Xpr6 endopeptidase to the Lys156-Arg157 cleavage site, because imprecise processing of the fusion junction has been previously noted due to a putative secondary structure (Park, C. S., et al., *J. Biol. Chem.*, 272:6876-6881 (1997)). Thus, one suitable Xpr2 pre/pro-region and N-terminal Xpr2 fragment of the present invention (i.e., "XPR2PP+13") is set forth herein as SEQ ID NOs:9 and 10.

Expression cassettes summarized below in Table 2 and illustrated in FIG. 1 were evaluated for invertase expression in transformed *Y. lipolytica*. More specifically, expression plasmid pYRH68 comprised the Suc2SS signal sequence fused to the gene encoding the mature SUC2 (i.e., SEQ ID NO:3; "m-ScSUC2"), expression plasmid pYRH70 comprised two copies of the Suc2SS signal sequence fused to SEQ ID NO:3, expression plasmid pYRH69 comprised both the Xpr2 pre/pro-region and N-terminal Xpr2 fragment and the Suc2SS signal sequence fused to SEQ ID NO:3, expression plasmid pYRH73 comprised only SEQ ID NO:3 (and neither the Xpr2 pre/pro-region and N-terminal Xpr2 fragment nor the Suc2SS signal sequence as a secretory signal sequence) and expression plasmid pYRH74 comprised the Xpr2 pre/pro-region and N-terminal Xpr2 fragment fused to SEQ ID NO:3. A "FBAINm promoter region" (i.e., derived from the 5' upstream untranslated region in front of the 'ATG' translation initiation codon of a fructose-bisphosphate aldolase enzyme (E.C. 4.1.2.13) encoded by the fba1 gene [U.S. Pat. No. 7,202,356]) was operably linked to the invertase gene construct.

TABLE 2

Summary Of *Yarrowia lipolytica* Extracellular Invertase Expression Cassettes

Figure 3:
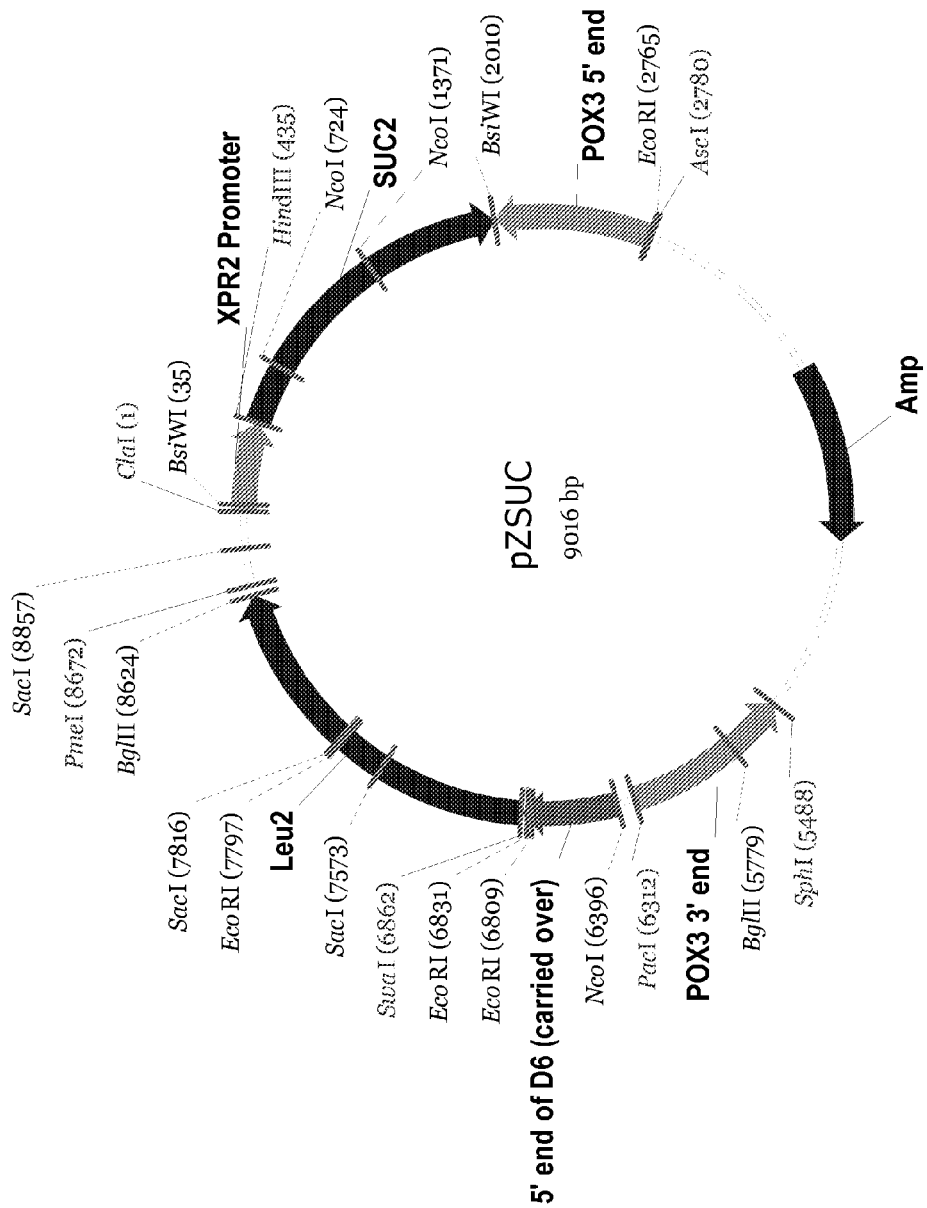
Figure 4:
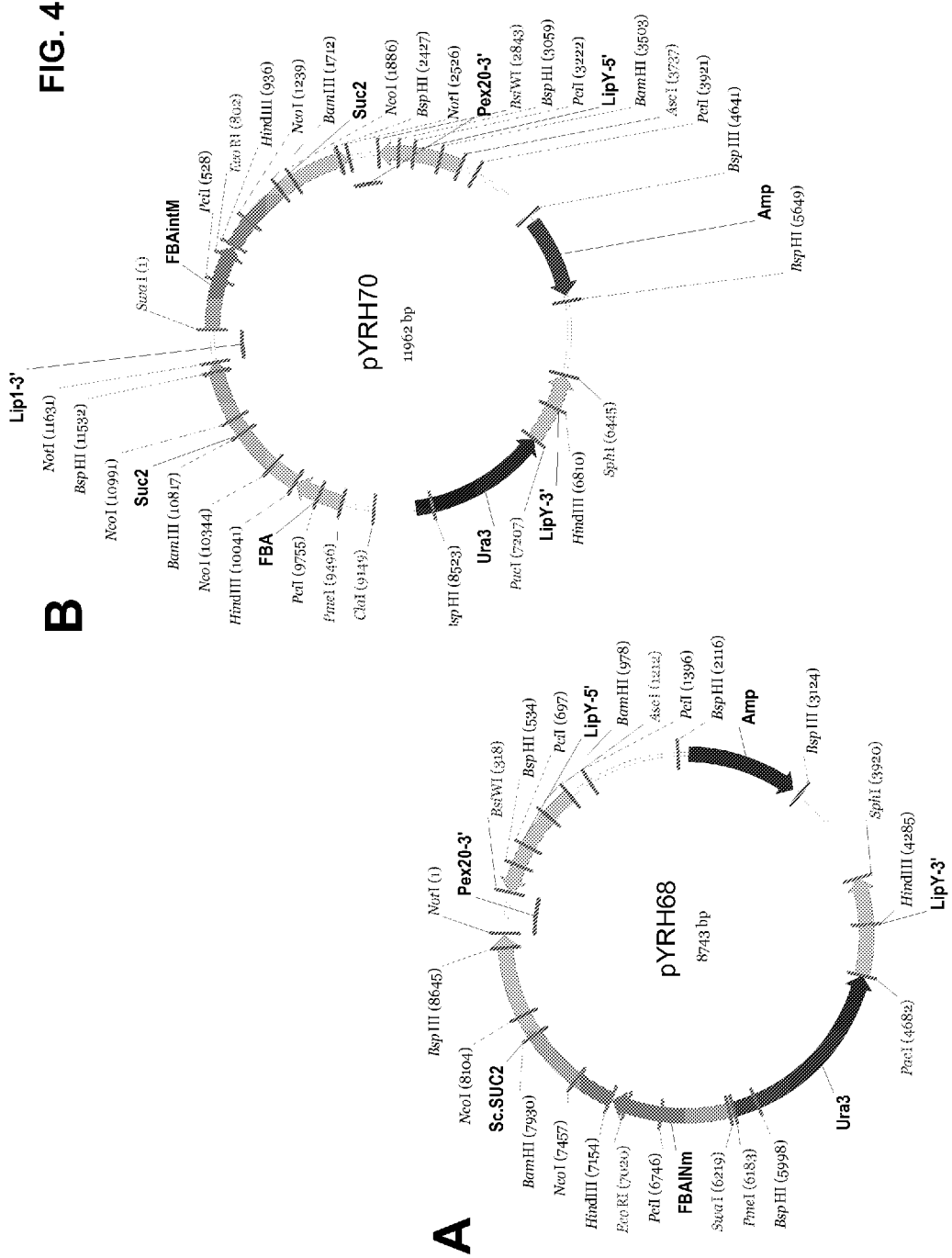
Figure 5:
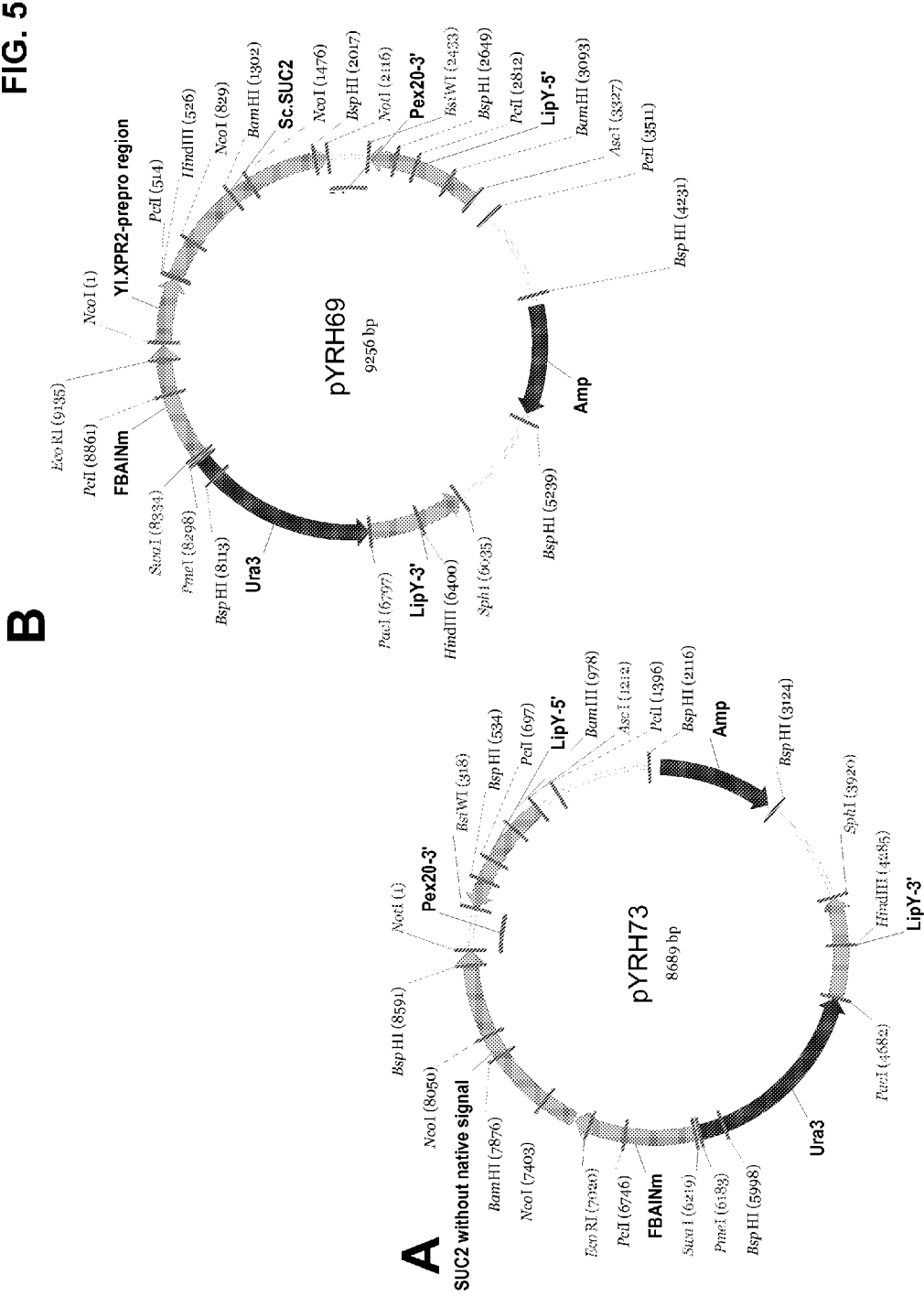

| Signal sequence | SEQ ID NO. of Xpr2 pre/pro-region and N-terminal Xpr2 fragment and/or SUC2 signal sequence/mature SUC2 | Plasmid Construct (SEQ ID NO; FIG. No.) | Phenotype of transformed *Y. lipolytica* |
|---|---|---|---|
| Suc2SS (SEQ ID NO: 8) | SEQ ID NOs: 11 and 12 | pYRH68 (SEQ ID NO: 13; FIG. 3A) | SUC+ |
| Suc2SS (SEQ ID NO: 8) | SEQ ID NOs: 11 and 12 | pYRH70 (SEQ ID NO: 14; FIG. 3B) | SUC+ |
| XPR2PP + 13 and Suc2SS (SEQ ID NO: 10 and SEQ ID NO: 8) | SEQ ID NOs: 16 and 17 | pYRH69 (SEQ ID NO: 18; FIG. 4B) | SUC− |
| — | SEQ ID NOs: 3 and 4 | pYRH73 (SEQ ID NO: 15; FIG. 4A) | SUC− |
| XPR2PP + 13 (SEQ ID NO: 10) | SEQ ID NO: 19 and 20 | pYRH74 (SEQ ID NO: 18; FIG. 5) | SUC+ |

*Y. lipolytica* transformants expressing each of the plasmid constructs above were grown on medium in which sucrose was the sole carbon source. Only those transformants expressing the Suc2SS signal sequence fused to the gene encoding the mature SUC2 (which effectively corresponds to the full-length gene encoding ScSuc2 [i.e., SEQ ID NO:2]) (i.e., pYRH68 and pYRH70) or the Xpr2 pre/pro-region and N-terminal Xpr2 fragment fused to the gene encoding the mature SUC2 (i.e., pYRH74) expressed invertase, i.e., a SUC+ phenotype. Thus, this illustrates those fusions resulting in functional expression of ScSUC2 in *Y. lipolytica*.

In one aspect, the instant invention concerns a transformed *Y. lipolytica* comprising an exogenous polynucleotide encoding a polypeptide having sucrose invertase activity, wherein:
 (a) said polypeptide comprises a signal sequence fused to a polypeptide sequence encoding mature sucrose invertase; and,
 (b) said signal sequence is selected from the group consisting of:
  (i) a Xpr2 pre/pro-region and a N-terminal Xpr2 fragment; and,
  (ii) a sucrose invertase signal sequence, wherein the second amino acid of the sucrose invertase signal sequence can be any hydrophobic amino acid; and,
 (c) said polypeptide sequence encoding mature sucrose invertase has at least 80% sequence identity based on the CLUSTALW method of alignment, when compared to SEQ ID NO:4 ("m-ScSUC2").

In preferred embodiments, the transformed *Y. lipolytica* of the present invention, when grown in a culture medium having at least sucrose as a carbon source, will be capable of secreting at least 80% of the sucrose invertase extracellularly (while intracellular [or periplasmic] invertase activity is equal to or less than 20% of the total invertase activity). More preferably, the extracellular invertase activity is at least 81%, 82%, 83%, 84%, 85%, 86%, 87%, 88%, 89%, 90%, 91%, 92%, 93%, 94%, 95%, 96%, 97%, 98%, 99% or 100% of the total invertase activity.

As previously described, the "mature" ScSUC2 protein ["m-ScSUC2"] set forth herein as SEQ ID NO:4 lacks the 19 amino acid length 5' signal sequence encoded by nucleotides 1-57 of SEQ ID NO:1. Preferably, the polypeptide sequence encoding mature sucrose invertase is set forth in SEQ ID NO:4 ("m-ScSUC2"). In alternate embodiments, the mature sucrose invertase has at least 80% sequence identity based on the CLUSTALW method of alignment, when compared to SEQ ID NO:4, i.e., the polypeptide may have at least 80%, 81%, 82%, 83%, 84%, 85%, 86%, 87%, 88%, 89%, 90%, 91%, 92%, 93%, 94%, 95%, 96%, 97%, 98%, 99%, or 100% identity when compared to SEQ ID NO:4.

In one embodiment, it may be desirable to codon-optimize SEQ ID NO:4 for expression in *Y. lipolytica*. This is possible based on previous determination of the *Y. lipolytica* codon usage profile, identification of those codons that are preferred, and determination of the consensus sequence around the 'ATG' initiation codon (see U.S. Pat. No. 7,238,482).

In another embodiment, the invertase sequences in Table 14 (Example 8), or portions of thereof, may be used in the present invention. Alternatively, any of these may be used to search for invertase homologs in the same or other species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul, et al., *Nucleic Acids Res.*, 25:3389-3402 (1997)), is well-known as a means for comparing any invertase protein in Table 14 against a database of nucleic or protein sequences and thereby identifying similar known sequences within a preferred organism.

Use of a software algorithm to comb through databases of known sequences is particularly suitable for the isolation of homologs having a relatively low percent identity to publicly available invertase sequences, such as those described in Table 14. It is predictable that isolation would be relatively easier for invertase homologs of at least about 80%-85% identity to publicly available invertase sequences. Further, those sequences that are at least about 85%-90% identical would be particularly suitable for isolation and those sequences that are at least about 90%-95% identical would be the most easily isolated.

Some invertase homologs have also been isolated by the use of motifs unique to invertase enzymes. Motifs are identified by their high degree of conservation in aligned sequences of a family of protein homologues. As unique "signatures", they can determine if a protein with a newly determined sequence belongs to a previously identified protein family. These motifs are useful as diagnostic tools for the rapid identification of novel invertase genes.

Any of the invertase nucleic acid fragments described herein or in public literature, or any identified homologs, may be used to isolate genes encoding homologous proteins from the same or other species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies, such as polymerase chain reaction ["PCR"] (U.S. Pat. No. 4,683, 202); ligase chain reaction ["LCR"] (Tabor, S. et al., *Proc. Natl. Acad. Sci. U.S.A.*, 82:1074 (1985)); or strand displacement amplification ["SDA"] (Walker, et al., *Proc. Natl. Acad. Sci. U.S.A.*, 89:392 (1992)); and, 3) methods of library construction and screening by complementation.

Transformed *Y. lipolytica* of the present invention comprise an exogenous polynucleotide encoding a polypeptide having sucrose invertase activity, wherein the polypeptide will comprise a signal sequence fused to an exogenous polynucleotide encoding mature sucrose invertase, wherein said signal sequence is selected from the group consisting of: 1) a Xpr2 pre/pro-region and a N-terminal Xpr2 fragment; and, 2) a sucrose invertase signal sequence, wherein the second amino acid of the sucrose invertase signal sequence can be any hydrophobic amino acid.

With respect to the signal sequence comprising a Xpr2 pre/pro-region and a N-terminal Xpr2 fragment, one of ordinary skill in the art will be able to analyze a suitable XPR2 gene encoding an alkaline extracellular protease (EC 3.4.21.-) to identify a sequence encoding the pre/pro-region versus sequence encoding the mature protein. For example, the SignalP 4.0 server (Center for Biological Sequence Analysis, Department of Systems Biology, Technical University of Denmark, DK-2800 Lyngby, Denmark) is useful to predict the presence and location of signal peptide cleavage sites in amino acid sequences from different organisms (Nielsen, H., et al., *Protein Engineering*, 10:1-6 (1997); Petersen, T. N., et al., *Nature Methods*, 8:785-786 (2011)). Following this identification, it is readily possible to isolate the appropriate sequence encoding the full length Xpr2 pre/pro-region, plus an additional N-terminal fragment of the mature Xpr2 protein (i.e., AEP).

This N-terminal Xpr2 fragment encodes at least about amino acids 1-10 of the mature protease and up to about amino acids 1-25 of the mature protease, to ensure access of the Xpr6 endopeptidase to the cleavage site between the pre/pro-region and the mature protein (although the exactly length of the N-terminal fragment will need to be experimentally determined for each XPR2 gene utilized).

More preferably, the N-terminal Xpr2 fragment of the mature protease will encode amino acids 1 to 11 of the mature protease, amino acids 1 to 12, amino acids 1 to 13, amino acids 1 to 14, amino acids 1 to 15, amino acids 1 to 16, amino acids 1 to 17, amino acids 1 to 18, amino acids 1 to 19, amino acids 1 to 20, amino acids 1 to 21, amino acids 1 to 22, amino acids 1 to 23 or amino acids 1 to 24 of the mature protease.

The Xpr2 pre/pro-region and N-terminal Xpr2 fragment from *Y. lipolytica* will comprise at least the 157 amino acids of the Xpr2 pre/pro-region (i.e., amino acids 1-157 of SEQ ID NO:6) and an additional N-terminal Xpr2 fragment encoding the mature protease (i.e., amino acids 158-167 or amino acids 158-168 or amino acids 158-169 or amino acids 158-170 or amino acids 158-171 or amino acids 158-172 or amino acids 158-173 or amino acids 158-174 or amino acids 158-175 or amino acids 158-176 or amino acids 158-177 or amino acids 158-178 or amino acids 158-179 or amino acids 158-180 or amino acids 158-181 or amino acids 158-182 of SEQ ID NO:6).

The preferred Xpr2 pre/pro-region and N-terminal Xpr2 fragment (i.e., "XPR2PP+13", as set forth in SEQ ID NO:10) included amino acids 1-170 of SEQ ID NO:6, which corresponded with an additional 13 amino acids after the Xpr2 pre/pro-region (i.e., amino acids 1 to 13 of the mature protease) to ensure access of the Xpr6 endopeptidase to the Lys156-Arg157 cleavage site. Thus, the Xpr2 pre/pro-region and N-terminal Xpr2 fragment comprises:

(a) a Xpr2 pre/pro-region comprising the N-terminal 157 amino acids of an AEP precursor; and,
(b) a N-terminal Xpr2 fragment comprising the N-terminal 13 amino acids of a mature AEP.

One preferred exogenous polynucleotide encoding a polypeptide having sucrose invertase activity that can be transformed into *Y. lipolytica* comprises the signal sequence of the Xpr2 pre/pro-region and N-terminal Xpr2 fragment of SEQ ID NO:10, fused to the mature sucrose invertase of SEQ ID NO:4 ("m-ScSUC2"), thereby producing a XPR2PP+13/m-ScSUC2 fusion, having the nucleotide sequence set forth as SEQ ID NO:19 and encoding the protein of SEQ ID NO:20.

The transformed *Y. lipolytica* comprising an exogenous polynucleotide encoding a polypeptide having sucrose invertase activity, wherein the polypeptide comprises a signal sequence fused to a polypeptide encoding mature sucrose invertase, may alternatively utilize a sucrose invertase signal sequence, wherein the second amino acid of the sucrose invertase signal sequence can be any hydrophobic amino acid.

One of skill in the art will be able to utilize similar methodology as described above to identify sequence encoding the invertase signal sequence versus sequence encoding the mature invertase protein. Once identified, it is readily possible to isolate the invertase signal sequence to construct a fusion polypeptide having sucrose invertase activity, as described herein. For clarity, the sucrose invertase signal sequence and mature sucrose invertase may be isolated from a single species (thereby effectively equivalent to that species' full-length invertase pre-protein); or, the sucrose invertase signal sequence may be isolated from species "A" while the mature sucrose invertase may be isolated from species "B". The second amino acid of the sucrose invertase signal sequence can be any hydrophobic amino acid, for example leucine, phenylalanine, isoleucine, valine or methionine.

Several previous studies examining invertase signal peptides have shown that at least 20% of essentially random amino acid sequences can act, at least partially, as an export signal for invertase. The export signal function is related to hydrophobicity rather than a defined structure or length of signal peptide (see, e.g., Kaiser et al., *Science*, 235:312-317 (1987); Kaiser and Botstein, *Mol. Cell. Biol.*, 6:2382-2391 (1986)). Further, the junction sequence between native ScSUC2 signal sequence and the mature ScSUC2 is known to be important for proper cleavage of the signal peptide. For example, if residue Ala19 of SEQ ID NO:2 is mutated to Val, ScSUC2 becomes defective (Schauer et al., *J. Cell Biol.*, 100:1664-1075 (1985)). For additional information on modification of the SUC2 signal sequence, see Ngsee et al. (*Mol. Cell. Biol.*, 9:3400-3410 (1989)).

In one embodiment, the sucrose invertase signal sequence can be from an organism of the genus *Saccharomyces*. More preferably, the sucrose invertase signal sequence is isolated from *Saccharomyces cerevisiae*, such as, for example, the sucrose invertase signal sequence set forth in SEQ ID NO:8 ["Suc2SS"]. It is expected that the second amino acid of SEQ ID NO:8 could readily be substituted with an alternate hydrophobic amino acid (i.e., Phe2 could alternatively be mutated to Leu2, Ile2, Val2 or Met2), thereby maintaining the hydrophobicity of the signal sequence without affecting the secretory process of the invertase. More specifically, the sucrose invertase signal sequence used in the transformed *Y. lipolytica* herein may have at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity when compared to SEQ ID NO:8, so long as it substantially maintains secretion activity (see, e.g., Kaiser and Botstein, *Mol. Cell. Biol.*, 6:2382-2391 (1986)).

One preferred exogenous polynucleotide encoding a polypeptide having sucrose invertase activity for transformation into *Y. lipolytica* comprises the sucrose invertase signal sequence of SEQ ID NO:8, fused to the mature sucrose invertase of SEQ ID NO:4 ("m-ScSUC2"), thereby producing a Suc2SS/m-ScSUC2 fusion, having the nucleotide sequence set forth as SEQ ID NO:11 and encoding the protein of SEQ ID NO:12.

It should be appreciated that the Suc2SS/m-ScSUC2 fusion of SEQ ID NO:12 is effectively equivalent to the full-length invertase pre-protein, for example as set forth in SEQ ID NO:2 (with the exception of the variation at amino acid 2), since the Suc2SS signal sequence corresponds to amino acids 1-19 while m-ScSUC2 corresponds to amino acids 20-532 of SEQ ID NO:2. Thus, for example, the polypeptide having sucrose invertase activity may have at least 80% sequence identity to SEQ ID NO:2 (based on the CLUSTALW method of alignment), although the polypeptide may more preferably have at least 81%, 82%, 83%, 84%, 85%, 86%, 87%, 88%, 89%, 90%, 91%, 92%, 93%, 94%, 95%, 96%, 97%, 98%, 99%, or 100% identity when compared to SEQ ID NO:2.

One of skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Maniatis, Silhavy, and Ausubel.

In general, the choice of sequences included in the construct depends on the desired expression products, the nature of the host cell and the proposed means of separating transformed cells versus non-transformed cells. Typically, a vector contains at least one expression cassette, a selectable marker and sequences allowing autonomous replication or chromosomal integration. Suitable expression cassettes typically comprise a promoter, the coding sequence of a selected gene, and a terminator (i.e., a chimeric gene). Preferably, both control regions are derived from genes from the transformed host cell.

Virtually any promoter (i.e., native, synthetic, or chimeric) capable of directing expression of an ORF encoding a polypeptide having sucrose invertase activity will be suitable, although transcriptional and translational regions from *Y. lipolytica* are particularly useful. Expression can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest.

A terminator can be derived from the 3' region of a gene from which the promoter was obtained or from a different gene. A large number of terminators are known and function satisfactorily in a variety of hosts, when utilized both in the same and different genera and species from which they were derived. The terminator usually is selected more as a matter of convenience rather than because of any particular property. Preferably, the terminator is derived from a yeast gene. The terminator can also be synthetic, as one of skill in the art can utilize available information to design and synthesize a terminator. A terminator may be unnecessary, but it is highly preferred.

Although not intended to be limiting, preferred promoters and terminators for use in a recombinant *Y. lipolytica* are those taught in U.S. Pat. Pub. No. 2009-0093543-A1, U.S. Pat. Pub. No. 2010-0068789-A1, U.S. Pat. Pub. No. 2011-0059496-A1, U.S. Provisional Pat. Appl. No. 61/469,933 (filed Mar. 31, 2011), U.S. Provisional Pat. Appl. No. 61/470,539 (filed Apr. 1, 2011), U.S. Provisional Pat. Appl. No. 61/471,736 (filed Apr. 5, 2011), and U.S. Provisional Pat. Appl. No. 61/472,742 (filed Apr. 7, 2011), the disclosure of each which is hereby incorporated herein by reference. More specifically, preferred promoters include: GPD, GPDIN, GPM, GPM/FBAIN, FBA, FBAIN, FBAINm, GPAT, YAT1, EXP1, DGAT2, ELI, ALK2, and SPS19.

Many specialized expression vectors have been created to obtain a high expression rate. Such vectors are made by adjusting certain properties that govern transcription, RNA stability, translation, protein stability and location, and secretion from the host cell. These properties include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the host cell genome; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell.

Once a DNA cassette (e.g., comprising a chimeric gene comprising a promoter, an ORF encoding a polypeptide having sucrose invertase activity and terminator) suitable for expression in *Y. lipolytica* has been obtained, it is placed in a plasmid vector capable of autonomous replication in the host cell, or DNA fragment containing the chimeric gene is directly integrated into the genome. Integration of expression cassettes can occur randomly within the *Y. lipolytica* genome or can be targeted through the use of constructs containing regions of homology with the genome sufficient to target recombination to a particular locus. Where constructs are targeted to an endogenous locus, all or some of the transcriptional and translational regulatory regions can be provided by the endogenous locus.

Constructs comprising a chimeric sucrose invertase gene(s) of interest may be introduced into *Y. lipolytica* by any standard technique. These techniques include transformation (e.g., lithium acetate transformation [*Methods in Enzymology*, 194:186-187 (1991)]), bolistic impact, electroporation, microinjection, or any other method that introduces the gene(s) of interest into the host cell. More specific teachings applicable for *Y. lipolytica* include U.S. Pat. No. 4,880,741 and U.S. Pat. No. 5,071,764 and Chen, D. C. et al. (*Appl. Microbiol. Biotechnol.*, 48(2):232-235 (1997)). Preferably, integration of a linear DNA fragment into the genome of the host is favored in transformation of *Y. lipolytica* host cells. Integration into multiple locations within the genome can be particularly useful when high level expression of genes are desired. Preferred loci include those taught in U.S. Pat. Pub. No. 2009-0093543-A1.

The terms "transformed", "transformant" or "recombinant" are used interchangeably herein. A transformed host will have at least one copy of an expression construct and may have two or more, depending upon whether the expression cassette is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media, which may incorporate an antibiotic or lack a factor necessary for growth of the untransformed host, such as a nutrient (e.g., sucrose) or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. No. 7,238,482, U.S. Pat. No. 7,259,255 and WO 2006/052870.

Stability of an integrated DNA fragment in *Y. lipolytica* is dependent on the individual transformants, the recipient strain and the targeting platform used. Thus, multiple transformants of a particular recombinant microbial host should be screened in order to obtain a strain displaying the desired expression level and pattern. Southern analysis of DNA blots (Southern, *J. Mol. Biol.*, 98:503 (1975)), Northern analysis of mRNA expression (Kroczek, *J. Chromatogr. Biomed. Appl.*, 618 (1-2):133-145 (1993)), Western analysis of protein expression, phenotypic analysis or GC analysis are suitable screening methods.

Any *Y. lipolytica* can be transformed with an appropriate polypeptide sequence encoding mature sucrose invertase according to the present invention, to produce a transformed strain able to utilize sucrose as a carbon source. Examples of readily available *Y. lipolytica* strains that can be obtained through the American Type Culture Collection ["ATCC"], include, for example #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, or #201847. Similarly, the following strains of *Y. lipolytica* could be obtained from the Herman J. Phaff Yeast Culture Collection, University of California Davis (Davis, Calif.): *Y. lipolytica* 49-14, *Y. lipolytica* 49-49, *Y. lipolytica* 50-140, *Y. lipolytica* 50-46, *Y. lipolytica* 50-47, *Y. lipolytica* 51-30, *Y. lipolytica* 60-26, *Y. lipolytica* 70-17, *Y. lipolytica* 70-18, *Y. lipolytica* 70-19, *Y. lipolytica* 70-20, *Y. lipolytica* 74-78, *Y. lipolytica* 74-87, *Y. lipolytica* 74-88, *Y. lipolytica* 74-89, *Y. lipolytica* 76-72, *Y. lipolytica* 76-93, *Y. lipolytica* 77-12T and *Y. lipolytica* 77-17. Or, strains could be obtained from the Laboratoire de Microbiologie et Génétique Moléculaire of Dr. Jean-Marc Nicaud, INRA Centre de Grignon, France, including for example, *Y. lipolytica* JMY798 (Mličková, K. et al., *Appl. Environ. Microbiol.*, 70(7):3918-24 (2004)), *Y. lipolytica* JMY399 (Barth, G., and C. Gaillardin. In, *Nonconventional Yeasts In Biotechnology*; Wolf, W. K., Ed.; Springer-Verlag: Berlin, Germany, 1996; pp 313-388) and *Y. lipolytica* JMY154 (Wang, H. J., et al., *J. Bacteriol.*, 181(17): 5140-8 (1999)).

Preferably, the *Y. lipolytica* host cells are oleaginous, i.e., capable of oil synthesis and accumulation, wherein the total oil content can comprise greater than about 25% of the dry cell weight ["DCW"], more preferably greater than about 30% of the DCW, and most preferably greater than about 40% of the DCW. In one embodiment, the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)) are particularly suitable.

The present invention also concerns transformed *Y. lipolytica* comprising an exogenous polynucleotide encoding a polypeptide having sucrose invertase activity (wherein said polypeptide comprises a signal sequence fused to a polypeptide sequence encoding mature sucrose invertase) and further wherein the transformed *Y. lipolytica* is capable of producing at least one non-native product of interest. This at least one non-native product of interest is preferably produced when the transformed *Y. lipolytica* is grown using sucrose (or mixtures thereof) as a carbon source. The order in which *Y. lipolytica* is transformed with heterologous genes does not matter. Such transformation can be simultaneous as well.

Examples of suitable non-native products of interest include, e.g., polyunsaturated fatty acids, carotenoids, amino acids, vitamins, sterols, flavonoids, organic acids, polyols and hydroxyesters, quinone-derived compounds and resveratrol, although this is not intended to be limiting herein.

The health benefits associated with "polyunsaturated fatty acids" (or "PUFAs"), especially omega-3 and omega-6 PUFAs, have been well documented. More specifically, PUFAs refer herein to fatty acids having at least 18 carbon atoms and 2 or more double bounds. The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds.

Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["n-6"] versus "omega-3 fatty acids" ["n-3"] are provided in U.S. Pat. No. 7,238,482, which is hereby incorporated herein by reference. U.S. Pat. App. Pub. No. 2009-0093543-A1, Table 3, provides a detailed summary of the chemical and common names of omega-3 and omega-6 PUFAs and their precursors, and well as commonly used abbreviations.

Some examples of PUFAs, however, include, but are not limited to, linoleic acid ["LA", 18:2 ω-6], gamma-linolenic acid ["GLA", 18:3 ω-6], eicosadienoic acid ["EDA", 20:2 ω-6], dihomo-gamma-linolenic acid ["GLA", 20:3 ω-6], arachidonic acid ["ARA", 20:4 ω-6], docosatetraenoic acid ["DTA", 22:4 ω-6], docosapentaenoic acid ["DPAn-6", 22:5 ω-6], alpha-linolenic acid ["ALA", 18:3 ω-3], stearidonic acid ["STA", 18:4 ω-3], eicosatrienoic acid ["ETA", 20:3 ω-3], eicosatetraenoic acid ["ETrA", 20:4 ω-3], eicosapentaenoic acid ["EPA", 20:5 ω-3], docosapentaenoic acid ["DPAn-3", 22:5 ω-3] and docosahexaenoic acid ["DHA", 22:6 ω-3].

Much effort has been invested towards engineering strains of *Y. lipolytica* for PUFA production. For example, U.S. Pat. No. 7,238,482 demonstrated the feasibility of producing omega-6 and omega-3 fatty acids in the yeast. U.S. Pat. No. 7,932,077 demonstrated recombinant production of 28.1% EPA of total fatty acids; U.S. Pat. No. 7,588,931 demonstrated recombinant production of 14% ARA of total fatty acids; U.S. Pat. No. 7,550,286 demonstrated recombinant production of 5% DHA of total fatty acids; and, U.S. Pat. Appl. Pub. No. 2009-0093543-A1 describes optimized recombinant strains for EPA production and demonstrated production of up to 55.6% EPA of total fatty acids. U.S. Pat. Appl. Pub. No. 2010-0317072-A1 describes further optimized recombinant *Y. lipolytica* strains producing microbial oils comprising up to 50% EPA of TFAs and having a ratio of at least 3.1 of EPA, measured as a weight percent of TFAs, to linoleic acid, measured as a weight percent of TFAs. The transformant *Y. lipolytica* express various combinations of desaturase (i.e., delta-12 desaturase, delta-6 desaturase, delta-8 desaturase, delta-5 desaturase, delta-17 desaturase, delta-15 desaturase, delta-9 desaturase, delta-4 desaturase) and elongase (i.e., $C_{14/16}$ elongase, $C_{16/18}$ elongase, $C_{18/20}$ elongase, $C_{20/22}$ elongase and delta-9 elongase) genes for PUFA production. In all of these methods, however, the production of PUFAs was demonstrated using oleaginous yeast grown using glucose as the carbon source.

Table 3 provides information about some of the specific *Y. lipolytica* strains described in the above cited references, wherein said strains possess various combinations of desaturases and elongases, although it is to be recognized that the specific strains and the specific PUFAs produced (or quantities thereof) are by no means limiting to the invention herein.

Lipid Profile of Representative *Y. lipolytica* Strains Engineered to Produce Omega-3/Omega-6 PUFAs

| Strain | Reference | ATCC Deposit No. | 16:0 | 16:1 | 18:0 | 18:1 | 18:2 | 18:3 (ALA) | GLA | 20:2 (EDA) | DGLA | ARA | ETA | EPA | DPA | DHA | TFAs % DCW |
|---|---|---|---|---|---|---|---|---|---|---|---|---|---|---|---|---|---|
| pDMW-208 | U.S. Pat. No. 7,465,564 | — | 11.9 | 8.6 | 1.5 | 24.4 | 17.8 | 0 | 25.9 | — | — | — | — | — | — | — | — |
| pDMW-208D62 | | — | 16.2 | 1.5 | 0.1 | 17.8 | 22.2 | 0 | 34 | — | — | — | — | — | — | — | — |
| M4 | U.S. Pat. No. 7,932,077 | — | 15 | 4 | 2 | 5 | 27 | 0 | 35 | — | 8 | 0 | 0 | 0 | — | — | — |
| Y2034 | U.S. Pat. No. 7,588,931 | — | 13.1 | 8.1 | 1.7 | 7.4 | 14.8 | 0 | 25.2 | — | 8.3 | 11.2 | — | — | — | — | — |
| Y2047 | | PTA-7186 | 15.9 | 6.6 | 0.7 | 8.9 | 16.6 | 0 | 29.7 | — | 0 | 10.9 | — | — | — | — | — |
| Y2214 | | — | 7.9 | 15.3 | 0 | 13.7 | 37.5 | 0 | 0 | — | 7.9 | 14 | — | — | — | — | — |
| EU | U.S. Pat. No. 7,932,077 | — | 19 | 10.3 | 2.3 | 15.8 | 12 | 0 | 18.7 | — | 5.7 | 0.2 | 3 | 10.3 | — | — | 36 |
| Y2072 | | — | 7.6 | 4.1 | 2.2 | 16.8 | 13.9 | 0 | 27.8 | — | 3.7 | 1.7 | 2.2 | 15 | — | — | — |
| Y2102 | | — | 9 | 3 | 3.5 | 5.6 | 18.6 | 0 | 29.6 | — | 3.8 | 2.8 | 2.3 | 18.4 | — | — | — |
| Y2095 | | — | 13 | 0 | 2.6 | 5.1 | 16 | 0 | 29.1 | — | 3.1 | 1.9 | 2.7 | 19.3 | — | — | — |
| Y2090 | | — | 6 | 1 | 6.1 | 7.7 | 12.6 | 0 | 26.4 | — | 6.7 | 2.4 | 3.6 | 26.6 | — | — | 22.9 |
| Y2096 | | PTA-7184 | 8.1 | 1 | 6.3 | 8.5 | 11.5 | 0 | 25 | — | 5.8 | 2.1 | 2.5 | 28.1 | — | — | 20.8 |
| Y2201 | | PTA-7185 | 11 | 16.1 | 0.7 | 18.4 | 27 | 0 | — | 3.3 | 3.3 | 1 | 3.8 | 9 | — | — | — |
| Y3000 | U.S. Pat. No. 7,550,286 | PTA-7187 | 5.9 | 1.2 | 5.5 | 7.7 | 11.7 | 0 | 30.1 | — | 2.6 | 1.2 | 1.2 | 4.7 | 18.3 | 5.6 | — |
| Y4001 | U.S. Pat. Application Pub. No. 2009-0093543-A1 | — | 4.3 | 4.4 | 3.9 | 35.9 | 23 | 0 | — | 23.8 | 0 | 0 | 0 | — | — | — | — |
| Y4036 | | — | 7.7 | 3.6 | 1.1 | 14.2 | 32.6 | 0 | — | 15.6 | 18.2 | 0 | 0 | — | — | — | — |
| Y4070 | | — | 8 | 5.3 | 3.5 | 14.6 | 42.1 | 0 | — | 6.7 | 2.4 | 11.9 | — | — | — | — | — |
| Y4086 | | — | 3.3 | 2.2 | 4.6 | 26.3 | 27.9 | 6.9 | — | 7.6 | 1 | 0 | 2 | 9.8 | — | — | 28.6 |
| Y4128 | | PTA-8614 | 6.6 | 4 | 2 | 8.8 | 19 | 2.1 | — | 4.1 | 3.2 | 0 | 5.7 | 42.1 | — | — | 18.3 |
| Y4158 | | — | 3.2 | 1.2 | 2.7 | 14.5 | 30.4 | 5.3 | — | 6.2 | 3.1 | 0.3 | 3.4 | 20.5 | — | — | 27.3 |
| Y4184 | | — | 3.1 | 1.5 | 1.8 | 8.7 | 31.5 | 4.9 | — | 5.6 | 2.9 | 0.6 | 2.4 | 28.9 | — | — | 23.9 |
| Y4259 | | — | 4.4 | 1.4 | 1.5 | 3.9 | 19.7 | 2.1 | — | 3.5 | 1.9 | 0.6 | 1.8 | 46.1 | — | — | 23.7 |
| Y4305 | | — | 2.8 | 0.7 | 1.3 | 4.9 | 17.6 | 2.3 | — | 3.4 | 2 | 0.6 | 1.7 | 53.2 | — | — | 27.5 |
| Y4127 | Int'l. Application Pub. No. WO 2008/073367 | PTA-8802 | 4.1 | 2.3 | 2.9 | 15.4 | 30.7 | 8.8 | — | 4.5 | 3.0 | 3.0 | 2.8 | 18.1 | — | — | — |
| Y4184 | | — | 2.2 | 1.1 | 2.6 | 11.6 | 29.8 | 6.6 | — | 6.4 | 2.0 | 0.4 | 1.9 | 28.5 | — | — | 24.8 |
| Y8404 | U.S. Pat. | — | 2.8 | 0.8 | 1.8 | 5.1 | 20.4 | 2.1 | — | 2.9 | 2.5 | 0.6 | 2.4 | 51.1 | — | — | 27.3 |

Lipid Profile of Representative *Y. lipolytica* Strains Engineered to Produce Omega-3/Omega-6 PUFAs

| Strain | Reference | ATCC Deposit No. | 16:0 | 16:1 | 18:0 | 18:1 | 18:2 | 18.3 (ALA) | GLA | 20:2 (EDA) | DGLA | ARA | ETA | EPA | DPA | DHA | TFAs % DCW |
|---|---|---|---|---|---|---|---|---|---|---|---|---|---|---|---|---|---|
| Y8406 | Application Pub. No. 2010-0317072-A1 | PTA-10025 | 2.6 | 0.5 | 2.9 | 5.7 | 20.3 | 2.8 | | 2.8 | 2.1 | 0.5 | 2.1 | 51.2 | — | — | 30.7 |
| Y8412 | | PTA-10026 | 2.5 | 0.4 | 2.6 | 4.3 | 19.0 | 2.4 | | 2.2 | 2.0 | 0.5 | 1.9 | 55.8 | — | — | 27.0 |
| Y8647 | | — | 1.3 | 0.2 | 2.1 | 4.7 | 20.3 | 1.7 | | 3.3 | 3.6 | 0.7 | 3.0 | 53.6 | — | — | 37.6 |
| Y9028 | | — | 1.3 | 0.2 | 2.1 | 4.4 | 19.8 | 1.7 | | 3.2 | 2.5 | 0.8 | 1.9 | 54.5 | — | — | 39.6 |
| Y9477 | | — | 2.6 | 0.5 | 3.4 | 4.8 | 10.0 | 0.5 | | 2.5 | 3.7 | 1.0 | 2.1 | 61.4 | — | — | 32.6 |
| Y9497 | | — | 2.4 | 0.5 | 3.2 | 4.6 | 11.3 | 0.8 | | 3.1 | 3.6 | 0.9 | 2.3 | 58.7 | — | — | 33.7 |
| Y9502 | | — | 2.5 | 0.5 | 2.9 | 5.0 | 12.7 | 0.9 | | 3.5 | 3.3 | 0.8 | 2.4 | 57.0 | — | — | 37.1 |
| Y9508 | | — | 2.3 | 0.5 | 2.7 | 4.4 | 13.1 | 0.9 | | 2.9 | 3.3 | 0.9 | 2.3 | 58.7 | — | — | 34.9 |
| Y8145 | | — | 4.3 | 1.7 | 1.4 | 4.8 | 18.6 | 2.8 | | 2.2 | 1.5 | 0.6 | 1.5 | 48.5 | — | — | 23.1 |
| Y8259 | | PTA-10027 | 3.5 | 1.3 | 1.3 | 4.8 | 16.9 | 2.3 | | 1.9 | 1.7 | 0.6 | 1.6 | 53.9 | — | — | 20.5 |
| Y8370 | | — | 3.4 | 1.1 | 1.4 | 4.0 | 15.7 | 1.9 | | 1.7 | 1.9 | 0.6 | 1.5 | 56.4 | — | — | 23.3 |
| Y8672 | | — | 2.3 | 0.4 | 2.0 | 4.0 | 16.1 | 1.4 | | 1.8 | 1.6 | 0.7 | 1.1 | 61.8 | — | — | 26.5 |

Notes:
The term "total fatty acids" ("TFAs") refer to the sum of all cellular fatty acids that can be derivitized to fatty acid methyl esters ("FAMEs") by the base transesterification method (as known in the art) in a given sample, which may be the biomass or oil, for example. Thus, total fatty acids include fatty acids from neutral lipid fractions (including diacylglycerols, monoacylglycerols and triacylglycerols) and from polar lipid fractions but not free fatty acids. The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).
The term "total lipid content" of cells is a measure of TFAs as a percent of the dry cell weight ("DCW"), although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.
Fatty acids are 16:0 (palmitate), 16:1 (palmitoleic acid), 18:0 (stearic acid), 18:1 (oleic acid), 18:2 (linoleic acid), 18:3 (ALA or alpha-linolenic acid), GLA (gamma-linolenic acid), 20:2 (EDA or eicosadienoic acid), DGLA (dihomo-gamma-linolenic acid), ARA (arachidonic acid), ETA (eicosatetraenoic acid), EPA (eicosapentaenoic acid), DPA (docosapentaenoic acid) and DHA (docosahexaenoic acid).

Carotenoids are also contemplated as suitable non-native products of interest that could be produced in transformed *Y. lipolytica*, when grown with sucrose as a carbon source. As used herein, the term "carotenoid" refers to a class of hydrocarbons having a conjugated polyene carbon skeleton formally derived from isoprene. This class of molecules is composed of triterpenes ["$C_{30}$ diapocarotenoids"] and tetraterpenes ["$C_{40}$ carotenoids"] and their oxygenated derivatives; and, these molecules typically have strong light absorbing properties and may range in length in excess of $C_{200}$. Other "carotenoid compounds" are known which are $C_{35}$, $C_{50}$, $C_{60}$, $C_{70}$ and $C_{80}$ in length, for example. The term "carotenoid" may include both carotenes and xanthophylls. A "carotene" refers to a hydrocarbon carotenoid (e.g., phytoene, β-carotene and lycopene). In contrast, the term "xanthophyll" refers to a $C_{40}$ carotenoid that contains one or more oxygen atoms in the form of hydroxy-, methoxy-, oxo-, epoxy-, carboxy-, or aldehydic functional groups. Xanthophylls are more polar than carotenes and this property dramatically reduces their solubility in fats and lipids. Thus, suitable examples of carotenoids include: antheraxanthin, adonirubin, adonixanthin, astaxanthin (i.e., 3,3"-dihydroxy-β,β-carotene-4,4"-dione), canthaxanthin (i.e., β,β-carotene-4,4"-dione), capsorubin, β-cryptoxanthin, α-carotene, β,ψ-carotene, δ-carotene, ε-carotene, β-carotene keto-γ-carotene, echinenone, 3-hydroxyechinenone, 3'-hydroxyechinenone, γ-carotene, ψ-carotene, ζ-carotene, zeaxanthin, adonirubin, tetrahydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal, 4-keto-γ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, phytofluene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, and combinations thereof.

Wildtype *Y. lipolytica* is not normally carotenogenic. However, Int'l App. Publications No. WO 2008/073367 and WO 2009/126890 describe the production of a suite of carotenoids in recombinant *Y. lipolytica* via introduction of carotenoid biosynthetic pathway genes, such as crtE encoding a geranyl geranyl pyrophosphate synthase, crtB encoding phytoene synthase, crtI encoding phytoene desaturase, crtY encoding lycopene cyclase, crtZ encoding carotenoid hydroxylase and/or crtW encoding carotenoid ketolase.

Other non-native products of interest that could be produced in transformed *Y. lipolytica*, when grown with sucrose as a carbon source, include, e.g., quinine-derived compounds, sterols and resveratrol. The term "at least one quinone derived compound" refers to compounds having a redox-active quinone ring structure and includes compounds selected from the group consisting of: quinones of the CoQ series (i.e., that is $Q_6$, $Q_7$, $Q_8$, $Q_9$ and $Q_{10}$), vitamin K compounds, vitamin E compounds, and combinations thereof. For example, the term coenzyme $Q_{10}$ ["$CoQ_{10}$"] refers to 2,3-dimethoxy-dimethyl-6-decaprenyl-1,4-benzoquinone, also known as ubiquinone-10 (CAS Registry No. 303-98-0). The benzoquinone portion of $CoQ_{10}$ is synthesized from tyrosine, whereas the isoprene sidechain is synthesized from acetyl-CoA through the mevalonate pathway. Thus, biosynthesis of CoQ compounds such as $CoQ_{10}$ requires NADPH. A "vitamin K compound" includes, e.g., menaquinone or phylloquinone, while a vitamin E compound includes, e.g., tocopherol, tocotrienol or an α-tocopherol. The term "resveratrol" refers to 3,4',5-trihydroxystilbene.

U.S. Pat. App. Pub. No. 2009/0142322-A1 and WO 2007/120423 describe production of various quinone derived compounds in *Y. lipolytica* via introduction of heterologous quinone biosynthetic pathway genes, such as ddsA encoding decaprenyl diphosphate synthase for production of coenzyme $Q_{10}$, genes encoding the MenF, MenD, MenC, MenE, MenB, MenA, UbiE, and/or MenG polypeptides for production of vitamin K compounds, and genes encoding the tyrA, pds1 (hppd), VTEI, HPT1(VTE2), VTE3, VTE4, and/or GGH polypeptides for production of vitamin E compounds, etc. Intl App. Pub. No. WO 2008/130372 describes production of sterols in *Y. lipolytica* via introduction of ERG9/SQS1 encoding squalene synthase and ERGI encoding squalene epoxidase. And, U.S. Pat. No. 7,772,444 describes production of resveratrol in *Y. lipolytica* via introduction of a gene encoding resveratrol synthase.

Transformed host cells are grown under conditions that optimize expression of chimeric genes (e.g., encoding invertase, genes that enable biosynthesis of the non-native product of interest, etc.). In general, media conditions that may be optimized include: the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Oleaginous yeast are often grown in a complex medium (e.g., yeast extract-peptone-dextrose broth ["YPD"]) or a defined minimal medium that lacks a component necessary for growth and thereby forces selection of the desired expression cassettes (e.g., Yeast Nitrogen Base (DIFCO Laboratories, Detroit, Mich.)).

Fermentation media in the present invention comprise a fermentable carbon source. The fermentable carbon source can be, for example, sucrose, invert sucrose, glucose, fructose, and combinations of these. Invert sucrose refers to herein to a mixture comprising approximately equal parts of fructose and glucose resulting from the hydrolysis of sucrose. Invert sucrose may be a mixture comprising 25 to 50% glucose and 25 to 50% fructose, although invert sucrose may also comprise sucrose, the amount of which depends on the degree of hydrolysis. Invert sucrose may be obtained by hydrolysis of sucrose, which can be obtained from various sources such as sugar cane or sugar beets. The hydrolysis of sucrose to glucose and fructose can be catalyzed by acid (e.g., addition of citric or ascorbic acid) or by enzymes (e.g., invertases or β-fructofuranosidases), as is known in the art.

In some embodiments, a *Y. lipolytica* disclosed herein is grown in a medium containing sucrose in the presence of other sugars ("mixed sugars"). The mixed sugars include at least one additional sugar, in addition to sucrose. Any sugar that may provide an energy source for metabolism of the *Y. lipolytica* cells, or any sugar that is present in a mixture containing sucrose may be included. However, like the wild type *Y. lipolytica* cells, a sucrose-utilizing *Y. lipolytica* disclosed herein can still use glucose as sole carbon source.

Additionally, the fermentation medium comprises a suitable nitrogen source. Nitrogen may be supplied from an inorganic (e.g., $(NH_4)_2SO_4$) or organic (e.g., urea, glutamate, or yeast extract) source. In addition to sucrose and nitrogen sources, the fermentation medium also contains suitable minerals, salts, cofactors, buffers, vitamins and other components known to those skilled in the art suitable for the growth of the microorganism.

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage fermentation process, since the metabolic state should be "balanced" between growth and synthesis/storage of fats. Thus, most preferably, a two-stage fermentation process is employed for the production of PUFAs in oleaginous yeast. This process is described in U.S. Pat. No. 7,238,482, as are various suitable fermentation process designs (i.e., batch, fed-batch and continuous) and considerations during growth).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature For Expression Cassettes

The structure of an expression cassette is represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*

*Y. lipolytica* strain ATCC #20362 was purchased from the American Type Culture Collection (Rockville, Md.). *Y. lipolytica* strains were routinely grown at 28-30° C. in several media, according to the recipes shown below.

High Glucose Media ["HGM"] (Per Liter):
80 glucose, 2.58 g $KH_2PO_4$ and 5.36 g $K_2HPO_4$, pH 7.5 (do not need to adjust).

High Sucrose Media ["HSM"] (Per Liter):
80 sucrose, 2.58 g $KH_2PO_4$ and 5.36 g $K_2HPO_4$, pH 7.5 (do not need to adjust).

Synthetic Dextrose Media ["SD"] (Per Liter):
6.7 g Yeast Nitrogen base with ammonium sulfate and without amino acids; 20 g glucose.

Synthetic Sucrose Media ["SS"] (Per Liter):
6.7 g Yeast Nitrogen base with ammonium sulfate and without amino acids; 20 g sucrose.

Fermentation Medium ["FM"] (Per Liter):
6.7 g/L YNB without amino acids; 6 g/L $KH_2PO_4$; 2 g/L $K_2HPO_4$; 1.5 g/L $MgSO_4$-heptahydrate; 5 g/L yeast extract; 2% carbon source (wherein the carbon source is either glucose or sucrose).

Transformation of *Y. lipolytica* was performed as described in U.S. Pat. Appl. Pub. No. 2009-0093543-A1, hereby incorporated herein by reference.

Fatty Acid Analysis of *Yarrowia lipolytica*

For fatty acid ["FA"] analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I., *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 µl of 1%) and a known amount of C15:0 triacylglycerol (C15:0 TAG; Cat. No. T-145, Nu-Check Prep, Elysian, Minn.) was added to the sample, and then the sample was vortexed and rocked for 30 min at 50° C. After adding 3 drops of 1 M NaCl and 400 µl hexane, the sample was vortexed and spun. The upper layer was removed and analyzed by GC.

Alternately, a modification of the base-catalysed transesterification method described in *Lipid Analysis*, William W. Christie, 2003 was used for routine analysis of the broth samples from either fermentation or flask samples. Specifically, broth samples were rapidly thawed in room temperature water, then weighed (to 0.1 mg) into a tarred 2 mL microcentrifuge tube with a 0.22 µm Corning® Costar® Spin-X® centrifuge tube filter (Cat. No. 8161). Sample (75-800 µl) was used, depending on the previously determined DCW. Using an Eppendorf 5430 centrifuge, samples are centrifuged for 5-7 min at 14,000 rpm or as long as necessary to remove the broth. The filter was removed, liquid was drained, and ~500 µl of deionized water was added to the filter to wash the sample. After centrifugation to remove the water, the filter was again removed, the liquid drained and the filter re-inserted. The tube was then re-inserted into the centrifuge, this time with the top open, for ~3-5 min to dry. The filter was then cut approximately ½ way up the tube and inserted into a fresh 2 mL round bottom Eppendorf tube (Cat. No. 22 36 335-2).

The filter was pressed to the bottom of the tube with an appropriate tool that only touches the rim of the cut filter container and not the sample or filter material. A known amount of C15:0 TAG (above) in toluene was added and 500 µl of freshly made 1% sodium methoxide in methanol solution. The sample pellet was firmly broken up with the appropriate tool and the tubes were closed and placed in a 50° C. heat block (VWR Cat. No. 12621-088) for 30 min. The tubes were then allowed to cool for at least 5 min. Then, 400 µl of hexane and 500 µl of a 1 M NaCl in water solution were added, the tubes were vortexed for 2×6 sec and centrifuged for 1 min. Approximately 150 µl of the top (organic) layer was placed into a GC vial with an insert and analyzed by GC.

FAME peaks recorded via GC analysis were identified by their retention times, when compared to that of known fatty acids, and quantitated by comparing the FAME peak areas with that of the internal standard (C15:0 TAG) of known amount. Thus, the approximate amount (µg) of any fatty acid FAME ["µg FAME"] is calculated according to the formula: (area of the FAME peak for the specified fatty acid/area of the standard FAME peak)*(µg of the standard C15:0 TAG), while the amount (µg) of any fatty acid ["µg FA"] is calculated according to the formula: (area of the FAME peak for the specified fatty acid/area of the standard FAME peak)*(µg of the standard C15:0 TAG)*0.9503, since 1 µg of C15:0 TAG is equal to 0.9503 µg fatty acids. Note that the 0.9503 conversion factor is an approximation of the value determined for most fatty acids, which range between 0.95 and 0.96.

The lipid profile, summarizing the amount of each individual fatty acid as a wt % of TFAs, was determined by dividing the individual FAME peak area by the sum of all FAME peak areas and multiplying by 100.

Analysis of Total Lipid Content and Composition in *Yarrowia lipolytica* by Flask Assay For a detailed analysis of the total lipid content and composition in a particular strain of *Y. lipolytica*, flask assays were conducted as followed. Specifically, one loop of freshly streaked cells was inoculated into 3 mL FM medium and grown overnight at 250 rpm and 30° C. The $OD_{600nm}$ was measured and an aliquot of the cells were added to a final $OD_{600nm}$ of 0.3 in 25 mL FM medium in a 125 mL flask. After 2 days in a shaking incubator at 250 rpm and at 30° C., 6 mL of the culture was harvested by centrifugation and resuspended in 25 mL HGM in a 125 mL flask. After 5 days in a shaking incubator at 250 rpm and at 30° C., a 1 mL aliquot was used for fatty acid analysis (above) and 10 mL dried for dry cell weight ["DCW"] determination.

For DCW determination, 10 mL culture was harvested by centrifugation for 5 min at 4000 rpm in a Beckman GH-3.8 rotor in a Beckman GS-6R centrifuge. The pellet was resuspended in 25 mL of water and re-harvested as above. The washed pellet was re-suspended in 20 mL of water and transferred to a pre-weighed aluminum pan. The cell suspension was dried overnight in a vacuum oven at 80° C. The weight of the cells was determined.

Total lipid content of cells ["TFAs % DCW"] is calculated and considered in conjunction with data tabulating the concentration of each fatty acid as a weight percent of TFAs ["% TFAs"] and the EPA content as a percent of the dry cell weight ["EPA % DCW"].

Example 1

Construction and Expression of *Yarrowia lipolytica* Extracellular Invertase Expression Plasmid pZSUC The present Example describes the construction of plasmid pZSUC (SEQ ID NO:22) comprising a fusion of the XPR2 promoter and signal sequences to a truncated variant of the *Saccharomyces cerevisiae* SUC2 ["m-ScSuc2"] gene encoding invertase, in a manner similar to that reported by Nicaud et al. in *Current Genetics* (16:253-260 (1989)).

More specifically, Nicaud et al. reported the secretion of invertase into the periplasm of *Y. lipolytica*, when expressing the *S. cerevisiae* SUC2 gene under the control of the promoter and an N-terminal amino acid signal sequence of the *Y. lipolytica* XPR2 gene. It is stated therein (page 257) that the "fusion puts the 23 N-terminal amino acids from the XPR2 gene in front of invertase, starting at amino acid eleven" (i.e., thus the first 10 amino acids of the full-length invertase were truncated, while amino acids 11-19 of the signal sequence were included with the mature protein to be expressed). However, according to FIG. 1B of Nicaud et al. (page 255), it appears that the fusion construct instead included 23 N-terminal amino acids from the XPR2 gene as signal sequence, fused to invertase, starting at amino acid five (i.e., thus the first 4 amino acids of the full-length invertase were truncated, while amino acids 5-19 of the signal sequence were included with the mature protein to be expressed). Despite the lack of clarity concerning the fusion, Nicaud et al. reported that expression of the invertase conferred a sucrose-utilizing (Suc+) phenotype in the transformed *Y. lipolytica*.

A XPR2::SUC2 fusion construct was made ("pZSUC"; FIG. 2) in a manner similar to that of Nicaud et al., above. First, a 432 bp DNA fragment containing 369 bp XPR promoter (−369 to −1) plus 63 bp coding region (+1 to +63) was amplified by PCR using *Yarrowia* genomic DNA as template and oligonucleotides YL427 and YL428 (SEQ ID NOs:36 and 37) as primers. A ClaI site was added at the 5' end and a HindIII site was added at the 3' end of the designed PCR fragment (SEQ ID NO:38). The PCR amplification was carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer, 50 ng genomic DNA of *Y. lipolytica* (ATCC #76982) and 1 µl of Taq DNA polymerase (Epicentre Technologies). The thermocycler conditions were set for 35 cycles at 95° C. for 1 min, 56° C. for 30 sec, and 72° C. for 1 min, followed by a final extension at 72° C. for 10 min.

The PCR products were purified using a Qiagen PCR purification kit (Valencia, Calif.), and then digested with ClaI/HindIII; the digested products were separated by gel electrophoresis in 1% (w/v) agarose, and the ClaI/HindIII fragments were used for construction of pZSUC (infra).

A 1569 bp DNA fragment containing the *S. cerevisiae* SUC2 coding region except the first 10 amino acids was amplified by PCR using *S. cerevisiae* genomic DNA as template and oligonucleotides YL429 and YL430 (SEQ ID NOs: 39 and 40) as primers. A HindIII site was added at the 5' end in the same reading frame of the SUC2 coding region, and a BsiWI site was added after the stop codon of the SUC2 coding region (SEQ ID NO:41). The PCR amplification was carried out in a 50 µl total volume comprising the components set forth above, with the exception that 50 ng genomic DNA of *S. cerevisiae* was used instead of 50 ng genomic DNA of *Y. lipolytica* (ATCC #76982). The thermocycler conditions were set for 35 cycles at 95° C. for 1 min, 56° C. for 30 sec, and 72° C. for 2 min, followed by a final extension at 72° C. for 10 min.

The PCR products were purified using a Qiagen PCR purification kit (Valencia, Calif.), and then digested with HindIII/BsiWI; the digested products were separated by gel electrophoresis in 1% (w/v) agarose, and the HindIII/BsiWI fragments were used for construction of pZSUC (infra).

Thus, plasmid pZSUC2 contains the following components.

TABLE 4

Description of Plasmid pZSUC2

| RE Sites And Nucleotide position in SEQ ID NO: XX | Description Of Fragment And Chimeric Gene Components |
|---|---|
| AscI/BsiWI (2780-2010) | 770 bp 5' portion of *Yarrowia lipolytica* Pox3 (GenBank Accession No. XP_503244) |
| PacI/SphI (6312-5488) | 824 bp 3' portion of *Yarrowia* Pox3 gene (GenBank Accession No. AJ001301) |
| ClaI/BsiWI (2-2010) | XPR2 Promoter/SUC2 fusion, comprising: XPR2 Promoter: 432 bp *Y. lipolytica* XPR2 gene comprising 369 bp of the XPR2 promoter (−369 to −1) plus 63 bp coding region of the XPR2 pre/pro-region; SUC2: 1569 bp *S. cerevisiae* SUC2 coding region corresponding to amino acids 11-532 of SEQ ID NO: 2 |
| 3768-4628 | Ampicillin-resistance gene ($Amp^R$) for selection in *E. coli* |
| SwaI/PmeI (6862-8672) | Leu2: beta-isopropylmalate dehydrogenase gene of *Y. lipolytica* (GenBank Accession No. M37309) |

Expression plasmid pZSUC (SEQ ID NO:22) was then transformed into *Y. lipolytica* ATCC#76982 to test for invertase expression. Transformants were grown on Synthetic Sucrose Media ["SS"]. However, the transformed *Y. lipolytica* strain could not grow on sucrose medium.

In the XPR2::SUC2 fusion construct within pZSUC, the first 63 bp of the XPR2 coding sequence (i.e., the pre/pro-region) was used as "signal sequence", and the SUC2 gene was missing first 30 nucleotides (i.e., removing the first 10 amino acids of the SUC2 signal sequence). After careful studies of the description by Nicaud et al., it was realized that they used autoclaved sucrose media to test the grow of the engineered strains. The autoclave process could hydrolyze some sucrose into fructose and glucose, which could be used by *Y. lipolytica* as a carbon source (data not shown).

Data presented in this Example demonstrated that transformed *Y. lipolytica* strains expressing a fusion of the N-terminal 21 amino acids of the *Y. lipolytica* XPR2 fused with a truncated variant of ScSuc2 as described by Nicaud et al. could not use sucrose as a carbon source. It was reported that the hydrophobic core of the Suc2 signal sequence is associated with proper secretory process and its disruption led to intracellular accumulation of invertase (Kaiser and Botstein, *Mol. Cell. Biol.*, 6; 2382-2391 (1986); Perlman, et al., *Proc. Natl. Acad. Sci. U.S.A.*, 83:5033-5037 (1986)).

Example 2

Construction of *Yarrowia lipolytica* Extracellular Invertase Expression Plasmids: pYRH68, pYRH69, pYRH70, pYRH73 and pYRH74

The present Example describes the construction of a series of plasmids comprising various different combinations of the XPR2 prepro-region ["XPR2PP+13"] and/or SUC2 signal sequence ["Suc2SS"] fused to the "mature" *Saccharomyces cerevisiae* SUC2 ["m-ScSuc2"] gene encoding invertase. The heterologous gene in each construct was flanked by a strong *Y. lipolytica* promoter (FBAINm; see U.S. Pat. No. 7,202,356) and *Y. lipolytica* Pex20 terminator sequence.

Construction of pYRH68, Comprising SucSS/m-ScSUC2

Plasmid pYRH68 was constructed to overexpress the Suc2 signal sequence ("SucSS"; SEQ ID NO:8) fused to the "mature" ScSUC2 gene encoding invertase ("m-ScSUC2"; SEQ ID NO:4). Effectively, however, this artificial fusion described herein as SucSS/m-ScSUC2 corresponds with the wildtype full-length ScSUC2 gene which naturally contains 5'-signal sequence.

A 1.6 kB fragment encoding the ScSUC2 ORF was amplified from genomic DNA of *S. cerevisiae* BY4743 (Open Biosystems, Huntsville, Ala.) using primers Sc. SUC2-5' (SEQ ID NO:23) and Sc. SUC2-3' (SEQ ID NO:24). These primers were designed to introduce a PciI restriction enzyme site at amino acid position 2 (thereby altering the wildtype Leu2 residue to Phe2, maintaining the hydrophobicity of the signal sequence without affecting the secretory process for Suc2 [ Kaiser, et al., *Science*, 235:312-317 (1987)]). The reaction mixture contained 1 µl of the genomic DNA, 1 µl each of the primers, 2 µl water, and 45 µl AccuPrime™ Pfx SuperMix (Invitrogen; Carlsbad, Calif.). Amplification was carried out as follows: initial denaturation at 94° C. for 5 min, followed by 35 cycles of denaturation at 94° C. for 15 sec, annealing at 55° C. for 30 sec, and elongation at 68° C. for 2 min. A final elongation cycle at 68° C. for 7 min was carried out, followed by reaction termination at 4° C. The ScSUC2 ORF was then digested with PciI/NotI restriction enzymes and utilized to create plasmid pYRH68 (FIG. 3A; SEQ ID NO:13), containing the following components (NcoI and PciI are isoschizomers):

TABLE 5

Description of Plasmid pYRH68

| RE Sites And Nucleotides Within SEQ ID NO: 13 | Description Of Fragment And Chimeric Gene Components |
|---|---|
| PmeI/BsiWI (6204--317) | FBAINm::SucSS/m-ScSUC2::PEX20, comprising: FBAINm: *Yarrowia lipolytica* FBAINm promoter (U.S. Pat. No. 7,202,356); SucSS/m-ScSUC2: *Saccharomyces cerevisiae* 5'-SUC2 signal sequence fused to the *S. cerevisiae* "mature" SUC2 gene (SEQ ID NO: 11); PEX20: Pex20 terminator sequence from *Yarrowia* PEX20 gene (GenBank Accession No. AF054613) |
| BsiWI/AscI (318-1211) | 894 bp 5' portion of *Yarrowia* Lip7 gene (labeled as "LipY-5'" in Figure; GenBank Accession No. AJ549519) |
| PacI/SphI (3920/4681) | 762 bp 3' portion of *Yarrowia* Lip7 gene (labeled as "LipY-3'" in Figure; GenBank Accession No. AJ549519) |
| PacI/PmeI (4682-6182) | *Yarrowia* URA3 gene (GenBank Accession No. AJ306421) |
| 2200-3060 | Ampicillin-resistance gene (Amp$^R$) for selection in *E. coli* |

Construction of pYRH70, Comprising Two Copies of SucSS/m-ScSUC2

Plasmid pYRH70 was constructed to overexpress two copies of SucSS/m-ScSUC2 (SEQ ID NO:12), which corresponds with two copies of the wildtype full-length ScSUC2 gene which naturally contains 5'-signal sequence. The plasmid pYRH68 (SEQ ID NO:13) was cut with SaI/I/SwaI to insert a second copy of the 1.6 kB PciII/NotI ScSUC2 fragment. Specifically, a four-way ligation was prepared comprising: 1) the pYRH68 vector backbone; 2) the PciII/NotI digested ScSUC2 fragment; 3) a 533 bp Sa/I/NcoI-fragment comprising a *Y. lipolytica* FBA promoter (U.S. Pat. No. 7,202,356) that had been excised from plasmid pZKLY-PP2 (SEQ ID NO:25; described in U.S. Pat. Pub. No. 2011-0244512-A1); and, 4) a 322 bp NotI/SwaI-fragment comprising a Lip1 terminator sequence from the *Yarrowia* Lip1 gene (GenBank Accession No. Z50020), also excised from pZKLY-PP2 (SEQ ID NO:25). This resulted in synthesis of pYRH70 (FIG. 3B; SEQ ID NO:14).

Construction of pYRH73, Comprising m-ScSUC2 without XPR2PP+13 or SUC2SS

Plasmid pYRH73 was constructed to overexpress the "mature" ScSUC2 gene encoding invertase ("m-ScSUC2"; SEQ ID NO:4), lacking the Suc2 signal sequence ("SucSS"; SEQ ID NO:8). Thus, the 5'-signal sequence of SucSS (corresponding to nucleotides 1 to 57 of SEQ ID NO:2) were truncated from the wildtype full-length ScSUC2 gene which naturally contains 5'-signal sequence]). A 1.55 kB fragment spanning the mature ScSUC2 gene was amplified from genomic DNA of *S. cerevisiae* BY4743 using primers Sc.SUC2-5' (SEQ ID NO:23) and nSc.SUC2-3' (SEQ ID NO:26). This fragment was then cut with PciII/NotI and cloned into a *Y. lipolytica* vector in the same manner as described above to create plasmid pYRH73 (FIG. 4A; SEQ ID NO:15).

Construction of pYRH69, Comprising XPR2PP+13/SucSS/m-ScSUC2

Plasmid pYRH69 was constructed to overexpress the XPR2 prepro-region ["XPR2PP+13"; SEQ ID NO:10] fused to SUC2 signal sequence ["Suc2SS"; SEQ ID NO:8] fused to the "mature" ScSUC2 gene encoding invertase ("m-ScSUC2"; SEQ ID NO:4). As described previously with pYRH68, however, the artificial fusion described herein as SucSS/m-ScSUC2 corresponds with the wildtype full-length ScSUC2 gene which naturally contains 5'-signal sequence. Thus, this particular construct described herein as XPR2PP+13/SucSS/m-ScSUC2 and as set forth as SEQ ID NOs:16 and 17 effectively fuses XPR2PP+13 to the full-length ScSUC2 gene.

As discussed, above, the XPR2PP+13 region of SEQ ID NO:10 was designed to encode amino acids 1-170 of SEQ ID NO:6, thereby encoding an additional 13 amino acids of Xpr2 after the prepro-region to ensure access of the Xpr6 endopeptidase to the Lys156-Arg157 cleavage site.

First, a 1.6 kB fragment encoding the full-length ScSUC2 ORF was amplified and cut with PciI/NotI in a manner identical to that utilized during construction of plasmid pYRH68, above. Then, a fragment encoding the N-terminal 170 amino acids of the *Y. lipolytica* XPR2 gene (i.e., including the 157 amino acid preproregion plus the N-terminal 13 amino acids of the mature AEP protein) (i.e., SEQ ID NO:9 plus flanking sequence corresponding to NcoI and PciI restriction enzymes) was amplified from genomic DNA of *Y. lipolytica* ATCC #20362 using primers YI.XPR2-5' (SEQ ID NO:27) and YI.XPR2-3' (SEQ ID NO:28). Following digestion, a PciI/NcoI digested 513 bp XPR2PP+13 fragment was produced.

Since the PciI and NcoI digested ends are compatible, the PciI/NcoI digested 513 bp XPR2PP+13 fragment and the 1.6 kB PciI/NotI digested ScSUC2 fragment were inserted into PciI/NotI digested pYRH68 backbone to create pYRH69 (FIG. 4B; SEQ ID NO:18). The orientation of the PciI/NcoI digested 513 bp XPR2PP+13 fragment was verified.

Sequencing of pYRH69 with primers YI.XPR2-5' (SEQ ID NO:27) and YI.XPR2-3' (SEQ ID NO:28) confirmed that the XPR2PP+13 sequence as set forth in SEQ ID NO:9 of *Y. lipolytica* ATCC #20362 was 100% identical to the published XPR2 sequence (Matoba, S. et al., *Mol. Cell. Biol.*, 8:4904-4916 (1988)).

Construction of pYRH74, Comprising XPR2PP+13/m-ScSUC2

Plasmid pYRH74 was constructed to overexpress the XPR2 prepro-region ["XPR2PP+13"; SEQ ID NO:10] fused to the "mature" ScSUC2 gene encoding invertase ("m-ScSUC2"; SEQ ID NO:4).

A 1.55 kB fragment spanning the mature ScSUC2 gene was amplified from genomic DNA of *S. cerevisiae* BY4743 using primers Sc.SUC2-5' (SEQ ID NO:23) and nSc.SUC2-3' (SEQ ID NO:24).

Specifically, a 1.55 kB PciI/NotI fragment comprising the mature ScSUC2 gene and a 513 bp PciI/NcoI XPR2PP+13 fragment were prepared as described above for plasmid pYRH73 and plasmid pYRH69, respectively. These fragments were ligated together with the pYRH68 backbone to create plasmid pYRH74 (FIG. 5; SEQ ID NO:21).

Example 3

Transformation and Expression of Plasmids pYRH68, pYRH69, pYRH70, pYRH73 and pYRH74 in *Yarrowia lipolytica*, Grown with Either Sucrose or Glucose as the Sole Carbon Source Plasmids pYRH68, pYRH69, pYRH70, pYRH73, and pYRH74 were individually digested with AscI/SphI for transformation into *Y. lipolytica* strain Y4184U (Example 5) and *Y. lipolytica* strain Z1978U (Example 6), both genetically engineered to produce significant quantities of EPA % TFAs. Transformants were grown on a variety of media comprising either sucrose or glucose as the sole carbon source.

Specifically, transformants were first selected on SD media plates lacking uracil (General Methods). Various Y4184U and Z1978U transformant strains were produced, as described below in Table 6.

TABLE 6

Y4184U And Z1978 Transformant Strains of *Yarrowia lipolytica* Overexpressing Extracellular Invertase

| Plasmid (SEQ ID NO) | Chimeric Gene Expressed (SEQ ID NO) | Transformants Produced |
|---|---|---|
| pYRH68 (SEQ ID NO: 13) | Suc2SS/m-ScSUC2 (SEQ ID NO: 11) | Y4184U + Suc2SS/m-ScSUC2 Z1978U + Suc2SS/m-ScSUC2 |
| pYRH70 (SEQ ID NO: 14) | 2 copies of Suc2SS/m-ScSUC2 (SEQ ID NO: 11) | Z1978U + 2_Suc2SS/m-ScSUC2 |
| pYRH73 (SEQ ID NO: 15) | m-ScSUC2 (SEQ ID NO: 3) | Z1978U + m-ScSUC2 |
| pYRH69 (SEQ ID NO: 18) | XPR2PP + 13/ Suc2SS/ m-ScSUC2 (SEQ ID NO: 16) | Y4184U + XPR2PP + 13/Suc2SS/m-ScSUC2 Z1978U + XPR2PP + 13/ Suc2SS/m-ScSUC2 |
| pYRH74 (SEQ ID NO: 21) | XPR2PP + 13/m-ScSUC2 (SEQ ID NO: 19) | Z1978U + XPR2PP + 13/m-ScSUC2 |

Figure 6:
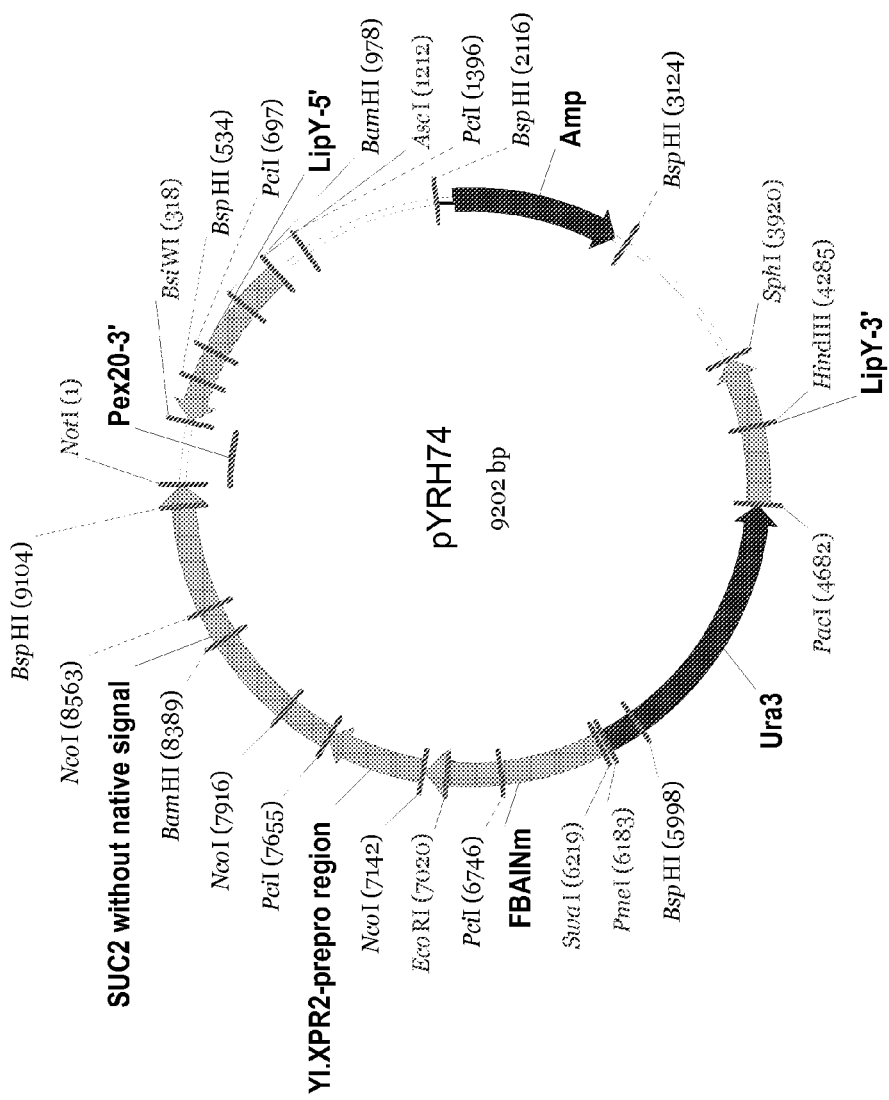
FIG. 6 is a plasmid map for pYRH74.

The growth of strains Y4184U+Suc2SS/m-ScSUC2 and Y4184 (control) was compared in SD (i.e., glucose) and SS (i.e., sucrose) medium. To avoid sucrose hydrolysis, the medium was sterilized by filtration instead of by autoclave. Specifically, cells were inoculated at an $OD_{600}$ of 0.03 and grown at 30° C. As shown in FIG. 6, the Y4184U+Suc2SS/m-ScSUC2 strain grew very well in sucrose, while control strain Y4184 failed to grow on sucrose as the sole carbon source. Both strains grew similarly when provided glucose as the sole carbon source. Strain Y4184U+XPR2PP+13/ Suc2SS/m-ScSUC2 also did not grow in sucrose (data not shown); it is hypothesized that the two different signal sequences may interfere with one another and prevent the secretory process.

Figure 7:
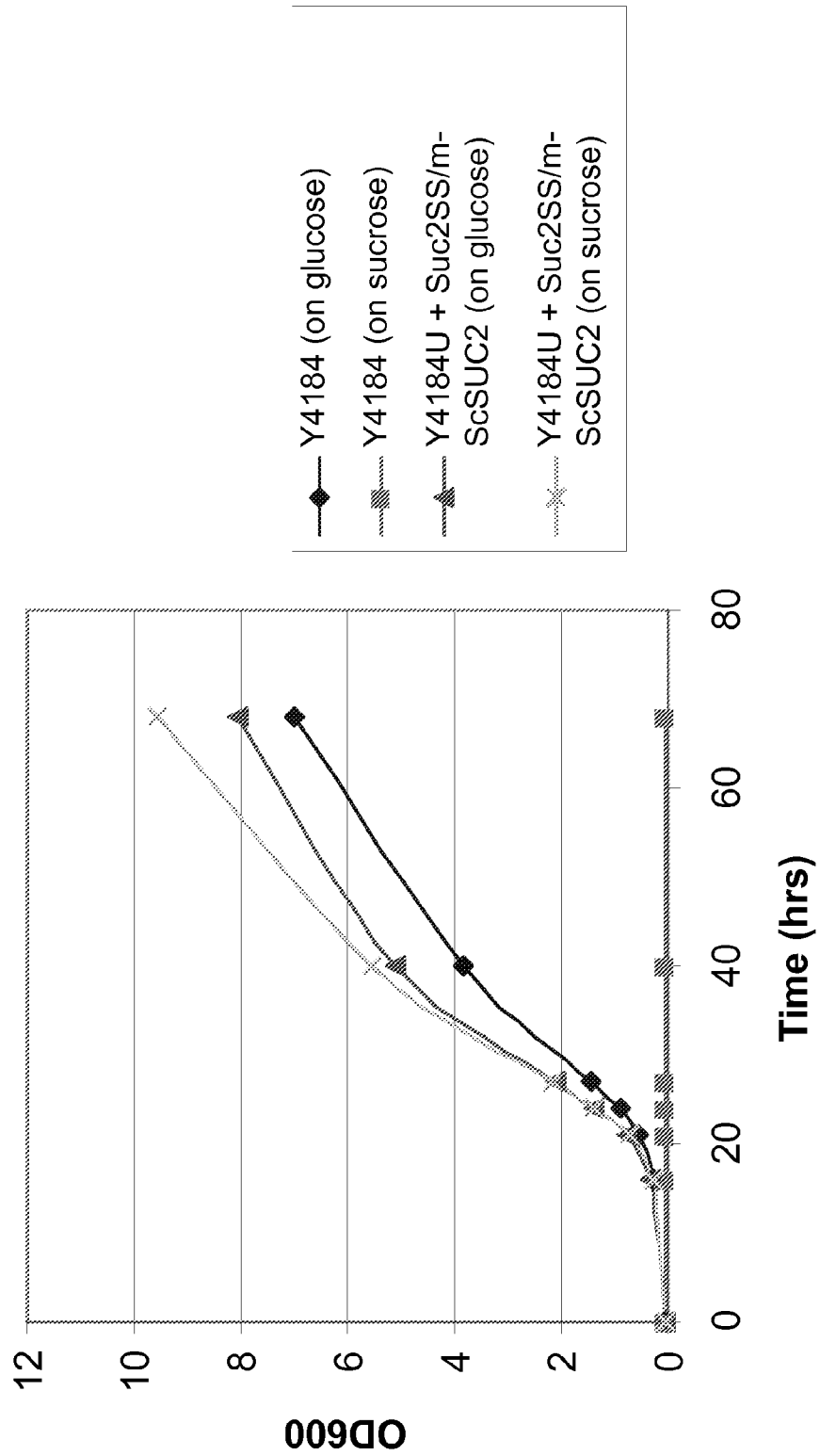
FIG. 7 shows growth of strains Y4184U+Suc2SS/m-Sc-SUC2 and Y4184 (control) on both glucose and sucrose media.

The growth of strains Z1978U+Suc2SS/m-ScSUC2, Z1978U+2_Suc2SS/m-ScSUC2, Z1978U+m-ScSUC2, Z1978U+XPR2PP+13/Suc2SS/m-ScSUC2, Z1978+ XPR2PP+13/m-ScSUC2 and Z1978 (control) was then compared in FM comprising either sucrose or glucose as the sole carbon source. To avoid sucrose hydrolysis, the medium was sterilized by filtration instead of by autoclave. Cells were inoculated at an $OD_{600}$ of 0.03 and grown at 30° C. All strains grew comparably in FM with glucose as the sole carbon source (FIG. 7A). In FM with sucrose as the sole carbon source (FIG. 7B), strains Z1978U+Suc2SS/m-ScSUC2, Z1978U+2_Suc2SS/m-ScSUC2 and Z1978+XPR2PP+13/ m-ScSUC2 grew very well but strains Z1978U+m-ScSUC2, Z1978U+XPR2PP+13/Suc2SS/m-ScSUC2 and Z1978 (control) grew very little; in fact, the residual growth could be due to the cells' ability to use yeast extract as a carbon source.

Thus, overexpression of both Suc2SS/m-ScSUC2 (SEQ ID NO:12) and XPR2PP+13/m-ScSUC2 (SEQ ID NO:20) resulted in transformed *Y. lipolytica* strains capable of growing in media with sucrose as the sole carbon source.

Example 4

Lipid Content and Composition in Transformant *Yarrowia lipolytica*, Grown with Either Sucrose or Glucose as the Sole Carbon Source The present Example examines lipid content and composition in Z1978 strains overexpressing the *S. cerevisiae* extracellular invertase (i.e., strains Z1978U+Suc2SS/m-ScSUC2, Z1978U+2_Suc2SS/m-ScSUC2 and Z1978+XPR2PP+13/ m-ScSUC2) when grown in media containing sucrose as the sole carbon source. The levels and composition of accumulated lipids in these strains were comparable to that of control strains grown in glucose as the sole carbon source.

To evaluate the effect of the sucrose utilization on total lipid content and fatty composition in strain Z1978U+ Suc2SS/m-ScSUC2, replicate cultures of the strain were grown under comparable oleaginous conditions in HSM (sucrose as the sole carbon source), as described in the General Methods. Thus, two cultures of Z1978U+Suc2SS/m-ScSUC2 (designated as cultures RHY243 and RHY244, respectively) were compared to duplicate samples of control strain Z1978, grown under comparable oleaginous conditions in HGM (glucose as the sole carbon source). More specifically, oleaginous conditions were achieved by first growing the cultures aerobically in 25 mL of SD or SS medium at 30° C. for 48 h, and then harvested by centrifugation. The pellets were then resuspended in 25 mL of either HGM or HSM, and the cultures were further incubated for 5 days in a shaker incubator at 250 rpm and 30° C.

The dry cell weight ["DCW"], total lipid content of cells ["TFAs DCW"], the concentration of each fatty acid as a weight percent of TFAs ["% TFAs"] and the EPA productivity (i.e., EPA content as its percent of the dry cell weight ["EPA % DCW"]) for the strains are shown below in Table 7, with averages highlighted in gray and indicated as "Ave". Abbreviations for fatty acids are as follows: oleic acid (18:1), linoleic acid (18:2), and eicosapentaenoic acid ("EPA", 20:5).

TABLE 7

Lipid Content And Composition Of Z1978 (Grown On Glucose) And Z1978U + Suc2SS/m-ScSUC2 (Grown On Sucrose)

| Strain | | TFAs | | % TFAs | | EPA |
|---|---|---|---|---|---|---|
| (Carbon Source) | Sample | DCW (g/L) | % DCW | 18:1 | 18:2 | 20:5 EPA | % DCW |
| Z1978 | Cont-1 | 4.40 | 33 | 5.3 | 11.5 | 53.7 | 17.7 |
| (Glucose) | Cont-2 | 4.48 | 32 | 4.4 | 11.1 | 53.8 | 17.1 |
| AVE | | 4.44 | 33 | 4.9 | 11.3 | 53.8 | 17.4 |
| Z1978U + Suc2SS/m-ScSUC2 (Sucrose) | RHY243 | 4.58 | 32 | 5.2 | 13.0 | 48.9 | 15.8 |
| | RHY244 | 4.62 | 32 | 5.3 | 13.1 | 48.8 | 15.4 |
| AVE | | 4.60 | 32 | 5.3 | 13.1 | 48.9 | 15.6 |

The results in Table 7 showed that TFAs % DCW in strain Z1978U+Suc2SS/m-ScSUC2 grown on sucrose was similar to that of strain Z1978 grown on glucose. However, a ~10% reduction in average EPA % DCW was observed when sucrose was the sole carbon source.

To determine if there were any changes in strain performance in strain Z1978U+Suc2SS/m-ScSUC2, RHY243 (Table 7) was grown in duplicate in either glucose or sucrose as the sole carbon source. Table 8 summarizes the DCW, TFAs % DCW, the concentration of each fatty acid as % TFAs, and EPA % DCW, in a format similar to that used in Table 7.

TABLE 8

Lipid Content And Composition Of Z1978 + Suc2SS/m-ScSUC2, Grown On Either Glucose Or Sucrose

| Carbon Source | Replicate | DCW (g/L) | TFAs % DCW | % TFAs | | | EPA % DCW |
|---|---|---|---|---|---|---|---|
| | | | | 18:1 | 18:2 | 20:5 EPA | |
| Glucose | 1 | 3.84 | 35 | 4.5 | 12.6 | 51.1 | 17.9 |
| | 2 | 4.34 | 34 | 4.6 | 12.8 | 51.0 | 17.2 |
| | AVE | 4.09 | 35 | 4.6 | 12.7 | 51.1 | 17.6 |
| Sucrose | 1 | 4.56 | 33 | 5.3 | 13.6 | 48.8 | 15.9 |
| | 2 | 4.56 | 32 | 5.3 | 13.5 | 48.8 | 15.5 |
| | AVE | 4.56 | 33 | 5.3 | 13.6 | 48.8 | 15.7 |

The results in Table 8 showed that TFAs % DCW in strain Z1978U+Suc2SS/m-ScSUC2 grown on sucrose was similar to lipid content of the same strain when it was grown on glucose. However, a ~10% reduction in average EPA % DCW was observed when sucrose was the sole carbon source.

Total lipid content and fatty acid composition was also compared in two cultures of Z1978U+Suc2SS/m-ScSUC2 (i.e., RHY243 and RHY244), three cultures of Z1978U+ 2_Suc2SS/m-ScSUC2 (designated as RHY248, RHY249 and RHY250) and three cultures of Z1978+XPR2PP+13/m-ScSUC2 (designated as RHY257, RHY258 and RHY259), when grown under comparable oleaginous conditions in HSM (sucrose as the sole carbon source), as described in the General Methods. These strains were compared to duplicate samples of control strain Z1978, grown under comparable oleaginous conditions in HGM (glucose as the sole carbon source).

Table 9 summarizes the DCW, TFAs % DCW, the concentration of each fatty acid as % TFAs, and EPA % DCW, in a format similar to that used in Table 7.

TABLE 9

Lipid Content And Composition Of Z1978 (Grown On Glucose) And Z1978U + Suc2SS/m-ScSUC2, Z1978U + 2 Suc2SS/m-ScSUC2 And Z1978U + XPR2PP + 13/m-ScSUC2 (Grown On Sucrose)

| Stain (Carbon Source) | Sample | DCW (g/L) | TFAs % DCW | % TFAs | | | EPA % DCW |
|---|---|---|---|---|---|---|---|
| | | | | 18:1 | 18:2 | 20:5 EPA | |
| Z1978 (Glucose) | Cont-1 | 4.30 | 31 | 4.8 | 11.4 | 54.8 | 16.8 |
| | Cont-2 | 4.34 | 32 | 4.8 | 11.5 | 54.7 | 17.5 |
| | AVE | 4.32 | 31 | 4.8 | 11.4 | 54.8 | 17.2 |
| Z1978U + Suc2SS/m-ScSUC2 (Sucrose) | RHY243 | 4.82 | 33 | 5.7 | 13.8 | 50.6 | 16.6 |
| | RHY244 | 5.04 | 33 | 5.8 | 13.7 | 50.0 | 16.6 |
| | AVE | 4.93 | 33 | 5.7 | 13.8 | 50.3 | 16.6 |
| Z1978U + XPR2PP + 13/m-ScSUC2 (Sucrose) | RHY257 | 4.44 | 33 | 4.9 | 13.4 | 51.4 | 16.8 |
| | RHY258 | 4.64 | 34 | 5.6 | 13.7 | 50.6 | 17.2 |
| | RHY259 | 4.20 | 35 | 5.8 | 14.2 | 50.1 | 17.4 |
| | AVE | 4.43 | 34 | 5.4 | 13.7 | 50.7 | 17.1 |
| Z1978U + 2_Suc2SS/m-ScSUC2 (Sucrose) | RHY248 | 4.76 | 33 | 5.4 | 13.4 | 50.2 | 16.8 |
| | RHY249 | 4.82 | 33 | 5.5 | 13.4 | 50.1 | 16.4 |
| | RHY250 | 4.48 | 31 | 4.2 | 11.6 | 54.0 | 16.5 |
| | AVE | 4.69 | 32 | 5.0 | 12.8 | 51.4 | 16.6 |

The results above showed that TFAs % DCW and EPA % DCW in strains Z1978U+Suc2SS/m-ScSUC2, Z1978U+ 2_Suc2SS/m-ScSUC2 and Z1978+XPR2PP+13/m-ScSUC2 grown in sucrose as the sole carbon source differed by less than 10% with the TFAs % DCW and EPA % DCW of control strain Z1978 grown in glucose. Of the three SUC2 engineered strains, strain Z1978+XPR2PP+13/m-ScSUC2 had the best EPA % DCW performance. All three SUC2 expressing strains consistently showed up to 14% higher final DCW (g/L) than control strain Z1978. Thus, the EPA volumetric productivity is similar between control strain Z1978 and the engineered sucrose-utilizing strains.

Example 5

Generation of *Yarrowia lipolytica* Strains Y4184 and Y4184U For High EPA Production

*Y. lipolytica* strain Y4184U was used as the host in Example 3, above. Strain Y4184U was derived from *Y. lipolytica* ATCC #20362 and is capable of producing high EPA relative to the total lipids via expression of a delta-9 elongase/delta-8 desaturase pathway. The strain has a Ura-phenotype and its construction is described in Example 7 of PCT Publication No. WO 2008/073367, hereby incorporated herein by reference.

The development of strain Y4184U required the construction of strains Y2224, Y4001, Y4001 U, Y4036, Y4036U, Y4069, Y4084, Y4084U1, Y4127 (deposited with the American Type Culture Collection on Nov. 29, 2007, under accession number ATCC PTA-8802), Y4127U2, Y4158, Y4158U1 and Y4184.

The final genotype of strain Y4184 (producing 30.7% EPA of total lipids) with respect to wildtype *Y. lipolytica* ATCC #20362 was unknown 1-, unknown 2-, unknown 4-, unknown 5-, unknown 6-, unknown 7-, YAT1::ME3S::Pex16, EXP1:: ME3S::Pex20 (2 copies), GPAT::EgD9e::Lip2, FBAINm:: EgD9eS::Lip2, EXP1::EgD9eS::Lip1, FBA::EgD9eS:: Pex20, YAT1::EgD9eS::Lip2, GPD::EgD9eS::Lip2, GPDIN::EgD8M::Lip1, YAT1::EgD8M::Aco, EXP1:: EgD8M::Pex16, FBAINm::EgD8M::Pex20, FBAIN:: EgD8M::Lip1 (2 copies), GPM/FBAIN::FmD12S::Oct, EXP1::FmD12S::Aco, YAT1::FmD12::Oct, GPD::FmD12:: Pex20, EXP1::EgD5S::Pex20, YAT1::EgD5S::Aco, YAT1:: Rd5S::Oct, FBAIN::EgD5::Aco, FBAINm::PaD17::Aco, EXP1::PaD17::Pex16, YAT1::PaD17S::Lip1, YAT1:: YICPT1::Aco, GPD::YICPT1::Aco.

Abbreviations above are as follows: ME3S is a codon-optimized $C_{16/18}$ elongase gene, derived from *Mortierella alpina* [U.S. Pat. No. 7,470,532]; EgD9e is a *Euglena gracilis* delta-9 elongase gene [U.S. Pat. No. 7,645,604]; EgD9eS is a codon-optimized delta-9 elongase gene, derived from *Euglena gracilis* [U.S. Pat. No. 7,645,604]; EgD8M is a synthetic mutant delta-8 desaturase [U.S. Pat. No. 7,709, 239], derived from *Euglena gracilis* [U.S. Pat. No. 7,256, 033]; FmD12 is a *Fusarium moniliforme* delta-12 desaturase gene [U.S. Pat. No. 7,504,259]; FmD12S is a codon-optimized delta-12 desaturase gene, derived from *Fusarium moniliforme* [U.S. Pat. No. 7,504,259]; EgD5 is a *Euglena gracilis* delta-5 desaturase [U.S. Pat. No. 7,678,560]; EgD5S is a codon-optimized delta-5 desaturase gene, derived from *Euglena gracilis* [U.S. Pat. No. 7,678,560]; RD5S is a codon-optimized delta-5 desaturase, derived from *Peridinium* sp. CCMP626 [U.S. Pat. No. 7,695,950]; PaD17 is a *Pythium aphanidermatum* delta-17 desaturase [U.S. Pat. No. 7,556, 949]; PaD17S is a codon-optimized delta-17 desaturase, derived from *Pythium aphanidermatum* [U.S. Pat. No. 7,556, 949]; and, YICPT1 is a *Yarrowia lipolytica* diacylglycerol cholinephosphotransferase gene [U.S. Pat. No. 7,932,077].

Finally, in order to disrupt the Ura3 gene in strain Y4184, construct pZKUE3S(PCT Publication No. WO 2008/073367, SEQ ID NO:78 therein) was used to integrate a EXP1:: ME3S::Pex20 chimeric gene into the Ura3 gene of strain Y4184 to result in strains Y4184U1 (11.2% EPA of total lipids), Y4184U2 (10.6% EPA of total lipids) and Y4184U4 (15.5% EPA of total lipids), respectively (collectively, Y4184U).

It is noted that PCT Publication No. WO 2008/073367 describes a discrepancy in the EPA % TFAs quantified in Y4184 (30.7%) versus Y4184U (average 12.4%) due to differing growth conditions.

Example 6

Generation of *Yarrowia lipolytica* Strains Z1978 and Z1978U for High EPA Production

*Y. lipolytica* strain Z1978U was used as the host in Example 3, above. Strain Z1978U was derived from *Y. lipolytica* ATCC #20362 and is capable of producing high EPA relative to the total lipids via expression of a delta-9 elongase/delta-8 desaturase pathway. The strain has a Ura-phenotype and its construction is described in Example 2 of U.S. patent application Ser. No. 13/218,708 (E.I. duPont de Nemours & Co., Inc., filed 26 Aug. 2011), hereby incorporated herein by reference.

The development of strain Z1978U required the construction of strains Y2224, Y4001, Y4001U, Y4036, Y4036U, L135, L135U9, Y8002, Y8006, Y8006U, Y8069, Y8069U, Y8154, Y8154U, Y8269, Y8269U, Y8412 (deposited with the American Type Culture Collection on May 14, 2009, under accession number ATCC PTA-10026), Y8412U, Y8647, Y8467U, Y9028, Y9028U, Y9502, Y9502U and Z1978.

Genotype of *Yarrowia lipolytica* Strain Y9502

The generation of strain Y9502 is described in U.S. Pat. Appl. Pub. No. 2010-0317072-A1. Strain Y9502, derived from *Y. lipolytica* ATCC #20362, was capable of producing about 57.0% EPA relative to the total lipids via expression of a delta-9 elongase/delta-8 desaturase pathway.

The final genotype of strain Y9502 with respect to wildtype *Y. lipolytica* ATCC #20362 was Ura+, Pex3-, unknown 1-, unknown 2-, unknown 3-, unknown 4-, unknown 5-, unknown6-, unknown 7-, unknown 8-, unknown9-, unknown 10-, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, GPDIN::EgD5SM::Aco, GPM::EgD5SM::Oct, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, YAT1::MCS::Lip1, FBA::MCS::Lip1, YAT1::MaLPAAT1S::Pex16.

Abbreviations used above and not set forth in Example 5 are as follows: EaD8S is a codon-optimized delta-8 desaturase gene, derived from *Euglena anabaena* [U.S. Pat. No. 7,790,156]; E389D9eS/EgD8M is a DGLA synthase created by linking a codon-optimized delta-9 elongase gene ("E389D9eS"), derived from *Eutreptiella* sp. CCMP389 (U.S. Pat. 7,645,604), to the delta-8 desaturase "EgD8M" (above) [U.S. Pat. Appl. Pub. No. 2008-0254191-A1]; EgD9eS/EgD8M is a DGLA synthase created by linking the delta-9 elongase "EgD9eS" (above) to the delta-8 desaturase "EgD8M" (above) [U.S. Pat. Appl. Pub. No. 2008-0254191-A1]; EaD9eS/EgD8M is a DGLA synthase created by linking a codon-optimized delta-9 elongase gene ("EaD9eS"), derived from *E. anabaena* [U.S. Pat. No. 7,794,701], to the delta-8 desaturase "EgD8M" (above) [U.S. Pat. Appl. Pub. No. 2008-0254191-A1]; EgDSM and EgDSSM are synthetic mutant delta-5 desaturase genes comprising a mutant HPGs motif [U.S. Pat. App. Pub. 2010-0075386-A1], derived from *Euglena gracilis* [U.S. Pat. No. 7,678,560]; EaD5SM is a synthetic mutant delta-5 desaturase gene comprising a mutant HaGG motif [U.S. Pat. App. Pub. 2010-0075386-A1], derived from *E. anabaena* [U.S. Pat. No. 7,943,365]; MCS is a codon-optimized malonyl-CoA synthetase gene, derived from *Rhizobium leguminosarum* by. viciae 3841 [U.S. Pat. App. Pub. 2010-0159558-A1], and, MaLPAAT1S is a codon-optimized lysophosphatidic acid acyltransferase gene, derived from *Mortierella alpina* [U.S. Pat. No. 7,879,591].

For a detailed analysis of the total lipid content and composition in strain Y9502, a flask assay was conducted wherein cells were grown in 2 stages for a total of 7 days. Based on analyses, strain Y9502 produced 3.8 g/L DCW, 37.1 TFAs % DCW, 21.3 EPA % DCW, and the lipid profile was as follows, wherein the concentration of each fatty acid is as a weight percent of TFAs ["% TFAs"]: 16:0 (palmitate)—2.5, 16:1 (palmitoleic acid)—0.5, 18:0 (stearic acid)—2.9, 18:1 (oleic acid)—5.0, 18:2 (LA)—12.7, ALA—0.9, EDA—3.5, DGLA—3.3, ARA—0.8, ETrA—0.7, ETA—2.4, EPA—57.0, other—7.5.

Generation of *Yarrowia lipolytica* Strain Z1978

The development of strain Z1978 from strain Y9502 was first described in U.S. Provisional Application No. 61/377,248 (corresponding to U.S. patent application Ser. No. 13/218,591) and U.S. Provisional Application No. 61/428,277 (corresponding to U.S. patent application Ser. No. 13/218,673), hereby incorporated herein by reference.

Figure 8:
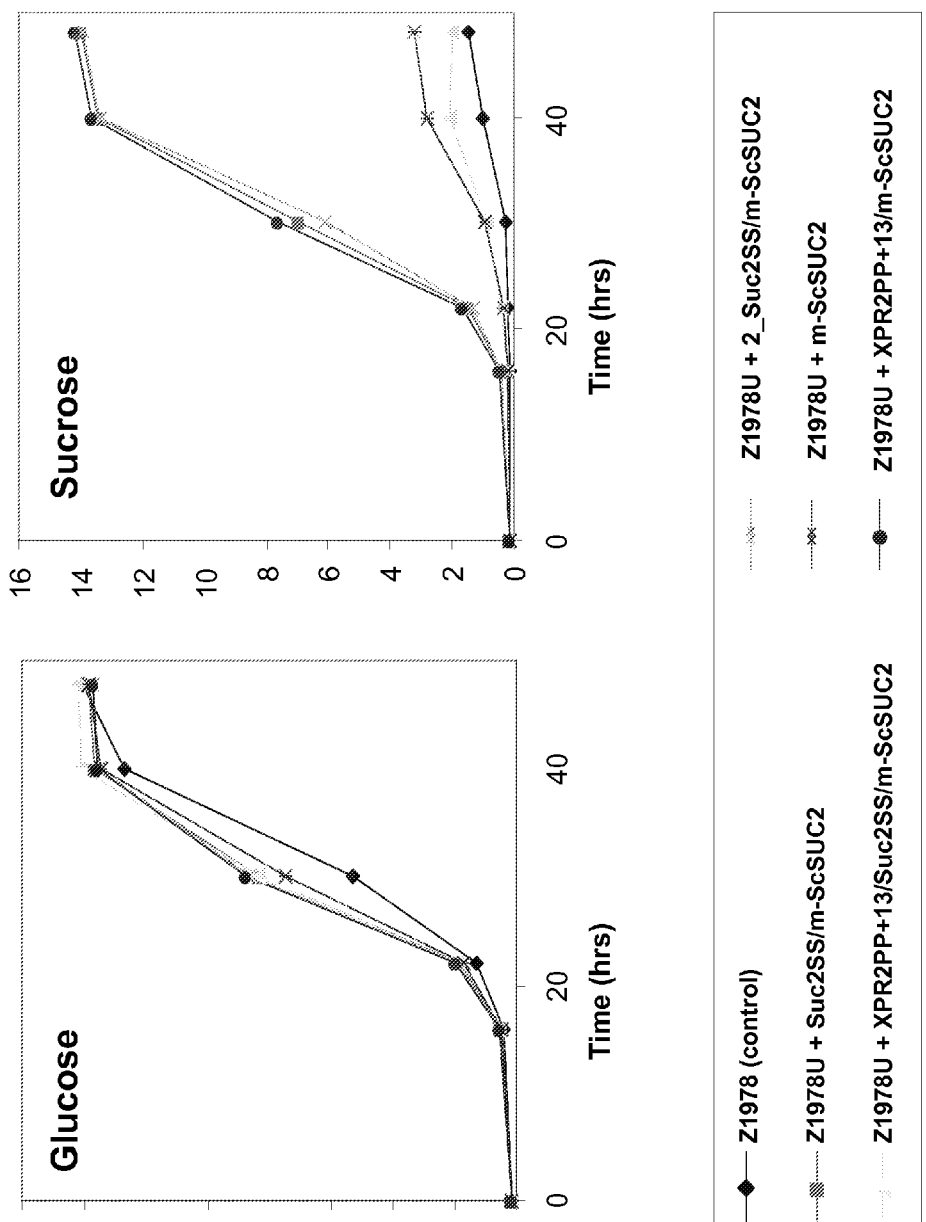
FIG. 8 shows growth of strains Z1978U+Suc2SS/m-Sc-SUC2, Z1978U+2_Suc2SS/m-ScSUC2, Z1978U+ XPR2PP+13/m-ScSUC2, Z1978U+m-ScSUC2, Z1978U+XPR2PP+13/Suc2SS/m-ScSUC2 and Z1978 (control) on media comprising: (A) glucose; and (B) sucrose.

Specifically, to disrupt the Ura3 gene in strain Y9502, Sal/I/PacI-digested construct pZKUM (see U.S. Pat. Appl. Pub. No. 2009-0093543-A1, Table 15, SEQ ID NO:133 and FIG. 8A therein) was used to integrate an Ura3 mutant gene into the Ura3 gene of strain Y9502, according to the General Methods. A total of 27 transformants (selected from a first group comprising 8 transformants, a second group comprising 8 transformants, and a third group comprising 11 transformants) were grown on Minimal Media+5-fluoroorotic acid ["MM+5-FOA"] selection plates and maintained at 30° C. for 2 to 5 days. MM+5-FOA comprises (per liter): 20 g glucose, 6.7 g Yeast Nitrogen base, 75 mg uracil, 75 mg uridine and an appropriate amount of FOA (Zymo Research Corp., Orange, Calif.), based on FOA activity testing against a range of concentrations from 100 mg/L to 1000 mg/L (since variation occurs within each batch received from the supplier).

Further experiments determined that only the third group of transformants possessed a real Ura-phenotype.

The Ura-cells were scraped from the MM+5-FOA plates and subjected to fatty acid analysis, according to the General Methods. In this way, GC analyses showed that there were 28.5%, 28.5%, 27.4%, 28.6%, 29.2%, 30.3% and 29.6% EPA of TFAs in pZKUM-transformants #1, #3, #6, #7, #8, #10 and #11 grown on MM+5-FOA plates of group 3, respectively. These seven strains were designated as strains Y9502U12, Y9502U14, Y9502U17, Y9502U18, Y9502U19, Y9502U21 and Y9502U22, respectively (collectively, Y9502U).

Figure 9:
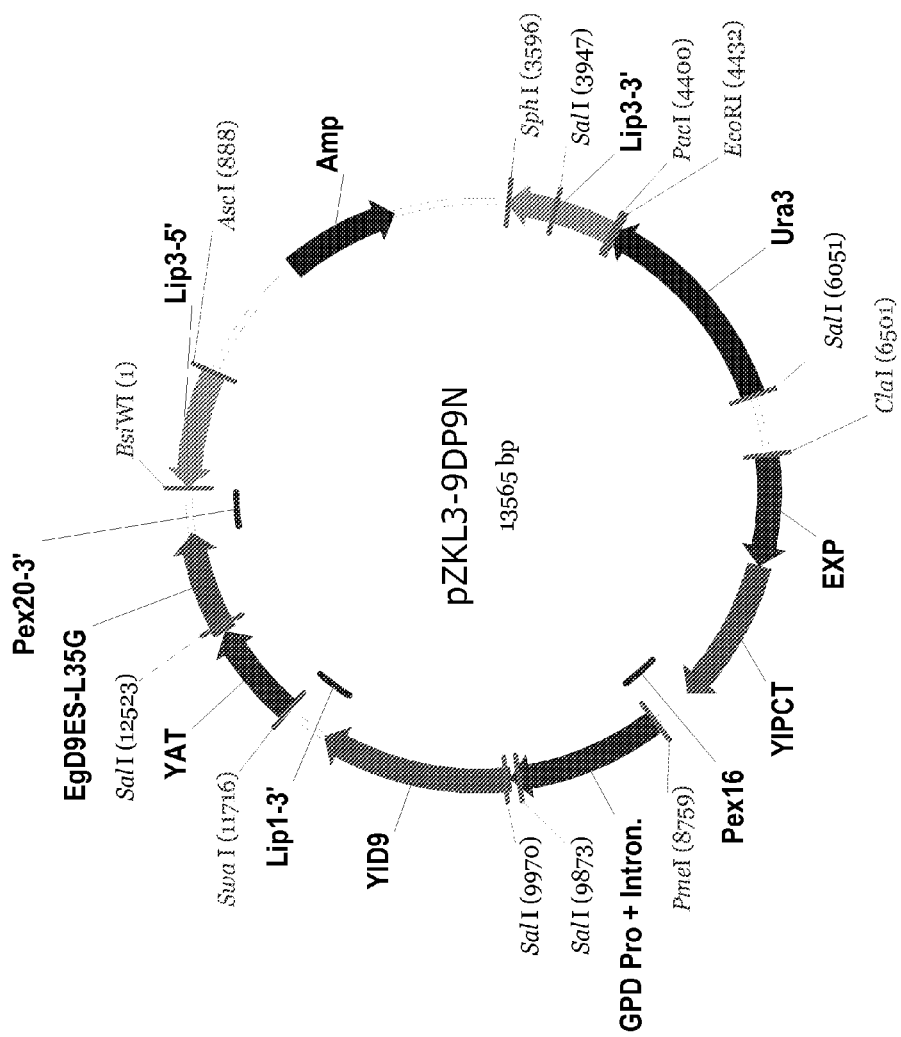
FIG. 9 is a plasmid map for pZKL3-9DP9N.

Construct pZKL3-9DP9N (FIG. 9; SEQ ID NO:29) was then generated to integrate one delta-9 desaturase gene, one choline-phosphate cytidylyl-transferase gene, and one delta-9 elongase mutant gene into the *Yarrowia* YALI0F32131p locus (GenBank Accession No. XM_506121) of strain Y9502U. Thus, the pZKL3-9DP9N plasmid contained the following components:

TABLE 10

Description of Plasmid pZKL3-9DP9N (SEQ ID NO: 29)

| RE Sites And Nucleotides Within SEQ ID NO: 29 | Description Of Fragment And Chimeric Gene Components |
|---|---|
| AscI/BsiWI (887-4) | 884 bp 5' portion of YALI0F32131p locus (GenBank Accession No. XM_506121, labeled as "Lip3-5" in Figure) |
| PacI/SphI (4396-3596) | 801 bp 3' portion of YALI0F32131p locus (GenBank Accession No. XM_506121, labeled as "Lip3-3" in Figure) |
| SwaI/BsiWI (11716-1) | YAT1::EgD9eS-L35G::Pex20, comprising:<br>YAT1: *Yarrowia lipolytica* YAT1 promoter (labeled as "YAT" in Figure; U.S. Pat. Appl. Pub. No. 2010-0068789-A1);<br>EgD9eS-L35G: Synthetic mutant of delta-9 elongase gene (SEQ ID NO: 30; U.S Pat. Application No. 13/218,591), derived from *Euglena gracilis* ("EgD9eS"; U.S. Pat. No. 7,645,604) (labeled as "EgD9ES-24" in Figure);<br>Pex20: Pex20 terminator sequence from *Yarrowia* Pex20 gene (GenBank Accession No. AF054613) |
| PmeI/SwaI (8759-11716) | GPDIN::YID9::Lip1, comprising:<br>GPDIN: *Y. lipolytica* GPDIN promoter (U.S. Pat. No. 7,459,546; labeled as "GPDPro + Intron" in Figure);<br>YID9: *Y. lipolytica* delta-9 desaturase gene (GenBank Accession No. XM_501496; SEQ ID NO: 32) (labeled as "YID9D" in Figure);<br>Lip1: Lip1 terminator sequence from *Yarrowia* Lip1 gene (GenBank Accession No. Z50020) |
| ClaII/PmeI (6501-8759) | EXP1::YIPCT::Pex16, comprising:<br>EXP1: *Y. lipolytica* export protein (EXP1) promoter (labeled as "EXP" in Figure; Intl. App. Pub. No. WO 2006/052870);<br>YIPCT: *Y. lipolytica* choline-phosphate cytidylyl-transferase ["PCT"] gene (GenBank Accession No. XM_502978; SEQ ID NO: 34);<br>Pex16: Pex16 terminator sequence from *Yarrowia* Pex16 gene (GenBank Accession No. U75433) |
| SalI/EcoRI (6501-4432) | *Yarrowia* Ura3 gene (GenBank Accession No. AJ306421) |

The pZKL3-9DP9N plasmid was digested with AscI/SphI, and then used for transformation of strain Y9502U17. The transformed cells were plated onto Minimal Media ["MM"] plates and maintained at 30° C. for 3 to 4 days. MM plates comprised (per liter): 20g glucose, 1.7 g yeast nitrogen base without amino acids, 1.0 g proline, and pH 6.1 (do not need to adjust). Single colonies were re-streaked onto MM plates, and then inoculated into liquid MM at 30° C. and shaken at 250 rpm/min for 2 days. The cells were collected by centrifugation, resuspended in HGM and then shaken at 250 rpm/min for 5 days. The cells were subjected to fatty acid analysis, above.

GC analyses showed that most of the selected 96 strains of Y9502U17 with pZKL3-9DP9N produced 50-56% EPA of TFAs. Five strains (i.e., #31, #32, #35, #70 and #80) that produced about 59.0%, 56.6%, 58.9%, 56.5%, and 57.6% EPA of TFAs were designated as strains Z1977, Z1978, Z1979, Z1980 and Z1981, respectively.

The final genotype of these pZKL3-9DP9N transformed strains with respect to wildtype *Y. lipolytica* ATCC #20362 was Ura+, Pex3-, unknown 1-, unknown 2-, unknown 3-, unknown 4-, unknown 5-, unknown6-, unknown 7-, unknown 8-, unknown9-, unknown 10-, unknown 11-, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, YAT1::EgD9eS-L35G::Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, GPDIN::YID9::Lip1, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, GPDIN::EgD5SM::Aco, GPM::EgD5SM::Oct, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, YAT1::MCS::Lip1, FBA::MCS::Lip1, YAT1::MaLPAAT1S::Pex16, EXP1::YIPCT::Pex16.

Knockout of the YALI0F32131p locus (GenBank Accession No. XM_50612) in strains Z1977, Z1978, Z1979, Z1980 and Z1981 was not confirmed in any of these EPA strains produced by transformation with pZKL3-9DP9N.

Cells from YPD plates of strains Z1977, Z1978, Z1979, Z1980 and Z1981 were grown and analyzed for total lipid content and composition. Specifically, flask assays were conducted as described in the General Methods. Table 11 below summarizes total lipid content and composition in each of these strains (i.e., the total DCW, the TFAs % DCW, the concentration of each fatty acid as a weight percent of TFAs ["% TFAs"] and the EPA % DCW). Fatty acids are 16:0 (palmitate), 16:1 (palmitoleic acid), 18:0 (stearic acid), 18:1 (oleic acid), 18:2 (linoleic acid), ALA (alpha-linolenic acid), EDA (eicosadienoic acid), DGLA (dihomo-gamma-linolenic acid), ARA (arachidonic acid), ETrA (eicosatrienoic acid), ETA (eicosatetraenoic acid), EPA (eicosapentaenoic acid) and other.

TABLE 11

Total Lipid Content And Composition In *Yarrowia* Strains Z1977, Z1978, Z1979, Z1980 and Z1981 By Flask Assay

| Strain | DCW (g/L) | TFAs % DCW | 16:0 | 16:1 | 18:0 | 18:1 | 18:2 | ALA | EDA | DGLA | ARA | EtrA | ETA | EPA | other | EPA % DCW |
|---|---|---|---|---|---|---|---|---|---|---|---|---|---|---|---|---|
| Z1977 | 3.8 | 34.3 | 2.0 | 0.5 | 1.9 | 4.6 | 11.2 | 0.7 | 3.1 | 3.3 | 0.9 | 0.7 | 2.2 | 59.1 | 9.9 | 20.3 |
| Z1978 | 3.9 | 38.3 | 2.4 | 0.4 | 2.4 | 4.8 | 11.1 | 0.7 | 3.2 | 3.3 | 0.8 | 0.6 | 2.1 | 58.7 | 9.5 | 22.5 |
| Z1979 | 3.7 | 33.7 | 2.3 | 0.4 | 2.4 | 4.1 | 10.5 | 0.6 | 3.2 | 3.6 | 0.9 | 0.6 | 2.2 | 59.4 | 9.8 | 20.0 |
| Z1980 | 3.6 | 32.7 | 2.1 | 0.4 | 2.2 | 4.0 | 10.8 | 0.6 | 3.1 | 3.5 | 0.9 | 0.7 | 2.2 | 59.5 | 10.0 | 19.5 |
| Z1981 | 3.5 | 34.3 | 2.2 | 0.4 | 2.1 | 4.2 | 10.6 | 0.6 | 3.3 | 3.4 | 1.0 | 0.8 | 2.2 | 58.5 | 10.7 | 20.1 |

Strain Z1978 was subsequently subjected to partial genome sequencing. This work, as described in U.S. patent application Ser. No. 13/218,673, determined that instead of six delta-5 desaturase genes integrated into the *Yarrowia* genome (i.e., chimeric genes EXP1::EgD5M::Pex16, FBAIN::EgD5SM::Pex20, GPDIN::EgD5SM::Aco, GPM::EgD5SM::Oct, EXP1::EgD5SM::Lip1, YAT1::EaD5SM::Oct), the engineered strain actually possessed only four delta-5 desaturase genes (i.e., EXP1::EgD5M::Pex16, FBAIN::EgD5SM::Pex20, EXP1::EgD5SM::Lip1, and YAT1::EaD5SM::Oct).

To disrupt the Ura3 gene in strain Z1978, construct pZKUM (see U.S. Pat. Appl. Pub. No. 2009-0093543-A1, Table 15, SEQ ID NO:133 and FIG. 8A therein) was used to integrate an Ura3 mutant gene into the Ura3 gene of strain Z1978 in a manner similar to that described for pZKUM transformation of strain Y9502 (above). A total of 16 transformants (selected from a first "B" group comprising 8 transformants and a second "C" group comprising 8 transformants) were grown and identified to possess a Ura- phenotype.

GC analyses showed the presence of 30.8%, 31%, 30.9% and 31.3% EPA of TFAs in the B group pZKUM-transformant strains #1, #2, #3, and #4, respectively, grown on MM+5-FOA plates. These 4 strains were designated as strains Z1978BU1, Z1978BU2, Z1978BU3 and Z1978BU4, respectively.

GC analyses showed the presence of 34.4%, 31.9%, 31.2% and 31% EPA of TFAs in the C group pZKUM-transformant strains #1, #2, #5, and #6, respectively, grown on MM+5-FOA plates. These 4 strains were designated as strains Z1978CU1, Z1978CU2, Z1978CU3 and Z1978CU4, respectively.

Strains Z1978BU1, Z1978BU2, Z1978BU3, Z1978BU4, Z1978CU1, Z1978CU2, Z1978CU3 and Z1978CU4 strains were collectively designated as strain Z1978U.

Example 7

Localization of Secreted Invertase in *Yarrowia lipolytica* Transformants

Plasmids pYRH68 (SEQ ID NO:13, comprising a Suc2SS/m-ScSUC2 fusion), pYRH73 (SEQ ID NO:15, comprising only m-ScSUC2), pYRH69 (SEQ ID NO:18, comprising a XPR2PP+13/Suc2SS/m-ScSUC2 fusion) and/or pYRH74 (SEQ ID NO:21, comprising a XPR2PP+13/m-ScSUC2 fusion) were individually digested with BsiWI/PacI for transformation into either *Y. lipolytica* strain Y2224U (a 5-fluoroorotic acid ["FOA"] resistant mutant from an autonomous mutation of the Ura3 gene of wildtype *Yarrowia* strain ATCC #20362) or *Y. lipolytica* strain Z1978U (Example 6). Invertase activity was determined in transformant whole cells and from the culture medium thereof.

Invertase Activity Assays

In vivo invertase activity was determined using whole cells as described in Silveira, et al. (*Anal. Biochem.*, 238:26-28 (1996)) with some modifications. Briefly, 40 mg (dry cell weight) of exponentially growing cells ($OD_{600}$ of 1.4-1.8) in SD or SS medium were collected by centrifugation at 4° C., washed three times in cold sodium acetate buffer (50 mM, pH 5.0). Cells were incubated in 8 mL of 100 mM NaF at 30° C. for 15 min with agitation. After addition of 4 mL 300 mM sucrose solution in 50 mM sodium acetate buffer, pH 5.0, invertase activity was determined with a glucose analyzer (YSI Life Sciences) after filtration using Nanosep MF 0.2μ (Pall Life Sciences; Port Washington, N.Y.) at different time intervals up to 10 min. One unit (U) of enzyme activity was defined as pmol of glucose produced per min, and yield was calculated to give units of invertase activity per gram of DCW.

Invertase activity from culture medium was measured from 1.5 mL of filtered medium. To remove any residual sugar in the sample, samples were dialyzed against 0.1 M acetate buffer (pH 5.0) at 4° C. overnight. Dialyzed sample (200 μl) was incubated with 100 μl of 300 mM sucrose solution in 50 mM sodium acetate buffer, pH 5.0, for up to 30 min. Reaction was stopped by adding 50 μl of 1.0 M $K_2HPO_4$ and immediately placing in a 95° C. heat block for 10 min. Invertase activity was measured with a glucose analyzer (YSI Life Sciences). Protein concentration was measured by Coomassie Plus Bradford Assay kit (Thermo Scientific; Rockford, Ill.) with bovine serum albumin as standard. Activity was calculated as units (U) of invertase activity per liter of culture medium and the specific activity as units per mg of protein. Yield was calculated to give units of invertase activity per gram of DCW of the culture.

Extracellular and Whole-Cell Invertase Activities in Transformant *Y. lipolytica* Y2224U $SUC^+$ Strains The extracellular and whole-cell invertase activities were measured from exponentially growing cells using culture supernatant and whole-cells, respectively. At least four assays from two independent experiments were conducted and average values are reported, as shown below in Table 12.

TABLE 12

| Invertase Activities From Culture Media And Whole Cells Of *Y. lipolytica* Strain Y2224U $SUC^+$ strains. | | | | | |
|---|---|---|---|---|---|
| Plasmid (SUC2 Construct) | Type of sample | Substrate | Activity (U/L) | Specific Activity (U/mg protein) | Yield (U/g DCW) |
| pRHY68 (Suc2SS/m-ScSuc2) | Culture medium | Glucose | 44.8 ± 3.8 | 10.1 ± 0.7 | 2431 ± 355 |
| | | Sucrose | 44.8 ± 8.9 | 10.9 ± 1.1 | 2361 ± 256 |
| | Whole Cells | Glucose | — | — | 32 ± 9 |
| | | Sucrose | — | — | 28 ± 3 |
| pYRH74 (XPR2PP + 13/m-ScSuc2) | Culture medium | Glucose | 38.8 ± 2.2 | 8.7 ± 1.4 | 1934 ± 62 |
| | | Sucrose | 29.9 ± 3.3 | 7.5 ± 1.1 | 1612 ± 183 |
| | Whole Cells | Glucose | — | — | 19 ± 4 |
| | | Sucrose | — | — | 28 ± 3 |

Consistent with the result of growth studies, invertase activities were observed with *Y. lipolytica* strains transformed with pYRH68 or pYRH74 from culture supernatant and whole-cells. *Y. lipolytica* transformants of pRH69 and pRH73 did not grow on sucrose medium, and there were no detectable extracellular or whole-cell invertase activities from cell cultures grown in glucose medium.

Invertase activities were slightly higher with transformants of Suc2SS/m-ScSuc2 versus XPR2PP+13/m-ScSuc2. It is possible that there still was some secondary structure hindrance for the access to the endopeptidase required for secretion signal processing even with the additional 13 amino acids of mature Xpr2. However, more than 98% of invertase activity was detected in the culture media for both $SUC^+$ strains and higher extracellular invertase activities per biomass in culture supernatant were observed than previously reported.

Extracellular and Whole-Cell Invertase Activities in Transformant in Transformant *Y. lipolytica* Strain Y1978U $SUC^+$ Strains Invertase activity was determined in transformant whole cells and from the culture medium thereof. The cultures were grown in YP (10 g/L Bacto Yeast extract and 20 g/L Bacto Peptone) media with glucose or sucrose as sole carbon source. Two different transformants were tested for each of the SUC2 constructs and average values are reported, as shown below in Table 13.

TABLE 13

Invertase Activities From Culture Media And Whole Cells Of *Y. lipolytica* Z1978U SUC+ Strains

| Plasmid (SUC2 Construct) | Type of sample | Substrate | Activity (U/L) | Specific Activity (U/mg protein) | Yield (U/g DCW) |
|---|---|---|---|---|---|
| pRHY68 (Suc2SS/m-ScSuc2) | Culture medium | Glucose | 15.2 ± 2.5 | 0.6 ± 0.1 | 761 ± 123 |
|  | Culture medium | Sucrose | 13.0 ± 4.7 | 0.5 ± 0.2 | 648 ± 235 |
|  | Whole Cells | Glucose | — | — | 35 ± 6 |
|  | Whole Cells | Sucrose | — | — | 28 ± 3 |
| pYRH74 (XPR2PP + 13/m-ScSuc2) | Culture medium | Glucose | 40.0 ± 21.4 | 1.5 ± 0.8 | 1999 ± 1068 |
|  | Culture medium | Sucrose | 38.1 ± 23.9 | 1.5 ± 1.0 | 1906 ± 1196 |
|  | Whole Cells | Glucose | — | — | 79 ± 34 |
|  | Whole Cells | Sucrose | — | — | 66 ± 28 |

Protein concentrations in YP-based culture media were significantly higher than those of synthetic based culture media (Table 12), reducing the invertase specific activities (U/mg protein). In spite of this, the pRHY68 transformants showed similar invertase activities between glucose and sucrose cultures, and more than 90% of the invertase activity was detected in the culture media. For pYRH74 transformants, one transformant showed much higher invertase activity in all conditions tested than the other transformant. Therefore, average invertase activities were elevated with a large standard error. Even so, more than 90% of invertase activity was detected in the culture media with either glucose or sucrose as sole carbon source.

Example 8

Identification of Publicly Available Genes Encoding Invertase

The *Saccharomyces cerevisiae* invertase is encoded by the SUC2 gene, set forth herein as SEQ ID NO:1. This 1599 bp gene encodes the full-length invertase of 532 amino acids (SEQ ID NO:2) that is secreted into the periplasm of *S. cerevisiae* in glycosylated form. In contrast, the "mature" ScSUC2 gene ["m-ScSUC2"] lacking the 19 amino acid length 5' signal sequence (i.e., encoded by nucleotides 1-57 of SEQ ID NO:1) is set forth as SEQ ID NO:3 and encodes the protein of SEQ ID NO:4.

Using the protein sequence encoding m-ScSUC2 (SEQ ID NO:4), National Center for Biotechnology Information ["NCBI"] BLASTP 2.2.26+(Basic Local Alignment Search Tool; Altschul, S. F., et al., *Nucleic Acids Res.*, 25:3389-3402 (1997); Altschul, S. F., et al., *FEBS J.*, 272:5101-5109 (2005)) searches were conducted to identify sequences having similarity within the BLAST "nr" database (comprising all non-redundant GenBank CDS translations, the Protein Data Bank ["PDB"] protein sequence database, the SWISS-PROT protein sequence database, the Protein Information Resource ["PIR"] protein sequence database and the Protein Research Foundation ["PRF"] protein sequence database, excluding environmental samples from whole genome shotgun ["WGS"] projects).

The results of the BLASTP comparison summarizing the sequence to which SEQ ID NO:4 has the most similarity may be reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

A large number of proteins were identified as sharing significant similarity to m-ScSUC2 (SEQ ID NO:4). Table 14 provides a partial summary of those hits having an Expectation value greater or equal to "4e-90" and annotation that specifically identified the protein as either an "invertase" or a "beta-fructofuranosidase", although this should not be considered as limiting to the disclosure herein. All hits to *Saccharomyces cerevisiae* were excluded from the results reported below. The proteins in Table 14 shared between 91% to 99% query coverage with SEQ ID NO:4.

TABLE 14

Some Publicly Available Genes Encoding Invertase

| Accession | Description | Query coverage | E value |
|---|---|---|---|
| BAJ07830.1, BAJ07833.1, BAJ07829.1 | invertase [*Saccharomyces paradoxus*] | 99% | 0.0 |
| CBK52121.1 | invertase [*Saccharomyces bayanus*] | 99% | 0.0 |
| AAX82487.1 | beta-fructosidase [*Saccharomyces cariocanus*] | 96% | 0.0 |
| XP_461505.2 | Beta-fructofuranosidase [*Debaryomyces hansenii* CBS767] | 98% | 5e-174 |
| XP_451456.1 | Invertase [*Kluyveromyces lactis* NRRL Y-1140] | 98% | 1e-172 |
| P24133.1 | Invertase [*Schwanniomyces occidentalis*] | 98% | 2e-151 |
| P40912.1 | Invertase [*Wickerhamomyces anomalus*] | 98% | 6e-150 |

TABLE 14-continued

Some Publicly Available Genes Encoding Invertase

| Accession | Description | Query coverage | E value |
|---|---|---|---|
| XP_002175417.1 | invertase [*Schizosaccharomyces japonicus* yFS275] | 98% | 3e−108 |
| XP_003196854.1 | beta-fructofuranosidase [*Cryptococcus gattii* WM276] | 92% | 1e−107 |
| XP_567775.1 | beta-fructofuranosidase [*Cryptococcus neoformans* var. *neoformans* JEC21] | 92% | 6e−106 |
| EFZ01512.1 | beta-fructofuranosidase [*Metarhizium anisopliae* ARSEF 23] | 92% | 2e−104 |
| NP_588300.1 | beta-fructofuranosidase [*Schizosaccharomyces pombe* 972h-] | 94% | 2e−104 |
| CBQ72191.1 | probable SUC2-invertase (sucrose hydrolyzing enzyme) [*Sporisorium reilianum* SRZ2] | 96% | 5e−104 |
| EGX95794.1 | beta-fructofuranosidase [*Cordyceps militaris* CM01] | 95% | 2e−103 |
| XP_001823245.1, ABY49829.1 | beta-fructofuranosidase [*Aspergillus oryzae* RIB40] | 92% | 3e−95 |
| YP_001603959.1 | invertase [*Gluconacetobacter diazotrophicus* PAl 5] | 91% | 1e−91 |
| XP_001265685.1 | beta-fructofuranosidase, putative [*Neosartorya fischeri* NRRL 181] | 92% | 2e−91 |
| XP_001273181.1 | beta-fructofuranosidase, putative [*Aspergillus clavatus* NRRL 1] | 92% | 2e−90 |
| XP_749260.1, EDP53788.1 | beta-fructofuranosidase [*Aspergillus fumigatus*] | 92% | 4e−90 |

What is claimed is:

1. A transformed *Yarrowia lipolytica* comprising an exogenous polynucleotide encoding a polypeptide having sucrose invertase activity, wherein:
   (a) said polypeptide comprises a signal sequence fused to a mature sucrose invertase;
   (b) said signal sequence is
   an Xpr2 pre/pro-region and an N-terminal Xpr2 fragment that are both from *Yarrowia lipolytica*; and
   (c) said mature sucrose invertase has at least 90% sequence identity based on the CLUSTALW method of alignment, when compared to SEQ ID NO:4.

2. The transformed *Yarrowia lipolytica* of claim 1, wherein said mature sucrose invertase is set forth in SEQ ID NO:4.

3. The transformed *Yarrowia lipolytica* of claim 1, wherein said
   Xpr2 pre/pro-region comprises the N-terminal 157 amino acids of an alkaline extracellular protease precursor; and
   a said N-terminal Xpr2 fragment comprises the N-terminal 13 amino acids of a mature alkaline extracellular protease.

4. The transformed *Yarrowia lipolytica* of claim 3, wherein said Xpr2 pre/pro-region and N-terminal Xpr2 fragment are set forth in SEQ ID NO:10.

5. The transformed *Yarrowia lipolytica* of claim 1, wherein said polypeptide having sucrose invertase activity comprises SEQ ID NO:20.

6. The transformed *Yarrowia lipolytica* of claim 1, wherein said transformed *Yarrowia lipolytica* is capable of growing under conditions wherein sucrose is the sole carbon source.

7. The transformed *Yarrowia lipolytica* of claim 1, wherein said transformed *Yarrowia lipolytica* is capable of producing at least one non-native product of interest.

8. The transformed *Yarrowia lipolytica* of claim 7, wherein the at least one non-native product of interest is selected from the group consisting of: polyunsaturated fatty acids, carotenoids, amino acids, vitamins, sterols, flavonoids, organic acids, polyols, hydroxyesters, quinone-derived compounds and resveratrol.

9. The transformed *Yarrowia lipolytica* of either claim 1 or claim 7, wherein said transformed *Yarrowia lipolytica* is capable of secreting at least 80% of the sucrose invertase extracellularly.

10. A method of producing at least one non-native product of interest comprising growing the transformed *Yarrowia lipolytica* of claim 7 in a culture medium having at least one carbon source selected from the group consisting of:
    a) sucrose; and,
    b) glucose;
    whereby the at least one non-native product of interest is produced, and optionally, recovering the at least one non-native product of interest.

11. The method of claim 10, wherein the at least one non-native product of interest is selected from the group consisting of: polyunsaturated fatty acids, carotenoids, amino acids, vitamins, sterols, flavonoids, organic acids, polyols, hydroxyesters, quinone-derived compounds and resveratrol.

12. The method of claim 10, wherein said transformed *Yarrowia lipolytica* is capable of secreting at least 80% of the sucrose invertase extracellularly.

* * * * *

SEQUENCE LISTING

<160> NUMBER OF SEQ ID NOS: 41

<210> SEQ ID NO 1
<211> LENGTH: 1599
<212> TYPE: DNA
<213> ORGANISM: Saccharomyces cerevisiae
<220> FEATURE:
<221> NAME/KEY: CDS
<222> LOCATION: (1)..(1599)
<220> FEATURE:
<221> NAME/KEY: sig_peptide
<222> LOCATION: (1)..(57)

<400> SEQUENCE: 1

```
atg ctt ttg caa gct ttc ctt ttc ctt ttg gct ggt ttt gca gcc aaa      48
Met Leu Leu Gln Ala Phe Leu Phe Leu Leu Ala Gly Phe Ala Ala Lys
1               5                   10                  15 ata tct gca tca atg aca aac gaa act agc gat aga cct ttg gtc cac      96
Ile Ser Ala Ser Met Thr Asn Glu Thr Ser Asp Arg Pro Leu Val His
                20                  25                  30 ttc aca ccc aac aag ggc tgg atg aat gac cca aat ggg ttg tgg tac     144
Phe Thr Pro Asn Lys Gly Trp Met Asn Asp Pro Asn Gly Leu Trp Tyr
            35                  40                  45 gat gaa aaa gat gcc aaa tgg cat ctg tac ttt caa tac aac cca aat     192
Asp Glu Lys Asp Ala Lys Trp His Leu Tyr Phe Gln Tyr Asn Pro Asn
        50                  55                  60 gac acc gta tgg ggt acg cca ttg ttt tgg ggc cat gct act tcc gat     240
Asp Thr Val Trp Gly Thr Pro Leu Phe Trp Gly His Ala Thr Ser Asp
65                  70                  75                  80 gat ttg act aat tgg gaa gat caa ccc att gct atc gct ccc aag cgt     288
Asp Leu Thr Asn Trp Glu Asp Gln Pro Ile Ala Ile Ala Pro Lys Arg
                85                  90                  95 aac gat tca ggt gct ttc tct ggc tcc atg gtg gtt gat tac aac aac     336
Asn Asp Ser Gly Ala Phe Ser Gly Ser Met Val Val Asp Tyr Asn Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     |     | 100 |     |     |     |     | 105 |     |     |     |     | 110 |     |     |      |
| acg | agt | ggg | ttt | ttc | aat | gat | act | att | gat | cca | aga | caa | aga | tgc | gtt | 384  |
| Thr | Ser | Gly | Phe | Phe | Asn | Asp | Thr | Ile | Asp | Pro | Arg | Gln | Arg | Cys | Val |      |
|     |     | 115 |     |     |     |     | 120 |     |     |     |     | 125 |     |     |     |      |
| gcg | att | tgg | act | tat | aac | act | cct | gaa | agt | gaa | gag | caa | tac | att | agc | 432  |
| Ala | Ile | Trp | Thr | Tyr | Asn | Thr | Pro | Glu | Ser | Glu | Glu | Gln | Tyr | Ile | Ser |      |
|     | 130 |     |     |     |     | 135 |     |     |     |     | 140 |     |     |     |     |      |
| tat | tct | ctt | gat | ggt | ggt | tac | act | ttt | act | gaa | tac | caa | aag | aac | cct | 480  |
| Tyr | Ser | Leu | Asp | Gly | Gly | Tyr | Thr | Phe | Thr | Glu | Tyr | Gln | Lys | Asn | Pro |      |
| 145 |     |     |     |     | 150 |     |     |     |     | 155 |     |     |     |     | 160 |      |
| gtt | tta | gct | gcc | aac | tcc | act | caa | ttc | aga | gat | cca | aag | gtt | ttc | tgg | 528  |
| Val | Leu | Ala | Ala | Asn | Ser | Thr | Gln | Phe | Arg | Asp | Pro | Lys | Val | Phe | Trp |      |
|     |     |     |     | 165 |     |     |     |     | 170 |     |     |     |     | 175 |     |      |
| tat | gaa | cct | tct | caa | aaa | tgg | att | atg | acg | gct | gcc | aaa | tca | caa | gac | 576  |
| Tyr | Glu | Pro | Ser | Gln | Lys | Trp | Ile | Met | Thr | Ala | Ala | Lys | Ser | Gln | Asp |      |
|     |     |     | 180 |     |     |     |     | 185 |     |     |     |     | 190 |     |     |      |
| tac | aaa | att | gaa | att | tac | tcc | tct | gat | gac | ttg | aag | tcc | tgg | aag | cta | 624  |
| Tyr | Lys | Ile | Glu | Ile | Tyr | Ser | Ser | Asp | Asp | Leu | Lys | Ser | Trp | Lys | Leu |      |
|     | 195 |     |     |     |     | 200 |     |     |     |     | 205 |     |     |     |     |      |
| gaa | tct | gca | ttt | gcc | aat | gaa | ggt | ttc | tta | ggc | tac | caa | tac | gaa | tgt | 672  |
| Glu | Ser | Ala | Phe | Ala | Asn | Glu | Gly | Phe | Leu | Gly | Tyr | Gln | Tyr | Glu | Cys |      |
| 210 |     |     |     |     | 215 |     |     |     |     | 220 |     |     |     |     |     |      |
| cca | ggt | ttg | att | gaa | gtc | cca | act | gag | caa | gat | cct | tcc | aaa | tct | tat | 720  |
| Pro | Gly | Leu | Ile | Glu | Val | Pro | Thr | Glu | Gln | Asp | Pro | Ser | Lys | Ser | Tyr |      |
| 225 |     |     |     |     | 230 |     |     |     |     | 235 |     |     |     |     | 240 |      |
| tgg | gtc | atg | ttt | att | tct | atc | aac | cca | ggt | gca | cct | gct | ggc | ggt | tcc | 768  |
| Trp | Val | Met | Phe | Ile | Ser | Ile | Asn | Pro | Gly | Ala | Pro | Ala | Gly | Gly | Ser |      |
|     |     |     |     | 245 |     |     |     |     | 250 |     |     |     |     | 255 |     |      |
| ttc | aac | caa | tat | ttt | gtt | gga | tcc | ttc | aat | ggt | act | cat | ttt | gaa | gcg | 816  |
| Phe | Asn | Gln | Tyr | Phe | Val | Gly | Ser | Phe | Asn | Gly | Thr | His | Phe | Glu | Ala |      |
|     |     | 260 |     |     |     |     | 265 |     |     |     |     | 270 |     |     |     |      |
| ttt | gac | aat | caa | tct | aga | gtg | gta | gat | ttt | ggt | aag | gac | tac | tat | gcc | 864  |
| Phe | Asp | Asn | Gln | Ser | Arg | Val | Val | Asp | Phe | Gly | Lys | Asp | Tyr | Tyr | Ala |      |
|     | 275 |     |     |     |     | 280 |     |     |     |     | 285 |     |     |     |     |      |
| ttg | caa | act | ttc | ttc | aac | act | gac | cca | acc | tac | ggt | tca | gca | tta | ggt | 912  |
| Leu | Gln | Thr | Phe | Phe | Asn | Thr | Asp | Pro | Thr | Tyr | Gly | Ser | Ala | Leu | Gly |      |
| 290 |     |     |     |     | 295 |     |     |     |     | 300 |     |     |     |     |     |      |
| att | gcc | tgg | gct | tca | aac | tgg | gag | tac | agt | gcc | ttt | gtc | cca | act | aac | 960  |
| Ile | Ala | Trp | Ala | Ser | Asn | Trp | Glu | Tyr | Ser | Ala | Phe | Val | Pro | Thr | Asn |      |
| 305 |     |     |     |     | 310 |     |     |     |     | 315 |     |     |     |     | 320 |      |
| cca | tgg | aga | tca | tcc | atg | tct | ttg | gtc | cgc | aag | ttt | tct | ttg | aac | act | 1008 |
| Pro | Trp | Arg | Ser | Ser | Met | Ser | Leu | Val | Arg | Lys | Phe | Ser | Leu | Asn | Thr |      |
|     |     |     |     | 325 |     |     |     |     | 330 |     |     |     |     | 335 |     |      |
| gaa | tat | caa | gct | aat | cca | gag | act | gaa | ttg | atc | aat | ttg | aaa | gcc | gaa | 1056 |
| Glu | Tyr | Gln | Ala | Asn | Pro | Glu | Thr | Glu | Leu | Ile | Asn | Leu | Lys | Ala | Glu |      |
|     |     | 340 |     |     |     |     | 345 |     |     |     |     | 350 |     |     |     |      |
| cca | ata | ttg | aac | att | agt | aat | gct | ggt | ccc | tgg | tct | cgt | ttt | gct | act | 1104 |
| Pro | Ile | Leu | Asn | Ile | Ser | Asn | Ala | Gly | Pro | Trp | Ser | Arg | Phe | Ala | Thr |      |
|     | 355 |     |     |     |     | 360 |     |     |     |     | 365 |     |     |     |     |      |
| aac | aca | act | cta | act | aag | gcc | aat | tct | tac | aat | gtc | gat | ttg | agc | aac | 1152 |
| Asn | Thr | Thr | Leu | Thr | Lys | Ala | Asn | Ser | Tyr | Asn | Val | Asp | Leu | Ser | Asn |      |
| 370 |     |     |     |     | 375 |     |     |     |     | 380 |     |     |     |     |     |      |
| tcg | act | ggt | acc | cta | gag | ttt | gag | ttg | gtt | tac | gct | gtt | aac | acc | aca | 1200 |
| Ser | Thr | Gly | Thr | Leu | Glu | Phe | Glu | Leu | Val | Tyr | Ala | Val | Asn | Thr | Thr |      |
| 385 |     |     |     |     | 390 |     |     |     |     | 395 |     |     |     |     | 400 |      |
| caa | acc | ata | tcc | aaa | tcc | gtc | ttt | gcc | gac | tta | tca | ctt | tgg | ttc | aag | 1248 |
| Gln | Thr | Ile | Ser | Lys | Ser | Val | Phe | Ala | Asp | Leu | Ser | Leu | Trp | Phe | Lys |      |
|     |     |     |     | 405 |     |     |     |     | 410 |     |     |     |     | 415 |     |      |
| ggt | tta | gaa | gat | cct | gaa | gaa | tat | ttg | aga | atg | ggt | ttt | gaa | gtc | agt | 1296 |
| Gly | Leu | Glu | Asp | Pro | Glu | Glu | Tyr | Leu | Arg | Met | Gly | Phe | Glu | Val | Ser |      |

```
                       420              425              430
gct tct tcc ttc ttt ttg gac cgt ggt aac tct aag gtc aag ttt gtc    1344
Ala Ser Ser Phe Phe Leu Asp Arg Gly Asn Ser Lys Val Lys Phe Val
        435              440              445 aag gag aac cca tat ttc aca aac aga atg tct gtc aac aac caa cca    1392
Lys Glu Asn Pro Tyr Phe Thr Asn Arg Met Ser Val Asn Asn Gln Pro
    450              455              460 ttc aag tct gag aac gac cta agt tac tat aaa gtg tac ggc cta ctg    1440
Phe Lys Ser Glu Asn Asp Leu Ser Tyr Tyr Lys Val Tyr Gly Leu Leu
465              470              475              480 gat caa aac atc ttg gaa ttg tac ttc aac gat gga gat gtg gtt tct    1488
Asp Gln Asn Ile Leu Glu Leu Tyr Phe Asn Asp Gly Asp Val Val Ser
            485              490              495 aca aat acc tac ttc atg acc acc ggt aac gct cta gga tct gtg aac    1536
Thr Asn Thr Tyr Phe Met Thr Thr Gly Asn Ala Leu Gly Ser Val Asn
        500              505              510 atg acc act ggt gtc gat aat ttg ttc tac att gac aag ttc caa gta    1584
Met Thr Thr Gly Val Asp Asn Leu Phe Tyr Ile Asp Lys Phe Gln Val
    515              520              525 agg gaa gta aaa tag                                                1599
Arg Glu Val Lys
    530

<210> SEQ ID NO 2
<211> LENGTH: 532
<212> TYPE: PRT
<213> ORGANISM: Saccharomyces cerevisiae

<400> SEQUENCE: 2

Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220
```

| Pro | Gly | Leu | Ile | Glu | Val | Pro | Thr | Glu | Gln | Asp | Pro | Ser | Lys | Ser | Tyr |
| 225 | | | | 230 | | | | | 235 | | | | | 240 | |

| Trp | Val | Met | Phe | Ile | Ser | Ile | Asn | Pro | Gly | Ala | Pro | Ala | Gly | Gly | Ser |
| | | | 245 | | | | | 250 | | | | | 255 | | |

| Phe | Asn | Gln | Tyr | Phe | Val | Gly | Ser | Phe | Asn | Gly | Thr | His | Phe | Glu | Ala |
| | | | 260 | | | | | 265 | | | | | 270 | | |

| Phe | Asp | Asn | Gln | Ser | Arg | Val | Val | Asp | Phe | Gly | Lys | Asp | Tyr | Tyr | Ala |
| | | 275 | | | | | 280 | | | | | 285 | | | |

| Leu | Gln | Thr | Phe | Phe | Asn | Thr | Asp | Pro | Thr | Tyr | Gly | Ser | Ala | Leu | Gly |
| | | 290 | | | | | 295 | | | | | 300 | | | |

| Ile | Ala | Trp | Ala | Ser | Asn | Trp | Glu | Tyr | Ser | Ala | Phe | Val | Pro | Thr | Asn |
| 305 | | | | | 310 | | | | | 315 | | | | | 320 |

| Pro | Trp | Arg | Ser | Ser | Met | Ser | Leu | Val | Arg | Lys | Phe | Ser | Leu | Asn | Thr |
| | | | | 325 | | | | | 330 | | | | | 335 | |

| Glu | Tyr | Gln | Ala | Asn | Pro | Glu | Thr | Glu | Leu | Ile | Asn | Leu | Lys | Ala | Glu |
| | | | 340 | | | | | 345 | | | | | 350 | | |

| Pro | Ile | Leu | Asn | Ile | Ser | Asn | Ala | Gly | Pro | Trp | Ser | Arg | Phe | Ala | Thr |
| | | | 355 | | | | | 360 | | | | | 365 | | |

| Asn | Thr | Thr | Leu | Thr | Lys | Ala | Asn | Ser | Tyr | Asn | Val | Asp | Leu | Ser | Asn |
| 370 | | | | | 375 | | | | | 380 | | | | | |

| Ser | Thr | Gly | Thr | Leu | Glu | Phe | Glu | Leu | Val | Tyr | Ala | Val | Asn | Thr | Thr |
| 385 | | | | | 390 | | | | | 395 | | | | | 400 |

| Gln | Thr | Ile | Ser | Lys | Ser | Val | Phe | Ala | Asp | Leu | Ser | Leu | Trp | Phe | Lys |
| | | | | 405 | | | | | 410 | | | | | 415 | |

| Gly | Leu | Glu | Asp | Pro | Glu | Glu | Tyr | Leu | Arg | Met | Gly | Phe | Glu | Val | Ser |
| | | | 420 | | | | | 425 | | | | | 430 | | |

| Ala | Ser | Ser | Phe | Phe | Leu | Asp | Arg | Gly | Asn | Ser | Lys | Val | Lys | Phe | Val |
| | | 435 | | | | | 440 | | | | | 445 | | | |

| Lys | Glu | Asn | Pro | Tyr | Phe | Thr | Asn | Arg | Met | Ser | Val | Asn | Asn | Gln | Pro |
| | 450 | | | | | 455 | | | | | 460 | | | | |

| Phe | Lys | Ser | Glu | Asn | Asp | Leu | Ser | Tyr | Tyr | Lys | Val | Tyr | Gly | Leu | Leu |
| 465 | | | | | 470 | | | | | 475 | | | | | 480 |

| Asp | Gln | Asn | Ile | Leu | Glu | Leu | Tyr | Phe | Asn | Asp | Gly | Asp | Val | Val | Ser |
| | | | | 485 | | | | | 490 | | | | | 495 | |

| Thr | Asn | Thr | Tyr | Phe | Met | Thr | Thr | Gly | Asn | Ala | Leu | Gly | Ser | Val | Asn |
| | | | 500 | | | | | 505 | | | | | 510 | | |

| Met | Thr | Thr | Gly | Val | Asp | Asn | Leu | Phe | Tyr | Ile | Asp | Lys | Phe | Gln | Val |
| | | | 515 | | | | | 520 | | | | | 525 | | |

| Arg | Glu | Val | Lys |
| | 530 | | |

```
<210> SEQ ID NO 3
<211> LENGTH: 1542
<212> TYPE: DNA
<213> ORGANISM: Saccharomyces cerevisiae
<220> FEATURE:
<221> NAME/KEY: CDS
<222> LOCATION: (1)..(1542)

<400> SEQUENCE: 3
```

| tca | atg | aca | aac | gaa | act | agc | gat | aga | cct | ttg | gtc | cac | ttc | aca | ccc | 48 |
| Ser | Met | Thr | Asn | Glu | Thr | Ser | Asp | Arg | Pro | Leu | Val | His | Phe | Thr | Pro | |
| 1 | | | | 5 | | | | | 10 | | | | | 15 | | |

| aac | aag | ggc | tgg | atg | aat | gac | cca | aat | ggg | ttg | tgg | tac | gat | gaa | aaa | 96 |
| Asn | Lys | Gly | Trp | Met | Asn | Asp | Pro | Asn | Gly | Leu | Trp | Tyr | Asp | Glu | Lys | |
| | | 20 | | | | | 25 | | | | | 30 | | | | |

| gat | gcc | aaa | tgg | cat | ctg | tac | ttt | caa | tac | aac | cca | aat | gac | acc | gta | 144 |

```
                Asp Ala Lys Trp His Leu Tyr Phe Gln Tyr Asn Pro Asn Asp Thr Val
                            35                  40                  45 tgg ggt acg cca ttg ttt tgg ggc cat gct act tcc gat gat ttg act              192
Trp Gly Thr Pro Leu Phe Trp Gly His Ala Thr Ser Asp Asp Leu Thr
 50                  55                  60 aat tgg gaa gat caa ccc att gct atc gct ccc aag cgt aac gat tca              240
Asn Trp Glu Asp Gln Pro Ile Ala Ile Ala Pro Lys Arg Asn Asp Ser
 65                  70                  75                  80 ggt gct ttc tct ggc tcc atg gtg gtt gat tac aac aac acg agt ggg              288
Gly Ala Phe Ser Gly Ser Met Val Val Asp Tyr Asn Asn Thr Ser Gly
                 85                  90                  95 ttt ttc aat gat act att gat cca aga caa aga tgc gtt gcg att tgg              336
Phe Phe Asn Asp Thr Ile Asp Pro Arg Gln Arg Cys Val Ala Ile Trp
                100                 105                 110 act tat aac act cct gaa agt gaa gag caa tac att agc tat tct ctt              384
Thr Tyr Asn Thr Pro Glu Ser Glu Glu Gln Tyr Ile Ser Tyr Ser Leu
            115                 120                 125 gat ggt ggt tac act ttt act gaa tac caa aag aac cct gtt tta gct              432
Asp Gly Gly Tyr Thr Phe Thr Glu Tyr Gln Lys Asn Pro Val Leu Ala
130                 135                 140 gcc aac tcc act caa ttc aga gat cca aag gtg ttc tgg tat gaa cct              480
Ala Asn Ser Thr Gln Phe Arg Asp Pro Lys Val Phe Trp Tyr Glu Pro
145                 150                 155                 160 tct caa aaa tgg att atg acg gct gcc aaa tca caa gac tac aaa att              528
Ser Gln Lys Trp Ile Met Thr Ala Ala Lys Ser Gln Asp Tyr Lys Ile
                165                 170                 175 gaa att tac tcc tct gat gac ttg aag tcc tgg aag cta gaa tct gca              576
Glu Ile Tyr Ser Ser Asp Asp Leu Lys Ser Trp Lys Leu Glu Ser Ala
            180                 185                 190 ttt gcc aat gaa ggt ttc tta ggc tac caa tac gaa tgt cca ggt ttg              624
Phe Ala Asn Glu Gly Phe Leu Gly Tyr Gln Tyr Glu Cys Pro Gly Leu
            195                 200                 205 att gaa gtc cca act gag caa gat cct tcc aaa tct tat tgg gtc atg              672
Ile Glu Val Pro Thr Glu Gln Asp Pro Ser Lys Ser Tyr Trp Val Met
210                 215                 220 ttt att tct atc aac cca ggt gca cct gct ggc ggt tcc ttc aac caa              720
Phe Ile Ser Ile Asn Pro Gly Ala Pro Ala Gly Gly Ser Phe Asn Gln
225                 230                 235                 240 tat ttt gtt gga tcc ttc aat ggt act cat ttt gaa gcg ttt gac aat              768
Tyr Phe Val Gly Ser Phe Asn Gly Thr His Phe Glu Ala Phe Asp Asn
                245                 250                 255 caa tct aga gtg gta gat ttt ggt aag gac tac tat gcc ttg caa act              816
Gln Ser Arg Val Val Asp Phe Gly Lys Asp Tyr Tyr Ala Leu Gln Thr
            260                 265                 270 ttc ttc aac act gac cca acc tac ggt tca gca tta ggt att gcc tgg              864
Phe Phe Asn Thr Asp Pro Thr Tyr Gly Ser Ala Leu Gly Ile Ala Trp
            275                 280                 285 gct tca aac tgg gag tac agt gcc ttt gtc cca act aac cca tgg aga              912
Ala Ser Asn Trp Glu Tyr Ser Ala Phe Val Pro Thr Asn Pro Trp Arg
290                 295                 300 tca tcc atg tct ttg gtc cgc aag ttt tct ttg aac act gaa tat caa              960
Ser Ser Met Ser Leu Val Arg Lys Phe Ser Leu Asn Thr Glu Tyr Gln
305                 310                 315                 320 gct aat cca gag act gaa ttg atc aat ttg aaa gcc gaa cca ata ttg             1008
Ala Asn Pro Glu Thr Glu Leu Ile Asn Leu Lys Ala Glu Pro Ile Leu
                325                 330                 335 aac att agt aat gct ggt ccc tgg tct cgt ttt gct act aac aca act             1056
Asn Ile Ser Asn Ala Gly Pro Trp Ser Arg Phe Ala Thr Asn Thr Thr
            340                 345                 350 cta act aag gcc aat tct tac aat gtc gat ttg agc aac tcg act ggt             1104
```

```
Leu Thr Lys Ala Asn Ser Tyr Asn Val Asp Leu Ser Asn Ser Thr Gly
        355                 360                 365 acc cta gag ttt gag ttg gtt tac gct gtt aac acc aca caa acc ata      1152
Thr Leu Glu Phe Glu Leu Val Tyr Ala Val Asn Thr Thr Gln Thr Ile
    370                 375                 380 tcc aaa tcc gtc ttt gcc gac tta tca ctt tgg ttc aag ggt tta gaa      1200
Ser Lys Ser Val Phe Ala Asp Leu Ser Leu Trp Phe Lys Gly Leu Glu
385                 390                 395                 400 gat cct gaa gaa tat ttg aga atg ggt ttt gaa gtc agt gct tct tcc      1248
Asp Pro Glu Glu Tyr Leu Arg Met Gly Phe Glu Val Ser Ala Ser Ser
                405                 410                 415 ttc ttt ttg gac cgt ggt aac tct aag gtc aag ttt gtc aag gag aac      1296
Phe Phe Leu Asp Arg Gly Asn Ser Lys Val Lys Phe Val Lys Glu Asn
            420                 425                 430 cca tat ttc aca aac aga atg tct gtc aac aac caa cca ttc aag tct      1344
Pro Tyr Phe Thr Asn Arg Met Ser Val Asn Asn Gln Pro Phe Lys Ser
        435                 440                 445 gag aac gac cta agt tac tat aaa gtg tac ggc cta ctg gat caa aac      1392
Glu Asn Asp Leu Ser Tyr Tyr Lys Val Tyr Gly Leu Leu Asp Gln Asn
    450                 455                 460 atc ttg gaa ttg tac ttc aac gat gga gat gtg gtt tct aca aat acc      1440
Ile Leu Glu Leu Tyr Phe Asn Asp Gly Asp Val Val Ser Thr Asn Thr
465                 470                 475                 480 tac ttc atg acc acc ggt aac gct cta gga tct gtg aac atg acc act      1488
Tyr Phe Met Thr Thr Gly Asn Ala Leu Gly Ser Val Asn Met Thr Thr
                485                 490                 495 ggt gtc gat aat ttg ttc tac att gac aag ttc caa gta agg gaa gta      1536
Gly Val Asp Asn Leu Phe Tyr Ile Asp Lys Phe Gln Val Arg Glu Val
            500                 505                 510 aaa tag                                                              1542
Lys

<210> SEQ ID NO 4
<211> LENGTH: 513
<212> TYPE: PRT
<213> ORGANISM: Saccharomyces cerevisiae

<400> SEQUENCE: 4

Ser Met Thr Asn Glu Thr Ser Asp Arg Pro Leu Val His Phe Thr Pro
1               5                   10                  15

Asn Lys Gly Trp Met Asn Asp Pro Asn Gly Leu Trp Tyr Asp Glu Lys
            20                  25                  30

Asp Ala Lys Trp His Leu Tyr Phe Gln Tyr Asn Pro Asn Asp Thr Val
        35                  40                  45

Trp Gly Thr Pro Leu Phe Trp Gly His Ala Thr Ser Asp Asp Leu Thr
    50                  55                  60

Asn Trp Glu Asp Gln Pro Ile Ala Ile Ala Pro Lys Arg Asn Asp Ser
65                  70                  75                  80

Gly Ala Phe Ser Gly Ser Met Val Val Asp Tyr Asn Asn Thr Ser Gly
                85                  90                  95

Phe Phe Asn Asp Thr Ile Asp Pro Arg Gln Arg Cys Val Ala Ile Trp
            100                 105                 110

Thr Tyr Asn Thr Pro Glu Ser Glu Glu Gln Tyr Ile Ser Tyr Ser Leu
        115                 120                 125

Asp Gly Gly Tyr Thr Phe Thr Glu Tyr Gln Lys Asn Pro Val Leu Ala
    130                 135                 140

Ala Asn Ser Thr Gln Phe Arg Asp Pro Lys Val Phe Trp Tyr Glu Pro
145                 150                 155                 160
```

```
Ser Gln Lys Trp Ile Met Thr Ala Ala Lys Ser Gln Asp Tyr Lys Ile
            165                 170                 175

Glu Ile Tyr Ser Ser Asp Leu Lys Ser Trp Lys Leu Glu Ser Ala
        180                 185                 190

Phe Ala Asn Glu Gly Phe Leu Gly Tyr Gln Tyr Glu Cys Pro Gly Leu
            195                 200                 205

Ile Glu Val Pro Thr Glu Gln Asp Pro Ser Lys Ser Tyr Trp Val Met
        210                 215                 220

Phe Ile Ser Ile Asn Pro Gly Ala Pro Ala Gly Gly Ser Phe Asn Gln
225                 230                 235                 240

Tyr Phe Val Gly Ser Phe Asn Gly Thr His Phe Glu Ala Phe Asp Asn
                245                 250                 255

Gln Ser Arg Val Val Asp Phe Gly Lys Asp Tyr Tyr Ala Leu Gln Thr
            260                 265                 270

Phe Phe Asn Thr Asp Pro Thr Tyr Gly Ser Ala Leu Gly Ile Ala Trp
        275                 280                 285

Ala Ser Asn Trp Glu Tyr Ser Ala Phe Val Pro Thr Asn Pro Trp Arg
290                 295                 300

Ser Ser Met Ser Leu Val Arg Lys Phe Ser Leu Asn Thr Glu Tyr Gln
305                 310                 315                 320

Ala Asn Pro Glu Thr Glu Leu Ile Asn Leu Lys Ala Glu Pro Ile Leu
                325                 330                 335

Asn Ile Ser Asn Ala Gly Pro Trp Ser Arg Phe Ala Thr Asn Thr Thr
            340                 345                 350

Leu Thr Lys Ala Asn Ser Tyr Asn Val Asp Leu Ser Asn Ser Thr Gly
        355                 360                 365

Thr Leu Glu Phe Glu Leu Val Tyr Ala Val Asn Thr Thr Gln Thr Ile
    370                 375                 380

Ser Lys Ser Val Phe Ala Asp Leu Ser Leu Trp Phe Lys Gly Leu Glu
385                 390                 395                 400

Asp Pro Glu Glu Tyr Leu Arg Met Gly Phe Glu Val Ser Ala Ser Ser
                405                 410                 415

Phe Phe Leu Asp Arg Gly Asn Ser Lys Val Lys Phe Val Lys Glu Asn
            420                 425                 430

Pro Tyr Phe Thr Asn Arg Met Ser Val Asn Asn Gln Pro Phe Lys Ser
        435                 440                 445

Glu Asn Asp Leu Ser Tyr Tyr Lys Val Tyr Gly Leu Leu Asp Gln Asn
    450                 455                 460

Ile Leu Glu Leu Tyr Phe Asn Asp Gly Asp Val Val Ser Thr Asn Thr
465                 470                 475                 480

Tyr Phe Met Thr Thr Gly Asn Ala Leu Gly Ser Val Asn Met Thr Thr
                485                 490                 495

Gly Val Asp Asn Leu Phe Tyr Ile Asp Lys Phe Gln Val Arg Glu Val
            500                 505                 510

Lys

<210> SEQ ID NO 5
<211> LENGTH: 1365
<212> TYPE: DNA
<213> ORGANISM: Yarrowia lipolytica
        <220> FEATURE:
<221> NAME/KEY: CDS
<222> LOCATION: (1)..(1365)
        <220> FEATURE:
<221> NAME/KEY: sig_peptide
<222> LOCATION: (1)..(471)
```

<400> SEQUENCE: 5

```
atg aag ctc gct acc gcc ttt act att ctc act gcc gtt ctg gcc gct      48
Met Lys Leu Ala Thr Ala Phe Thr Ile Leu Thr Ala Val Leu Ala Ala
1               5                   10                  15 ccc ctg gcc gcc cct gcc cct gct cct gat gct gcc cct gct gct gtg      96
Pro Leu Ala Ala Pro Ala Pro Ala Pro Asp Ala Ala Pro Ala Ala Val
            20                  25                  30 cct gag ggc cct gcc gcc gct gcc tac tca tct att ctg tcc gtg gtc     144
Pro Glu Gly Pro Ala Ala Ala Ala Tyr Ser Ser Ile Leu Ser Val Val
        35                  40                  45 gct aag cag tcc aag aag ttt aag cac cac aag cga gat ctt gat gag     192
Ala Lys Gln Ser Lys Lys Phe Lys His His Lys Arg Asp Leu Asp Glu
50                  55                  60 aag gat cag ttc atc gtt gtc ttt gac agt agc gct act gtt gac cag     240
Lys Asp Gln Phe Ile Val Val Phe Asp Ser Ser Ala Thr Val Asp Gln
65                  70                  75                  80 atc gcc tcc gaa atc cag aag ctg gac tct ctg gtc gac gag gac tcg     288
Ile Ala Ser Glu Ile Gln Lys Leu Asp Ser Leu Val Asp Glu Asp Ser
                85                  90                  95 tcc aac ggt atc acc tct gct ctt gat ctt cct gtc tac acg gat gga     336
Ser Asn Gly Ile Thr Ser Ala Leu Asp Leu Pro Val Tyr Thr Asp Gly
            100                 105                 110 tct ggc ttt ctc gga ttt gtt gga aag ttc aac tcc act atc gtt gac     384
Ser Gly Phe Leu Gly Phe Val Gly Lys Phe Asn Ser Thr Ile Val Asp
        115                 120                 125 aag ctc aag gag tcg tct gtt ctg acg gtc gag ccc gat acc att gtg     432
Lys Leu Lys Glu Ser Ser Val Leu Thr Val Glu Pro Asp Thr Ile Val
130                 135                 140 tct ctc ccc gag att cct gct tct tct aat gcc aag cga gct atc cag     480
Ser Leu Pro Glu Ile Pro Ala Ser Ser Asn Ala Lys Arg Ala Ile Gln
145                 150                 155                 160 act act ccc gtc act caa tgg ggc ctg tct aga atc tct cat aag aag     528
Thr Thr Pro Val Thr Gln Trp Gly Leu Ser Arg Ile Ser His Lys Lys
                165                 170                 175 gcc cag act gga aac tac gcc tac gtt cga gag aca gtt ggc aag cac     576
Ala Gln Thr Gly Asn Tyr Ala Tyr Val Arg Glu Thr Val Gly Lys His
            180                 185                 190 ccc acc gtt tct tac gtt gtt gac tct ggt atc cga acc acc cac tcc     624
Pro Thr Val Ser Tyr Val Val Asp Ser Gly Ile Arg Thr Thr His Ser
        195                 200                 205 gag ttc gga ggc cga gct gtc tgg gga gcc aac ttc gct gac aca cag     672
Glu Phe Gly Gly Arg Ala Val Trp Gly Ala Asn Phe Ala Asp Thr Gln
210                 215                 220 aac gct gat ctt ctc ggt cac ggc act cac gtt gca ggt acc gtg gga     720
Asn Ala Asp Leu Leu Gly His Gly Thr His Val Ala Gly Thr Val Gly
225                 230                 235                 240 gga aag aca tac gga gtc gac gcc aac acc aag ctg gtg gcc gtc aag     768
Gly Lys Thr Tyr Gly Val Asp Ala Asn Thr Lys Leu Val Ala Val Lys
                245                 250                 255 gtg ttt gca ggc cga tcc gca gct ctc tcc gtc atc aac cag ggc ttc     816
Val Phe Ala Gly Arg Ser Ala Ala Leu Ser Val Ile Asn Gln Gly Phe
            260                 265                 270 acc tgg gct ctc aac gac tac atc tcc aag cga gac act ctg cct cga     864
Thr Trp Ala Leu Asn Asp Tyr Ile Ser Lys Arg Asp Thr Leu Pro Arg
        275                 280                 285 gga gtg ctg aac ttc tct gga gga gga ccc aag tcc gct tcc cag gac     912
Gly Val Leu Asn Phe Ser Gly Gly Gly Pro Lys Ser Ala Ser Gln Asp
290                 295                 300 gcc cta tgg tct cga gct acc cag gag ggt ctg ctt gtc gcc atc gct     960
Ala Leu Trp Ser Arg Ala Thr Gln Glu Gly Leu Leu Val Ala Ile Ala
```

```
                    305                 310                 315                 320
gcg gga aac gat gcc gtg gac gcc tgt aac gac tct ccc ggt aac att          1008
Ala Gly Asn Asp Ala Val Asp Ala Cys Asn Asp Ser Pro Gly Asn Ile
            325                 330                 335 gga ggc tcc acc tct ggt atc atc act gtg ggt tcc att gac tct agc          1056
Gly Gly Ser Thr Ser Gly Ile Ile Thr Val Gly Ser Ile Asp Ser Ser
            340                 345                 350 gat aag atc tcc gtc tgg tcc ggt gga cag gga tcc aac tac gga act          1104
Asp Lys Ile Ser Val Trp Ser Gly Gly Gln Gly Ser Asn Tyr Gly Thr
            355                 360                 365 tgt gtt gat gtc ttt gcc ccc ggc tcc gat atc atc tct gcc tct tac          1152
Cys Val Asp Val Phe Ala Pro Gly Ser Asp Ile Ile Ser Ala Ser Tyr
        370                 375                 380 cag tcc gac tct ggt act ttg gtc tac tcc ggt acc tcc atg gcc tgt          1200
Gln Ser Asp Ser Gly Thr Leu Val Tyr Ser Gly Thr Ser Met Ala Cys
385                 390                 395                 400 ccc cac gtt gcc ggt ctt gcc tcc tac tac ctg tcc atc aat gac gag          1248
Pro His Val Ala Gly Leu Ala Ser Tyr Tyr Leu Ser Ile Asn Asp Glu
                405                 410                 415 gtt ctc acc cct gcc cag gtc gag gct ctt att act gag tcc aac acc          1296
Val Leu Thr Pro Ala Gln Val Glu Ala Leu Ile Thr Glu Ser Asn Thr
            420                 425                 430 ggt gtt ctt ccc acc acc aac ctc aag ggc tct ccc aac gct gtt gcc          1344
Gly Val Leu Pro Thr Thr Asn Leu Lys Gly Ser Pro Asn Ala Val Ala
            435                 440                 445 tac aac ggt gtt ggc att tag                                              1365
Tyr Asn Gly Val Gly Ile
        450

<210> SEQ ID NO 6
<211> LENGTH: 454
<212> TYPE: PRT
<213> ORGANISM: Yarrowia lipolytica

<400> SEQUENCE: 6

Met Lys Leu Ala Thr Ala Phe Thr Ile Leu Thr Ala Val Leu Ala Ala
1               5                   10                  15

Pro Leu Ala Ala Pro Ala Pro Ala Asp Ala Ala Pro Ala Ala Val
            20                  25                  30

Pro Glu Gly Pro Ala Ala Ala Tyr Ser Ser Ile Leu Ser Val Val
        35                  40                  45

Ala Lys Gln Ser Lys Lys Phe Lys His His Lys Arg Asp Leu Asp Glu
    50                  55                  60

Lys Asp Gln Phe Ile Val Val Phe Asp Ser Ser Ala Thr Val Asp Gln
65                  70                  75                  80

Ile Ala Ser Glu Ile Gln Lys Leu Asp Ser Leu Val Asp Glu Asp Ser
                85                  90                  95

Ser Asn Gly Ile Thr Ser Ala Leu Asp Leu Pro Val Tyr Thr Asp Gly
            100                 105                 110

Ser Gly Phe Leu Gly Phe Val Gly Lys Phe Asn Ser Thr Ile Val Asp
        115                 120                 125

Lys Leu Lys Glu Ser Ser Val Leu Thr Val Glu Pro Asp Thr Ile Val
    130                 135                 140

Ser Leu Pro Glu Ile Pro Ala Ser Ser Asn Ala Lys Arg Ala Ile Gln
145                 150                 155                 160

Thr Thr Pro Val Thr Gln Trp Gly Leu Ser Arg Ile Ser His Lys Lys
                165                 170                 175

Ala Gln Thr Gly Asn Tyr Ala Tyr Val Arg Glu Thr Val Gly Lys His
```

```
                    180                 185                 190
Pro Thr Val Ser Tyr Val Val Asp Ser Gly Ile Arg Thr Thr His Ser
            195                 200                 205

Glu Phe Gly Gly Arg Ala Val Trp Gly Ala Asn Phe Ala Asp Thr Gln
        210                 215                 220

Asn Ala Asp Leu Leu Gly His Gly Thr His Val Ala Gly Thr Val Gly
225                 230                 235                 240

Gly Lys Thr Tyr Gly Val Asp Ala Asn Thr Lys Leu Val Ala Val Lys
                245                 250                 255

Val Phe Ala Gly Arg Ser Ala Ala Leu Ser Val Ile Asn Gln Gly Phe
            260                 265                 270

Thr Trp Ala Leu Asn Asp Tyr Ile Ser Lys Arg Asp Thr Leu Pro Arg
        275                 280                 285

Gly Val Leu Asn Phe Ser Gly Gly Pro Lys Ser Ala Ser Gln Asp
290                 295                 300

Ala Leu Trp Ser Arg Ala Thr Gln Glu Gly Leu Leu Val Ala Ile Ala
305                 310                 315                 320

Ala Gly Asn Asp Ala Val Asp Ala Cys Asn Asp Ser Pro Gly Asn Ile
                325                 330                 335

Gly Gly Ser Thr Ser Gly Ile Ile Thr Val Gly Ser Ile Asp Ser Ser
            340                 345                 350

Asp Lys Ile Ser Val Trp Ser Gly Gln Gly Ser Asn Tyr Gly Thr
        355                 360                 365

Cys Val Asp Val Phe Ala Pro Gly Ser Asp Ile Ile Ser Ala Ser Tyr
370                 375                 380

Gln Ser Asp Ser Gly Thr Leu Val Tyr Ser Gly Thr Ser Met Ala Cys
385                 390                 395                 400

Pro His Val Ala Gly Leu Ala Ser Tyr Tyr Leu Ser Ile Asn Asp Glu
                405                 410                 415

Val Leu Thr Pro Ala Gln Val Glu Ala Leu Ile Thr Glu Ser Asn Thr
            420                 425                 430

Gly Val Leu Pro Thr Thr Asn Leu Lys Gly Ser Pro Asn Ala Val Ala
        435                 440                 445

Tyr Asn Gly Val Gly Ile
    450

<210> SEQ ID NO 7
<211> LENGTH: 57
<212> TYPE: DNA
<213> ORGANISM: Saccharomyces cerevisiae
<220> FEATURE:
<221> NAME/KEY: CDS
<222> LOCATION: (1)..(57)
<223> OTHER INFORMATION: SucSS

<400> SEQUENCE: 7 atg ttt ttg caa gct ttc ctt ttc ctt ttg gct ggt ttt gca gcc aaa    48
Met Phe Leu Gln Ala Phe Leu Phe Leu Leu Ala Gly Phe Ala Ala Lys
1               5                   10                  15 ata tct gca                                                        57
Ile Ser Ala <210> SEQ ID NO 8
<211> LENGTH: 19
<212> TYPE: PRT
<213> ORGANISM: Saccharomyces cerevisiae

<400> SEQUENCE: 8
```

Met Phe Leu Gln Ala Phe Leu Phe Leu Leu Ala Gly Phe Ala Ala Lys
1               5                   10                  15

Ile Ser Ala

<210> SEQ ID NO 9
<211> LENGTH: 510
<212> TYPE: DNA
<213> ORGANISM: Yarrowia lipolytica
<220> FEATURE:
<221> NAME/KEY: CDS
<222> LOCATION: (1)..(510)

<400> SEQUENCE: 9

| atg aag ctc gct acc gcc ttt act att ctc act gcc gtt ctg gcc gct | 48 |
| Met Lys Leu Ala Thr Ala Phe Thr Ile Leu Thr Ala Val Leu Ala Ala | |
| 1               5                   10                  15 | |

| ccc ctg gcc gcc cct gcc cct gct cct gat gct gcc cct gct gct gtg | 96 |
| Pro Leu Ala Ala Pro Ala Pro Ala Pro Asp Ala Ala Pro Ala Ala Val | |
|                 20                  25                  30 | |

| cct gag ggc cct gcc gcc gct gcc tac tca tct att ctg tcc gtg gtc | 144 |
| Pro Glu Gly Pro Ala Ala Ala Ala Tyr Ser Ser Ile Leu Ser Val Val | |
|         35                  40                  45 | |

| gct aag cag tcc aag aag ttt aag cac cac aag cga gat ctt gat gag | 192 |
| Ala Lys Gln Ser Lys Lys Phe Lys His His Lys Arg Asp Leu Asp Glu | |
| 50                  55                  60 | |

| aag gat cag ttc atc gtt gtc ttt gac agt agc gct act gtt gac cag | 240 |
| Lys Asp Gln Phe Ile Val Val Phe Asp Ser Ser Ala Thr Val Asp Gln | |
| 65                  70                  75                  80 | |

| atc gcc tcc gaa atc cag aag ctg gac tct ctg gtc gac gag gac tcg | 288 |
| Ile Ala Ser Glu Ile Gln Lys Leu Asp Ser Leu Val Asp Glu Asp Ser | |
|                 85                  90                  95 | |

| tcc aac ggt atc acc tct gct ctt gat ctt cct gtc tac acg gat gga | 336 |
| Ser Asn Gly Ile Thr Ser Ala Leu Asp Leu Pro Val Tyr Thr Asp Gly | |
|             100                 105                 110 | |

| tct ggc ttt ctc gga ttt gtt gga aag ttc aac tcc act atc gtt gac | 384 |
| Ser Gly Phe Leu Gly Phe Val Gly Lys Phe Asn Ser Thr Ile Val Asp | |
|         115                 120                 125 | |

| aag ctc aag gag tcg tct gtt ctg acg gtc gag ccc gat acc att gtg | 432 |
| Lys Leu Lys Glu Ser Ser Val Leu Thr Val Glu Pro Asp Thr Ile Val | |
|     130                 135                 140 | |

| tct ctc ccc gag att cct gct tct tct aat gcc aag cga gct atc cag | 480 |
| Ser Leu Pro Glu Ile Pro Ala Ser Ser Asn Ala Lys Arg Ala Ile Gln | |
| 145                 150                 155                 160 | |

| act act ccc gtc act caa tgg ggc ctg tct | 510 |
| Thr Thr Pro Val Thr Gln Trp Gly Leu Ser | |
|                 165                 170 | |

<210> SEQ ID NO 10
<211> LENGTH: 170
<212> TYPE: PRT
<213> ORGANISM: Yarrowia lipolytica

<400> SEQUENCE: 10

Met Lys Leu Ala Thr Ala Phe Thr Ile Leu Thr Ala Val Leu Ala Ala
1               5                   10                  15

Pro Leu Ala Ala Pro Ala Pro Ala Pro Asp Ala Ala Pro Ala Ala Val
                20                  25                  30

Pro Glu Gly Pro Ala Ala Ala Ala Tyr Ser Ser Ile Leu Ser Val Val
        35                  40                  45

Ala Lys Gln Ser Lys Lys Phe Lys His His Lys Arg Asp Leu Asp Glu
50                  55                  60

```
Lys Asp Gln Phe Ile Val Val Phe Asp Ser Ser Ala Thr Val Asp Gln
 65                  70                  75                  80

Ile Ala Ser Glu Ile Gln Lys Leu Asp Ser Leu Val Asp Glu Asp Ser
                 85                  90                  95

Ser Asn Gly Ile Thr Ser Ala Leu Asp Leu Pro Val Tyr Thr Asp Gly
            100                 105                 110

Ser Gly Phe Leu Gly Phe Val Gly Lys Phe Asn Ser Thr Ile Val Asp
        115                 120                 125

Lys Leu Lys Glu Ser Ser Val Leu Thr Val Glu Pro Asp Thr Ile Val
130                 135                 140

Ser Leu Pro Glu Ile Pro Ala Ser Ser Asn Ala Lys Arg Ala Ile Gln
145                 150                 155                 160

Thr Thr Pro Val Thr Gln Trp Gly Leu Ser
                165                 170

<210> SEQ ID NO 11
<211> LENGTH: 1599
<212> TYPE: DNA
<213> ORGANISM: Saccharomyces cerevisiae
<220> FEATURE:
<221> NAME/KEY: CDS
<222> LOCATION: (1)..(1599)
<223> OTHER INFORMATION: Suc2SS/m-ScSUC2

<400> SEQUENCE: 11 atg ttt ttg caa gct ttc ctt ttc ctt ttg gct ggt ttt gca gcc aaa     48
Met Phe Leu Gln Ala Phe Leu Phe Leu Leu Ala Gly Phe Ala Ala Lys
1               5                   10                  15 ata tct gca tca atg aca aac gaa act agc gat aga cct ttg gtc cac     96
Ile Ser Ala Ser Met Thr Asn Glu Thr Ser Asp Arg Pro Leu Val His
            20                  25                  30 ttc aca ccc aac aag ggc tgg atg aat gac cca aat ggg ttg tgg tac    144
Phe Thr Pro Asn Lys Gly Trp Met Asn Asp Pro Asn Gly Leu Trp Tyr
        35                  40                  45 gat gaa aaa gat gcc aaa tgg cat ctg tac ttt caa tac aac cca aat    192
Asp Glu Lys Asp Ala Lys Trp His Leu Tyr Phe Gln Tyr Asn Pro Asn
    50                  55                  60 gac acc gta tgg ggt acg cca ttg ttt tgg ggc cat gct act tcc gat    240
Asp Thr Val Trp Gly Thr Pro Leu Phe Trp Gly His Ala Thr Ser Asp
65                  70                  75                  80 gat ttg act aat tgg gaa gat caa ccc att gct atc gct ccc aag cgt    288
Asp Leu Thr Asn Trp Glu Asp Gln Pro Ile Ala Ile Ala Pro Lys Arg
                85                  90                  95 aac gat tca ggt gct ttc tct ggc tcc atg gtg gtt gat tac aac aac    336
Asn Asp Ser Gly Ala Phe Ser Gly Ser Met Val Val Asp Tyr Asn Asn
            100                 105                 110 acg agt ggg ttt ttc aat gat act att gat cca aga caa aga tgc gtt    384
Thr Ser Gly Phe Phe Asn Asp Thr Ile Asp Pro Arg Gln Arg Cys Val
        115                 120                 125 gcg att tgg act tat aac act cct gaa agt gaa gag caa tac att agc    432
Ala Ile Trp Thr Tyr Asn Thr Pro Glu Ser Glu Glu Gln Tyr Ile Ser
    130                 135                 140 tat tct ctt gat ggt ggt tac act ttt act gaa tac caa aag aac cct    480
Tyr Ser Leu Asp Gly Gly Tyr Thr Phe Thr Glu Tyr Gln Lys Asn Pro
145                 150                 155                 160 gtt tta gct gcc aac tcc act caa ttc aga gat cca aag gtg ttc tgg    528
Val Leu Ala Ala Asn Ser Thr Gln Phe Arg Asp Pro Lys Val Phe Trp
                165                 170                 175 tat gaa cct tct caa aaa tgg att atg acg gct gcc aaa tca caa gac    576
Tyr Glu Pro Ser Gln Lys Trp Ile Met Thr Ala Ala Lys Ser Gln Asp
            180                 185                 190
```

```
tac aaa att gaa att tac tcc tct gat gac ttg aag tcc tgg aag cta     624
Tyr Lys Ile Glu Ile Tyr Ser Ser Asp Asp Leu Lys Ser Trp Lys Leu
        195                 200                 205 gaa tct gca ttt gcc aat gaa ggt ttc tta ggc tac caa tac gaa tgt     672
Glu Ser Ala Phe Ala Asn Glu Gly Phe Leu Gly Tyr Gln Tyr Glu Cys
210                 215                 220 cca ggt ttg att gaa gtc cca act gag caa gat cct tcc aaa tct tat     720
Pro Gly Leu Ile Glu Val Pro Thr Glu Gln Asp Pro Ser Lys Ser Tyr
225                 230                 235                 240 tgg gtc atg ttt att tct atc aac cca ggt gca cct gct ggc ggt tcc     768
Trp Val Met Phe Ile Ser Ile Asn Pro Gly Ala Pro Ala Gly Gly Ser
            245                 250                 255 ttc aac caa tat ttt gtt gga tcc ttc aat ggt act cat ttt gaa gcg     816
Phe Asn Gln Tyr Phe Val Gly Ser Phe Asn Gly Thr His Phe Glu Ala
            260                 265                 270 ttt gac aat caa tct aga gtg gta gat ttt ggt aag gac tac tat gcc     864
Phe Asp Asn Gln Ser Arg Val Val Asp Phe Gly Lys Asp Tyr Tyr Ala
        275                 280                 285 ttg caa act ttc ttc aac act gac cca acc tac ggt tca gca tta ggt     912
Leu Gln Thr Phe Phe Asn Thr Asp Pro Thr Tyr Gly Ser Ala Leu Gly
290                 295                 300 att gcc tgg gct tca aac tgg gag tac agt gcc ttt gtc cca act aac     960
Ile Ala Trp Ala Ser Asn Trp Glu Tyr Ser Ala Phe Val Pro Thr Asn
305                 310                 315                 320 cca tgg aga tca tcc atg tct ttg gtc cgc aag ttt tct ttg aac act    1008
Pro Trp Arg Ser Ser Met Ser Leu Val Arg Lys Phe Ser Leu Asn Thr
            325                 330                 335 gaa tat caa gct aat cca gag act gaa ttg atc aat ttg aaa gcc gaa    1056
Glu Tyr Gln Ala Asn Pro Glu Thr Glu Leu Ile Asn Leu Lys Ala Glu
            340                 345                 350 cca ata ttg aac att agt aat gct ggt ccc tgg tct cgt ttt gct act    1104
Pro Ile Leu Asn Ile Ser Asn Ala Gly Pro Trp Ser Arg Phe Ala Thr
        355                 360                 365 aac aca act cta act aag gcc aat tct tac aat gtc gat ttg agc aac    1152
Asn Thr Thr Leu Thr Lys Ala Asn Ser Tyr Asn Val Asp Leu Ser Asn
370                 375                 380 tcg act ggt acc cta gag ttt gag ttg gtt tac gct gtt aac acc aca    1200
Ser Thr Gly Thr Leu Glu Phe Glu Leu Val Tyr Ala Val Asn Thr Thr
385                 390                 395                 400 caa acc ata tcc aaa tcc gtc ttt gcc gac tta tca ctt tgg ttc aag    1248
Gln Thr Ile Ser Lys Ser Val Phe Ala Asp Leu Ser Leu Trp Phe Lys
            405                 410                 415 ggt tta gaa gat cct gaa gaa tat ttg aga atg ggt ttt gaa gtc agt    1296
Gly Leu Glu Asp Pro Glu Glu Tyr Leu Arg Met Gly Phe Glu Val Ser
            420                 425                 430 gct tct tcc ttc ttt ttg gac cgt ggt aac tct aag gtc aag ttt gtc    1344
Ala Ser Ser Phe Phe Leu Asp Arg Gly Asn Ser Lys Val Lys Phe Val
        435                 440                 445 aag gag aac cca tat ttc aca aac aga atg tct gtc aac aac caa cca    1392
Lys Glu Asn Pro Tyr Phe Thr Asn Arg Met Ser Val Asn Asn Gln Pro
450                 455                 460 ttc aag tct gag aac gac cta agt tac tat aaa gtg tac ggc cta ctg    1440
Phe Lys Ser Glu Asn Asp Leu Ser Tyr Tyr Lys Val Tyr Gly Leu Leu
465                 470                 475                 480 gat caa aac atc ttg gaa ttg tac ttc aac gat gga gat gtg gtt tct    1488
Asp Gln Asn Ile Leu Glu Leu Tyr Phe Asn Asp Gly Asp Val Val Ser
            485                 490                 495 aca aat acc tac ttc atg acc acc ggt aac gct cta gga tct gtg aac    1536
Thr Asn Thr Tyr Phe Met Thr Thr Gly Asn Ala Leu Gly Ser Val Asn
            500                 505                 510
```

```
atg acc act ggt gtc gat aat ttg ttc tac att gac aag ttc caa gta    1584
Met Thr Thr Gly Val Asp Asn Leu Phe Tyr Ile Asp Lys Phe Gln Val
        515                 520                 525 agg gaa gta aaa tag                                                1599
Arg Glu Val Lys
        530
```

<210> SEQ ID NO 12
<211> LENGTH: 532
<212> TYPE: PRT
<213> ORGANISM: Saccharomyces cerevisiae

<400> SEQUENCE: 12

```
Met Phe Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
                20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
        50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335
```

```
Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Phe Ala Thr
        355                 360                 365

Asn Thr Thr Leu Thr Lys Ala Asn Ser Tyr Val Asp Leu Ser Asn
370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
                500                 505                 510

Met Thr Thr Gly Val Asp Asn Leu Phe Tyr Ile Asp Lys Phe Gln Val
            515                 520                 525

Arg Glu Val Lys
        530

<210> SEQ ID NO 13
<211> LENGTH: 8743
<212> TYPE: DNA
<213> ORGANISM: Artificial Sequence
<220> FEATURE:
<223> OTHER INFORMATION: Plasmid pYRH68

<400> SEQUENCE: 13
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt tcacttgag tgcagtggct      240 agtgctctta ctcgtacagt gtgcaatact gcgtatcata gtctttgatg tatatcgtat     300
tcattcatgt tagttgcgta cgttgattga ggtggagcca gatgggctat tgtttcatat     360
atagactggc agccacctct ttggcccagc atgtttgtat acctggaagg gaaaactaaa    420
gaagctggct agtttagttt gattattata gtagatgtcc taatcactag agattagaat    480
gtcttggcga tgattagtcg tcgtccctg tatcatgtct agaccaactg tgtcatgaag    540
ttggtgctgg tgttttacct gtgtactaca agtaggtgtc ctagatctag tgtacagagc    600
cgtttagacc catgtggact tcaccattaa cgatggaaaa tgttcattat atgacagtat     660
attacaatgg acttgctcca tttcttcctt gcatcacatg ttctccacct ccatagttga    720
tcaacacatc atagtagcta aggctgctgc tctcccacta cagtccacca caagttaagt   780
agcaccgtca gtacagctaa aagtacacgt ctagtacgtt tcataactag tcaagtagcc    840
cctattacag atatcagcac tatcacgcac gagttttct ctgtgctatc taatcaactt     900
gccaagtatt cggagaagat acactttctt ggcatcaggt atacgaggga gcctatcaga    960
```

```
tgaaaaaggg tatattggat ccattcatat ccacctacac gttgtcataa tctcctcatt    1020
cacgtgattc atttcgtgac actagtttct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga aagaacatgt gagcaaaagg ccagcaaaag gccaggaacc gtaaaaaggc    1440
cgcgttgctg gcgttttttcc ataggctccg cccccctgac gagcatcaca aaatcgacg    1500 ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca gctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc aacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaaagagt tggtagctct tgatccggca aacaaaccac    1980
cgctggtagc ggtggttttt ttgtttgcaa gcagcagatt acgcgcagaa aaaaggatc    2040 tcaagaagat cctttgatct tttctacggg gtctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atcccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcggggc gaaaactctc aaggatctta ccgctgttga tccagttc    2940 gatgtaaccc actcgtgcac ccaactgatc ttcagcatct tttactttca ccagcgtttc    3000
tgggtgagca aaaacaggaa ggcaaaatgc cgcaaaaaag gaataagggc gacacggaa    3060 atgttgaata ctcatactct tcctttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240 gaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
```

```
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagtttttt ggggtcgagg tgccgtaaag cactaaatcg    3540
gaaccctaaa gggagccccc gatttagagc ttgacgggga aagccggcga acgtggcgag    3600
aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aggggggatg tgctgcaagg cgattaagtt gggtaacgcc agggttttcc    3840
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaaccta ctttcatcaa gtgcaagaac    4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctccctt gtcgtcaaga cccacccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggagca    5580 cagtgccggc gtaggtgaag tcgtcaatga tgtcgatatg ggttttgatc atgcacacat    5640
aaggtccgac cttatcggca agctcaatga gctccttggt ggtggtaaca tccagagaag    5700
cacacaggtt ggttttcttg ctgccacga gcttgagcac tcgagcggca aggcggact    5760
```

```
tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300
ggggggcctt tttatatggc caagccaagc tctccacgtc ggttgggctg cacccaacaa    6360
taaatgggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gccttagag ctgcgaaagc gcgtatggat ttggctcatc    6720
aggccagatt gagggtctgt ggacacatgt catgttagtg tacttcaatc gcccctgga    6780 tatagccccg acataggcc gtggcctcat ttttttgcct tccgcacatt tccattgctc    6840
gatacccaca ccttgcttct cctgcacttg ccaaccttaa tactggttta cattgaccaa    6900
catcttacaa gcgggggct tgtctagggt atatataaac agtggctctc ccaatcggtt    6960
gccagtctct ttttcctttt cttcccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatgttttt gcaagctttc cttttccttt tggctggttt tgcagccaaa atatctgcat    7200
caatgacaaa cgaaactagc gatagacctt tggtccactt cacacccaac aagggctgga    7260
tgaatgaccc aaatggggttg tggtacgatg aaaaagatgc caaatggcat ctgtactttc    7320
aatacaaccc aaatgacacc gtatggggta cgccattgtt ttggggccat gctacttccg    7380
atgatttgac taattgggaa gatcaaccca ttgctatcgc tcccaagcgt aacgattcag    7440
gtgctttctc tggctccatg gtggttgatt acaacaacac gagtgggttt ttcaatgata    7500
ctattgatcc aagacaaaga tgcgttgcga tttggactta taacactcct gaaagtgaag    7560
agcaatacat tagctattct cttgatggtg gttacacttt tactgaatac caaaagaacc    7620
ctgttttagc tgccaactcc actcaattca gagatccaaa ggtgttctgg tatgaacctt    7680
ctcaaaaatg gattatgacg gctgccaaat cacaagacta caaaattgaa atttactcct    7740
ctgatgactt gaagtcctgg aagctagaat ctgcatttgc caatgaaggt ttcttaggct    7800
accaatacga atgtccaggt ttgattgaag tcccaactga gcaagatcct tccaaatctt    7860
attgggtcat gtttatttct atcaacccag gtgcacctgc tggcggttcc ttcaaccaat    7920
attttgttgg atccttcaat ggtactcatt ttgaagcgtt tgacaatcaa tctagagtgg    7980
tagattttgg taaggactac tatgccttgc aaactttctt caacactgac ccaacctacg    8040
gttcagcatt aggtattgcc tgggcttcaa actgggagta cagtgccttt gtcccaacta    8100
acccatggag atcatccatg tctttggtcc gcaagttttc tttgaacact gaatatcaag    8160
```

| | | | |
|---|---|---|---|
| ctaatccaga | gactgaattg | atcaatttga | aagccgaacc | aatattgaac | attagtaatg | 8220 |
| ctggtccctg | gtctcgtttt | gctactaaca | caactctaac | taaggccaat | tcttacaatg | 8280 |
| tcgatttgag | caactcgact | ggtaccctag | agtttgagtt | ggtttacgct | gttaacacca | 8340 |
| cacaaaccat | atccaaatcc | gtctttgccg | acttatcact | ttggttcaag | ggtttagaag | 8400 |
| atcctgaaga | atatttgaga | atgggttttg | aagtcagtgc | ttcttccttc | tttttggacc | 8460 |
| gtggtaactc | taaggtcaag | tttgtcaagg | agaacccata | tttcacaaac | agaatgtctg | 8520 |
| tcaacaacca | accattcaag | tctgagaacg | acctaagtta | ctataaagtg | tacggcctac | 8580 |
| tggatcaaaa | catcttggaa | ttgtacttca | acgatggaga | tgtggtttct | acaaatacct | 8640 |
| acttcatgac | caccggtaac | gctctaggat | ctgtgaacat | gaccactggt | gtcgataatt | 8700 |
| tgttctacat | tgacaagttc | caagtaaggg | aagtaaaata | ggc | | 8743 |

<210> SEQ ID NO 14
<211> LENGTH: 11962
<212> TYPE: DNA
<213> ORGANISM: Artificial Sequence
<220> FEATURE:
<223> OTHER INFORMATION: Plasmid pYRH70

<400> SEQUENCE: 14

| | | | |
|---|---|---|---|
| aaattgcccc | ggagaagacg | gccaggccgc | ctagatgaca | aattcaacaa | ctcacagctg | 60 |
| actttctgcc | attgccacta | gggggggggcc | ttttatatg | gccaagccaa | gctctccacg | 120 |
| tcggttgggc | tgcacccaac | aataaatggg | tagggttgca | ccaacaaagg | gatgggatgg | 180 |
| ggggtagaag | atacgaggat | aacggggctc | aatggcacaa | ataagaacga | atactgccat | 240 |
| taagactcgt | gatccagcga | ctgacaccat | tgcatcatct | aagggcctca | aaactacctc | 300 |
| ggaactgctg | cgctgatctg | gacaccacag | aggttccgag | cactttaggt | tgcaccaaat | 360 |
| gtcccaccag | gtgcaggcag | aaaacgctgg | aacagcgtgt | acagtttgtc | ttaacaaaaa | 420 |
| gtgagggcgc | tgaggtcgag | cagggtggtg | tgacttgtta | tagccttag | agctgcgaaa | 480 |
| gcgcgtatgg | atttggctca | tcaggccaga | ttgagggtct | gtggacacat | gtcatgttag | 540 |
| tgtacttcaa | tcgcccctg | gatatagccc | cgacaatagg | ccgtggcctc | attttttgc | 600 |
| cttccgcaca | tttccattgc | tcgatacca | caccttgctt | ctcctgcact | tgccaacctt | 660 |
| aatactggtt | tacattgacc | aacatcttac | aagcgggggg | cttgtctagg | gtatatataa | 720 |
| acagtggctc | tcccaatcgg | ttgccagtct | ctttttttcct | ttctttcccc | acagattcga | 780 |
| aatctaaact | acacatcaca | gaattccgag | ccgtgagtat | ccacgacaag | atcagtgtcg | 840 |
| agacgacgcg | ttttgtgtaa | tgacacaatc | cgaaagtcgc | tagcaacaca | cactctctac | 900 |
| acaaactaac | ccagctctgg | taccatgttt | ttgcaagctt | tcctttcct | tttggctggt | 960 |
| tttgcagcca | aaatatctgc | atcaatgaca | aacgaaacta | gcgatagacc | tttggtccac | 1020 |
| ttcacaccca | acaagggctg | gatgaatgac | ccaaatgggt | tgtggtacga | tgaaaaagat | 1080 |
| gccaaatggc | atctgtactt | tcaatacaac | ccaaatgaca | ccgtatgggg | tacgccattg | 1140 |
| ttttggggcc | atgctacttc | cgatgatttg | actaattggg | aagatcaacc | cattgctatc | 1200 |
| gctcccaagc | gtaacgattc | aggtgctttc | tctggctcca | tggtggttga | ttacaacaac | 1260 |
| acgagtgggt | ttttcaatga | tactattgat | ccaagacaaa | gatgcgttgc | gatttggact | 1320 |
| tataacactc | ctgaaagtga | agagcaatac | attagctatt | ctcttgatgg | tggttacact | 1380 |
| tttactgaat | accaaaagaa | ccctgtttta | gctgccaact | ccactcaatt | cagagatcca | 1440 |
| aaggtgttct | ggtatgaacc | ttctcaaaaa | tggattatga | cggctgccaa | atcacaagac | 1500 |

```
tacaaaattg aaatttactc ctctgatgac ttgaagtcct ggaagctaga atctgcattt    1560
gccaatgaag gtttcttagg ctaccaatac gaatgtccag gtttgattga agtcccaact    1620
gagcaagatc cttccaaatc ttattgggtc atgtttattt ctatcaaccc aggtgcacct    1680
gctggcggtt ccttcaacca atattttgtt ggatccttca atggtactca ttttgaagcg    1740
tttgacaatc aatctagagt ggtagatttt ggtaaggact actatgcctt gcaaactttc    1800
ttcaacactg acccaaccta cggttcagca ttaggtattg cctgggcttc aaactgggag    1860
tacagtgcct ttgtcccaac taacccatgg agatcatcca tgtctttggt ccgcaagttt    1920
tctttgaaca ctgaatatca agctaatcca gagactgaat tgatcaattt gaaagccgaa    1980
ccaatattga acattagtaa tgctggtccc tggtctcgtt ttgctactaa cacaactcta    2040
actaaggcca attcttacaa tgtcgatttg agcaactcga ctggtaccct agagtttgag    2100
ttggtttacg ctgttaacac cacacaaacc atatccaaat ccgtctttgc cgacttatca    2160 cttggttca agggtttaga agatcctgaa gaatatttga gaatgggttt tgaagtcagt    2220
gcttcttcct tcttttttgga ccgtggtaac tctaaggtca gtttgtcaa ggagaaccca    2280 tatttcacaa acagaatgtc tgtcaacaac caaccattca agtctgagaa cgacctaagt    2340
tactataaag tgtacggcct actggatcaa aacatcttgg aattgtactt caacgatgga    2400
gatgtggttt ctacaaatac ctacttcatg accaccggta acgctctagg atctgtgaac    2460
atgaccactg gtgtcgataa tttgttctac attgacaagt ccaagtaag ggaagtaaaa    2520 taggcggccg caagtgtgga tggggaagtg agtgcccggt tctgtgtgca caattggcaa    2580
tccaagatgg atggattcaa cacagggata tagcgagcta cgtggtggtg cgaggatata    2640
gcaacggata tttatgtttg acacttgaga atgtacgata caagcactgt ccaagtacaa    2700
tactaaacat actgtacata ctcatactcg tacccgggca acggtttcac ttgagtgcag    2760
tggctagtgc tcttactcgt acagtgtgca atactgcgta tcatagtctt tgatgtatat    2820
cgtattcatt catgttagtt gcgtacgttg attgaggtgg agccagatgg gctattgttt    2880
catatataga ctggcagcca cctctttggc ccagcatgtt tgtatacctg gaagggaaaa    2940
ctaaagaagc tggctagttt agtttgatta ttatagtaga tgtcctaatc actagagatt    3000
agaatgtctt ggcgatgatt agtcgtcgtc ccctgtatca tgtctagacc aactgtgtca    3060
tgaagttggt gctggtgttt tacctgtgta ctacaagtag gtgtcctaga tctagtgtac    3120
agagccgttt agaccccatgt ggacttcacc attaacgatg gaaaatgttc attatatgac    3180
agtatattac aatggacttg ctccatttct tccttgcatc acatgttctc cacctccata    3240
gttgatcaac acatcatagt agctaaggct gctgctctcc cactacagtc caccacaagt    3300
taagtagcac cgtcagtaca gctaaaagta cacgtctagt acgtttcata actagtcaag    3360
tagcccctat tacagatatc agcactatca cgcacgagtt tttctctgtg ctatctaatc    3420
aacttgccaa gtattcggag aagatacact ttcttggcat caggtatacg agggagccta    3480
tcagatgaaa aagggtatat tggatccatt catatccacc tacacgttgt cataatctcc    3540
tcattcacgt gattcatttc gtgacactag tttctcactt tcccccccgc acctatagtc    3600
aacttggcgg acacgctact tgtagctgac gttgatttat agacccaatc aaagcgggtt    3660
atcggtcagg tagcacttat cattcatcgt tcatactacg atgagcaatc tcgggcatgt    3720
ccggaaaagt gtcgggcgcg ccagctgcat taatgaatcg ccaacgcgc ggggagaggc    3780 ggtttgcgta ttgggcgctc ttccgcttcc tcgctcactg actcgctgcg ctcggtcgtt    3840
cggctgcggc gagcggtatc agctcactca aaggcggtaa tacggttatc cacagaatca    3900
```

```
ggggataacg caggaaagaa catgtgagca aaaggccagc aaaaggccag gaaccgtaaa    3960
aaggccgcgt tgctggcgtt tttccatagg ctccgccccc ctgacgagca tcacaaaaat    4020
cgacgctcaa gtcagaggtg gcgaaacccg acaggactat aaagatacca ggcgtttccc    4080
cctggaagct ccctcgtgcg ctctcctgtt ccgaccctgc cgcttaccgg atacctgtcc    4140
gcctttctcc cttcgggaag cgtggcgctt tctcatagct cacgctgtag gtatctcagt    4200
tcggtgtagg tcgttcgctc caagctgggc tgtgtgcacg aaccccccgt tcagcccgac    4260
cgctgcgcct tatccggtaa ctatcgtctt gagtccaacc cggtaagaca cgacttatcg    4320
ccactggcag cagccactgg taacaggatt agcagagcga ggtatgtagg cggtgctaca    4380
gagttcttga agtggtggcc taactacggc tacactagaa gaacagtatt tggtatctgc    4440
gctctgctga agccagttac cttcggaaaa agagttggta gctcttgatc cggcaaacaa    4500
accaccgctg gtagcggtgg ttttttttgtt tgcaagcagc agattacgcg cagaaaaaaa    4560
ggatctcaag aagatccttt gatcttttct acggggtctg acgctcagtg gaacgaaaac    4620
tcacgttaag ggattttggt catgagatta tcaaaaagga tcttcaccta gatccttttta    4680 aattaaaaat gaagttttaa atcaatctaa agtatatatg agtaaacttg gtctgacagt    4740
taccaatgct taatcagtga ggcacctatc tcagcgatct gtctatttcg ttcatccata    4800
gttgcctgac tccccgtcgt gtagataact acgatacggg agggcttacc atctggcccc    4860
agtgctgcaa tgataccgcg agacccacgc tcaccggctc cagatttatc agcaataaac    4920
cagccagccg aagggccga gcgcagaagt ggtcctgcaa cttatccgc ctccatccag    4980 tctattaatt gttgccggga agctagagta agtagttcgc cagttaatag tttgcgcaac    5040
gttgttgcca ttgctacagg catcgtggtg tcacgctcgt cgtttggtat ggcttcattc    5100
agctccggtt cccaacgatc aaggcgagtt acatgatccc ccatgttgtg caaaaaagcg    5160
gttagctcct tcggtcctcc gatcgttgtc agaagtaagt tggccgcagt gttatcactc    5220
atggttatgg cagcactgca taattctctt actgtcatgc catccgtaag atgcttttct    5280
gtgactggtg agtactcaac caagtcattc tgagaatagt gtatgcggcg accgagttgc    5340
tcttgcccgg cgtcaatacg ggataatacc gcgccacata gcagaacttt aaaagtgctc    5400
atcattggaa aacgttcttc ggggcgaaaa ctctcaagga tcttaccgct gttgagatcc    5460
agttcgatgt aacccactcg tgcacccaac tgatcttcag catctttttac tttcaccagc    5520 gtttctgggt gagcaaaaac aggaaggcaa aatgccgcaa aaaagggaat aagggcgaca    5580
cggaaatgtt gaatactcat actcttcctt tttcaatatt attgaagcat ttatcagggt    5640
tattgtctca tgagcggata catatttgaa tgtatttaga aaaataaaca ataggggtt    5700 ccgcgcacat ttccccgaaa agtgccacct gatgcggtgt gaaataccgc acagatgcgt    5760
aaggagaaaa taccgcatca ggaaattgta agcgttaata ttttgttaaa attcgcgtta    5820
aatttttgtt aaatcagctc attttttaac caataggccg aaatcggcaa aatcccttat    5880
aaatcaaaag aatagaccga gatagggttg agtgttgttc cagtttggaa caagagtcca    5940
ctattaaaga acgtggactc caacgtcaaa gggcgaaaaa ccgtctatca gggcgatggc    6000
ccactacgtg aaccatcacc ctaatcaagt tttttggggt cgaggtgccg taaagcacta    6060
aatcggaacc ctaaagggag cccccgattt agagcttgac ggggaaagcc ggcgaacgtg    6120
gcgagaaagg aagggaagaa agcgaaagga gcgggcgcta gggcgctggc aagtgtagcg    6180
gtcacgctgc gcgtaaccac cacacccgcc gcgcttaatg cgccgctaca gggcgcgtcc    6240
attcgccatt caggctgcgc aactgttggg aagggcgatc ggtgcgggcc tcttcgctat    6300
```

```
tacgccagct ggcgaaaggg ggatgtgctg caaggcgatt aagttgggta acgccagggt   6360
tttcccagtc acgacgttgt aaaacgacgg ccagtgaatt gtaatacgac tcactatagg   6420
gcgaattggg cccgacgtcg catgcattcc gacagcagcg actgggcacc atgatcaagc   6480
gaaacacctt cccccagctg ccctggcaaa ccatcaagaa ccctactttc atcaagtgca   6540
agaacggttc tactcttctc acctccggtg tctacggctg gtgccgaaag cctaactaca   6600
ccgctgattt catcatgtgc ctcacctggg ctctcatgtg cggtgttgct ctcccctgc    6660 cttacttcta cccggtcttc ttcttcctgg tgctcatcca ccgagcttac cgagactttg   6720
agcgactgga gcgaaagtac ggtgaggact accaggagtt caagcgacag gtcccttgga   6780
tcttcatccc ttatgttttc taaacgataa gcttagtgag cgaatggtga ggttacttaa   6840
ttgagtggcc agcctatggg attgtataac agacagtcaa tatattactg aaaagactga   6900
acagccagac ggagtgaggt tgtgagtgaa tcgtagaggg cggctattac agcaagtcta   6960
ctctacagtg tactaacaca gcagagaaca aatacaggtg tgcattcggc tatctgagaa   7020
ttagttggag agctcgagac cctcggcgat aaactgctcc tcggttttgt gtccatactt   7080
gtacggacca ttgtaatggg gcaagtcgtt gagttctcgt cgtccgacgt tcagagcaca   7140
gaaaccaatg taatcaatgt agcagagatg gttctgcaaa agattgattt gtgcgagcag   7200
gttaattaag tcatacacaa gtcagctttc ttcgagcctc atataagtat aagtagttca   7260
acgtattagc actgtaccca gcatctccgt atcgagaaac acaacaacat gccccattgg   7320
acagatcatg cggatacaca ggttgtgcag tatcatacat actcgatcag acaggtcgtc   7380
tgaccatcat acaagctgaa caagcgctcc atacttgcac gctctctata tacacagtta   7440
aattacatat ccatagtcta acctctaaca gttaatcttc tggtaagcct cccagccagc   7500
cttctggtat cgcttggcct cctcaatagg atctcggttc tggccgtaca gacctcggcc   7560
gacaattatg atatccgttc cggtagacat gacatcctca acagttcggt actgctgtcc   7620
gagagcgtct cccttgtcgt caagacccac cccggggtc agaataagcc agtcctcaga    7680
gtcgccctta ggtcggttct gggcaatgaa gccaaccaca aactcggggt cggatcgggc   7740
aagctcaatg gtctgcttgg agtactcgcc agtggccaga gagcccttgc aagacagctc   7800
ggccagcatg agcagacctc tggccagctt ctcgttggga gagggacta ggaactcctt    7860 gtactgggag ttctcgtagt cagagacgtc ctccttcttc tgttcagaga cagtttcctc   7920
ggcaccagct cgcaggccag caatgattcc ggttccgggt acaccgtggg cgttggtgat   7980
atcggaccac tcggcgattc ggtgacaccg gtactggtgc ttgacagtgt tgccaatatc   8040
tgcgaacttt ctgtcctcga acaggaagaa accgtgctta agagcaagtt ccttgagggg   8100
gagcacagtg ccggcgtagg tgaagtcgtc aatgatgtcg atatgggttt tgatcatgca   8160
cacataaggt ccgaccttat cggcaagctc aatgagctcc ttggtggtgg taacatccag   8220
agaagcacac aggttggttt tcttggctgc cacgagcttg agcactcgag cggcaaaggc   8280
ggacttgtgg acgttagctc gagcttcgta ggagggcatt ttggtggtga agaggagact   8340
gaaataaatt tagtctgcag aacttttat cggaacctta tctggggcag tgaagtatat    8400
gttatggtaa tagttacgag ttagttgaac ttatagatag actggactat acggctatcg   8460
gtccaaatta gaaagaacgt caatggctct ctgggcgtcg cctttgccga caaaatgtg    8520 atcatgatga aagccagcaa tgacgttgca gctgatattg ttgtcggcca accgcgccga   8580
aaacgcagct gtcagaccca cagcctccaa cgaagaatgt atcgtcaaag tgatccaagc   8640
acactcatag ttggagtcgt actccaaagg cggcaatgac gagtcagaca gatactcgtc   8700
```

```
gaccttttcc ttgggaacca ccaccgtcag cccttctgac tcacgtattg tagccaccga    8760
cacaggcaac agtccgtgga tagcagaata tgtcttgtcg gtccatttct caccaacttt    8820
aggcgtcaag tgaatgttgc agaagaagta tgtgccttca ttgagaatcg gtgttgctga    8880
tttcaataaa gtcttgagat cagtttggcc agtcatgttg tgggggtaa ttggattgag     8940 ttatcgccta cagtctgtac aggtatactc gctgcccact ttatacttttt tgattccgct   9000 gcacttgaag caatgtcgtt taccaaaagt gagaatgctc cacagaacac accccagggt    9060
atggttgagc aaaaaataaa cactccgata cggggaatcg aaccccggtc tccacggttc    9120
tcaagaagta ttcttgatga gagcgtatcg atgagcctaa aatgaacccg agtatatctc    9180
ataaaattct cggtgagagg tctgtgactg tcagtacaag gtgccttcat tatgccctca    9240
accttaccat acctcactga atgtagtgta cctctaaaaa tgaaatacag tgccaaaagc    9300
caaggcactg agctcgtcta acggacttga tatacaacca attaaaacaa atgaaaagaa    9360
atacagttct ttgtatcatt tgtaacaatt accctgtaca aactaaggta ttgaaatccc    9420
acaatattcc caaagtccac cccttttcca attgtcatgc ctacaactca tataccaagc    9480
actaacctac cgttaaacc atcatctaag ggcctcaaaa ctacctcgga actgctgcgc     9540
tgatctggac accacagagg ttccgagcac tttaggttgc accaaatgtc ccaccaggtg    9600
caggcagaaa acgctggaac agcgtgtaca gtttgtctta acaaaagtg agggcgctga     9660 ggtcgagcag ggtggtgtga cttgttatag cctttagagc tgcgaaagcg cgtatggatt    9720
tggctcatca ggccagattg agggtctgtg acacatgtc atgttagtgt acttcaatcg     9780 cccccctggat atagccccga caataggccg tggcctcatt tttttgcctt ccgcacattt    9840
ccattgctcg gtacccacac cttgcttctc ctgcacttgc aaccttaat actggtttac     9900 attgaccaac atcttacaag cggggggctt gtctagggta tatataaaca gtggctctcc    9960
caatcggttg ccagtctctt ttttcctttc tttccccaca gattcgaaat ctaaactaca   10020
catcacacca tgttttttgca agctttcctt ttccttttgg ctggttttgc agccaaaata   10080
tctgcatcaa tgacaaacga aactagcgat agacctttgg tccacttcac acccaacaag   10140
ggctggatga atgacccaaa tgggttgtgg tacgatgaaa aagatgccaa atggcatctg   10200
tactttcaat acaacccaaa tgacaccgta tggggtacgc cattgttttg gggccatgct   10260
acttccgatg atttgactaa ttgggaagat caacccattg ctatcgctcc caagcgtaac   10320
gattcaggtg cttttctctgg ctccatggtg gttgattaca caacacgag tgggttttc    10380 aatgatacta ttgatccaag acaaagatgc gttgcgattt ggacttataa cactcctgaa   10440
agtgaagagc aatacattag ctattctctt gatggtggtt acacttttac tgaataccaa   10500
aagaaccctg ttttagctgc caactccact caattcagag atccaaaggt gttctggtat   10560
gaaccttctc aaaaatggat tatgacggct gccaaatcac aagactacaa aattgaaatt   10620
tactcctctg atgacttgaa gtcctggaag ctagaatctg catttgccaa tgaaggtttc   10680
ttaggctacc aatacgaatg tccaggtttg attgaagtcc caactgagca agatccttcc   10740
aaatcttatt gggtcatgtt tatttctatc aacccaggtg cacctgctgg cggttccttc   10800
aaccaatatt ttgttggatc cttcaatggt actcattttg aagcgtttga caatcaatct   10860
agagtggtag attttggtaa ggactactat gccttgcaaa cttttcttcaa cactgaccca   10920 acctacggtt cagcattagg tattgcctgg gcttcaaact gggagtacag tgcctttgtc   10980
ccaactaacc catggagatc atccatgtct ttggtccgca gtttttctttt gaacactgaa   11040 tatcaagcta atccagagac tgaattgatc aatttgaaag ccgaaccaat attgaacatt   11100
```

```
agtaatgctg gtccctggtc tcgttttgct actaacacaa ctctaactaa ggccaattct    11160
tacaatgtcg atttgagcaa ctcgactggt accctagagt ttgagttggt ttacgctgtt    11220
aacaccacac aaaccatatc caaatccgtc tttgccgact tatcactttg gttcaagggt    11280
ttagaagatc ctgaagaata tttgagaatg ggttttgaag tcagtgcttc ttccttcttt    11340
ttggaccgtg gtaactctaa ggtcaagttt gtcaaggaga acccatattt cacaaacaga    11400
atgtctgtca acaaccaacc attcaagtct gagaacgacc taagttacta taaagtgtac    11460
ggcctactgg atcaaaacat cttggaattg tacttcaacg atggagatgt ggtttctaca    11520
aatacctact tcatgaccac cggtaacgct ctaggatctg tgaacatgac cactggtgtc    11580
gataatttgt tctacattga caagttccaa gtaaggaag taaaataggc ggccgcatga    11640
gaagataaat atataaatac attgagatat taaatgcgct agattagaga gcctcatact    11700
gctcggagag aagccaagac gagtactcaa aggggattac accatccata tccacagaca    11760
caagctgggg aaaggttcta tatacacttt ccggaatacc gtagtttccg atgttatcaa    11820
tgggggcagc caggatttca ggcacttcgg tgtctcgggg tgaaatggcg ttcttggcct    11880
ccatcaagtc gtaccatgtc ttcatttgcc tgtcaaagta aaacagaagc agatgaagaa    11940
tgaacttgaa gtgaaggaat tt                                              11962

<210> SEQ ID NO 15
<211> LENGTH: 8689
<212> TYPE: DNA
<213> ORGANISM: Artificial Sequence
<220> FEATURE:
<223> OTHER INFORMATION: Plasmid pYRH73

<400> SEQUENCE: 15
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgttgattga ggtggagcca gatgggctat tgtttcatat     360
atagactggc agccacctct ttggcccagc atgtttgtat acctggaagg gaaaactaaa     420
gaagctggct agtttagttt gattattata gtagatgtcc taatcactag agattagaat     480
gtcttggcga tgattagtcg tcgtcccctg tatcatgtct agaccaactg tgtcatgaag     540
ttggtgctgg tgttttacct gtgtactaca agtaggtgtc ctagatctag tgtacagagc     600
cgtttagacc catgtggact tcaccattaa cgatggaaaa tgttcattat atgacagtat     660
attacaatgg acttgctcca tttcttcctt gcatcacatg ttctccacct ccatagttga     720
tcaacacatc atagtagcta aggctgctgc tctcccacta cagtccacca caagttaagt     780
agcaccgtca gtacagctaa aagtacacgt ctagtacgtt tcataactag tcaagtagcc     840
cctattacag atatcagcac tatcacgcac gagttttttct ctgtgctatc taatcaactt     900
gccaagtatt cggagaagat acactttctt ggcatcaggt atacgaggga gcctatcaga     960
tgaaaaaggg tatattggat ccattcatat ccacctacac gttgtcataa tctcctcatt    1020
cacgtgattc atttcgtgac actagtttct cacttttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
```

```
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga agaacatgt gagcaaaagg ccagcaaaag gccaggaacc gtaaaaaggc    1440
cgcgttgctg gcgttttttcc ataggctccg ccccctgac gagcatcaca aaatcgacg    1500 ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc aacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaaagagt tggtagctct tgatccggca aacaaaccac    1980
cgctggtagc ggtggttttt ttgtttgcaa gcagcagatt acgcgcagaa aaaaggatc    2040 tcaagaagat cctttgatct tttctacggg gtctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atccccatg ttgtgcaaaa aagcggttag    2640
ctccttcggt cctccgatcg ttgtcagaag taagttggcc gcagtgttat cactcatggt    2700 tatgcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcggggc gaaaactctc aaggatctta ccgctgttga tccagttc    2940 gatgtaaccc actcgtgcac ccaactgatc ttcagcatct tttactttca ccagcgtttc    3000
tgggtgagca aaaacaggaa ggcaaaatgc cgcaaaaaag gaataagggg cgacacggaa    3060
atgttgaata ctcatactct tcctttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagttttttt ggggtcgagg tgccgtaaag cactaaatcg    3540
gaaccctaaa gggagccccc gatttagagc ttgacgggga aagccggcga acgtggcgag    3600
```

```
aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aaggggatg tgctgcaagg cgattaagtt gggtaacgcc agggttttcc    3840
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaaccccta cttttcatcaa gtgcaagaac    4020 ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctccctt gtcgtcaaga cccaccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggagca    5580 cagtgccggc gtaggtgaag tcgtcaatga tgtcgatatg gttttgatc atgcacacat    5640 aaggtccgac cttatcggca agctcaatga gctccttggt ggtggtaaca tccagagaag    5700
cacacaggtt ggttttcttg gctgccacga gcttgagcac tcgagcggca aggcggact    5760 tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
```

```
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300
gggggccctt tttatatggc caagccaagc tctccacgtc ggttgggctg cacccaacaa    6360
taaatgggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gcccctgga    6780 tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcgggggct tgtctagggt atatataaac agtggctctc ccaatcggtt    6960
gccagtctct ttttccttt ctttccccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatgtcaat gacaaacgaa actagcgata gaccttttggt ccacttcaca cccaacaagg    7200
gctggatgaa tgacccaaat gggttgtggt acgatgaaaa agatgccaaa tggcatctgt    7260
actttcaata caacccaaat gacaccgtat ggggtacgcc attgttttgg ggccatgcta    7320
cttccgatga tttgactaat tgggaagatc aacccattgc tatcgctccc aagcgtaacg    7380
attcaggtgc tttctctggc tccatggtgg ttgattacaa caacacgagt gggttttca    7440 atgatactat tgatccaaga caaagatgcg ttgcgatttg gacttataac actcctgaaa    7500
gtgaagagca atacattagc tattctcttg atggtggtta cacttttact gaataccaaa    7560
agaaccctgt tttagctgcc aactccactc aattcagaga tccaaaggtg ttctggtatg    7620
aaccttctca aaaatggatt atgacggctg ccaaatcaca agactacaaa attgaaattt    7680
actcctctga tgacttgaag tcctggaagc tagaatctgc atttgccaat gaaggtttct    7740
taggctacca atacgaatgt ccaggtttga ttgaagtccc aactgagcaa gatccttcca    7800
aatcttattg ggtcatgttt atttctatca acccaggtgc acctgctggc ggttccttca    7860
accaatattt tgttggatcc ttcaatggta ctcattttga agcgtttgac aatcaatcta    7920
gagtggtaga ttttggtaag gactactatg ccttgcaaac tttcttcaac actgacccaa    7980
cctacggttc agcattaggt attgcctggg cttcaaactg ggagtacagt gcctttgtcc    8040
caactaaccc atggagatca tccatgtctt tggtccgcaa gttttctttg aacactgaat    8100
atcaagctaa tccagagact gaattgatca atttgaaagc cgaaccaata ttgaacatta    8160
gtaatgctgg tccctggtct cgttttgcta ctaacacaac tctaactaag gccaattctt    8220
acaatgtcga tttgagcaac tcgactggta ccctagagtt tgagttggtt tacgctgtta    8280
acaccacaca aaccatatcc aaatccgtct ttgccgactt atcactttgg ttcaagggtt    8340
tagaagatcc tgaagaatat ttgagaatgg gttttgaagt cagtgcttct tccttctttt    8400
```

```
tggaccgtgg taactctaag gtcaagtttg tcaaggagaa cccatatttc acaaacagaa      8460
tgtctgtcaa caaccaacca ttcaagtctg agaacgacct aagttactat aaagtgtacg      8520
gcctactgga tcaaaacatc ttggaattgt acttcaacga tggagatgtg gtttctacaa      8580
atacctactt catgaccacc ggtaacgctc taggatctgt gaacatgacc actggtgtcg      8640
ataatttgtt ctacattgac aagttccaag taagggaagt aaaataggc                  8689
```

```
<210> SEQ ID NO 16
<211> LENGTH: 2112
<212> TYPE: DNA
<213> ORGANISM: Artificial Sequence
<220> FEATURE:
<223> OTHER INFORMATION: fusion
<220> FEATURE:
<221> NAME/KEY: CDS
<222> LOCATION: (1)..(2112)
<223> OTHER INFORMATION: XPR2PP+13/Suc2SS/m-ScSUC2

<400> SEQUENCE: 16
```

```
atg gag ctc gct acc gcc ttt act att ctc act gcc gtt ctg gcc gct        48
Met Glu Leu Ala Thr Ala Phe Thr Ile Leu Thr Ala Val Leu Ala Ala
1               5                   10                  15 ccc ctg gcc gcc cct gcc cct gct cct gat gct gcc cct gct gct gtg        96
Pro Leu Ala Ala Pro Ala Pro Ala Pro Asp Ala Ala Pro Ala Ala Val
            20                  25                  30 cct gag ggc cct gcc gcc gct gcc tac tca tct att ctg tcc gtg gtc       144
Pro Glu Gly Pro Ala Ala Ala Ala Tyr Ser Ser Ile Leu Ser Val Val
        35                  40                  45 gct aag cag tcc aag aag ttt aag cac cac aag cga gat ctt gat gag       192
Ala Lys Gln Ser Lys Lys Phe Lys His His Lys Arg Asp Leu Asp Glu
    50                  55                  60 aag gat cag ttc atc gtt gtc ttt gac agt agc gct act gtt gac cag       240
Lys Asp Gln Phe Ile Val Val Phe Asp Ser Ser Ala Thr Val Asp Gln
65                  70                  75                  80 atc gcc tcc gaa atc cag aag ctg gac tct ctg gtc gac gag gac tcg       288
Ile Ala Ser Glu Ile Gln Lys Leu Asp Ser Leu Val Asp Glu Asp Ser
                85                  90                  95 tcc aac ggt atc acc tct gct ctt gat ctt cct gtc tac acg gat gga       336
Ser Asn Gly Ile Thr Ser Ala Leu Asp Leu Pro Val Tyr Thr Asp Gly
            100                 105                 110 tct ggc ttt ctc gga ttt gtt gga aag ttc aac tcc act atc gtt gac       384
Ser Gly Phe Leu Gly Phe Val Gly Lys Phe Asn Ser Thr Ile Val Asp
        115                 120                 125 aag ctc aag gag tcg tct gtt ctg acg gtc gag ccc gat acc att gtg       432
Lys Leu Lys Glu Ser Ser Val Leu Thr Val Glu Pro Asp Thr Ile Val
    130                 135                 140 tct ctc ccc gag att cct gct tct tct aat gcc aag cga gct atc cag       480
Ser Leu Pro Glu Ile Pro Ala Ser Ser Asn Ala Lys Arg Ala Ile Gln
145                 150                 155                 160 act act ccc gtc act caa tgg ggc ctg tct aac atg ttt ttg caa gct       528
Thr Thr Pro Val Thr Gln Trp Gly Leu Ser Asn Met Phe Leu Gln Ala
                165                 170                 175 ttc ctt ttc ctt ttg gct ggt ttt gca gcc aaa ata tct gca tca atg       576
Phe Leu Phe Leu Leu Ala Gly Phe Ala Ala Lys Ile Ser Ala Ser Met
            180                 185                 190 aca aac gaa act agc gat aga cct ttg gtc cac ttc aca ccc aac aag       624
Thr Asn Glu Thr Ser Asp Arg Pro Leu Val His Phe Thr Pro Asn Lys
        195                 200                 205 ggc tgg atg aat gac cca aat ggg ttg tgg tac gat gaa aaa gat gcc       672
Gly Trp Met Asn Asp Pro Asn Gly Leu Trp Tyr Asp Glu Lys Asp Ala
    210                 215                 220
```

```
aaa tgg cat ctg tac ttt caa tac aac cca aat gac acc gta tgg ggt      720
Lys Trp His Leu Tyr Phe Gln Tyr Asn Pro Asn Asp Thr Val Trp Gly
225                 230                 235                 240 acg cca ttg ttt tgg ggc cat gct act tcc gat gat ttg act aat tgg      768
Thr Pro Leu Phe Trp Gly His Ala Thr Ser Asp Asp Leu Thr Asn Trp
                245                 250                 255 gaa gat caa ccc att gct atc gct ccc aag cgt aac gat tca ggt gct      816
Glu Asp Gln Pro Ile Ala Ile Ala Pro Lys Arg Asn Asp Ser Gly Ala
        260                 265                 270 ttc tct ggc tcc atg gtg gtt gat tac aac aac acg agt ggg ttt ttc      864
Phe Ser Gly Ser Met Val Val Asp Tyr Asn Asn Thr Ser Gly Phe Phe
            275                 280                 285 aat gat act att gat cca aga caa aga tgc gtt gcg att tgg act tat      912
Asn Asp Thr Ile Asp Pro Arg Gln Arg Cys Val Ala Ile Trp Thr Tyr
290                 295                 300 aac act cct gaa agt gaa gag caa tac att agc tat tct ctt gat ggt      960
Asn Thr Pro Glu Ser Glu Glu Gln Tyr Ile Ser Tyr Ser Leu Asp Gly
305                 310                 315                 320 ggt tac act ttt act gaa tac caa aag aac cct gtt tta gct gcc aac     1008
Gly Tyr Thr Phe Thr Glu Tyr Gln Lys Asn Pro Val Leu Ala Ala Asn
                325                 330                 335 tcc act caa ttc aga gat cca aag gtg ttc tgg tat gaa cct tct caa     1056
Ser Thr Gln Phe Arg Asp Pro Lys Val Phe Trp Tyr Glu Pro Ser Gln
        340                 345                 350 aaa tgg att atg acg gct gcc aaa tca caa gac tac aaa att gaa att     1104
Lys Trp Ile Met Thr Ala Ala Lys Ser Gln Asp Tyr Lys Ile Glu Ile
            355                 360                 365 tac tcc tct gat gac ttg aag tcc tgg aag cta gaa tct gca ttt gcc     1152
Tyr Ser Ser Asp Asp Leu Lys Ser Trp Lys Leu Glu Ser Ala Phe Ala
370                 375                 380 aat gaa ggt ttc tta ggc tac caa tac gaa tgt cca ggt ttg att gaa     1200
Asn Glu Gly Phe Leu Gly Tyr Gln Tyr Glu Cys Pro Gly Leu Ile Glu
385                 390                 395                 400 gtc cca act gag caa gat cct tcc aaa tct tat tgg gtc atg ttt att     1248
Val Pro Thr Glu Gln Asp Pro Ser Lys Ser Tyr Trp Val Met Phe Ile
                405                 410                 415 tct atc aac cca ggt gca cct gct ggc ggt tcc ttc aac caa tat ttt     1296
Ser Ile Asn Pro Gly Ala Pro Ala Gly Gly Ser Phe Asn Gln Tyr Phe
        420                 425                 430 gtt gga tcc ttc aat ggt act cat ttt gaa gcg ttt gac aat caa tct     1344
Val Gly Ser Phe Asn Gly Thr His Phe Glu Ala Phe Asp Asn Gln Ser
            435                 440                 445 aga gtg gta gat ttt ggt aag gac tac tat gcc ttg caa act ttc ttc     1392
Arg Val Val Asp Phe Gly Lys Asp Tyr Tyr Ala Leu Gln Thr Phe Phe
450                 455                 460 aac act gac cca acc tac ggt tca gca tta ggt att gcc tgg gct tca     1440
Asn Thr Asp Pro Thr Tyr Gly Ser Ala Leu Gly Ile Ala Trp Ala Ser
465                 470                 475                 480 aac tgg gag tac agt gcc ttt gtc cca act aac cca tgg aga tca tcc     1488
Asn Trp Glu Tyr Ser Ala Phe Val Pro Thr Asn Pro Trp Arg Ser Ser
                485                 490                 495 atg tct ttg gtc cgc aag ttt tct ttg aac act gaa tat caa gct aat     1536
Met Ser Leu Val Arg Lys Phe Ser Leu Asn Thr Glu Tyr Gln Ala Asn
        500                 505                 510 cca gag act gaa ttg atc aat ttg aaa gcc gaa cca ata ttg aac att     1584
Pro Glu Thr Glu Leu Ile Asn Leu Lys Ala Glu Pro Ile Leu Asn Ile
            515                 520                 525 agt aat gct ggt ccc tgg tct cgt ttt gct act aac aca act cta act     1632
Ser Asn Ala Gly Pro Trp Ser Arg Phe Ala Thr Asn Thr Thr Leu Thr
530                 535                 540
```

-continued

```
aag gcc aat tct tac aat gtc gat ttg agc aac tcg act ggt acc cta    1680
Lys Ala Asn Ser Tyr Asn Val Asp Leu Ser Asn Ser Thr Gly Thr Leu
545                 550                 555                 560 gag ttt gag ttg gtt tac gct gtt aac acc aca caa acc ata tcc aaa    1728
Glu Phe Glu Leu Val Tyr Ala Val Asn Thr Thr Gln Thr Ile Ser Lys
                565                 570                 575 tcc gtc ttt gcc gac tta tca ctt tgg ttc aag ggt tta gaa gat cct    1776
Ser Val Phe Ala Asp Leu Ser Leu Trp Phe Lys Gly Leu Glu Asp Pro
            580                 585                 590 gaa gaa tat ttg aga atg ggt ttt gaa gtc agt gct tct tcc ttc ttt    1824
Glu Glu Tyr Leu Arg Met Gly Phe Glu Val Ser Ala Ser Ser Phe Phe
        595                 600                 605 ttg gac cgt ggt aac tct aag gtc aag ttt gtc aag gag aac cca tat    1872
Leu Asp Arg Gly Asn Ser Lys Val Lys Phe Val Lys Glu Asn Pro Tyr
    610                 615                 620 ttc aca aac aga atg tct gtc aac aac caa cca ttc aag tct gag aac    1920
Phe Thr Asn Arg Met Ser Val Asn Asn Gln Pro Phe Lys Ser Glu Asn
625                 630                 635                 640 gac cta agt tac tat aaa gtg tac ggc cta ctg gat caa aac atc ttg    1968
Asp Leu Ser Tyr Tyr Lys Val Tyr Gly Leu Leu Asp Gln Asn Ile Leu
                645                 650                 655 gaa ttg tac ttc aac gat gga gat gtg gtt tct aca aat acc tac ttc    2016
Glu Leu Tyr Phe Asn Asp Gly Asp Val Val Ser Thr Asn Thr Tyr Phe
            660                 665                 670 atg acc acc ggt aac gct cta gga tct gtg aac atg acc act ggt gtc    2064
Met Thr Thr Gly Asn Ala Leu Gly Ser Val Asn Met Thr Thr Gly Val
        675                 680                 685 gat aat ttg ttc tac att gac aag ttc caa gta agg gaa gta aaa tag    2112
Asp Asn Leu Phe Tyr Ile Asp Lys Phe Gln Val Arg Glu Val Lys
    690                 695                 700
```

<210> SEQ ID NO 17
<211> LENGTH: 703
<212> TYPE: PRT
<213> ORGANISM: Artificial Sequence
<220> FEATURE:
<223> OTHER INFORMATION: Synthetic Construct

<400> SEQUENCE: 17

```
Met Glu Leu Ala Thr Ala Phe Thr Ile Leu Thr Ala Val Leu Ala Ala
1               5                   10                  15

Pro Leu Ala Ala Pro Ala Pro Ala Pro Asp Ala Ala Pro Ala Ala Val
            20                  25                  30

Pro Glu Gly Pro Ala Ala Ala Tyr Ser Ser Ile Leu Ser Val Val
        35                  40                  45

Ala Lys Gln Ser Lys Lys Phe Lys His His Lys Arg Asp Leu Asp Glu
    50                  55                  60

Lys Asp Gln Phe Ile Val Val Phe Asp Ser Ser Ala Thr Val Asp Gln
65                  70                  75                  80

Ile Ala Ser Glu Ile Gln Lys Leu Asp Ser Leu Val Asp Glu Asp Ser
                85                  90                  95

Ser Asn Gly Ile Thr Ser Ala Leu Asp Leu Pro Val Tyr Thr Asp Gly
            100                 105                 110

Ser Gly Phe Leu Gly Phe Val Gly Lys Phe Asn Ser Thr Ile Val Asp
        115                 120                 125

Lys Leu Lys Glu Ser Val Leu Thr Val Glu Pro Asp Thr Ile Val
    130                 135                 140

Ser Leu Pro Glu Ile Pro Ala Ser Ser Asn Ala Lys Arg Ala Ile Gln
145                 150                 155                 160
```

```
Thr Thr Pro Val Thr Gln Trp Gly Leu Ser Asn Met Phe Leu Gln Ala
            165                 170                 175

Phe Leu Phe Leu Leu Ala Gly Phe Ala Ala Lys Ile Ser Ala Ser Met
            180                 185                 190

Thr Asn Glu Thr Ser Asp Arg Pro Leu Val His Phe Thr Pro Asn Lys
            195                 200                 205

Gly Trp Met Asn Asp Pro Asn Gly Leu Trp Tyr Asp Glu Lys Asp Ala
            210                 215                 220

Lys Trp His Leu Tyr Phe Gln Tyr Asn Pro Asn Asp Thr Val Trp Gly
225                 230                 235                 240

Thr Pro Leu Phe Trp Gly His Ala Thr Ser Asp Leu Thr Asn Trp
                245                 250                 255

Glu Asp Gln Pro Ile Ala Ile Ala Pro Lys Arg Asn Asp Ser Gly Ala
            260                 265                 270

Phe Ser Gly Ser Met Val Val Asp Tyr Asn Asn Thr Ser Gly Phe Phe
            275                 280                 285

Asn Asp Thr Ile Asp Pro Arg Gln Arg Cys Val Ala Ile Trp Thr Tyr
290                 295                 300

Asn Thr Pro Glu Ser Glu Glu Gln Tyr Ile Ser Tyr Ser Leu Asp Gly
305                 310                 315                 320

Gly Tyr Thr Phe Thr Glu Tyr Gln Lys Asn Pro Val Leu Ala Ala Asn
            325                 330                 335

Ser Thr Gln Phe Arg Asp Pro Lys Val Phe Trp Tyr Glu Pro Ser Gln
            340                 345                 350

Lys Trp Ile Met Thr Ala Ala Lys Ser Gln Asp Tyr Lys Ile Glu Ile
            355                 360                 365

Tyr Ser Ser Asp Asp Leu Lys Ser Trp Lys Leu Glu Ser Ala Phe Ala
            370                 375                 380

Asn Glu Gly Phe Leu Gly Tyr Gln Tyr Glu Cys Pro Gly Leu Ile Glu
385                 390                 395                 400

Val Pro Thr Glu Gln Asp Pro Ser Lys Ser Tyr Trp Val Met Phe Ile
            405                 410                 415

Ser Ile Asn Pro Gly Ala Pro Ala Gly Gly Ser Phe Asn Gln Tyr Phe
            420                 425                 430

Val Gly Ser Phe Asn Gly Thr His Phe Glu Ala Phe Asp Asn Gln Ser
            435                 440                 445

Arg Val Val Asp Phe Gly Lys Asp Tyr Tyr Ala Leu Gln Thr Phe Phe
450                 455                 460

Asn Thr Asp Pro Thr Tyr Gly Ser Ala Leu Gly Ile Ala Trp Ala Ser
465                 470                 475                 480

Asn Trp Glu Tyr Ser Ala Phe Val Pro Thr Asn Pro Trp Arg Ser Ser
                485                 490                 495

Met Ser Leu Val Arg Lys Phe Ser Leu Asn Thr Glu Tyr Gln Ala Asn
            500                 505                 510

Pro Glu Thr Glu Leu Ile Asn Leu Lys Ala Glu Pro Ile Leu Asn Ile
            515                 520                 525

Ser Asn Ala Gly Pro Trp Ser Arg Phe Ala Thr Asn Thr Thr Leu Thr
            530                 535                 540

Lys Ala Asn Ser Tyr Asn Val Asp Leu Ser Asn Ser Thr Gly Thr Leu
545                 550                 555                 560

Glu Phe Glu Leu Val Tyr Ala Val Asn Thr Thr Gln Thr Ile Ser Lys
                565                 570                 575

Ser Val Phe Ala Asp Leu Ser Leu Trp Phe Lys Gly Leu Glu Asp Pro
```

```
                     580                 585                 590
Glu Glu Tyr Leu Arg Met Gly Phe Glu Val Ser Ala Ser Ser Phe Phe
                595                 600                 605
Leu Asp Arg Gly Asn Ser Lys Val Lys Phe Val Lys Glu Asn Pro Tyr
            610                 615                 620
Phe Thr Asn Arg Met Ser Val Asn Asn Gln Pro Phe Lys Ser Glu Asn
625                 630                 635                 640
Asp Leu Ser Tyr Tyr Lys Val Tyr Gly Leu Leu Asp Gln Asn Ile Leu
                645                 650                 655
Glu Leu Tyr Phe Asn Asp Gly Asp Val Val Ser Thr Asn Thr Tyr Phe
            660                 665                 670
Met Thr Thr Gly Asn Ala Leu Gly Ser Val Asn Met Thr Thr Gly Val
                675                 680                 685
Asp Asn Leu Phe Tyr Ile Asp Lys Phe Gln Val Arg Glu Val Lys
            690                 695                 700

<210> SEQ ID NO 18
<211> LENGTH: 9256
<212> TYPE: DNA
<213> ORGANISM: Artificial Sequence
<220> FEATURE:
<223> OTHER INFORMATION: Plasmid pYRH69

<400> SEQUENCE: 18
catggagctc gctaccgcct ttactattct cactgccgtt ctggccgctc ccctggccgc      60
ccctgcccct gctcctgatg ctgccccctgc tgctgtgcct gagggccctg ccgccgctgc     120
ctactcatct attctgtccg tggtcgctaa gcagtccaag aagtttaagc accacaagcg     180
agatcttgat gagaaggatc agttcatcgt tgtctttgac agtagcgcta ctgttgacca     240
gatcgcctcc gaaatccaga agctggactc tctggtcgac gaggactcgt ccaacggtat     300
cacctctgct cttgatcttc ctgtctacac ggatggatct ggctttctcg gatttgttgg     360
aaagttcaac tccactatcg ttgacaagct caaggagtcg tctgttctga cggtcgagcc     420
cgataccatt gtgtctctcc ccgagattcc tgcttcttct aatgccaagc gagctatcca     480
gactactccc gtcactcaat ggggcctgtc taacatgttt ttgcaagctt cctttttcct     540
tttggctggt tttgcagcca aaatatctgc atcaatgaca aacgaaacta gcgatagacc     600
tttggtccac ttcacaccca caagggctg gatgaatgac ccaaatgggt tgtggtacga     660
tgaaaaagat gccaaatggc atctgtactt caatacaac ccaaatgaca ccgtatgggg     720
tacgccattg ttttggggcc atgctacttc cgatgatttg actaattggg aagatcaacc     780
cattgctatc gctcccaagc gtaacgattc aggtgctttc tctggctcca tggtggttga     840
ttacaacaac acgagtgggt ttttcaatga tactattgat ccaagacaaa gatgcgttgc     900
gatttggact tataacactc ctgaaagtga agagcaatac attagctatt ctcttgatgg     960
tggttacact tttactgaat accaaaagaa ccctgtttta gctgccaact ccactcaatt    1020
cagagatcca aaggtgttct ggtatgaacc ttctcaaaaa tggattatga cggctgccaa    1080
atcacaagac tacaaaattg aaatttactc ctctgatgac ttgaagtcct ggaagctaga    1140
atctgcattt gccaatgaag gtttcttagg ctaccaatac gaatgtccag gtttgattga    1200
agtcccaact gagcaagatc cttccaaatc ttattgggtc atgtttattt ctatcaaccc    1260
aggtgcacct gctggcggtt ccttcaacca atattttgtt ggatccttca atggtactca    1320
ttttgaagcg tttgacaatc aatctagagt ggtagatttt ggtaaggact actatgcctt    1380
gcaaactttc ttcaacactg acccaaccta cggttcagca ttaggtattg cctgggcttc    1440
```

```
aaactgggag tacagtgcct ttgtcccaac taacccatgg agatcatcca tgtctttggt   1500
ccgcaagttt tctttgaaca ctgaatatca agctaatcca gagactgaat tgatcaattt   1560
gaaagccgaa ccaatattga acattagtaa tgctggtccc tggtctcgtt ttgctactaa   1620
cacaactcta actaaggcca attcttacaa tgtcgatttg agcaactcga ctggtaccct   1680
agagtttgag ttggtttacg ctgttaacac cacacaaacc atatccaaat ccgtctttgc   1740
cgacttatca ctttggttca agggtttaga agatcctgaa gaatatttga gaatgggttt   1800
tgaagtcagt gcttcttcct tcttttttgga ccgtggtaac tctaaggtca agttgtcaa    1860
ggagaaccca tatttcacaa acagaatgtc tgtcaacaac caaccattca agtctgagaa   1920
cgacctaagt tactataaag tgtacggcct actggatcaa acatcttgg aattgtactt     1980
caacgatgga gatgtggttt ctacaaatac ctacttcatg accaccggta acgctctagg   2040
atctgtgaac atgaccactg gtgtcgataa tttgttctac attgacaagt tccaagtaag   2100
ggaagtaaaa taggcggccg caagtgtgga tggggaagtg agtgcccggt tctgtgtgca   2160
caattggcaa tccaagatgg atggattcaa cacagggata tagcgagcta cgtggtggtg   2220
cgaggatata gcaacggata tttatgtttg acacttgaga atgtacgata caagcactgt   2280
ccaagtacaa tactaaacat actgtacata ctcatactcg tacccgggca acggtttcac    2340
ttgagtgcag tggctagtgc tcttactcgt acagtgtgca atactgcgta tcatagtctt    2400
tgatgtatat cgtattcatt catgttagtt gcgtacgttg attgaggtgg agccagatgg   2460
gctattgttt catatataga ctggcagcca cctctttggc ccagcatgtt tgtatacctg   2520
gaagggaaaa ctaaagaagc tggctagttt agtttgatta ttatagtaga tgtcctaatc    2580
actagagatt agaatgtctt ggcgatgatt agtcgtcgtc ccctgtatca tgtctagacc   2640
aactgtgtca tgaagttggt gctggtgttt tacctgtgta ctacaagtag gtgtcctaga   2700
tctagtgtac agagccgttt agacccatgt ggacttcacc attaacgatg gaaaatgttc   2760
attatatgac agtatattac aatggacttg ctccatttct tccttgcatc acatgttctc   2820
cacctccata gttgatcaac acatcatagt agctaaggct gctgctctcc cactacagtc   2880
caccacaagt taagtagcac cgtcagtaca gctaaaagta cacgtctagt acgtttcata   2940
actagtcaag tagcccctat tacagatatc agcactatca cgcacgagtt tttctctgtg   3000
ctatctaatc aacttgccaa gtattcggag aagatacact ttcttggcat caggtatacg   3060
agggagccta tcagatgaaa aagggtatat tggatccatt catatccacc tacacgttgt   3120
cataatctcc tcattcacgt gattcatttc gtgacactag tttctcactt tcccccccgc   3180
acctatagtc aacttggcgg acacgctact tgtagctgac gttgatttat agacccaatc   3240
aaagcgggtt atcggtcagg tagcacttat cattcatcgt tcatactacg atgagcaatc   3300
tcgggcatgt ccggaaaagt gtcgggcgcg ccagctgcat taatgaatcg gccaacgcgc   3360
ggggagaggc ggtttgcgta ttgggcgctc ttccgcttcc tcgctcactg actcgctgcg   3420
ctcggtcgtt cggctgcggc gagcggtatc agctcactca aaggcggtaa tacggttatc   3480
cacagaatca ggggataacg caggaaagaa catgtgagca aaaggccagc aaaaggccag   3540
gaaccgtaaa aaggccgcgt tgctggcgtt tttccatagg ctccgccccc ctgacgagca   3600
tcacaaaaat cgacgctcaa gtcagaggtg gcgaaacccg acaggactat aaagatacca   3660
ggcgtttccc cctggaagct ccctcgtgcg ctctcctgtt ccgaccctgc cgcttaccgg   3720
atacctgtcc gcctttctcc cttcgggaag cgtggcgctt tctcatagct cacgctgtag   3780
gtatctcagt tcggtgtagg tcgttcgctc caagctgggc tgtgtgcacg aaccccccgt   3840
```

```
tcagcccgac cgctgcgcct tatccggtaa ctatcgtctt gagtccaacc cggtaagaca   3900
cgacttatcg ccactggcag cagccactgg taacaggatt agcagagcga ggtatgtagg   3960
cggtgctaca gagttcttga agtggtggcc taactacggc tacactagaa gaacagtatt   4020
tggtatctgc gctctgctga agccagttac cttcggaaaa agagttggta gctcttgatc   4080
cggcaaacaa accaccgctg gtagcggtgg ttttttttgtt tgcaagcagc agattacgcg   4140
cagaaaaaaa ggatctcaag aagatccttt gatcttttct acggggtctg acgctcagtg   4200
gaacgaaaac tcacgttaag ggattttggt catgagatta tcaaaaagga tcttcaccta   4260 gatccttttaa aattaaaaat gaagttttaa atcaatctaa agtatatatg agtaaacttg   4320
gtctgacagt taccaatgct taatcagtga ggcacctatc tcagcgatct gtctatttcg   4380
ttcatccata gttgcctgac tccccgtcgt gtagataact acgatacggg agggcttacc   4440
atctggcccc agtgctgcaa tgataccgcg agacccacgc tcaccggctc cagatttatc   4500
agcaataaac cagccagccg gaagggccga gcgcagaagt ggtcctgcaa ctttatccgc   4560
ctccatccag tctattaatt gttgccggga agctagagta agtagttcgc cagttaatag   4620
tttgcgcaac gttgttgcca ttgctacagg catcgtggtg tcacgctcgt cgtttggtat   4680
ggcttcattc agctccggtt cccaacgatc aaggcgagtt acatgatccc ccatgttgtg   4740
caaaaaagcg gttagctcct tcggtcctcc gatcgttgtc agaagtaagt tggccgcagt   4800
gttatcactc atggttatgg cagcactgca taattctctt actgtcatgc catccgtaag   4860
atgcttttct gtgactggtg agtactcaac caagtcattc tgagaatagt gtatgcggcg   4920
accgagttgc tcttgcccgg cgtcaatacg ggataatacc gcgccacata gcagaacttt   4980
aaaagtgctc atcattggaa aacgttcttc ggggcgaaaa ctctcaagga tcttaccgct   5040
gttgagatcc agttcgatgt aacccactcg tgcacccaac tgatcttcag catcttttac   5100
tttcaccagc gtttctgggt gagcaaaaac aggaaggcaa aatgccgcaa aaaagggaat   5160
aagggcgaca cggaaatgtt gaatactcat actcttcctt tttcaatatt attgaagcat   5220
ttatcagggt tattgtctca tgagcggata catatttgaa tgtatttaga aaaataaaca   5280
aataggggtt ccgcgcacat ttccccgaaa agtgccacct gatgcggtgt gaaataccgc   5340
acagatgcgt aaggagaaaa taccgcatca ggaaattgta agcgttaata ttttgttaaa   5400
attcgcgtta aattttttgtt aaatcagctc attttttaac caataggccg aaatcggcaa   5460
aatcccttat aaatcaaaag aatagaccga gatagggttg agtgttgttc cagtttggaa   5520
caagagtcca ctattaaaga acgtggactc caacgtcaaa gggcgaaaaa ccgtctatca   5580
gggcgatggc ccactacgtg aaccatcacc ctaatcaagt tttttggggt cgaggtgccg   5640
taaagcacta aatcggaacc ctaaagggag cccccgattt agagcttgac ggggaaagcc   5700
ggcgaacgtg gcgagaaagg aagggaagaa agcgaaagga gcgggcgcta gggcgctggc   5760
aagtgtagcg gtcacgctgc gcgtaaccac cacacccgcc gcgcttaatg cgccgctaca   5820
gggcgcgtcc attcgccatt caggctgcgc aactgttggg aagggcgatc ggtgcgggcc   5880
tcttcgctat tacgccagct ggcgaaaggg ggatgtgctg caaggcgatt aagttgggta   5940
acgccagggt tttcccagtc acgacgttgt aaaacgacgg ccagtgaatt gtaatacgac   6000
tcactatagg gcgaattggg cccgacgtcg catgcattcc gacagcagcg actgggcacc   6060
atgatcaagc gaaacacctt ccccccagctg ccctggcaaa ccatcaagaa ccctactttc   6120
atcaagtgca gaacggttc tactcttctc acctccggtg tctacggctg gtgccgaaag   6180
cctaactaca ccgctgattt catcatgtgc ctcacctggg ctctcatgtg cggtgttgct   6240
```

```
tctcccctgc cttacttcta cccggtcttc ttcttcctgg tgctcatcca ccgagcttac   6300
cgagactttg agcgactgga gcgaaagtac ggtgaggact accaggagtt caagcgacag   6360
gtcccttgga tcttcatccc ttatgttttc taaacgataa gcttagtgag cgaatggtga   6420
ggttacttaa ttgagtggcc agcctatggg attgtataac agacagtcaa tatattactg   6480
aaaagactga acagccagac ggagtgaggt tgtgagtgaa tcgtagaggg cggctattac   6540
agcaagtcta ctctacagtg tactaacaca gcagagaaca aatacaggtg tgcattcggc   6600
tatctgagaa ttagttggag agctcgagac cctcggcgat aaactgctcc tcggttttgt   6660
gtccatactt gtacggacca ttgtaatggg gcaagtcgtt gagttctcgt cgtccgacgt   6720
tcagagcaca gaaaccaatg taatcaatgt agcagagatg gttctgcaaa agattgattt   6780
gtgcgagcag gttaattaag tcatacacaa gtcagctttc ttcgagcctc atataagtat   6840
aagtagttca acgtattagc actgtaccca gcatctccgt atcgagaaac acaacaacat   6900
gccccattgg acagatcatg cggatacaca ggttgtgcag tatcatacat actcgatcag   6960
acaggtcgtc tgaccatcat acaagctgaa caagcgctcc atacttgcac gctctctata   7020
tacacagtta aattacatat ccatagtcta acctctaaca gttaatcttc tggtaagcct   7080
cccagccagc cttctggtat cgcttggcct cctcaatagg atctcggttc tggccgtaca   7140
gacctcggcc gacaattatg atatccgttc cggtagacat gacatcctca acagttcggt   7200
actgctgtcc gagagcgtct cccttgtcgt caagacccac cccgggggtc agaataagcc   7260
agtcctcaga gtcgcccta ggtcggttct gggcaatgaa gccaaccaca aactcggggt   7320
cggatcgggc aagctcaatg gtctgcttgg agtactcgcc agtggccaga gagcccttgc   7380
aagacagctc ggccagcatg agcagacctc tggccagctt ctcgttggga gaggggacta   7440
ggaactcctt gtactgggag ttctcgtagt cagagacgtc ctccttcttc tgttcagaga   7500
cagtttcctc ggcaccagct cgcaggccag caatgattcc ggttccgggt acaccgtggg   7560
cgttggtgat atcggaccac tcggcgattc ggtgacaccg gtactggtgc ttgacagtgt   7620
tgccaatatc tgcgaacttt ctgtcctcga acaggaagaa accgtgctta agagcaagtt   7680
ccttgagggg gagcacagtg ccggcgtagg tgaagtcgtc aatgatgtcg atatgggttt   7740
tgatcatgca cacataaggt ccgacccttat cggcaagctc aatgagctcc ttggtggtgg   7800
taacatccag agaagcacac aggttggttt tcttggctgc cacgagcttg agcactcgag   7860
cggcaaaggc ggacttgtgg acgttagctc gagcttcgta ggagggcatt ttggtggtga   7920
agaggagact gaaataaatt tagtctgcag aacttttat cggaaccta tctggggcag   7980 tgaagtatat gttatggtaa tagttacgag ttagttgaac ttatagatag actggactat   8040
acggctatcg gtccaaatta gaaagaacgt caatggctct ctgggcgtcg cctttgccga   8100
caaaaatgtg atcatgatga aagccagcaa tgacgttgca gctgatattg ttgtcggcca   8160
accgcgccga aaacgcagct gtcagaccca cagcctccaa cgaagaatgt atcgtcaaag   8220
tgatccaagc acactcatag ttggagtcgt actccaaagg cggcaatgac gagtcagaca   8280
gatactcgtc gacgtttaaa cagtgtacgc agatctacta tagaggaaca tttaaattgc   8340
cccggagaag acggccaggc cgcctagatg acaaattcaa caactcacag ctgactttct   8400
gccattgcca ctagggggg ggccttttat atggccaagc caagctctcc acgtcggttg   8460
ggctgcaccc aacaataaat gggtagggtt gcaccaacaa agggatggga tggggggtag   8520
aagatacgag gataacgggg ctcaatggca caaataagaa cgaatactgc cattaagact   8580
cgtgatccag cgactgacac cattgcatca tctaagggcc tcaaaactac ctcggaactg   8640
```

-continued

```
ctgcgctgat ctggacacca cagaggttcc gagcacttta ggttgcacca aatgtcccac   8700
caggtgcagg cagaaaacgc tggaacagcg tgtacagttt gtcttaacaa aaagtgaggg   8760
cgctgaggtc gagcagggtg gtgtgacttg ttatagcctt tagagctgcg aaagcgcgta   8820
tggatttggc tcatcaggcc agattgaggg tctgtggaca catgtcatgt tagtgtactt   8880
caatcgcccc ctggatatag ccccgacaat aggccgtggc ctcattttt tgccttccgc    8940 acatttccat tgctcgatac ccacaccttg cttctcctgc acttgccaac cttaatactg   9000
gtttacattg accaacatct tacaagcggg gggcttgtct agggtatata taaacagtgg   9060
ctctcccaat cggttgccag tctcttttt cctttctttc cccacagatt cgaaatctaa    9120
actacacatc acagaattcc gagccgtgag tatccacgac aagatcagtg tcgagacgac   9180
gcgttttgtg taatgacaca atccgaaagt cgctagcaac acacactctc tacacaaact   9240
aacccagctc tggtac                                                    9256

<210> SEQ ID NO 19
<211> LENGTH: 2058
<212> TYPE: DNA
<213> ORGANISM: Artificial Sequence
<220> FEATURE:
<223> OTHER INFORMATION: Fusion
<220> FEATURE:
<221> NAME/KEY: CDS
<222> LOCATION: (1)..(2058)
<223> OTHER INFORMATION: XPR2PP+13/m-ScSUC2

<400> SEQUENCE: 19 atg gag ctc gct acc gcc ttt act att ctc act gcc gtt ctg gcc gct     48
Met Glu Leu Ala Thr Ala Phe Thr Ile Leu Thr Ala Val Leu Ala Ala
1               5                   10                  15 ccc ctg gcc gcc cct gcc cct gct cct gat gct gcc cct gct gct gtg     96
Pro Leu Ala Ala Pro Ala Pro Ala Pro Asp Ala Ala Pro Ala Ala Val
            20                  25                  30 cct gag ggc cct gcc gcc gct gcc tac tca tct att ctg tcc gtg gtc    144
Pro Glu Gly Pro Ala Ala Ala Ala Tyr Ser Ser Ile Leu Ser Val Val
        35                  40                  45 gct aag cag tcc aag aag ttt aag cac cac aag cga gat ctt gat gag    192
Ala Lys Gln Ser Lys Lys Phe Lys His His Lys Arg Asp Leu Asp Glu
    50                  55                  60 aag gat cag ttc atc gtt gtc ttt gac agt agc gct act gtt gac cag    240
Lys Asp Gln Phe Ile Val Val Phe Asp Ser Ser Ala Thr Val Asp Gln
65                  70                  75                  80 atc gcc tcc gaa atc cag aag ctg gac tct ctg gtc gac gag gac tcg    288
Ile Ala Ser Glu Ile Gln Lys Leu Asp Ser Leu Val Asp Glu Asp Ser
                85                  90                  95 tcc aac ggt atc acc tct gct ctt gat ctt cct gtc tac acg gat gga    336
Ser Asn Gly Ile Thr Ser Ala Leu Asp Leu Pro Val Tyr Thr Asp Gly
            100                 105                 110 tct ggc ttt ctc gga ttt gtt gga aag ttc aac tcc act atc gtt gac    384
Ser Gly Phe Leu Gly Phe Val Gly Lys Phe Asn Ser Thr Ile Val Asp
        115                 120                 125 aag ctc aag gag tcg tct gtt ctg acg gtc gag ccc gat acc att gtg    432
Lys Leu Lys Glu Ser Ser Val Leu Thr Val Glu Pro Asp Thr Ile Val
    130                 135                 140 tct ctc ccc gag att cct gct tct tct aat gcc aag cga gct atc cag    480
Ser Leu Pro Glu Ile Pro Ala Ser Ser Asn Ala Lys Arg Ala Ile Gln
145                 150                 155                 160 act act ccc gtc act caa tgg ggc ctg tct aac atg tca atg aca aac    528
Thr Thr Pro Val Thr Gln Trp Gly Leu Ser Asn Met Ser Met Thr Asn
                165                 170                 175
```

```
                                          -continued gaa act agc gat aga cct ttg gtc cac ttc aca ccc aac aag ggc tgg        576
Glu Thr Ser Asp Arg Pro Leu Val His Phe Thr Pro Asn Lys Gly Trp
        180                 185                 190 atg aat gac cca aat ggg ttg tgg tac gat gaa aaa gat gcc aaa tgg        624
Met Asn Asp Pro Asn Gly Leu Trp Tyr Asp Glu Lys Asp Ala Lys Trp
            195                 200                 205 cat ctg tac ttt caa tac aac cca aat gac acc gta tgg ggt acg cca        672
His Leu Tyr Phe Gln Tyr Asn Pro Asn Asp Thr Val Trp Gly Thr Pro
    210                 215                 220 ttg ttt tgg ggc cat gct act tcc gat gat ttg act aat tgg gaa gat        720
Leu Phe Trp Gly His Ala Thr Ser Asp Asp Leu Thr Asn Trp Glu Asp
225                 230                 235                 240 caa ccc att gct atc gct ccc aag cgt aac gat tca ggt gct ttc tct        768
Gln Pro Ile Ala Ile Ala Pro Lys Arg Asn Asp Ser Gly Ala Phe Ser
                245                 250                 255 ggc tcc atg gtg gtt gat tac aac aac acg agt ggg ttt ttc aat gat        816
Gly Ser Met Val Val Asp Tyr Asn Asn Thr Ser Gly Phe Phe Asn Asp
            260                 265                 270 act att gat cca aga caa aga tgc gtt gcg att tgg act tat aac act        864
Thr Ile Asp Pro Arg Gln Arg Cys Val Ala Ile Trp Thr Tyr Asn Thr
    275                 280                 285 cct gaa agt gaa gag caa tac att agc tat tct ctt gat ggt ggt tac        912
Pro Glu Ser Glu Glu Gln Tyr Ile Ser Tyr Ser Leu Asp Gly Gly Tyr
290                 295                 300 act ttt act gaa tac caa aag aac cct gtt tta gct gcc aac tcc act        960
Thr Phe Thr Glu Tyr Gln Lys Asn Pro Val Leu Ala Ala Asn Ser Thr
305                 310                 315                 320 caa ttc aga gat cca aag gtg ttc tgg tat gaa cct tct caa aaa tgg       1008
Gln Phe Arg Asp Pro Lys Val Phe Trp Tyr Glu Pro Ser Gln Lys Trp
                325                 330                 335 att atg acg gct gcc aaa tca caa gac tac aaa att gaa att tac tcc       1056
Ile Met Thr Ala Ala Lys Ser Gln Asp Tyr Lys Ile Glu Ile Tyr Ser
            340                 345                 350 tct gat gac ttg aag tcc tgg aag cta gaa tct gca ttt gcc aat gaa       1104
Ser Asp Asp Leu Lys Ser Trp Lys Leu Glu Ser Ala Phe Ala Asn Glu
    355                 360                 365 ggt ttc tta ggc tac caa tac gaa tgt cca ggt ttg att gaa gtc cca       1152
Gly Phe Leu Gly Tyr Gln Tyr Glu Cys Pro Gly Leu Ile Glu Val Pro
370                 375                 380 act gag caa gat cct tcc aaa tct tat tgg gtc atg ttt att tct atc       1200
Thr Glu Gln Asp Pro Ser Lys Ser Tyr Trp Val Met Phe Ile Ser Ile
385                 390                 395                 400 aac cca ggt gca cct gct ggc ggt tcc ttc aac caa tat ttt gtt gga       1248
Asn Pro Gly Ala Pro Ala Gly Gly Ser Phe Asn Gln Tyr Phe Val Gly
                405                 410                 415 tcc ttc aat ggt act cat ttt gaa gcg ttt gac aat caa tct aga gtg       1296
Ser Phe Asn Gly Thr His Phe Glu Ala Phe Asp Asn Gln Ser Arg Val
            420                 425                 430 gta gat ttt ggt aag gac tac tat gcc ttg caa act ttc ttc aac act       1344
Val Asp Phe Gly Lys Asp Tyr Tyr Ala Leu Gln Thr Phe Phe Asn Thr
    435                 440                 445 gac cca acc tac ggt tca gca tta ggt att gcc tgg gct tca aac tgg       1392
Asp Pro Thr Tyr Gly Ser Ala Leu Gly Ile Ala Trp Ala Ser Asn Trp
450                 455                 460 gag tac agt gcc ttt gtc cca act aac cca tgg aga tca tcc atg tct       1440
Glu Tyr Ser Ala Phe Val Pro Thr Asn Pro Trp Arg Ser Ser Met Ser
465                 470                 475                 480 ttg gtc cgc aag ttt tct ttg aac act gaa tat caa gct aat cca gag       1488
Leu Val Arg Lys Phe Ser Leu Asn Thr Glu Tyr Gln Ala Asn Pro Glu
                485                 490                 495
```

```
act gaa ttg atc aat ttg aaa gcc gaa cca ata ttg aac att agt aat      1536
Thr Glu Leu Ile Asn Leu Lys Ala Glu Pro Ile Leu Asn Ile Ser Asn
            500                 505                 510 gct ggt ccc tgg tct cgt ttt gct act aac aca act cta act aag gcc      1584
Ala Gly Pro Trp Ser Arg Phe Ala Thr Asn Thr Thr Leu Thr Lys Ala
        515                 520                 525 aat tct tac aat gtc gat ttg agc aac tcg act ggt acc cta gag ttt      1632
Asn Ser Tyr Asn Val Asp Leu Ser Asn Ser Thr Gly Thr Leu Glu Phe
    530                 535                 540 gag ttg gtt tac gct gtt aac acc aca caa acc ata tcc aaa tcc gtc      1680
Glu Leu Val Tyr Ala Val Asn Thr Thr Gln Thr Ile Ser Lys Ser Val
545                 550                 555                 560 ttt gcc gac tta tca ctt tgg ttc aag ggt tta gaa gat cct gaa gaa      1728
Phe Ala Asp Leu Ser Leu Trp Phe Lys Gly Leu Glu Asp Pro Glu Glu
                565                 570                 575 tat ttg aga atg ggt ttt gaa gtc agt gct tct tcc ttc ttt ttg gac      1776
Tyr Leu Arg Met Gly Phe Glu Val Ser Ala Ser Ser Phe Phe Leu Asp
            580                 585                 590 cgt ggt aac tct aag gtc aag ttt gtc aag gag aac cca tat ttc aca      1824
Arg Gly Asn Ser Lys Val Lys Phe Val Lys Glu Asn Pro Tyr Phe Thr
        595                 600                 605 aac aga atg tct gtc aac aac caa cca ttc aag tct gag aac gac cta      1872
Asn Arg Met Ser Val Asn Asn Gln Pro Phe Lys Ser Glu Asn Asp Leu
    610                 615                 620 agt tac tat aaa gtg tac ggc cta ctg gat caa aac atc ttg gaa ttg      1920
Ser Tyr Tyr Lys Val Tyr Gly Leu Leu Asp Gln Asn Ile Leu Glu Leu
625                 630                 635                 640 tac ttc aac gat gga gat gtg gtt tct aca aat acc tac ttc atg acc      1968
Tyr Phe Asn Asp Gly Asp Val Val Ser Thr Asn Thr Tyr Phe Met Thr
                645                 650                 655 acc ggt aac gct cta gga tct gtg aac atg acc act ggt gtc gat aat      2016
Thr Gly Asn Ala Leu Gly Ser Val Asn Met Thr Thr Gly Val Asp Asn
            660                 665                 670 ttg ttc tac att gac aag ttc caa gta agg gaa gta aaa tag              2058
Leu Phe Tyr Ile Asp Lys Phe Gln Val Arg Glu Val Lys
        675                 680                 685

<210> SEQ ID NO 20
<211> LENGTH: 685
<212> TYPE: PRT
<213> ORGANISM: Artificial Sequence
<220> FEATURE:
<223> OTHER INFORMATION: Synthetic Construct

<400> SEQUENCE: 20

Met Glu Leu Ala Thr Ala Phe Thr Ile Leu Thr Ala Val Leu Ala Ala
1               5                   10                  15

Pro Leu Ala Ala Pro Ala Pro Ala Pro Asp Ala Ala Pro Ala Ala Val
            20                  25                  30

Pro Glu Gly Pro Ala Ala Ala Tyr Ser Ser Ile Leu Ser Val Val
        35                  40                  45

Ala Lys Gln Ser Lys Lys Phe Lys His His Lys Arg Asp Leu Asp Glu
    50                  55                  60

Lys Asp Gln Phe Ile Val Val Phe Asp Ser Ser Ala Thr Val Asp Gln
65                  70                  75                  80

Ile Ala Ser Glu Ile Gln Lys Leu Asp Ser Leu Val Asp Glu Asp Ser
                85                  90                  95

Ser Asn Gly Ile Thr Ser Ala Leu Asp Leu Pro Val Tyr Thr Asp Gly
            100                 105                 110
```

-continued

```
Ser Gly Phe Leu Gly Phe Val Gly Lys Phe Asn Ser Thr Ile Val Asp
        115                 120                 125
Lys Leu Lys Glu Ser Ser Val Leu Thr Val Glu Pro Asp Thr Ile Val
130                 135                 140
Ser Leu Pro Glu Ile Pro Ala Ser Ser Asn Ala Lys Arg Ala Ile Gln
145                 150                 155                 160
Thr Thr Pro Val Thr Gln Trp Gly Leu Ser Asn Met Ser Met Thr Asn
                165                 170                 175
Glu Thr Ser Asp Arg Pro Leu Val His Phe Thr Pro Asn Lys Gly Trp
            180                 185                 190
Met Asn Asp Pro Asn Gly Leu Trp Tyr Asp Lys Ala Lys Trp
        195                 200                 205
His Leu Tyr Phe Gln Tyr Asn Pro Asn Asp Thr Val Trp Gly Thr Pro
    210                 215                 220
Leu Phe Trp Gly His Ala Thr Ser Asp Asp Leu Thr Asn Trp Glu Asp
225                 230                 235                 240
Gln Pro Ile Ala Ile Ala Pro Lys Arg Asn Asp Ser Gly Ala Phe Ser
                245                 250                 255
Gly Ser Met Val Val Asp Tyr Asn Asn Thr Ser Gly Phe Phe Asn Asp
            260                 265                 270
Thr Ile Asp Pro Arg Gln Arg Cys Val Ala Ile Trp Thr Tyr Asn Thr
    275                 280                 285
Pro Glu Ser Glu Glu Gln Tyr Ile Ser Tyr Ser Leu Asp Gly Gly Tyr
290                 295                 300
Thr Phe Thr Glu Tyr Gln Lys Asn Pro Val Leu Ala Ala Asn Ser Thr
305                 310                 315                 320
Gln Phe Arg Asp Pro Lys Val Phe Trp Tyr Glu Pro Ser Gln Lys Trp
                325                 330                 335
Ile Met Thr Ala Ala Lys Ser Gln Asp Tyr Lys Ile Glu Ile Tyr Ser
            340                 345                 350
Ser Asp Asp Leu Lys Ser Trp Lys Leu Glu Ser Ala Phe Ala Asn Glu
    355                 360                 365
Gly Phe Leu Gly Tyr Gln Tyr Glu Cys Pro Gly Leu Ile Glu Val Pro
370                 375                 380
Thr Glu Gln Asp Pro Ser Lys Ser Tyr Trp Val Met Phe Ile Ser Ile
385                 390                 395                 400
Asn Pro Gly Ala Pro Ala Gly Gly Ser Phe Asn Gln Tyr Phe Val Gly
                405                 410                 415
Ser Phe Asn Gly Thr His Phe Glu Ala Phe Asp Asn Gln Ser Arg Val
            420                 425                 430
Val Asp Phe Gly Lys Asp Tyr Tyr Ala Leu Gln Thr Phe Phe Asn Thr
    435                 440                 445
Asp Pro Thr Tyr Gly Ser Ala Leu Gly Ile Ala Trp Ala Ser Asn Trp
450                 455                 460
Glu Tyr Ser Ala Phe Val Pro Thr Asn Pro Trp Arg Ser Ser Met Ser
465                 470                 475                 480
Leu Val Arg Lys Phe Ser Leu Asn Thr Glu Tyr Gln Ala Asn Pro Glu
                485                 490                 495
Thr Glu Leu Ile Asn Leu Lys Ala Glu Pro Ile Leu Asn Ile Ser Asn
            500                 505                 510
Ala Gly Pro Trp Ser Arg Phe Ala Thr Asn Thr Thr Leu Thr Lys Ala
    515                 520                 525
Asn Ser Tyr Asn Val Asp Leu Ser Asn Ser Thr Gly Thr Leu Glu Phe
530                 535                 540
```

```
Glu Leu Val Tyr Ala Val Asn Thr Thr Gln Thr Ile Ser Lys Ser Val
545                 550                 555                 560

Phe Ala Asp Leu Ser Leu Trp Phe Lys Gly Leu Glu Asp Pro Glu Glu
                565                 570                 575

Tyr Leu Arg Met Gly Phe Glu Val Ser Ala Ser Ser Phe Phe Leu Asp
            580                 585                 590

Arg Gly Asn Ser Lys Val Lys Phe Val Lys Glu Asn Pro Tyr Phe Thr
        595                 600                 605

Asn Arg Met Ser Val Asn Asn Gln Pro Phe Lys Ser Glu Asn Asp Leu
    610                 615                 620

Ser Tyr Tyr Lys Val Tyr Gly Leu Leu Asp Gln Asn Ile Leu Glu Leu
625                 630                 635                 640

Tyr Phe Asn Asp Gly Asp Val Val Ser Thr Asn Thr Tyr Phe Met Thr
                645                 650                 655

Thr Gly Asn Ala Leu Gly Ser Val Asn Met Thr Thr Gly Val Asp Asn
            660                 665                 670

Leu Phe Tyr Ile Asp Lys Phe Gln Val Arg Glu Val Lys
        675                 680                 685

<210> SEQ ID NO 21
<211> LENGTH: 9202
<212> TYPE: DNA
<213> ORGANISM: Artificial Sequence
<220> FEATURE:
<223> OTHER INFORMATION: Plasmid pYRH74

<400> SEQUENCE: 21
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt tcacttgag tgcagtggct      240 agtgctctta ctcgtacagt gtgcaatact gcgtatcata gtctttgatg tatatcgtat     300
tcattcatgt tagttgcgta cgttgattga ggtggagcca gatgggctat tgtttcatat     360
atagactggc agccacctct ttggcccagc atgtttgtat acctggaagg gaaaactaaa     420
gaagctggct agtttagttt gattattata gtagatgtcc taatcactag agattagaat     480
gtcttggcga tgattagtcg tcgtcccctg tatcatgtct agaccaactg tgtcatgaag     540
ttggtgctgg tgttttacct gtgtactaca agtaggtgtc ctagatctag tgtacagagc     600
cgtttagacc catgtggact tcaccattaa cgatggaaaa tgttcattat atgacagtat     660
attacaatgg acttgctcca tttcttcctt gcatcacatg ttctccacct ccatagttga     720
tcaacacatc atagtagcta aggctgctgc tctcccacta cagtccacca caagttaagt     780
agcaccgtca gtacagctaa agtacacgt ctagtacgtt tcataactag tcaagtagcc     840
cctattacag atatcagcac tatcacgcac gagtttttct ctgtgctatc taatcaactt     900
gccaagtatt cggagaagat acactttctt ggcatcaggt atacgaggga gcctatcaga     960
tgaaaaaggg tatattggat ccattcatat ccacctacac gttgtcataa tctcctcatt    1020
cacgtgattc atttcgtgac actagtttct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
```

```
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga agaacatgt gagcaaaagg ccagcaaaag gccaggaacc gtaaaaaggc     1440
cgcgttgctg gcgttttcc ataggctccg ccccctgac gagcatcaca aaatcgacg      1500 ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc caacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaaagagt tggtagctct tgatccggca acaaaccac     1980 cgctggtagc ggtggttttt tgtttgcaa gcagcagatt acgcgcagaa aaaaggatc     2040 tcaagaagat cctttgatct tttctacggg gtctgacgct cagtggaacg aaaactcacg    2100
ttaagggatt ttggtcatga gattatcaaa aaggatcttc acctagatcc ttttaaatta    2160 aaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca tacgggata ataccgcgcc acatagcaga actttaaaag tgctcatcat     2880
tggaaaacgt tcttcggggc gaaaactctc aaggatctta ccgctgttga tccagttc     2940 gatgtaaccc actcgtgcac ccaactgatc ttcagcatct tttactttca ccagcgtttc    3000
tgggtgagca aaaacaggaa ggcaaaatgc cgcaaaaaag gaataaggg cgacacggaa    3060 atgttgaata ctcatactct ccttttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagttttt ggggtcgagg tgccgtaaag cactaaatcg     3540
gaaccctaaa gggagccccc gatttagagc ttgacgggga agccggcgaa cgtggcgag    3600 aaaggaaggg aagaaagcga aaggagcggg cgctagggcg ctggcaagtg tagcggtcac    3660
```

```
gctgcgcgta accaccacac ccgccgcgct taatgcgccg ctacagggcg cgtccattcg   3720
ccattcaggc tgcgcaactg ttgggaaggg cgatcggtgc gggcctcttc gctattacgc   3780
cagctggcga aaggggatg tgctgcaagg cgattaagtt gggtaacgcc aggggttttcc   3840 cagtcacgac gttgtaaaac gacgccagt gaattgtaat acgactcact atagggcgaa   3900
ttgggcccga cgtcgcatgc attccgacag cagcgactgg gcaccatgat caagcgaaac   3960
acctttcccc agctgccctg gcaaaccatc aagaaccta ctttcatcaa gtgcaagaac   4020
ggttctactc ttctcaccte cggtgtctac ggctggtgcc gaaagcctaa ctacaccgct   4080
gatttcatca tgtgcctcac ctgggctctc atgtgcggtg ttgcttctcc cctgccttac   4140
ttctacccgg tcttcttctt cctggtgctc atccaccgag cttaccgaga ctttgagcga   4200
ctggagcgaa agtacggtga ggactaccag gagttcaagc gacaggtccc ttggatcttc   4260
atcccttatg ttttctaaac gataagctta gtgagcgaat ggtgaggtta cttaattgag   4320
tggccagcct atgggattgt ataacagaca gtcaatatat tactgaaaag actgaacagc   4380
cagacggagt gaggttgtga gtgaatcgta gagggcggct attacagcaa gtctactcta   4440
cagtgtacta acacagcaga gaacaaatac aggtgtgcat tcggctatct gagaattagt   4500
tggagagctc gagacccteg gcgataaact gctcctcggt tttgtgtcca tacttgtacg   4560
gaccattgta atggggcaag tcgttgagtt ctcgtcgtcc gacgttcaga gcacagaaac   4620
caatgtaatc aatgtagcag agatggttct gcaaaagatt gatttgtgcg agcaggttaa   4680
ttaagtcata cacaagtcag ctttcttcga gcctcatata agtataagta gttcaacgta   4740
ttagcactgt acccagcatc tccgtatcga gaaacacaac aacatgcccc attggacaga   4800
tcatgcggat acacaggttg tgcagtatca tacatactcg atcagacagg tcgtctgacc   4860
atcatacaag ctgaacaagc gctccatact tgcacgctct ctatatacac agttaaatta   4920
catatccata gtctaaccte taacagttaa tcttctggta agcctcccag ccagccttct   4980
ggtatcgctt ggcctcctca ataggatctc ggttctggcc gtacagacct cggccgacaa   5040
ttatgatatc cgttccggta gacatgacat cctcaacagt tcggtactgc tgtccgagag   5100 cgtctcccett gtcgtcaaga cccacccegg gggtcagaat aagccagtcc tcagagtcgc   5160
ccttaggtcg gttctgggca atgaagccaa ccacaaactc ggggtcggat cgggcaagct   5220
caatggtctg cttggagtac tcgccagtgg ccagagagcc cttgcaagac agctcggcca   5280
gcatgagcag acctctggcc agcttctcgt tgggagaggg gactaggaac tccttgtact   5340
gggagttctc gtagtcagag acgtcctcct tcttctgttc agagacagtt tcctcggcac   5400
cagctcgcag gccagcaatg attccggttc cgggtacacc gtgggcgttg gtgatatcgg   5460
accactcggc gattcggtga caccggtact ggtgcttgac agtgttgcca atatctgcga   5520
actttctgtc ctcgaacagg aagaaaccgt gcttaagagc aagttccttg aggggagca   5580 cagtgccggg gtaggtgaag tcgtcaatga tgtcgatatg gttttgatc atgcacacat   5640 aaggtccgac cttatcggca agctcaatga gctccttggt ggtggtaaca tccagagaag   5700
cacacaggtt ggttttcttg gctgccacga gcttgagcac tcgagcggca aggcggact   5760 tgtggacgtt agctcgagct tcgtaggagg gcattttggt ggtgaagagg agactgaaat   5820
aaatttagtc tgcagaactt tttatcggaa ccttatctgg ggcagtgaag tatatgttat   5880
ggtaatagtt acgagttagt tgaacttata gatagactgg actatacggc tatcggtcca   5940
aattagaaag aacgtcaatg gctctctggg cgtcgccttt gccgacaaaa atgtgatcat   6000
gatgaaagcc agcaatgacg ttgcagctga tattgttgtc ggccaaccgc gccgaaaacg   6060
```

```
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300
ggggggcctt tttatatggc caagccaagc tctccacgtc ggttgggctg cacccaacaa    6360
taaatgggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gcccctggaa    6780
tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcggggggct tgtctagggt atatataaac agtggctctc ccaatcggtt    6960
gccagtctct tttttccttt ctttccccac agattcgaaa tctaaactac acatcacaga    7020
attccgagcc gtgagtatcc acgacaagat cagtgtcgag acgacgcgtt tgtgtaatg    7080 acacaatccg aaagtcgcta gcaacacaca ctctctacac aaactaaccc agctctggta    7140
ccatggagct cgctaccgcc tttactattc tcactgccgt tctggccgct cccctggccg    7200
cccctgcccc tgctcctgat gctgcccctg ctgctgtgcc tgagggccct gccgccgctg    7260
cctactcatc tattctgtcc gtggtcgcta agcagtccaa gaagtttaag caccacaagc    7320
gagatcttga tgagaaggat cagttcatcg ttgtctttga cagtagcgct actgttgacc    7380
agatcgcctc cgaaatccag aagctggact ctctggtcga cgaggactcg tccaacggta    7440
tcacctctgc tcttgatctt cctgtctaca cggatggatc tggctttctc ggatttgttg    7500
gaaagttcaa ctccactatc gttgacaagc tcaaggagtc gtctgttctg acggtcgagc    7560
ccgataccat tgtgtctctc cccgagattc ctgcttcttc taatgccaag cgagctatcc    7620
agactactcc cgtcactcaa tggggcctgt ctaacatgtc aatgacaaac gaaactagcg    7680
atagaccttt ggtccacttc acacccaaca agggctggat gaatgaccca aatgggttgt    7740
ggtacgatga aaaagatgcc aaatggcatc tgtactttca atacaaccca aatgacaccg    7800
tatggggtac gccattgttt tggggccatg ctacttccga tgatttgact aattgggaag    7860
atcaacccat tgctatcgct cccaagcgta acgattcagg tgctttctct ggctccatgg    7920
tggttgatta caacaacacg agtgggtttt tcaatgatac tattgatcca agacaaagat    7980
gcgttgcgat ttggacttat aacactcctg aaagtgaaga gcaatacatt agctattctc    8040
ttgatggtgg ttacactttt actgaatacc aaaagaaccc tgttttagct gccaactcca    8100
ctcaattcag agatccaaag gtgttctggt atgaaccttc tcaaaaatgg attatgacgg    8160
ctgccaaatc acaagactac aaaattgaaa tttactcctc tgatgacttg aagtcctgga    8220
agctagaatc tgcatttgcc aatgaaggtt tcttaggcta ccaatacgaa tgtccaggtt    8280
tgattgaagt cccaactgag caagatcctt ccaaatctta ttgggtcatg tttatttcta    8340
tcaacccagg tgcacctgct ggcggttcct caaccaata ttttgttgga tccttcaatg    8400
gtactcattt tgaagcgttt gacaatcaat ctagagtggt agattttggt aaggactact    8460
```

-continued

| | |
|---|---|
| atgccttgca aactttcttc aacactgacc caacctacgg ttcagcatta ggtattgcct | 8520 |
| gggcttcaaa ctgggagtac agtgcctttg tcccaactaa cccatggaga tcatccatgt | 8580 |
| ctttggtccg caagttttct ttgaacactg aatatcaagc taatccagag actgaattga | 8640 |
| tcaatttgaa agccgaacca atattgaaca ttagtaatgc tggtccctgg tctcgttttg | 8700 |
| ctactaacac aactctaact aaggccaatt cttacaatgt cgatttgagc aactcgactg | 8760 |
| gtaccctaga gtttgagttg gtttacgctg ttaacaccac acaaaccata tccaaatccg | 8820 |
| tctttgccga cttatcactt tggttcaagg gtttagaaga tcctgaagaa tatttgagaa | 8880 |
| tgggttttga agtcagtgct tcttccttct ttttggaccg tggtaactct aaggtcaagt | 8940 |
| ttgtcaagga gaacccatat ttcacaaaca gaatgtctgt caacaaccaa ccattcaagt | 9000 |
| ctgagaacga cctaagttac tataaagtgt acggcctact ggatcaaaac atcttggaat | 9060 |
| tgtacttcaa cgatggagat gtggtttcta caaatacctta cttcatgacc accggtaacg | 9120 |
| ctctaggatc tgtgaacatg accactggtg tcgataattt gttctacatt gacaagttcc | 9180 |
| aagtaaggga agtaaaatag gc | 9202 |

<210> SEQ ID NO 22
<211> LENGTH: 9016
<212> TYPE: DNA
<213> ORGANISM: Artificial Sequence
<220> FEATURE:
<223> OTHER INFORMATION: Plasmid pZSUC

<400> SEQUENCE: 22

| | |
|---|---|
| cgatcccact acttgtagtc aggccatctt ttacgtacgc actgtaccat gatgtcaatg | 60 |
| gagtatgatg aaccgacttt gagagactca catctgcaca acaccatgtt tcagcggaat | 120 |
| ccgacttcca acccaaaccc aagcccctgt cagatatcgt gagaaggcac ggcaccaact | 180 |
| aatgcacaca ctccacctgt attgcaccaa gataatgagg gcatcgtctt ggcgcgtctt | 240 |
| ggcgagagcc gtgtttcgtg acgcaatcag agcagtttct ggatagtatc ttgtccagaa | 300 |
| acacgatata aacccatcg acgggcccgt tgaagagcac caacccacta tccaatcctc | 360 |
| caatccaaca atgaagctcg ctaccgcctt tactattctc actgccgttc tggccgctcc | 420 |
| cctggccgcc cctaagcttg ctggttttgc agccaaaata tctgcatcaa tgacaaacga | 480 |
| aactagcgat agacctttgg tccacttcac acccaacaag ggctggatga atgacccaaa | 540 |
| tgggttgtgg tacgatgaaa aagatgccaa atggcatctg tactttcaat acaacccaaa | 600 |
| tgacaccgta tggggtacgc cattgttttg gggccatgct acttccgatg atttgactaa | 660 |
| ttgggaagat caacccattg ctatcgctcc caagcgtaac gattcaggtg cttttctctgg | 720 |
| ctccatggtg gttgattaca acaacacgag tgggtttttc aatgatacta ttgatccaag | 780 |
| acaaagatgc gttgcgattt ggacttataa cactcctgaa agtgaagagc aatacattag | 840 |
| ctattctctt gatggtggtt acacttttac tgaataccaa aagaaccctg ttttagctgc | 900 |
| caactccact caattcagag atccaaaggt gttctggtat gaaccttctc aaaaatggat | 960 |
| tatgacggct gccaaatcac aagactacaa aattgaaatt tactcctctg atgacttgaa | 1020 |
| gtcctggaag ctagaatctg catttgccaa cgaaggtttc ttaggctacc aatacgaatg | 1080 |
| tccaggtttg attgaagtcc caactgagca agatccttcc aaatcttatt gggtcatgtt | 1140 |
| tatttctatc aacccaggtg cacctgctgg cggttccttc aaccaatatt tgttggatc | 1200 |
| cttcaatggt actcattttg aagcgtttga caatcaatct agagtggtag attttggtaa | 1260 |
| ggactactat gccttgcaaa cttttcttca cactgaccca acctacggtt cagcattagg | 1320 |

```
tattgcctgg gcttcaaact gggagtacag tgcctttgtc ccaactaacc catggagatc    1380
atccatgtct ttggtccgca agttttcttt gaacactgaa tatcaagcta atccagagac    1440
tgaattgatc aatttgaaag ccgaaccaat attgaacatt agtaatgctg gtccctggtc    1500
tcgttttgct actaacacaa ctctaactaa ggccaattct tacaatgtcg atttgagcaa    1560
ctcgactggt accctagagt ttgagttggt ttacgctgtt aacaccacac aaaccatatc    1620
caaatccgtc tttgccgact tatcactttg gttcaagggt ttagaagatc ctgaagaata    1680
tttgagaatg ggttttgaag tcagtgcttc ttccttcttt ttggaccgtg gtaactctaa    1740
ggtcaagttt gtcaaggaga acccatattt cacaaacaga atgtctgtca acaaccaacc    1800
attcaagtct gagaacgacc taagttacta taaagtgtac ggcctactgg atcaaaacat    1860
cttggaattg tacttcaacg atggagatgt ggtttctaca aatacctact tcatgaccac    1920
cggtaacgct ctaggatctg tgaacatgac cactggtgtc gataatttgt tctacattga    1980
caagttccaa gtaagggaag taaaatagcg tacggtgtgt atcgtagagg tagtgacgtg    2040
ttgtccacag ggcgactgtg tccgtgtata tatatattcc tcggcccgag cttatttgtg    2100
tggggttgag gaaatcaaac caaatcggta gtcagagaaa taaaacaaaa agaaataaaa    2160
agaaatagag gacgcacaac gccatcaccg tcggagagac aggagaaggg aaaatgggca    2220
aaaatgccct tatcacaccc gcccgctttg tgctctcatt cggctcccac aagagcctct    2280
tgtcctggtt ccccccccccc acattttaac accccacacg acgttgctgc acgtggaatt    2340
ttcggccgaa aacctgtggg gtacttactt ttggcactgg agagaagcat ctgggatttt    2400
gggaacctag gcagaagatg aggaaaaaaa taagaggaac cgttgtgagc ttgcttatca    2460
gtgtcatata ctcccccctc cttgcgtttt tgcgtctttt cccctatttt ttcaaatttt    2520
gcgatttttt ttctcttttt ttccgctttt ttccgctttt ttttggccg gcttttatcc     2580 atttctccaa gccgaggatc acatctatgc agcccagtcc gttggagcat atctgcggta    2640
gagtttcgga acggcgttaa gcactgtgtc cgggtcggtc tggaacgaga ttgagcggga    2700
aattcggggg aataagacca ccgttggact ccccgcaatg aggagatcaa gatgtgcttt    2760
tcagaattct gattggtggc gcgccagctg cattaatgaa tcggccaacg cgcgggagaa    2820
ggcggtttgc gtattgggcg ctcttccgct tcctcgctca ctgactcgct gcgctcggtc    2880
gttcggctgc ggcgagcggt atcagctcac tcaaaggcgg taatacggtt atccacagaa    2940
tcaggggata acgcaggaaa gaacatgtga gcaaaaggcc agcaaaaggc caggaaccgt    3000
aaaaaggccg cgttgctggc gttttccat aggctccgcc cccctgacga gcatcacaaa    3060
aatcgacgct caagtcagag gtggcgaaac ccgacaggac tataaagata ccaggcgttt    3120
ccccctggaa gctccctcgt gcgctctcct gttccgaccc tgccgcttac cggatacctg    3180
tccgcctttc tcccttcggg aagcgtggcg ctttctcata gctcacgctg taggtatctc    3240
agttcggtgt aggtcgttcg ctccaagctg ggctgtgtgc acgaaccccc cgttcagccc    3300
gaccgctgcg ccttatccgg taactatcgt cttgagtcca acccggtaag acacgactta    3360
tcgccactgg cagcagccac tggtaacagg attagcagag cgaggtatgt aggcggtgct    3420
acagagttct tgaagtggtg gcctaactac ggctacacta agaacagt atttggtatc    3480 tgcgctctgc tgaagccagt taccttcgga aaaagagttg gtagctcttg atccggcaaa    3540
caaaccaccg ctggtagcgg tggttttttt gtttgcaagc agcagattac gcgcagaaaa    3600
aaaggatctc aagaagatcc tttgatcttt tctacgggt ctgacgctca gtggaacgaa    3660
aactcacgtt aagggatttt ggtcatgaga ttatcaaaaa ggatcttcac ctagatcctt    3720
```

-continued

```
ttaaattaaa aatgaagttt taaatcaatc taaagtatat atgagtaaac ttggtctgac    3780
agttaccaat gcttaatcag tgaggcacct atctcagcga tctgtctatt tcgttcatcc    3840
atagttgcct gactccccgt cgtgtagata actacgatac gggagggctt accatctggc    3900
cccagtgctg caatgatacc gcgagaccca cgctcaccgg ctccagattt atcagcaata    3960
aaccagccag ccggaagggc cgagcgcaga agtggtcctg caactttatc cgcctccatc    4020
cagtctatta attgttgccg ggaagctaga gtaagtagtt cgccagttaa tagtttgcgc    4080
aacgttgttg ccattgctac aggcatcgtg gtgtcacgct cgtcgtttgg tatggcttca    4140
ttcagctccg gttcccaacg atcaaggcga gttacatgat cccccatgtt gtgcaaaaaa    4200
gcggttagct ccttcggtcc tccgatcgtt gtcagaagta agttggccgc agtgttatca    4260
ctcatggtta tggcagcact gcataattct cttactgtca tgccatccgt aagatgcttt    4320
tctgtgactg gtgagtactc aaccaagtca ttctgagaat agtgtatgcg gcgaccgagt    4380
tgctcttgcc cggcgtcaat acgggataat accgcgccac atagcagaac tttaaaagtg    4440
ctcatcattg gaaaacgttc ttcggggcga aaactctcaa ggatcttacc gctgttgaga    4500
tccagttcga tgtaacccac tcgtgcaccc aactgatctt cagcatcttt tactttcacc    4560
agcgtttctg ggtgagcaaa aacaggaagg caaaatgccg caaaaaaggg aataagggcg    4620
acacggaaat gttgaatact catactcttc ctttttcaat attattgaag catttatcag    4680
ggttattgtc tcatgagcgg atacatattt gaatgtattt agaaaaataa acaaataggg    4740
gttccgcgca catttccccg aaaagtgcca cctgatgcgg tgtgaaatac cgcacagatg    4800
cgtaaggaga aaataccgca tcaggaaatt gtaagcgtta atattttgtt aaaattcgcg    4860
ttaaattttt gttaaatcag ctcattttt aaccaatagg ccgaaatcgg caaaatccct    4920
tataaatcaa agaatagac cgagataggg ttgagtgttg ttccagtttg gaacaagagt    4980
ccactattaa agaacgtgga ctccaacgtc aaagggcgaa aaaccgtcta tcagggcgat    5040
ggcccactac gtgaaccatc accctaatca agttttttgg ggtcgaggtg ccgtaaagca    5100
ctaaatcgga acctaaagg agccccga tttagagctt gacggggaaa gccggcgaac    5160
gtggcgagaa aggaagggaa gaaagcgaaa ggagcgggcg ctagggcgct ggcaagtgta    5220
gcggtcacgc tgcgcgtaac caccacaccc gccgcgctta atgcgccgct acagggcgcg    5280
tccattcgcc attcaggctg cgcaactgtt gggaagggcg atcggtgcgg gcctcttcgc    5340
tattacgcca gctggcgaaa gggggatgtg ctgcaaggcg attaagttgg gtaacgccag    5400
ggttttccca gtcacgacgt tgtaaaacga cggccagtga attgtaatac gactcactat    5460
agggcgaatt gggcccgacg tcgcatgcgt cgagatatcg acattgttcc atctccagtt    5520
taacccccaac ttatcgagag tatttgtgag acacgcaata aatgaattta taccaatcaa    5580
atccatattc tacgctgtct acatatagat acttttgtc atctcttgcc ctactatttc    5640
gtcgatatat gaaggatacg ccaaccgaac ccatactcca cgctacacac gcgccttttc    5700
acgcatttct ggggaaaata gacacccttg gtgtcacctg aagaatatga aagaagatat    5760
tcattgtatt gagctgtaga tctgtgtatt tcttgacctc atcaatgact tctgggctct    5820
ttacctcgaa tcatggtggt actgtaccac atctcaacac cttgtagcac acctatggga    5880
aaattgagac tatgaatgga ttcccgtgcc cgtattactc tactaatttg atcttggaac    5940
gcgaaaatac gtttctagga ctccaaagaa tctcaactct tgtccttact aaatatacta    6000
cccatagttg atggtttact tgaacagaga ggacatgttc acttgaccca agtttctcg    6060
catctcttgg atatttgaac aacggcgtcc actgaccgtc agttatccag tcacaaaacc    6120
```

```
cccacattca tacattccca tgtacgttta caaagttctc aattccatcg tgcaaatcaa    6180
aatcacatct attcattcat catatataaa cccatcatgt ctactaacac tcacaactcc    6240
atagaaaaca tcgactcaga acacacgctc catctattcc tcgtccagct cgcaaatgtc    6300
gtcatcttaa ttaagttgcg acacatgtct tgatagtatc ttggcttctc tctcttgagc    6360
ttttccataa caagttcttc tgcctccagg aagtccatgg tgaatgattc ttatactcag    6420
aaggaaatgc ttaacgattt cgggtgtgag ttgacaagga gagagagaaa agaagaggaa    6480
aggtaattcg gggacggtgg tcttttatac ccttggctaa agtcccaacc acaaagcaaa    6540
aaaattttca gtagtctatt ttgcgtccgg catgggttac ccggatggcc agacaaagaa    6600
actagtacaa agtctgaaca agcgtagatt ccagactgca gtaccctacg cccttaacgg    6660
caagtgtggg aaccggggga ggtttgatat gtggggtgaa gggggctctc gccggggttg    6720
ggcccgctac tgggtcaatt tggggtcaat tgggcaatt ggggctgttt tttgggacac    6780
aaatacgccg ccaacccggt ctctcctgaa ttctgcagat gggctgcagg aattccgtcg    6840
tcgcctgagt cgacatcatt taaataccag ttggccacaa acccttgacg atctcgtatg    6900 tccctccga catactcccg gccggctggg gtacgttcga tagcgctatc ggcatcgaca    6960
aggtttgggt ccctagccga taccgcacta cctgagtcac aatcttcgga ggtttagtct    7020
tccacatagc acgggcaaaa gtgcgtatat atacaagagc gtttgccagc cacagatttt    7080
cactccacac accacatcac acatacaacc acacacatcc acaatggaac ccgaaactaa    7140
gaagaccaag actgactcca agaagattgt tcttctcggc ggcgacttct gtggccccga    7200
ggtgattgcc gaggccgtca aggtgctcaa gtctgttgct gaggcctccg gcaccgagtt    7260
tgtgtttgag gaccgactca ttggaggagc tgccattgag aaggagggcg agcccatcac    7320
cgacgctact ctcgacatct gccgaaaggc tgactctatt atgctcggtg ctgtcggagg    7380
cgctgccaac accgtatgga ccactcccga cggacgaacc gacgtgcgac ccgagcaggg    7440
tctcctcaag ctgcgaaagg acctgaacct gtacgccaac ctgcgaccct gccagctgct    7500
gtcgcccaag ctcgccgatc tctcccccat ccgaaacgtt gagggcaccg acttcatcat    7560
tgtccgagag ctcgtcggag gtatctactt tggagagcga aaggaggatg acggatctgg    7620
cgtcgcttcc gacaccgaga cctactccgt tcctgaggtt gagcgaattg cccgaatggc    7680
cgccttcctg gcccttcagc acaaccccc tcttcccgtg tggtctcttg acaaggccaa    7740
cgtgctggcc tcctctcgac tttggcgaaa gactgtcact cgagtcctca aggacgaatt    7800
cccccagctc gagctcaacc accagctgat cgactcggcc gccatgatcc tcatcaagca    7860
gccctccaag atgaatggta tcatcatcac caccaacatg tttggcgata tcatctccga    7920
cgaggcctcc gtcatccccg gttctctggg tctgctgccc tccgcctctc tggcttctct    7980
gcccgacacc aacgaggcgt tcggtctgta cgagccctgt cacggatctg cccccgatct    8040
cggcaagcag aaggtcaacc ccattgccac cattctgtct gccgccatga tgctcaagtt    8100
ctctcttaac atgaagcccg ccggtgacgc tgttgaggct gccgtcaagg agtccgtcga    8160
ggctggtatc actaccgccg atatcggagg ctcttcctcc acctccgagg tcggagactt    8220
gttgccaaca aggtcaagga gctgctcaag aaggagtaag tcgtttctac gacgcattga    8280
tggaaggagc aaactgacgc gcctgcgggt tggtctaccg gcagggtccg ctagtgtata    8340
agactctata aaagggccc tgccctgcta atgaaatgat gatttataat ttaccggtgt    8400
agcaaccttg actagaagaa gcagattggg tgtgtttgta gtggaggaca gtggtacgtt    8460
ttggaaacag tcttcttgaa agtgtcttgt ctacagtata ttcactcata acctcaatag    8520
```

-continued

```
ccaagggtgt agtcggttta ttaaaggaag ggagttgtgg ctgatgtgga tagatatctt    8580
taagctggcg actgcaccca acgagtgtgg tggtagcttg ttagatctgt atattcggta    8640
agatatattt tgtggggttt tagtggtgtt taaacggtag gttagtgctt ggtatatgag    8700
ttgtaggcat gacaatttgg aaaggggtgg actttgggaa tattgtggga tttcaatacc    8760
ttagtttgta cagggtaatt gttacaaatg atacaaagaa ctgtatttct tttcatttgt    8820
tttaattggt tgtatatcaa gtccgttaga cgagctcagt gccttggctt ttggcactgt    8880
atttcatttt tagaggtaca ctacattcag tgaggtatgg taaggttgag ggcataatga    8940
aggcaccttg tactgacagt cacagacctc tcaccgagaa ttttatgaga tatactcggg    9000
ttcattttag gctcat                                                    9016

<210> SEQ ID NO 23
<211> LENGTH: 43
<212> TYPE: DNA
<213> ORGANISM: Artificial Sequence
<220> FEATURE:
<223> OTHER INFORMATION: primer

<400> SEQUENCE: 23
gatcaaacat gttttgcaa gctttccttt tccttttggc tgg                       43

<210> SEQ ID NO 24
<211> LENGTH: 44
<212> TYPE: DNA
<213> ORGANISM: Artificial Sequence
<220> FEATURE:
<223> OTHER INFORMATION: primer

<400> SEQUENCE: 24
gatcaagcgg ccgcctattt tacttccctt acttggaact tgtc                     44

<210> SEQ ID NO 25
<211> LENGTH: 11180
<212> TYPE: DNA
<213> ORGANISM: Artificial Sequence
<220> FEATURE:
<223> OTHER INFORMATION: Plasmid pZKLY-PP2

<400> SEQUENCE: 25
aaatgcgttt ggatagcact agtctatgag gagcgtttta tgttgcggtg agggcgattg     60
gtgctcatat gggttcaatt gaggtggcgg aacgagctta gtcttcaatt gaggtgcgag    120
cgacacaatt gggtgtcacg tggcctaatt gacctcgggt cgtggagtcc ccagttatac    180
agcaaccacg aggtgcatgg gtaggagacg tcaccagaca atagggtttt ttttggactg    240
gagagggttg ggcaaaagcg ctcaacgggc tgtttgggga gctgtggggg aggaattggc    300
gatatttgtg aggttaacgg ctccgatttg cgtgttttgt cgctcctgca tctccccata    360
cccatatctt ccctccccac ctctttccac gataaattta cggatcagca ataaggttcc    420
ttctcctagt ttccacgtcc atatatatct atgctgcgtc gtccttttcg tgacatcacc    480
aaaacacata caaccatggc tggcacctta cccaagttcg gcgacggaac caccattgtg    540
gttcttggag cctccggcga cctcgctaag aagaagaccg tgagtattga accagactga    600
ggtcaattga agagtaggag agtctgagaa cattcgacgg acctgattgt gctctggacc    660
actcaattga ctcgttgaga gccccaatgg gtcttggcta gccgagtcgt tgacttgttg    720
acttgttgag cccagaaccc caactttttg ccaccataca ccgccatcac catgacaccc    780
agatgtgcgt gcgtatgtga gagtcaattg ttccgtggca aggcacagct tattccaccg    840
```

```
tgttccttgc acaggtggtc tttacgctct cccactctat ccgagcaata aaagcggaaa    900
aacagcagca agtcccaaca gacttctgct ccgaataagg cgtctagcaa gtgtgcccaa    960
aactcaattc aaaaatgtca gaaacctgat atcaacccgt cttcaaaagc taaccccagt   1020
tccccgccct cttcggcctt taccgaaacg gcctgctgcc caaaaatgtt gaaatcatcg   1080
gctacgcacg gtcgaaaatg actcaggagg agtaccacga gcgaatcagc cactacttca   1140
agaccccga cgaccagtcc aaggagcagg ccaagaagtt ccttgagaac acctgctacg   1200
tccagggccc ttacgacggt gccgagggct accagcgact gaatgaaaag attgaggagt   1260
ttgagaagaa gaagcccgag ccccactacc gtcttttcta cctggctctg cccccagcg   1320
tcttccttga ggctgccaac ggtctgaaga agtatgtcta ccccggcgag ggcaaggccc   1380
gaatcatcat cgagaagccc tttggccacg acctggcctc gtcacgagag ctccaggacg   1440
gccttgctcc tctctggaag gagtctgaga tcttccgaat cgaccactac ctcggaaagg   1500
agatggtcaa gaacctcaac attctgcgat tggcaaccca gttcctgtcc gccgtgtggg   1560
acaagaacac catttccaac gtccagatct ccttcaagga gccctttggc actgagggcc   1620
gaggtggata cttcaacgac attggaatca tccgagacgt tattcagaac catctgttgc   1680
aggttctgtc cattctagcc atggagcgac ccgtcacttt cggcgccgag gacattcgag   1740
atgagaaggt caaggtgctc cgatgtgtcg acattctcaa cattgacgac gtcattctcg   1800
gccagtacgg cccctctgaa gacggaaaga agcccggata caccgatgac gatggcgttc   1860
ccgatgactc ccgagctgtg accttgctg ctctccatct ccagatccac aacgacagat   1920
gggagggtgt tcctttcatc ctccgagccg gtaaggctct ggacgagggc aaggtcgaga   1980
tccgagtgca gttccgagac gtgaccaagg gcgttgtgga ccatctgcct cgaaatgagc   2040
tcgtcatccg aatccagccc tccgagtcca tctacatgaa gatgaactcc aagctgcctg   2100
gccttactgc caagaacatt gtcaccgacc tggatctgac ctacaaccga cgatactcgg   2160
acgtgcgaat ccctgaggct tacgagtctc tcattctgga ctgcctcaag ggtgaccaca   2220
ccaactttgt gcgaaacgac gagctggaca tttcctggaa gatttttcacc gatctgctgc   2280
acaagattga cgaggacaag agcattgtgc ccgagaagta cgcctacggc tctcgtggcc   2340
ccgagcgact caagcagtgg ctccgagacc gaggctacgt gcgaaacggc accgagctgt   2400
accaatggcc tgtcaccaag ggctcctcgt gagcggccgc aagtgtggat ggggaagtga   2460
gtgcccggtt ctgtgtgcac aattggcaat ccaagatgga tggattcaac acagggatat   2520
agcgagctac gtggtggtgc gaggatatag caacggatat ttatgtttga cacttgagaa   2580
tgtacgatac aagcactgtc caagtacaat actaaacata ctgtacatac tcatactcgt   2640
acccgggcaa cggtttcact tgagtgcagt ggctagtgct cttactcgta cagtgtgcaa   2700
tactgcgtat catagtcttt gatgtatatc gtattcattc atgttagttg cgtacgttga   2760
ttgaggtgga gccagatggg ctattgtttc atatatagac tggcagccac ctctttggcc   2820
cagcatgttt gtatacctgg aagggaaaac taaagaagct ggctagttta gtttgattat   2880
tatagtagat gtcctaatca ctagagatta gaatgtcttg gcgatgatta gtcgtcgtcc   2940
cctgtatcat gtctagacca actgtgtcat gaagttggtg ctggtgtttt acctgtgtac   3000
tacaagtagg tgtcctagat ctagtgtaca gagccgttta gacccatgtg gacttccacca  3060
ttaacgatgg aaaatgttca ttatatgaca gtatattaca atggacttgc tccatttctt   3120
ccttgcatca catgttctcc acctccatag ttgatcaaca catcatagta gctaaggctg   3180
ctgctctccc actacagtcc accacaagtt aagtagcacc gtcagtacag ctaaaagtac   3240
```

```
acgtctagta cgtttcataa ctagtcaagt agcccctatt acagatatca gcactatcac   3300
gcacgagttt ttctctgtgc tatctaatca acttgccaag tattcggaga agatacactt   3360
tcttggcatc aggtatacga gggagcctat cagatgaaaa agggtatatt ggatccattc   3420
atatccacct acacgttgtc ataatctcct cattcacgtg attcatttcg tgacactagt   3480
ttctcacttt ccccccccgca cctatagtca acttggcgga cacgctactt gtagctgacg   3540
ttgatttata gacccaatca aagcgggtta tcggtcaggt agcacttatc attcatcgtt   3600
catactacga tgagcaatct cgggcatgtc cggaaaagtg tcgggcgcgc agctgcatt    3660
aatgaatcgg ccaacgcgcg gggagaggcg gtttgcgtat tgggcgctct tccgcttcct   3720
cgctcactga ctcgctgcgc tcggtcgttc ggctgcggcg agcggtatca gctcactcaa   3780
aggcggtaat acggttatcc acagaatcag gggataacgc aggaaagaac atgtgagcaa   3840
aaggccagca aaaggccagg aaccgtaaaa aggccgcgtt gctggcgttt ttccataggc   3900
tccgcccccc tgacgagcat cacaaaaatc gacgctcaag tcagaggtgg cgaaacccga   3960
caggactata aagataccag gcgtttcccc ctggaagctc cctcgtgcgc tctcctgttc   4020
cgaccctgcc gcttaccgga tacctgtccg cctttctccc ttcgggaagc gtggcgcttt   4080
ctcatagctc acgctgtagg tatctcagtt cggtgtaggt cgttcgctcc aagctgggct   4140
gtgtgcacga accccccgtt cagcccgacc gctgcgcctt atccggtaac tatcgtcttg   4200
agtccaaccc ggtaagacac gacttatcgc cactggcagc agccactggt aacaggatta   4260
gcagagcgag gtatgtaggc ggtgctacag agttcttgaa gtggtggcct aactacggct   4320
acactagaag aacagtattt ggtatctgcg ctctgctgaa gccagttacc ttcggaaaaa   4380
gagttggtag ctcttgatcc ggcaaacaaa ccaccgctgg tagcggtggt ttttttgttt   4440
gcaagcagca gattacgcgc agaaaaaaag gatctcaaga agatcctttg atcttttcta   4500
cggggtctga cgctcagtgg aacgaaaact cacgttaagg gattttggtc atgagattat   4560
caaaaaggat cttcacctag atcctttta attaaaaatg aagttttaaa tcaatctaaa   4620
gtatatatga gtaaacttgg tctgacagtt accaatgctt aatcagtgag gcacctatct   4680
cagcgatctg tctatttcgt tcatccatag ttgcctgact ccccgtcgtg tagataacta   4740
cgatacggga gggcttacca tctggcccca gtgctgcaat gataccgcga gacccacgct   4800
caccggctcc agatttatca gcaataaacc agccagccgg aagggccgag cgcagaagtg   4860
gtcctgcaac tttatccgcc tccatccagt ctattaattg ttgccgggaa gctagagtaa   4920
gtagttcgcc agttaatagt ttgcgcaacg ttgttgccat tgctacaggc atcgtggtgt   4980
cacgctcgtc gtttggtatg gcttcattca gctccggttc ccaacgatca aggcgagtta   5040
catgatcccc catgttgtgc aaaaaagcgg ttagctcctt cggtcctccg atcgttgtca   5100
gaagtaagtt ggccgcagtg ttatcactca tggttatggc agcactgcat aattctctta   5160
ctgtcatgcc atccgtaaga tgcttttctg tgactggtga gtactcaacc aagtcattct   5220
gagaatagtg tatgcggcga ccgagttgct cttgcccggc gtcaatacgg gataataccg   5280
cgccacatag cagaacttta aaagtgctca tcattggaaa acgttcttcg ggcgaaaac    5340
tctcaaggat cttaccgctg ttgagatcca gttcgatgta acccactcgt gcacccaact   5400
gatcttcagc atcttttact ttcaccagcg tttctgggtg agcaaaaaca ggaaggcaaa   5460
atgccgcaaa aaagggaata agggcgacac ggaaatgttg aatactcata ctcttccttt   5520
ttcaatatta ttgaagcatt tatcagggtt attgtctcat gagcggatac atatttgaat   5580
gtatttagaa aaataaacaa ataggggttc cgcgcacatt tccccgaaaa gtgccacctg   5640
```

```
atgcggtgtg aaataccgca cagatgcgta aggagaaaat accgcatcag gaaattgtaa    5700
gcgttaatat tttgttaaaa ttcgcgttaa atttttgtta aatcagctca ttttttaacc    5760
aataggccga aatcggcaaa atcccttata aatcaaaaga atagaccgag atagggttga    5820
gtgttgttcc agtttggaac aagagtccac tattaaagaa cgtggactcc aacgtcaaag    5880
ggcgaaaaac cgtctatcag ggcgatggcc cactacgtga accatcaccc taatcaagtt    5940
ttttggggtc gaggtgccgt aaagcactaa atcggaaccc taagggagc ccccgattta    6000
gagcttgacg gggaaagccg gcgaacgtgg cgagaaagga agggaagaaa gcgaaggag    6060
cgggcgctag ggcgctggca agtgtagcgg tcacgctgcg cgtaaccacc acacccgccg    6120
cgcttaatgc gccgctacag ggcgcgtcca ttcgccattc aggctgcgca actgttggga    6180
agggcgatcg gtgcgggcct cttcgctatt acgccagctg gcgaaagggg gatgtgctgc    6240
aaggcgatta agttgggtaa cgccagggtt ttcccagtca cgacgttgta aaacgacggc    6300
cagtgaattg taatacgact cactataggg cgaattgggc ccgacgtcgc atgcattccg    6360
acagcagcga ctgggcacca tgatcaagcg aaacaccttc ccccagctgc cctggcaaac    6420
catcaagaac cctactttca tcaagtgcaa gaacggttct actcttctca cctccggtgt    6480
ctacggctgg tgccgaaagc ctaactacac cgctgatttc atcatgtgcc tcacctgggc    6540
tctcatgtgc ggtgttgctt ctcccctgcc ttacttctac ccggtcttct tcttcctggt    6600
gctcatccac cgagcttacc gagactttga gcgactggag cgaaagtacg gtgaggacta    6660
ccaggagttc aagcgacagg tcccttggat cttcatccct tatgttttct aaacgataag    6720
cttagtgagc gaatggtgag gttacttaat tgagtggcca gccatgggga ttgtataaca    6780
gacagtcaat atattactga aaagactgaa cagccagacg gagtgaggtt gtgagtgaat    6840
cgtagagggc ggctattaca gcaagtctac tctacagtgt actaacacag cagagaacaa    6900
atacaggtgt gcattcggct atctgagaat tagttggaga gctcgagacc ctcggcgata    6960
aactgctcct cggttttgtg tccatacttg tacggaccat tgtaatgggg caagtcgttg    7020
agttctcgtc gtccgacgtt cagagcacag aaaccaatgt aatcaatgta gcagagatgg    7080
ttctgcaaaa gattgatttg tgcgagcagg ttaattaagt tgcgacacat gtcttgatag    7140
tatcttgaat tctctctctt gagcttttcc ataacaagtt cttctgcctc caggaagtcc    7200
atgggtggtt tgatcatggt tttggtgtag tggtagtgca gtggtggtat tgtgactggg    7260
gatgtagttg agaataagtc atacacaagt cagctttctt cgagcctcat ataagtataa    7320
gtagttcaac gtattagcac tgtacccagc atctccgtat cgagaaacac aacaacatgc    7380
cccattggac agatcatgcg gatacacagg ttgtgcagta tcatacatac tcgatcagac    7440
aggtcgtctg accatcatac aagctgaaca agcgctccat acttgcacgc tctctatata    7500
cacagttaaa ttacatatcc atagtctaac ctctaacagt taatcttctg gtaagcctcc    7560
cagccagcct tctggtatcg cttggcctcc tcaataggat ctcggttctg gccgtacaga    7620
cctcggccga caattatgat atccgttccg gtagacatga catcctcaac agttcggtac    7680
tgctgtccga gagcgtctcc cttgtcgtca agacccaccc cggggtcag aataagccag    7740
tcctcagagt cgcccttagg tcggttctgg gcaatgaagc caaccacaaa ctcggggtcg    7800
gatcgggcaa gctcaatggt ctgcttggag tactcgccag tggccagaga gcccttgcaa    7860
gacagctcgg ccagcatgag cagacctctg gccagcttct cgttgggaga ggggactagg    7920
aactccttgt actgggagtt ctcgtagtca gagacgtcct ccttcttctg ttcagagaca    7980
gtttcctcgg caccagctcg caggccagca atgattccgg ttccgggtac accgtgggcg    8040
```

```
ttggtgatat cggaccactc ggcgattcgg tgacaccggt actggtgctt gacagtgttg    8100
ccaatatctg cgaactttct gtcctcgaac aggaagaaac cgtgcttaag agcaagttcc    8160
ttgaggggga gcacagtgcc ggcgtaggtg aagtcgtcaa tgatgtcgat atgggttttg    8220
atcatgcaca cataaggtcc gaccttatcg gcaagctcaa tgagctcctt ggtggtggta    8280
acatccagag aagcacacag gttggttttc ttggctgcca cgagcttgag cactcgagcg    8340
gcaaaggcgg acttgtggac gttagctcga gcttcgtagg agggcatttt ggtggtgaag    8400
aggagactga aataaattta gtctgcagaa ctttttatcg gaaccttatc tggggcagtg    8460
aagtatatgt tatggtaata gttacgagtt agttgaactt atagatagac tggactatac    8520
ggctatcggt ccaaattaga agaacgtca atggctctct gggcgtcgcc tttgccgaca     8580
aaaatgtgat catgatgaaa gccagcaatg acgttgcagc tgatattgtt gtcggccaac    8640
cgcgccgaaa acgcagctgt cagacccaca gcctccaacg aagaatgtat cgtcaaagtg    8700
atccaagcac actcatagtt ggagtcgtac tccaaaggcg gcaatgacga gtcagacaga    8760
tactcgtcga ccttttcctt gggaaccacc accgtcagcc cttctgactc acgtattgta    8820
gccaccgaca caggcaacag tccgtggata gcagaatatg tcttgtcggt ccatttctca    8880
ccaactttag gcgtcaagtg aatgttgcag aagaagtatg tgccttcatt gagaatcggt    8940
gttgctgatt tcaataaagt cttgagatca gtttggccag tcatgttgtg gggggtaatt    9000
ggattgagtt atcgcctaca gtctgtacag gtatactcgc tgcccacttt atacttttg    9060 attccgctgc acttgaagca atgtcgttta ccaaaagtga gaatgctcca cagaacacac    9120
cccagggtat ggttgagcaa aaaataaaca ctccgatacg gggaatcgaa ccccggtctc    9180
cacggttctc aagaagtatt cttgatgaga gcgtatcgat gagcctaaaa tgaacccgag    9240
tatatctcat aaaattctcg gtgagaggtc tgtgactgtc agtacaaggt gccttcatta    9300
tgccctcaac cttaccatac ctcactgaat gtagtgtacc tctaaaaatg aaatacagtg    9360
ccaaaagcca aggcactgag ctcgtctaac ggacttgata tacaaccaat taaaacaaat    9420
gaaaagaaat acagttcttt gtatcatttg taacaattac cctgtacaaa ctaaggtatt    9480
gaaatcccac aatattccca aagtccaccc ctttccaaat tgtcatgcct acaactcata    9540
taccaagcac taacctaccg tttaaaccat catctaaggg cctcaaaact acctcggaac    9600
tgctgcgctg atctggacac cacagaggtt ccgagcactt taggttgcac caaatgtccc    9660
accaggtgca ggcagaaaac gctggaacag cgtgtacagt ttgtcttaac aaaaagtgag    9720
ggcgctgagg tcgagcaggg tggtgtgact tgttatagcc tttagagctg cgaaagcgcg    9780
tatggatttg gctcatcagg ccagattgag ggtctgtgga cacatgtcat gttagtgtac    9840
ttcaatcgcc ccctggatat agccccgaca ataggccgtg gcctcatttt tttgccttcc    9900
gcacatttcc attgctcggt acccacacct tgcttctcct gcacttgcca accttaatac    9960
tggtttacat tgaccaacat cttacaagcg ggggcttgt ctagggtata tataaacagt    10020
ggctctccca atcggttgcc agtctctttt ttcctttctt tccccacaga ttcgaaatct    10080
aaactacaca tcacaccatg gctcccaagg tcatctctaa gaacgaatcg caactggtcg    10140
ctgaggctgc tgccgctgag atcattcgac tccagaacga gtcaattgct gccactggag    10200 cttttccatgt tgccgtatct ggaggctctc tggtgtctgc tctccgaaag ggtctggtca    10260
acaactcgga gaccaagttc cccaagtgga agattttctt ctccgacgaa cggctggtca    10320
agctggacga tgccgactcc aactacggtc tcctcaagaa ggatctgctc gatcacatcc    10380
ccaaggatca gcaaccacag gtcttcaccg tcaaggagtc tcttctgaac gactctgatg    10440
```

-continued

```
ccgtctccaa ggactaccag gagcagattg tcaagaatgt gcctctcaac ggccagggag    10500
tgcctgtttt cgatctcatt ctgctcggat gcggtcctga tggccacact tgctcgctgt    10560
tccctggaca cgctctgctc aaggaggaga ccaagtttgt cgccaccatt gaggactctc    10620
ccaagcctcc tcctcgacga atcaccatca ctttccccgt tctcaaggct gccaaggcca    10680
tcgctttcgt cgccgaggga gccggaaagg ccctgtcct caagcagatc ttcgaggagc    10740
ccgagcccac tcttccctct gccattgtca acaaggtcgc taccggaccc gttttctggt    10800
ttgtttccga ctctgccgtt gagggcgtca acctctccaa gatctagcgg ccgcatgaga    10860
agataaatat ataaatacat tgagatatta aatgcgctag attagagagc ctcatactgc    10920
tcggagagaa gccaagacga gtactcaaag gggattacac catccatatc cacagacaca    10980
agctggggaa aggttctata tacactttcc ggaataccgt agtttccgat gttatcaatg    11040
ggggcagcca ggatttcagg cacttcggtg tctcggggtg aaatggcgtt cttggcctcc    11100
atcaagtcgt accatgtctt catttgcctg tcaaagtaaa acagaagcag atgaagaatg    11160
aacttgaagt gaaggaattt                                                11180
```

<210> SEQ ID NO 26
<211> LENGTH: 45
<212> TYPE: DNA
<213> ORGANISM: Artificial Sequence
<220> FEATURE:
<223> OTHER INFORMATION: primer

<400> SEQUENCE: 26

```
gatcaaacat gtcaatgaca aacgaaacta gcgatagacc tttgg              45
```

<210> SEQ ID NO 27
<211> LENGTH: 43
<212> TYPE: DNA
<213> ORGANISM: Artificial Sequence
<220> FEATURE:
<223> OTHER INFORMATION: primer

<400> SEQUENCE: 27

```
gatcaaccat ggagctcgct accgccttta ctattctcac tgc                43
```

<210> SEQ ID NO 28
<211> LENGTH: 43
<212> TYPE: DNA
<213> ORGANISM: Artificial Sequence
<220> FEATURE:
<223> OTHER INFORMATION: primer

<400> SEQUENCE: 28

```
gatcaaacat gttagacagg ccccattgag tgacgggagt agt                43
```

<210> SEQ ID NO 29
<211> LENGTH: 13565
<212> TYPE: DNA
<213> ORGANISM: Artificial Sequence
<220> FEATURE:
<223> OTHER INFORMATION: Plasmid pZKL3-9DP9N

<400> SEQUENCE: 29

```
gtacggattg tgtatgtccc tgtacctgca tcttgatgga gagagctccg gaaagcggat    60
caggagctgt ccaattttaa ttttataaca tggaaacgag tccttggagc tagaagacca    120 tttttttcaac tgccctatcg actatatttta tctactccaa aaccgactgc ttcccaagaa    180
tcttcagcca aggcttccaa agtaaccct cgcttcccga cacttaattg aaaccttaga    240
```

```
tgcagtcact gcgagtgaag tggactctaa catctccaac atagcgacga tattgcgagg    300
gtttgaatat aactaagatg catgatccat tacatttgta gaaatatcat aaacaacgaa    360
gcacatagac agaatgctgt tggttgttac atctgaagcc gaggtaccga tgtcattttc    420
agctgtcact gcagagacag gggtatgtca catttgaaga tcatacaacc gacgtttatg    480
aaaaccagag atatagagaa tgtattgacg gttgtggcta tgtcataagt gcagtgaagt    540
gcagtgatta taggtatagt acacttactg tagctacaag tacatactgc tacagtaata    600
ctcatgtatg caaaccgtat tctgtgtcta cagaaggcga tacggaagag tcaatctctt    660
atgtagagcc atttctataa tcgaagggc cttgtaattt ccaaacgagt aattgagtaa    720
ttgaagagca tcgtagacat tacttatcat gtattgtgag agggaggaga tgcagctgta    780
gctactgcac atactgtact cgcccatgca gggataatgc atagcgagac ttggcagtag    840
gtgacagttg ctagctgcta cttgtagtcg ggtgggtgat agcatggcgc gccagctgca    900
ttaatgaatc ggccaacgcg cggggagagg cggtttgcgt attgggcgct cttccgcttc    960
ctcgctcact gactcgctgc gctcggtcgt tcggctgcgg cgagcggtat cagctcactc    1020
aaaggcggta atacggttat ccacagaatc aggggataac gcaggaaaga acatgtgagc    1080
aaaaggccag caaaaggcca ggaaccgtaa aaaggccgcg ttgctggcgt ttttccatag    1140
gctccgcccc cctgacgagc atcacaaaaa tcgacgctca agtcagaggt ggcgaaaccc    1200
gacaggacta taaagatacc aggcgtttcc ccctggaagc tccctcgtgc gctctcctgt    1260
tccgaccctg ccgcttaccg gatacctgtc cgcctttctc ccttcgggaa gcgtggcgct    1320
ttctcatagc tcacgctgta ggtatctcag ttcggtgtag tcgttcgct ccaagctggg    1380 ctgtgtgcac gaaccccccg ttcagcccga ccgctgcgcc ttatccggta actatcgtct    1440
tgagtccaac ccggtaagac acgacttatc gccactggca gcagccactg gtaacaggat    1500
tagcagagcg aggtatgtag gcggtgctac agagttcttg aagtggtggc ctaactacgg    1560
ctacactaga agaacagtat ttggtatctg cgctctgctg aagccagtta ccttcggaaa    1620
aagagttggt agctcttgat ccggcaaaca aaccaccgct ggtagcggtg ttttttttgt    1680
ttgcaagcag cagattacgc gcagaaaaaa aggatctcaa gaagatcctt tgatcttttc    1740
tacggggtct gacgctcagt ggaacgaaaa ctcacgttaa gggattttgg tcatgagatt    1800
atcaaaaagg atcttcacct agatcctttt aaattaaaaa tgaagtttta atcaatcta    1860 aagtatatat gagtaaactt ggtctgacag ttaccaatgc ttaatcagtg aggcacctat    1920
ctcagcgatc tgtctatttc gttcatccat agttgcctga ctccccgtcg tgtagataac    1980
tacgatacgg gagggcttac catctggccc cagtgctgca atgataccgc gagacccacg    2040
ctcaccggct ccagatttat cagcaataaa ccagccagcc ggaagggccg agcgcagaag    2100
tggtcctgca actttatccg cctccatcca gtctattaat tgttgccggg aagctagagt    2160
aagtagttcg ccagttaata gtttgcgcaa cgttgttgcc attgctacag gcatcgtggt    2220
gtcacgctcg tcgtttggta tggcttcatt cagctccggt tcccaacgat caaggcgagt    2280
tacatgatcc cccatgttgt gcaaaaaagc ggttagctcc ttcggtcctc cgatcgttgt    2340
cagaagtaag ttggccgcag tgttatcact catggttatg gcagcactgc ataattctct    2400
tactgtcatg ccatccgtaa gatgcttttc tgtgactggt gagtactcaa ccaagtcatt    2460
ctgagaatag tgtatgcggc gaccgagttg ctcttgcccg gcgtcaatac gggataatac    2520
cgcgccacat agcagaactt taaaagtgct catcattgga aaacgttctt cggggcgaaa    2580
actctcaagg atcttaccgc tgttgagatc cagttcgatg taacccactc gtgcacccaa    2640
```

```
ctgatcttca gcatctttta cttctcaccag cgtttctggg tgagcaaaaa caggaaggca    2700
aaatgccgca aaaagggaa taagggcgac acggaaatgt tgaatactca tactcttcct    2760
ttttcaatat tattgaagca tttatcaggg ttattgtctc atgagcggat acatatttga    2820
atgtatttag aaaaataaac aaatagggggt tccgcgcaca tttccccgaa aagtgccacc    2880
tgatgcggtg tgaaataccg cacagatgcg taaggagaaa ataccgcatc aggaaattgt    2940
aagcgttaat attttgttaa aattcgcgtt aaatttttgt taaatcagct cattttttaa    3000
ccaataggcc gaaatcggca aaatccctta taaatcaaaa gaatagaccg agatagggtt    3060
gagtgttgtt ccagtttgga acaagagtcc actattaaag aacgtggact ccaacgtcaa    3120
agggcgaaaa accgtctatc agggcgatgg cccactacgt gaaccatcac cctaatcaag    3180
ttttttgggg tcgaggtgcc gtaaagcact aaatcggaac cctaaaggga gcccccgatt    3240
tagagcttga cggggaaagc cggcgaacgt ggcgagaaag gaagggaaga aagcgaaagg    3300
agcgggcgct agggcgctgg caagtgtagc ggtcacgctg cgcgtaacca ccacacccgc    3360
cgcgcttaat gcgccgctac agggcgcgtc cattcgccat tcaggctgcg caactgttgg    3420
gaagggcgat cggtgcgggc ctcttcgcta ttacgccagc tggcgaaagg gggatgtgct    3480
gcaaggcgat taagttgggt aacgccaggg ttttcccagt cacgacgttg taaaacgacg    3540
gccagtgaat tgtaatacga ctcactatag ggcgaattgg gcccgacgtc gcatgcagga    3600
atagacatct tcaataggag cattaatacc tgtgggatca ctgatgtaaa cttctcccag    3660
agtatgtgaa taaccagcgg gccatccaac aaagaagtcg ttccagtgag tgactcggta    3720
catccgtctt tcggggttga tggtaagtcc gtcgtctcct tgcttaaaga acagagcgtc    3780
cacgtagtct gcaaaagcct tgttttccaag tcgaggctgc ccatagttga ttagcgttgg    3840
atcatatcca agattcttca ggttgatgcc catgaataga gcagtgacag ctcctagaga    3900
gtggccagtt acgatcaatt tgtagtcagt gttgtttcca aggaagtcga ccagacgatc    3960
ctgtacgttc accatagtct ctctgtatgc cttctgaaag ccatcatgaa cttggcagcc    4020
aggacaattg atactggcag aagggttttgt ggagtttatg tcagtagtgt taagaggagg    4080
gatactggtc atgtagggtt gttggatcgt ttggatgtca gtaatagcgt ctgcaatgga    4140
gaaagtgcct cggaaaacaa tatacttttc cttttggtg tgatcgtggg ccaaaaatcc    4200
agtaactgaa gtcgagaaga aatttcctcc aaactggtag tcaagagtca catcgggaaa    4260
atgagcgcaa gagtttccac aggtaaaatc gctctgcagg gcaaatgggc caggggctct    4320
gacacaatag gccacgttag atagccatcc gtacttgaga acaaagtcgt atgtctcctg    4380
ggtgatagga gccgttaatt aagttgcgac acatgtcttg atagtatctt gaattctctc    4440
tcttgagctt ttccataaca agttcttctg cctccaggaa gtccatgggt ggtttgatca    4500
tggttttggt gtagtggtag tgcagtggtg gtattgtgac tggggatgta gttgagaata    4560
agtcatacac aagtcagctt tcttcgagcc tcatataagt ataagtagtt caacgtatta    4620
gcactgtacc cagcatctcc gtatcgagaa acacaacaac atgccccatt ggacagatca    4680
tgcggataca caggttgtgc agtatcatac atactcgatc agacaggtcg tctgaccatc    4740
atacaagctg aacaagcgct ccatacttgc acgctctcta tatacacagt taaattacat    4800
atccatagtc taacctctaa cagttaatct tctggtaagc ctcccagcca gccttctggt    4860
atcgcttggc ctcctcaata ggatctcggt tctggccgta cagacctcgg ccgacaatta    4920
tgatatccgt tccggtagac atgacatcct caacagttcg gtactgctgt ccgagagcgt    4980
ctcccttgtc gtcaagaccc accccgggggg tcagaataag ccagtcctca gagtcgccct    5040
```

```
taggtcggtt ctgggcaatg aagccaacca caaactcggg gtcggatcgg gcaagctcaa   5100
tggtctgctt ggagtactcg ccagtggcca gagagccctt gcaagacagc tcggccagca   5160
tgagcagacc tctggccagc ttctcgttgg gagaggggac taggaactcc ttgtactggg   5220
agttctcgta gtcagagacg tcctccttct tctgttcaga cacagtttcc tcggcaccag   5280
ctcgcaggcc agcaatgatt ccggttccgg gtacaccgtg ggcgttggtg atatcggacc   5340
actcggcgat tcggtgacac cggtactggt gcttgacagt gttgccaata tctgcgaact   5400
ttctgtcctc gaacaggaag aaaccgtgct taagagcaag ttccttgagg gggagcacag   5460
tgccggcgta ggtgaagtcg tcaatgatgt cgatatgggg tttgatcatg cacacataag   5520
gtccgacctt atcggcaagc tcaatgagct ccttggtggt ggtaacatcc agagaagcac   5580
acaggttggt tttcttggct gccacgagct tgagcactcg agcggcaaag gcggacttgt   5640
ggacgttagc tcgagcttcg taggagggca ttttggtggt gaagaggaga ctgaaataaa   5700
tttagtctgc agaactttt atcggaacct tatctgggc agtgaagtat atgttatggt    5760
aatagttacg agttagttga acttatagat agactggact atacggctat cggtccaaat   5820
tagaaagaac gtcaatggct ctctgggcgt cgcctttgcc gacaaaaatg tgatcatgat   5880
gaaagccagc aatgacgttg cagctgatat tgttgtcggc caaccgcgcc gaaaacgcag   5940
ctgtcagacc cacagcctcc aacgaagaat gtatcgtcaa agtgatccaa gcacactcat   6000
agttggagtc gtactccaaa ggcggcaatg acgagtcaga cagatactcg tcgacctttt   6060
ccttgggaac caccaccgtc agcccttctg actcacgtat tgtagccacc gacacaggca   6120
acagtccgtg gatagcagaa tatgtcttgt cggtccattt ctcaccaact ttaggcgtca   6180
agtgaatgtt gcagaagaag tatgtgcctt cattgagaat cggtgttgct gatttcaata   6240
aagtcttgag atcagtttgg ccagtcatgt tgtgggggt aattggattg agttatcgcc     6300
tacagtctgt acaggtatac tcgctgccca ctttatactt tttgattccg ctgcacttga   6360
agcaatgtcg tttaccaaaa gtgagaatgc tccacagaac acaccccagg gtatggttga   6420
gcaaaaaata aacactccga tacggggaat cgaaccccgg tctccacggt tctcaagaag   6480
tattcttgat gagagcgtat cgatggttaa tgctgctgtg tgctgtgtgt gtgtgttgtt   6540
tggcgctcat tgttgcgtta tgcagcgtac accacaatat tggaagctta ttagcctttc   6600
tatttttcg tttgcaaggc ttaacaacat tgctgtggag agggatgggg atatggaggc    6660
cgctggaggg agtcggagag gcgttttgga gcggcttggc ctggcgccca gctcgcgaaa   6720
cgcacctagg acccttggc acgccgaaat gtgccacttt tcagtctagt aacgccttac    6780
ctacgtcatt ccatgcgtgc atgtttgcgc cttttttccc ttgcccttga tcgccacaca   6840
gtacagtgca ctgtacagtg gaggtttgg ggggtctta gatgggagct aaaagcggcc     6900
tagcggtaca ctagtgggat tgtatggagt ggcatggagc ctaggtggag cctgacagga   6960
cgcacgaccg gctagcccgt gacagacgat gggtggctcc tgttgtccac cgcgtacaaa   7020
tgtttgggcc aaagtcttgt cagccttgct tgcgaaccta attcccaatt ttgtcacttc   7080
gcaccccat tgatcgagcc ctaacccctg cccatcaggc aatccaatta agctcgcatt    7140
gtctgccttg tttagtttgg ctcctgcccg tttcggcgtc cacttgcaca aacacaaaca   7200
agcattatat ataaggctcg tctctccctc ccaaccacac tcacttttt gcccgtcttc    7260
ccttgctaac acaaaagtca agaacacaaa caaccacccc aaccccctta cacacaagac   7320
atatctacag caatggccat ggccaaaagc aaacgacggt cggaggctgt ggaagagcac   7380
gtgaccggct cggacgaggg cttgaccgat acttcgggtc acgtgagccc tgccgccaag   7440
```

-continued

```
aagcagaaga actcggagat tcatttcacc acccaggctg cccagcagtt ggatcgggag    7500
cgcaaggagg agtatctgga ctcgctgatc gacaacaagg actatctcaa gtaccgtcct    7560
cgaggctgga agctcaacaa cccgcctacc gaccgacctg tgcgaatcta cgccgatgga    7620
gtgtttgatt tgttccatct gggacacatg cgtcagctgg agcagtccaa gaaggccttc    7680
cccaacgcag tgttgattgt gggcattccc agcgacaagg agacccacaa gcggaaggga    7740
ttgaccgtgc tgagtgacgt ccagcggtac gagacggtgc gacactgcaa gtgggtggac    7800
gaggtggtgg aggatgctcc ctggtgtgtc accatggact ttctggaaaa acacaaaatc    7860
gactacgtgg cccatgacga tctgccctac gcttccggca acgacgatga tatctacaag    7920
cccatcaagg agaagggcat gtttctggcc acccagcgaa ccgagggcat ttccacctcg    7980
gacatcatca ccaagattat ccgagactac gacaagtatt taatgcgaaa ctttgcccgg    8040
ggtgctaacc gaaaggatct caacgtctcg tggctcaaga gaacgagct ggacttcaag     8100
cgtcatgtgg ccgagttccg aaactcgttc aagcgaaaga aggtcggtaa ggatctctac    8160
ggcgagattc gcggtctgct gcagaatgtg ctcatttgga acggcgacaa ctccggcact    8220
tccactcccc agcgaaagac gctgcagacc aacgccaaga gatgtacat gaacgtgctc     8280
aagactctgc aggctcctga cgctgttgac gtggactcct cggagaacgt gtctgagaac    8340
gtcactgatg aggaggagga agacgacgac gaggttgatg aggacgaaga agccgacgac    8400
gacgacgaag acgacgaaga cgaggaagac gacgagtagg cggccgcatt gatgattgga    8460
aacacacaca tgggttatat ctaggtgaga gttagttgga cagttatata ttaaatcagc    8520
tatgccaacg gtaacttcat tcatgtcaac gaggaaccag tgactgcaag taatatagaa    8580
tttgaccacc ttgccattct cttgcactcc tttactatat ctcatttatt cttatatac     8640
aaatcacttc ttcttcccag catcgagctc ggaaacctca tgagcaataa catcgtggat    8700
ctcgtcaata gagggcttt tggactcctt gctgttggcc accttgtcct tgctgtttaa     8760
acacgcagta ggatgtcctg cacgggtctt tttgtggggt gtggagaaag gggtgcttgg    8820
agatggaagc cggtagaacc gggctgcttg tgcttggaga tggaagccgg tagaaccggg    8880
ctgcttgggg ggatttgggg ccgctgggct ccaaagaggg gtaggcattt cgttgggtt     8940
acgtaattgc ggcatttggg tcctgcgcgc atgtcccatt ggtcagaatt agtccggata    9000
ggagacttat cagccaatca cagcgccgga tccacctgta ggttgggttg ggtgggagca    9060
cccctccaca gagtagagtc aaacagcagc agcaacatga tagttggggg tgtgcgtgtt    9120
aaaggaaaaa aaagaagctt gggttatatt cccgctctat ttagaggttg cgggatagac    9180
gccgacggag ggcaatggcg ctatggaacc ttgcggatat ccatacgccg cggcggactg    9240
cgtccgaacc agctccagca gcgttttttc cgggccattg agccgactgc gaccccgcca    9300
acgtgtcttg gcccacgcac tcatgtcatg ttggtgttgg gaggccactt tttaagtagc    9360
acaaggcacc tagctcgcag caaggtgtcc gaaccaaaga agcggctgca gtggtgcaaa    9420
cggggcggaa acggcgggaa aaagccacgg gggcacgaat tgaggcacgc cctcgaattt    9480
gagacgagtc acgcccccat tcgccgcgcg aatggctcgc caacgcccgg tcttttgcac    9540
cacatcaggt taccccaagc caaacctttg tgttaaaaag cttaacatat tataccgaac    9600
gtaggtttgg gcgggcttgc tccgtctgtc caaggcaaca tttatataag ggtctgcatc    9660
gccggctcaa ttgaatcttt tttcttcttc tcttctctat attcattctt gaattaaaca    9720
cacatcaaca tggccatcaa agtcggtatt aacggattcg ggcgaatcgg acgaattgtg    9780
agtaccatag aaggtgatgg aaacatgacc caacagaaac agatgacaag tgtcatcgac    9840
```

```
ccaccagagc ccaattgagc tcatactaac agtcgacaac ctgtcgaacc aattgatgac   9900
tccccgacaa tgtactaaca caggtcctgc ccatggtgaa aaacgtggac caagtggatc   9960
tctcgcaggt cgacaccatt gcctccggcc gagatgtcaa ctacaaggtc aagtacacct  10020
ccggcgttaa gatgagccag ggcgcctacg acgacaaggg ccgccacatt tccgagcagc  10080
ccttcacctg ggccaactgg caccagcaca tcaactggct caacttcatt ctggtgattg  10140
cgctgcctct gtcgtccttt gctgccgctc ccttcgtctc cttcaactgg aagaccgccg  10200
cgtttgctgt cggctattac atgtgcaccg gtctcggtat caccgccggc taccaccgaa  10260
tgtgggccca tcgagcctac aaggccgctc tgcccgttcg aatcatcctt gctctgtttg  10320
gaggaggagc tgtcgagggc tccatccgat ggtgggcctc gtctcaccga gtccaccacc  10380
gatggaccga ctccaacaag gacccttacg acgcccgaaa gggattctgg ttctcccact  10440
ttggctggat gctgcttgtg cccaacccca agaacaaggg ccgaactgac atttctgacc  10500
tcaacaacga ctgggttgtc cgactccagc acaagtacta cgtttacgtt ctcgtcttca  10560
tggccattgt tctgcccacc ctcgtctgtg gctttggctg gggcgactgg aagggaggtc  10620
ttgtctacgc cggtatcatg cgatacacct ttgtgcagca ggtgactttc tgtgtcaact  10680
cccttgccca ctggattgga gagcagccct tcgacgaccg acgaactccc cgagaccacg  10740
ctcttaccgc cctggtcacc tttggagagg gctaccacaa cttccaccac gagttccccct  10800
cggactaccg aaacgccctc atctggtacc agtacgaccc caccaagtgg ctcatctgga  10860
ccctcaagca ggttggtctc gcctgggacc tccagacctt ctcccagaac gccatcgagc  10920
agggtctcgt gcagcagcga cagaagaagc tggacaagtg gcgaaacaac ctcaactggg  10980
gtatccccat tgagcagctg cctgtcattg agtttgagga gttccaagag caggccaaga  11040
cccgagatct ggttctcatt tctggcattg tccacgacgt gtctgccttt gtcgagcacc  11100
accctggtgg aaaggccctc attatgagcg ccgtcggcaa ggacggtacc gctgtcttca  11160
acggaggtgt ctaccgacac tccaacgctg gccacaacct gcttgccacc atgcgagttt  11220
cggtcattcg aggcggcatg gaggttgagg tgtggaagac tgcccagaac gaaaagaagg  11280
accagaacat tgtctccgat gagagtggaa accgaatcca ccgagctggt ctccaggcca  11340
cccgggtcga gaaccccggt atgtctggca tggctgctta ggcggccgca tgagaagata  11400
aatatataaa tacattgaga tattaaatgc gctagattag agagcctcat actgctcgga  11460
gagaagccaa gacgagtact caaaggggat tacaccatcc atatccacag acacaagctg  11520
gggaaaggtt ctatatacac tttccggaat accgtagttt ccgatgttat caatgggggc  11580
agccaggatt tcaggcactt cggtgtctcg gggtgaaatg gcgttcttgg cctccatcaa  11640
gtcgtaccat gtcttcatt gcctgtcaaa gtaaaacaga agcagatgaa gaatgaactt  11700
gaagtgaagg aatttaaata gttggagcaa gggagaaatg tagagtgtga aagactcact  11760
atggtccggg cttatctcga ccaatagcca aagtctggag tttctgagag aaaaaggcaa  11820
gatacgtatg taacaaagcg acgcatggta caataatacc ggaggcatgt atcatagaga  11880
gttagtggtt cgatgatggc actggtgcct ggtatgactt tatacggctg actacatatt  11940
tgtcctcaga catacaatta cagtcaagca cttacccttg gacatctgta ggtaccccc  12000
ggccaagacg atctcagcgt gtcgtatgtc ggattggcgt agctccctcg ctcgtcaatt  12060
ggctcccatc tactttcttc tgcttggcta cacccagcat gtctgctatg gctcgttttc  12120
gtgccttatc tatcctccca gtattaccaa ctctaaatga catgatgtga ttgggtctac  12180
actttcatat cagagataag gagtagcaca gttgcataaa aagcccaact ctaatcagct  12240
```

```
tcttcctttc ttgtaattag tacaaaggtg attagcgaaa tctggaagct tagttggccc    12300
taaaaaaatc aaaaaaagca aaaaacgaaa acgaaaaaac cacagttttg agaacaggga    12360
ggtaacgaag gatcgtatat atatatatat atatatatac ccacggatcc cgagaccggc    12420
ctttgattct tccctacaac caaccattct caccaccta attcacaacc atggaggtcg     12480
tgaacgaaat cgtctccatt ggccaggagg ttcttcccaa ggtcgactat gctcagctct    12540
ggtctgatgc ctcgcactgc gaggtgctgt acctctccat cgccttcgtc atcctgaagt    12600
tcacccttgg tcctctcgga cccaagggtc agtctcgaat gaagtttgtg ttcaccaact    12660
acaacctgct catgtccatc tactcgctgg gctccttcct ctctatggcc tacgccatgt    12720
acaccattgg tgtcatgtcc gacaactgcg agaaggcttt cgacaacaat gtcttccgaa    12780
tcaccactca gctgttctac ctcagcaagt tcctcgagta cattgactcc ttctatctgc    12840
ccctcatggg caagcctctg acctggttgc agttcttttca ccatctcgga gctcctatgg    12900
acatgtggct gttctacaac taccgaaacg aagccgtttg gatctttgtg ctgctcaacg    12960
gcttcattca ctggatcatg tacggctact attggacccg actgatcaag ctcaagttcc    13020
ctatgcccaa gtccctgatt acttctatgc agatcattca gttcaacgtt ggcttctaca    13080
tcgtctggaa gtaccggaac attccctgct accgacaaga tggaatgaga atgtttggct    13140 ggttttttcaa ctacttctac gttggtactg tcctgtgtct gttcctcaac ttctacgtgc    13200
agacctacat cgtccgaaag cacaagggag ccaaaaagat tcagtgagcg gccgcaagtg    13260
tggatgggga agtgagtgcc cggttctgtg tgcacaattg gcaatccaag atggatggat    13320
tcaacacagg gatatagcga gctacgtggt ggtgcgagga tatagcaacg gatatttatg    13380
tttgacactt gagaatgtac gatacaagca ctgtccaagt acaatactaa acatactgta    13440
catactcata ctcgtacccg gcaacggttt cacttgagtg cagtggctag tgctcttact    13500
cgtacagtgt gcaatactgc gtatcatagt ctttgatgta tatcgtattc attcatgtta    13560
gttgc                                                               13565

<210> SEQ ID NO 30
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-L35G"

<400> SEQUENCE: 30 atg gag gtc gtg aac gaa atc gtc tcc att ggc cag gag gtt ctt ccc     48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg     96
Lys Val Asp Tyr Ala Gln Leu Trp Ser Asp Ala Ser His Cys Glu Val
            20                  25                  30 ctg tac ggg tcc atc gcc ttc gtc atc ctg aag ttc acc ctt ggt cct    144
Leu Tyr Gly Ser Ile Ala Phe Val Ile Leu Lys Phe Thr Leu Gly Pro
        35                  40                  45 ctc gga ccc aag ggt cag tct cga atg aag ttt gtg ttc acc aac tac    192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc    240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct    288
Tyr Ala Met Tyr Thr Ile Gly Val Met Ser Asp Asn Cys Glu Lys Ala
```

```
ttc gac aac aat gtc ttc cga atc acc act cag ctg ttc tac ctc agc    336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag    384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac    432
Pro Leu Thr Trp Leu Gln Phe Phe His His Leu Gly Ala Pro Met Asp
130                 135                 140 atg tgg ctg ttc tac aac tac cga aac gaa gcc gtt tgg atc ttt gtg    480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc    528
Leu Leu Asn Gly Phe Ile His Trp Ile Met Tyr Gly Tyr Tyr Trp Thr
                165                 170                 175 cga ctg atc aag ctc aag ttc cct atg ccc aag tcc ctg att act tct    576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac    624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg    672
Arg Asn Ile Pro Cys Tyr Arg Gln Asp Gly Met Arg Met Phe Gly Trp
210                 215                 220 ttt ttc aac tac ttc tac gtt ggt act gtc ctg tgt ctg ttc ctc aac    720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag    768
Phe Tyr Val Gln Thr Tyr Ile Val Arg Lys His Lys Gly Ala Lys Lys
                245                 250                 255 att cag tga                                                        777
Ile Gln

<210> SEQ ID NO 31
<211> LENGTH: 258
<212> TYPE: PRT
<213> ORGANISM: Euglena gracilis

<400> SEQUENCE: 31

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Gly Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140
```

```
Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 32
<211> LENGTH: 1449
<212> TYPE: DNA
<213> ORGANISM: Yarrowia lipolytica
<220> FEATURE:
<221> NAME/KEY: CDS
<222> LOCATION: (1)..(1449)
<223> OTHER INFORMATION: delta-9 desaturase; GenBank Accession No.
      XM_501496

<400> SEQUENCE: 32 atg gtg aaa aac gtg gac caa gtg gat ctc tcg cag gtc gac acc att      48
Met Val Lys Asn Val Asp Gln Val Asp Leu Ser Gln Val Asp Thr Ile
1               5                   10                  15 gcc tcc ggc cga gat gtc aac tac aag gtc aag tac acc tcc ggc gtt      96
Ala Ser Gly Arg Asp Val Asn Tyr Lys Val Lys Tyr Thr Ser Gly Val
            20                  25                  30 aag atg agc cag ggc gcc tac gac gac aag ggc cgc cac att tcc gag     144
Lys Met Ser Gln Gly Ala Tyr Asp Asp Lys Gly Arg His Ile Ser Glu
        35                  40                  45 cag ccc ttc acc tgg gcc aac tgg cac cag cac atc aac tgg ctc aac     192
Gln Pro Phe Thr Trp Ala Asn Trp His Gln His Ile Asn Trp Leu Asn
50                  55                  60 ttc att ctg gtg att gcg ctg cct ctg tcg tcc ttt gct gcc gct ccc     240
Phe Ile Leu Val Ile Ala Leu Pro Leu Ser Ser Phe Ala Ala Ala Pro
65                  70                  75                  80 ttc gtc tcc ttc aac tgg aag acc gcc gcg ttt gct gtc ggc tat tac     288
Phe Val Ser Phe Asn Trp Lys Thr Ala Ala Phe Ala Val Gly Tyr Tyr
                85                  90                  95 atg tgc acc ggt ctc ggt atc acc gcc ggc tac cac cga atg tgg gcc     336
Met Cys Thr Gly Leu Gly Ile Thr Ala Gly Tyr His Arg Met Trp Ala
            100                 105                 110 cat cga gcc tac aag gcc gct ctg ccc gtt cga atc atc ctt gct ctg     384
His Arg Ala Tyr Lys Ala Ala Leu Pro Val Arg Ile Ile Leu Ala Leu
        115                 120                 125 ttt gga gga gga gct gtc gag ggc tcc atc cga tgg tgg gcc tcg tct     432
Phe Gly Gly Gly Ala Val Glu Gly Ser Ile Arg Trp Trp Ala Ser Ser
    130                 135                 140 cac cga gtc cac cac cga tgg acc gac tcc aac aag gac cct tac gac     480
His Arg Val His His Arg Trp Thr Asp Ser Asn Lys Asp Pro Tyr Asp
145                 150                 155                 160 gcc cga aag gga ttc tgg ttc tcc cac ttt ggc tgg atg ctg ctt gtg     528
Ala Arg Lys Gly Phe Trp Phe Ser His Phe Gly Trp Met Leu Leu Val
                165                 170                 175
```

```
ccc aac ccc aag aac aag ggc cga act gac att tct gac ctc aac aac    576
Pro Asn Pro Lys Asn Lys Gly Arg Thr Asp Ile Ser Asp Leu Asn Asn
            180                 185                 190 gac tgg gtt gtc cga ctc cag cac aag tac tac gtt tac gtt ctc gtc    624
Asp Trp Val Val Arg Leu Gln His Lys Tyr Tyr Val Tyr Val Leu Val
            195                 200                 205 ttc atg gcc att gtt ctg ccc acc ctc gtc tgt ggc ttt ggc tgg ggc    672
Phe Met Ala Ile Val Leu Pro Thr Leu Val Cys Gly Phe Gly Trp Gly
    210                 215                 220 gac tgg aag gga ggt ctt gtc tac gcc ggt atc atg cga tac acc ttt    720
Asp Trp Lys Gly Gly Leu Val Tyr Ala Gly Ile Met Arg Tyr Thr Phe
225                 230                 235                 240 gtg cag cag gtg act ttc tgt gtc aac tcc ctt gcc cac tgg att gga    768
Val Gln Gln Val Thr Phe Cys Val Asn Ser Leu Ala His Trp Ile Gly
                245                 250                 255 gag cag ccc ttc gac gac cga cga act ccc cga gac cac gct ctt acc    816
Glu Gln Pro Phe Asp Asp Arg Arg Thr Pro Arg Asp His Ala Leu Thr
            260                 265                 270 gcc ctg gtc acc ttt gga gag ggc tac cac aac ttc cac cac gag ttc    864
Ala Leu Val Thr Phe Gly Glu Gly Tyr His Asn Phe His His Glu Phe
            275                 280                 285 ccc tcg gac tac cga aac gcc ctc atc tgg tac cag tac gac ccc acc    912
Pro Ser Asp Tyr Arg Asn Ala Leu Ile Trp Tyr Gln Tyr Asp Pro Thr
    290                 295                 300 aag tgg ctc atc tgg acc ctc aag cag gtt ggt ctc gcc tgg gac ctc    960
Lys Trp Leu Ile Trp Thr Leu Lys Gln Val Gly Leu Ala Trp Asp Leu
305                 310                 315                 320 cag acc ttc tcc cag aac gcc atc gag cag ggt ctc gtg cag cag cga   1008
Gln Thr Phe Ser Gln Asn Ala Ile Glu Gln Gly Leu Val Gln Gln Arg
                325                 330                 335 cag aag aag ctg gac aag tgg cga aac aac ctc aac tgg ggt atc ccc   1056
Gln Lys Lys Leu Asp Lys Trp Arg Asn Asn Leu Asn Trp Gly Ile Pro
            340                 345                 350 att gag cag ctg cct gtc att gag ttt gag gag ttc caa gag cag gcc   1104
Ile Glu Gln Leu Pro Val Ile Glu Phe Glu Glu Phe Gln Glu Gln Ala
            355                 360                 365 aag acc cga gat ctg gtt ctc att tct ggc att gtc cac gac gtg tct   1152
Lys Thr Arg Asp Leu Val Leu Ile Ser Gly Ile Val His Asp Val Ser
    370                 375                 380 gcc ttt gtc gag cac cac cct ggt gga aag gcc ctc att atg agc gcc   1200
Ala Phe Val Glu His His Pro Gly Gly Lys Ala Leu Ile Met Ser Ala
385                 390                 395                 400 gtc ggc aag gac ggt acc gct gtc ttc aac gga ggt gtc tac cga cac   1248
Val Gly Lys Asp Gly Thr Ala Val Phe Asn Gly Gly Val Tyr Arg His
                405                 410                 415 tcc aac gct ggc cac aac ctg ctt gcc acc atg cga gtt tcg gtc att   1296
Ser Asn Ala Gly His Asn Leu Leu Ala Thr Met Arg Val Ser Val Ile
            420                 425                 430 cga ggc ggc atg gag gtt gag gtg tgg aag act gcc cag aac gaa aag   1344
Arg Gly Gly Met Glu Val Glu Val Trp Lys Thr Ala Gln Asn Glu Lys
            435                 440                 445 aag gac cag aac att gtc tcc gat gag agt gga aac cga atc cac cga   1392
Lys Asp Gln Asn Ile Val Ser Asp Glu Ser Gly Asn Arg Ile His Arg
    450                 455                 460 gct ggt ctc cag gcc acc cgg gtc gag aac ccc ggt atg tct ggc atg   1440
Ala Gly Leu Gln Ala Thr Arg Val Glu Asn Pro Gly Met Ser Gly Met
465                 470                 475                 480 gct gct tag                                                        1449
Ala Ala
```

```
<210> SEQ ID NO 33
<211> LENGTH: 482
<212> TYPE: PRT
<213> ORGANISM: Yarrowia lipolytica

<400> SEQUENCE: 33

Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
        35                  40                  45

Gln Pro Phe Thr Trp Ala Asn Trp His Gln His Ile Asn Trp Leu Asn
    50                  55                  60

Phe Ile Leu Val Ile Ala Leu Pro Leu Ser Ser Phe Ala Ala Ala Pro
65                  70                  75                  80

Phe Val Ser Phe Asn Trp Lys Thr Ala Ala Phe Ala Val Gly Tyr Tyr
                85                  90                  95

Met Cys Thr Gly Leu Gly Ile Thr Ala Gly Tyr His Arg Met Trp Ala
            100                 105                 110

His Arg Ala Tyr Lys Ala Ala Leu Pro Val Arg Ile Ile Leu Ala Leu
        115                 120                 125

Phe Gly Gly Gly Ala Val Glu Gly Ser Ile Arg Trp Trp Ala Ser Ser
    130                 135                 140

His Arg Val His His Arg Trp Thr Asp Ser Asn Lys Asp Pro Tyr Asp
145                 150                 155                 160

Ala Arg Lys Gly Phe Trp Phe Ser His Phe Gly Trp Met Leu Leu Val
                165                 170                 175

Pro Asn Pro Lys Asn Lys Gly Arg Thr Asp Ile Ser Asp Leu Asn Asn
            180                 185                 190

Asp Trp Val Val Arg Leu Gln His Lys Tyr Tyr Val Tyr Val Leu Val
        195                 200                 205

Phe Met Ala Ile Val Leu Pro Thr Leu Val Cys Gly Phe Gly Trp Gly
    210                 215                 220

Asp Trp Lys Gly Gly Leu Val Tyr Ala Gly Ile Met Arg Tyr Thr Phe
225                 230                 235                 240

Val Gln Gln Val Thr Phe Cys Val Asn Ser Leu Ala His Trp Ile Gly
                245                 250                 255

Glu Gln Pro Phe Asp Asp Arg Arg Thr Pro Arg Asp His Ala Leu Thr
            260                 265                 270

Ala Leu Val Thr Phe Gly Glu Gly Tyr His Asn Phe His His Glu Phe
        275                 280                 285

Pro Ser Asp Tyr Arg Asn Ala Leu Ile Trp Tyr Gln Tyr Asp Pro Thr
    290                 295                 300

Lys Trp Leu Ile Trp Thr Leu Lys Gln Val Gly Leu Ala Trp Asp Leu
305                 310                 315                 320

Gln Thr Phe Ser Gln Asn Ala Ile Glu Gln Gly Leu Val Gln Arg
                325                 330                 335

Gln Lys Lys Leu Asp Lys Trp Arg Asn Asn Leu Asn Trp Gly Ile Pro
            340                 345                 350

Ile Glu Gln Leu Pro Val Ile Glu Phe Glu Phe Gln Glu Gln Ala
        355                 360                 365

Lys Thr Arg Asp Leu Val Leu Ile Ser Gly Ile Val His Asp Val Ser
    370                 375                 380

Ala Phe Val Glu His His Pro Gly Gly Lys Ala Leu Ile Met Ser Ala
```

```
385                 390                 395                 400
Val Gly Lys Asp Gly Thr Ala Val Phe Asn Gly Gly Val Tyr Arg His
                405                 410                 415

Ser Asn Ala Gly His Asn Leu Leu Ala Thr Met Arg Val Ser Val Ile
                420                 425                 430

Arg Gly Gly Met Glu Val Glu Val Trp Lys Thr Ala Gln Asn Glu Lys
                435                 440                 445

Lys Asp Gln Asn Ile Val Ser Asp Glu Ser Gly Asn Arg Ile His Arg
                450                 455                 460

Ala Gly Leu Gln Ala Thr Arg Val Glu Asn Pro Gly Met Ser Gly Met
465                 470                 475                 480

Ala Ala

<210> SEQ ID NO 34
<211> LENGTH: 1101
<212> TYPE: DNA
<213> ORGANISM: Yarrowia lipolytica
<220> FEATURE:
<221> NAME/KEY: CDS
<222> LOCATION: (1)..(1101)
<223> OTHER INFORMATION: cholinephosphate cytidylyltransferase; GenBank
      Accession No. XM_502978

<400> SEQUENCE: 34 atg gcc aaa agc aaa cga cgg tcg gag gct gtg gaa gag cac gtg acc        48
Met Ala Lys Ser Lys Arg Arg Ser Glu Ala Val Glu Glu His Val Thr
1               5                   10                  15 ggc tcg gac gag ggc ttg acc gat act tcg ggt cac gtg agc cct gcc        96
Gly Ser Asp Glu Gly Leu Thr Asp Thr Ser Gly His Val Ser Pro Ala
            20                  25                  30 gcc aag aag cag aag aac tcg gag att cat ttc acc acc cag gct gcc       144
Ala Lys Lys Gln Lys Asn Ser Glu Ile His Phe Thr Thr Gln Ala Ala
        35                  40                  45 cag cag ttg gat cgg gag cgc aag gag gag tat ctg gac tcg ctg atc       192
Gln Gln Leu Asp Arg Glu Arg Lys Glu Glu Tyr Leu Asp Ser Leu Ile
    50                  55                  60 gac aac aag gac tat ctc aag tac cgt cct cga ggc tgg aag ctc aac       240
Asp Asn Lys Asp Tyr Leu Lys Tyr Arg Pro Arg Gly Trp Lys Leu Asn
65                  70                  75                  80 aac ccg cct acc gac cga cct gtg cga atc tac gcc gat gga gtg ttt       288
Asn Pro Pro Thr Asp Arg Pro Val Arg Ile Tyr Ala Asp Gly Val Phe
                85                  90                  95 gat ttg ttc cat ctg gga cac atg cgt cag ctg gag cag tcc aag aag       336
Asp Leu Phe His Leu Gly His Met Arg Gln Leu Glu Gln Ser Lys Lys
            100                 105                 110 gcc ttc ccc aac gca gtg ttg att gtg ggc att ccc agc gac aag gag       384
Ala Phe Pro Asn Ala Val Leu Ile Val Gly Ile Pro Ser Asp Lys Glu
        115                 120                 125 acc cac aag cgg aag gga ttg acc gtg ctg agt gac gtc cag cgg tac       432
Thr His Lys Arg Lys Gly Leu Thr Val Leu Ser Asp Val Gln Arg Tyr
    130                 135                 140 gag acg gtg cga cac tgc aag tgg gtg gac gag gtg gtg gag gat gct       480
Glu Thr Val Arg His Cys Lys Trp Val Asp Glu Val Val Glu Asp Ala
145                 150                 155                 160 ccc tgg tgt gtc acc atg gac ttt ctg gaa aaa cac aaa atc gac tac       528
Pro Trp Cys Val Thr Met Asp Phe Leu Glu Lys His Lys Ile Asp Tyr
                165                 170                 175 gtg gcc cat gac gat ctg ccc tac gct tcc ggc aac gac gat gat atc       576
Val Ala His Asp Asp Leu Pro Tyr Ala Ser Gly Asn Asp Asp Asp Ile
            180                 185                 190
```

```
tac aag ccc atc aag gag aag ggc atg ttt ctg gcc acc cag cga acc      624
Tyr Lys Pro Ile Lys Glu Lys Gly Met Phe Leu Ala Thr Gln Arg Thr
        195                 200                 205 gag ggc att tcc acc tcg gac atc atc acc aag att atc cga gac tac      672
Glu Gly Ile Ser Thr Ser Asp Ile Ile Thr Lys Ile Ile Arg Asp Tyr
    210                 215                 220 gac aag tat tta atg cga aac ttt gcc cgg ggt gct aac cga aag gat      720
Asp Lys Tyr Leu Met Arg Asn Phe Ala Arg Gly Ala Asn Arg Lys Asp
225                 230                 235                 240 ctc aac gtc tcg tgg ctc aag aag aac gag ctg gac ttc aag cgt cat      768
Leu Asn Val Ser Trp Leu Lys Lys Asn Glu Leu Asp Phe Lys Arg His
            245                 250                 255 gtg gcc gag ttc cga aac tcg ttc aag cga aag aag gtc ggt aag gat      816
Val Ala Glu Phe Arg Asn Ser Phe Lys Arg Lys Lys Val Gly Lys Asp
        260                 265                 270 ctc tac ggc gag att cgc ggt ctg ctg cag aat gtg ctc att tgg aac      864
Leu Tyr Gly Glu Ile Arg Gly Leu Leu Gln Asn Val Leu Ile Trp Asn
    275                 280                 285 ggc gac aac tcc ggc act tcc act ccc cag cga aag acg ctg cag acc      912
Gly Asp Asn Ser Gly Thr Ser Thr Pro Gln Arg Lys Thr Leu Gln Thr
290                 295                 300 aac gcc aag aag atg tac atg aac gtg ctc aag act ctg cag gct cct      960
Asn Ala Lys Lys Met Tyr Met Asn Val Leu Lys Thr Leu Gln Ala Pro
305                 310                 315                 320 gac gct gtt gac gtg gac tcc tcg gag aac gtg tct gag aac gtc act     1008
Asp Ala Val Asp Val Asp Ser Ser Glu Asn Val Ser Glu Asn Val Thr
            325                 330                 335 gat gag gag gag gaa gac gac gag gtt gat gag gac gaa gaa gcc         1056
Asp Glu Glu Glu Glu Asp Asp Glu Val Asp Glu Asp Glu Glu Ala
        340                 345                 350 gac gac gac gac gaa gac gac gaa gac gag gaa gac gac gag tag         1101
Asp Asp Asp Asp Glu Asp Asp Glu Asp Glu Glu Asp Asp Glu
        355                 360                 365

<210> SEQ ID NO 35
<211> LENGTH: 366
<212> TYPE: PRT
<213> ORGANISM: Yarrowia lipolytica

<400> SEQUENCE: 35

Met Ala Lys Ser Lys Arg Arg Ser Glu Ala Val Glu Glu His Val Thr
1               5                   10                  15

Gly Ser Asp Glu Gly Leu Thr Asp Thr Ser Gly His Val Ser Pro Ala
            20                  25                  30

Ala Lys Lys Gln Lys Asn Ser Glu Ile His Phe Thr Thr Gln Ala Ala
        35                  40                  45

Gln Gln Leu Asp Arg Glu Arg Lys Glu Glu Tyr Leu Asp Ser Leu Ile
    50                  55                  60

Asp Asn Lys Asp Tyr Leu Lys Tyr Arg Pro Arg Gly Trp Lys Leu Asn
65                  70                  75                  80

Asn Pro Pro Thr Asp Arg Pro Val Arg Ile Tyr Ala Asp Gly Val Phe
                85                  90                  95

Asp Leu Phe His Leu Gly His Met Arg Gln Leu Glu Gln Ser Lys Lys
            100                 105                 110

Ala Phe Pro Asn Ala Val Leu Ile Val Gly Ile Pro Ser Asp Lys Glu
        115                 120                 125

Thr His Lys Arg Lys Gly Leu Thr Val Leu Ser Asp Val Gln Arg Tyr
    130                 135                 140

Glu Thr Val Arg His Cys Lys Trp Val Asp Glu Val Val Glu Asp Ala
```

```
       145                 150                 155                 160
Pro Trp Cys Val Thr Met Asp Phe Leu Glu Lys His Lys Ile Asp Tyr
                    165                 170                 175

Val Ala His Asp Asp Leu Pro Tyr Ala Ser Gly Asn Asp Asp Ile
                180                 185                 190

Tyr Lys Pro Ile Lys Glu Lys Gly Met Phe Leu Ala Thr Gln Arg Thr
                195                 200                 205

Glu Gly Ile Ser Thr Ser Asp Ile Ile Thr Lys Ile Ile Arg Asp Tyr
            210                 215                 220

Asp Lys Tyr Leu Met Arg Asn Phe Ala Arg Gly Ala Asn Arg Lys Asp
225                 230                 235                 240

Leu Asn Val Ser Trp Leu Lys Lys Asn Glu Leu Asp Phe Lys Arg His
                245                 250                 255

Val Ala Glu Phe Arg Asn Ser Phe Lys Arg Lys Val Gly Lys Asp
                260                 265                 270

Leu Tyr Gly Glu Ile Arg Gly Leu Leu Gln Asn Val Leu Ile Trp Asn
            275                 280                 285

Gly Asp Asn Ser Gly Thr Ser Thr Pro Gln Arg Lys Thr Leu Gln Thr
290                 295                 300

Asn Ala Lys Lys Met Tyr Met Asn Val Leu Lys Thr Leu Gln Ala Pro
305                 310                 315                 320

Asp Ala Val Asp Val Asp Ser Ser Glu Asn Val Ser Glu Asn Val Thr
                325                 330                 335

Asp Glu Glu Glu Glu Asp Asp Glu Val Asp Glu Asp Glu Ala
                340                 345                 350

Asp Asp Asp Asp Glu Asp Asp Glu Asp Glu Asp Asp Glu
            355                 360                 365

<210> SEQ ID NO 36
<211> LENGTH: 43
<212> TYPE: DNA
<213> ORGANISM: Artificial Sequence
<220> FEATURE:
<223> OTHER INFORMATION: Primer YL427

<400> SEQUENCE: 36
tttatcgatc ccactacttg tagtcaggcc atcttttacg tac          43

<210> SEQ ID NO 37
<211> LENGTH: 50
<212> TYPE: DNA
<213> ORGANISM: Artificial Sequence
<220> FEATURE:
<223> OTHER INFORMATION: Primer YL428

<400> SEQUENCE: 37
tttaagctta ggggcggcca ggggagcggc cagaacggca gtgagaatag      50

<210> SEQ ID NO 38
<211> LENGTH: 441
<212> TYPE: DNA
<213> ORGANISM: Yarrowia lipolytica

<400> SEQUENCE: 38
atcgatccca ctacttgtag tcaggccatc ttttacgtac gcactgtacc atgatgtcaa    60
tggagtatga tgaaccgact tgagagact cacatctgca caacaccatg tttcagcgga   120
atccgacttc caacccaaac ccaagcccct gtcagatatc gtgagaaggc acggcaccaa   180
ctaatgcaca cactccacct gtattgcacc aagataatga gggcatcgtc ttggcgcgtc   240
```

```
ttggcgagag ccgtgtttcg tgacgcaatc agagcagttt ctggatagta tcttgtccag    300
aaacacgata taaaccccat cgacgggccc gttgaagagc accaacccac tatccaatcc    360
tccaatccaa caatgaagct cgctaccgcc tttactattc tcactgccgt tctggccgct    420
cccctggccg cccctaagct t                                              441
```

```
<210> SEQ ID NO 39
<211> LENGTH: 38
<212> TYPE: DNA
<213> ORGANISM: Artificial Sequence
<220> FEATURE:
<223> OTHER INFORMATION: Primer YL429

<400> SEQUENCE: 39
cccaagcttg ctggttttgc agccaaaata tctgcatc                            38

<210> SEQ ID NO 40
<211> LENGTH: 37
<212> TYPE: DNA
<213> ORGANISM: Artificial Sequence
<220> FEATURE:
<223> OTHER INFORMATION: Primer YL430

<400> SEQUENCE: 40
cttcgtacgc tattttactt cccttacttg aacttg                              37

<210> SEQ ID NO 41
<211> LENGTH: 1581
<212> TYPE: DNA
<213> ORGANISM: Saccharomyces cerevisiae

<400> SEQUENCE: 41
```

```
aagcttgctg ttttgcagc caaaatatct gcatcaatga caaacgaaac tagcgataga    60
cctttggtcc acttcacacc caacaagggc tggatgaatg acccaaatgg gttgtggtac    120
gatgaaaaag atgccaaatg gcatctgtac tttcaataca acccaaatga caccgtatgg    180
ggtacgccat tgtttttggg gccatgctact tccgatgatt tgactaattg gaagatcaa    240 cccattgcta tcgctcccaa gcgtaacgat tcaggtgctt tctctggctc catggtggtt    300
gattacaaca cacgagtgg gttttttcaat gatactattg atccaagaca agatgcgtt    360 gcgatttgga cttataacac tcctgaaagt gaagagcaat acattagcta ttctcttgat    420
ggtggttaca cttttactga ataccaaaag aaccctgttt tagctgccaa ctccactcaa    480
ttcagagatc caaaggtgtt ctggtatgaa ccttctcaaa aatggattat gacggctgcc    540
aaatcacaag actacaaaat tgaaatttac tcctctgatg acttgaagtc ctggaagcta    600
gaatctgcat ttgccaacga aggtttctta ggctaccaat acgaatgtcc aggtttgatt    660
gaagtcccaa ctgagcaaga tccttccaaa tcttattggg tcatgtttat ttctatcaac    720
ccaggtgcac ctgctggcgg ttccttcaac caatattttg ttggatcctt caatggtact    780
cattttgaag cgtttgacaa tcaatctaga gtggtagatt ttggtaagga ctactatgcc    840
ttgcaaactt cttcaacac tgacccaacc tacggttcag cattaggtat tgcctgggct    900
tcaaactggg agtacagtgc ctttgtccca actaacccat ggagatcatc catgtctttg    960
gtccgcaagt tttcttgaa cactgaatat caagctaatc cagagactga attgatcaat    1020
ttgaaagccg aaccaatatt gaacattagt aatgctggtc cctggtctcg ttttgctact    1080
aacacaactc taactaaggc caattcttac aatgtcgatt tgagcaactc gactggtacc    1140
ctagagtttg agttggttta cgctgttaac accacacaaa ccatatccaa atccgtcttt    1200
```

```
gccgacttat cactttggtt caagggttta gaagatcctg aagaatattt gagaatgggt    1260
tttgaagtca gtgcttcttc cttctttttg gaccgtggta actctaaggt caagtttgtc    1320
aaggagaacc catatttcac aaacagaatg tctgtcaaca accaaccatt caagtctgag    1380
aacgacctaa gttactataa agtgtacggc ctactggatc aaaacatctt ggaattgtac    1440
ttcaacgatg gagatgtggt ttctacaaat acctacttca tgaccaccgg taacgctcta    1500
ggatctgtga acatgaccac tggtgtcgat aatttgttct acattgacaa gttccaagta    1560
agggaagtaa aatagcgtac g                                              1581
```